US010183015B2

(12) United States Patent
Bernales et al.

(10) Patent No.: US 10,183,015 B2
(45) Date of Patent: Jan. 22, 2019

(54) HETEROCYCLIC COMPOUNDS AND METHODS OF USE

(71) Applicant: Medivation Technologies LLC, San Francisco, CA (US)

(72) Inventors: Sebastian Bernales, San Francisco, CA (US); Jeffrey Lindquist, Redwood City, CA (US); Mausumee Guha, Trabuco Canyon, CA (US)

(73) Assignee: Medivation Technologies LLC, San Francisco, CA (US)

( * ) Notice: Subject to any disclaimer, the term of this patent is extended or adjusted under 35 U.S.C. 154(b) by 0 days.

(21) Appl. No.: 15/553,589

(22) PCT Filed: Mar. 3, 2016

(86) PCT No.: PCT/US2016/020644
§ 371 (c)(1),
(2) Date: Aug. 25, 2017

(87) PCT Pub. No.: WO2016/141159
PCT Pub. Date: Sep. 9, 2016

(65) Prior Publication Data
US 2018/0028518 A1  Feb. 1, 2018

Related U.S. Application Data

(60) Provisional application No. 62/128,251, filed on Mar. 4, 2015.

(51) Int. Cl.
*A61K 31/4439*   (2006.01)
(52) U.S. Cl.
CPC ................. *A61K 31/4439* (2013.01)
(58) Field of Classification Search
USPC ........................................................ 514/342
See application file for complete search history.

(56) References Cited

U.S. PATENT DOCUMENTS

| | | |
|---|---|---|
| 6,444,687 B1 | 9/2002 | Stamford et al. |
| 6,924,298 B2 | 8/2005 | Tisdell et al. |
| 7,244,739 B2 | 7/2007 | Cheng et al. |
| 8,063,080 B2 | 11/2011 | Fulp et al. |
| 8,207,196 B2 | 6/2012 | Uesugi et al. |
| 8,229,106 B2 | 7/2012 | Greiss et al. |
| 8,822,513 B2 | 9/2014 | Lu et al. |
| 8,907,099 B2 | 12/2014 | Learmonth et al. |
| 9,670,172 B2 | 6/2017 | Chakravarty et al. |
| 2001/0031781 A1 | 10/2001 | Illig et al. |
| 2013/0165472 A1 | 6/2013 | Chau et al. |
| 2014/0045854 A1 | 2/2014 | Uesugi et al. |
| 2014/0303213 A1 | 10/2014 | Uesugi et al. |

FOREIGN PATENT DOCUMENTS

| | | |
|---|---|---|
| EP | 0438230 A2 | 7/1991 |
| WO | 199940088 A1 | 8/1999 |
| WO | 2006131336 A1 | 12/2006 |
| WO | 2008097835 A2 | 8/2008 |
| WO | 2008114157 A1 | 9/2008 |
| WO | 2009080663 A1 | 7/2009 |
| WO | 2011085269 A1 | 7/2011 |
| WO | 2012084678 A1 | 6/2012 |
| WO | 2012099200 A1 | 7/2012 |
| WO | 2013038136 A1 | 3/2013 |
| WO | 2014199164 A1 | 12/2014 |
| WO | 2014210389 A1 | 12/2014 |
| WO | 2015031650 A1 | 3/2015 |
| WO | 2016141258 A1 | 9/2016 |

OTHER PUBLICATIONS

Kamisuki et. al. (Journal of Medicinal Chemistry (2011) 54:4923-4927). (Year: 2011).*
J. G. Cannon, Chapter Nineteen in Burger's Medicinal Chemistry and Drug Discovery, Fifth Edition, vol. I: Principles and Practice, Wiley-Interscience 1995. (Year: 1995).*
Bataller et. al. (Journal of Clinical Investigation (2005) 115:209-218). (Year: 2005).*
Bellale et al., "Diarylthiazole: An Antimycobacterial Scaffold Potentially Targeting PrrB-PrrA Two-Component System," Journal of Medicinal Chemistry, 2014, vol. 57, pp. 6572-6582.
International Search Report and Written Opinion for PCT/US2014/053215 dated Jan. 29, 2015, 11 pages.
International Preliminary Report on Patentability for PCT/US2016/020644, dated Sep. 5, 2017, 7 pages.
International Search Report for PCT/US2016/020644, dated Jun. 9, 2016, 6 pages.
International Search Report and Written Opinion for PCT/US2016/020802, dated Apr. 29, 2016, 17 pages.
Kamisuki et al., "Synthesis and Evaluation of Diarylthiazole Derivatives That Inhibit Activation of Sterol Regulatory Element-Binding Proteins," Journal of Medicinal Chemistry, vol. 54, No. 13, 2011, pp. 4923-4927.
Li et al., Synthesis and biological evaluation of 1,2,4-trisubstituted imidazoles and 1,3,5-trisubstituted pyrazoles as inhibitors of transforming growth factor b type 1 receptor (ALK5), Bioorganic & Medicinal Chemistry Letters 19, 2009, pp. 4868-4872.
Pujala et al., U.S. Appl. No. 15/553,622, amended claims filed Aug. 25, 2017, 29 pages.
Rice et al., "An Improved Synthesis of 1,2,4-Oxadiazoles on Solid Support," Bioorganic & Medicinal Chemistry Letters 11, 2001, pp. 753-755.
Shahlaei & Nazari, "Prediction of glucagon receptor antagonist activities of some substituted imidazoles using combined radial basis function neural network and density functional theory," Medicinal Chemistry Research, 2014, vol. 23, pp. 2744-2756.

(Continued)

*Primary Examiner* — Marcos L Sznaidman
(74) *Attorney, Agent, or Firm* — Banner & Witcoff, Ltd.

(57) ABSTRACT

This disclosure provides compounds and methods of using those compounds to treat liver fibrosis, including liver fibrosis which is a precursor to, is concurrent with, is associated with, or is secondary to nonalcoholic steatohepatitis (NASH); elevated cholesterol levels, and insulin resistance.

3 Claims, 9 Drawing Sheets

(56) References Cited

OTHER PUBLICATIONS

Tani et al., "Programmed synthesis of arylthiazoles through sequential C—H couplings," Chemical Science, 2014, vol. 5, pp. 123-135.

* cited by examiner

COMPOUND #37
MOUSE PK

| PO (10MG/KG) | |
|---|---|
| PK PARAMETERS | MEAN |
| C MAX (μM) | 32.4 |
| T MAX (h) | 1 |
| AUC FAST (μM*h) | 294 |
| TERMINAL t1/2(h) | 4.23 |
| BIOAVAILABILITY(%) | 151% |

FIG. 2A

COMPOUND #37
DOG ORAL PK

| PO DOSE LEVEL (MG/KG) | 2 (N=3) | | 10 (N=1) | |
|---|---|---|---|---|
| PK PARAMETERS | MEAN | SD | DOG2002 | SD |
| C<sub>MAX</sub> (μM) | 27.0 | 1.21 | 182 | - |
| T<sub>MAX</sub> (h) | 1.5 | 0 | 1.5 | - |
| AUC<sub>FAST</sub> (μM*h) | 449 | 17.3 | 4200 | - |
| TERMINAL t 1/2 (h) | 10.7 | 2.05 | 11.3 | - |
| BIOAVAILABILITY | 99.3% | 20.1% | 62.9% | - |

FIG. 2B

HETEROCYCLIC COMPOUNDS AND METHODS OF USE

This application claims priority to Ser. No. 62/128,251 filed on Mar. 5, 2015. Ser. No. 62/128,251 as well as each reference cited in this disclosure is incorporated herein by reference in its entirety.

TECHNICAL FIELD

This disclosure relates generally to therapeutics for treatment of liver fibrosis, elevated cholesterol levels, and insulin resistance.

BACKGROUND

Sterol regulatory element-binding proteins (SREBPs) are major transcription factors regulating the biosynthesis of cholesterol, fatty acid, and triglyceride. They control the expression of crucial genes involved in lipogenesis and uptake. Inhibition of the SREBP pathway can reduce lipid biosynthesis and thus can be a strategy to treat metabolic diseases, such as type II diabetes, insulin resistance, fatty liver and atherosclerosis [Xiao, et al. *Acta Biochim. Biophys. Sin* (2013) 45:1, pp 2-10]. In mammals, three SREBP isoforms are known, designated SREBP-1a, SREBP-1c, and SREBP-2. SREBP-1a controls a broad range of SREBP targets including production of fatty acids, triglycerides, phospholipids and cholesterol. SREBP-1c preferentially activates genes of fatty acid and triglyceride metabolism, whereas SREBP-2 preferentially activates genes of cholesterol metabolism, both of which have been studied in human and mice models [Horton, et al. J. Clin. Invest. (2002) 109:9, pp 1125-1131], as well as *Drosophila* [Rawson. Nature Rev. Mol. Cell Biol. (2003) 4:8, pp 631-640].

Recent studies have also presented a link between upregulation of lipid synthesis and prostate cancer [Suburu, et al. Prostaglandins Other Lipid Mediat. (2012) 98:0, pp 1-10]. The metabolic shift from catabolic to anabolic metabolism is a hallmark of cancer cells. Many cancers require synthesis of fatty acids, and other lipids such as cholesterol and androgens are implicated in prostate cancer. SREP-1c is the major transcriptional regulator of enzymes in the fatty acid synthesis pathway, and its expression can be stimulated by androgens and epidermal growth factor (EGF) in prostate cancer cells. Overexpression of SREP-1c is sufficient to cause tumorigenicity and invasion of prostate cancer cells. SREBP-1 can also increase expression of NOXS, a prominent producer of reactive oxygen species (ROS) and regulator of prostate cancer cell growth [Brar, et al. Am. J. Physiol. Cell Physiol. (2003) 285:2, pp C353-369; Huang, et al. Mol. Cancer Res. (2012) 10:1, pp 133-142; Huang, et al. Cancer Research (2012) 72:8, SUPPL. 1; Huang, et al. Mol. Cancer Res. (2014) 13:4, pp 855-866].

SREBP-2, a regulator of androgen synthesis, is also itself regulated by androgens, demonstrating a direct feedback circuit for regulation of androgen production. SREBP-2 expression increases during disease progression and is significantly higher after castration. This transcription factor also lacks its feedback inhibition in prostate cancer cells, implicating a role for cholesterol and androgen synthesis in prostate cancer [Eberle, et al. Biochimie (2004) 86:11, pp 839-848; Ettinger, et al. Cancer Res. (2004), 64:6, pp 2212-2221; Chen, et al. Int. J. Cancer (2001), 91:1, pp 41-45].

Blocking SREBP functions linked to disease states therefore represents an important therapeutic approach for limiting lipid/cholesterol synthesis in membrane production which occurs in metabolic diseases and in cancer progression, as well as in viral pathogenesis [Naar, et al. Clin. Lipidol. (2012) 7:1, pp 27-36]. Small molecule therapeutics affecting metabolic regulators such as mTOR, AMPK or SIRT1, including Rapamycin, Metformin, or Resveratrol, respectively, may impinge on the transcriptional activity of SREBPs. Recently, two non-sterol small molecules, fatostatin and betulin have been found to inhibit SREBP processing [Kamisuki, et al. Chem. Biol. (2009) 16:8, pp 882-892; Tang, et al. Cell. Metab. (2011) 13:1, pp 44-56]. Methods for the treatment of cancers having a p53 mutation, such as breast cancer cells, using SREBP inhibitors have been presented [Freed-Pastor, et al. PCT. Publication WO2013-110007A1].

Fatostatin analogs have recently been described as potential therapeutics for the treatment of metabolic disorders [Uesugi, et al. U.S. Pat. No. 8,207,196]. Key compounds presented therein are based around Formula X:

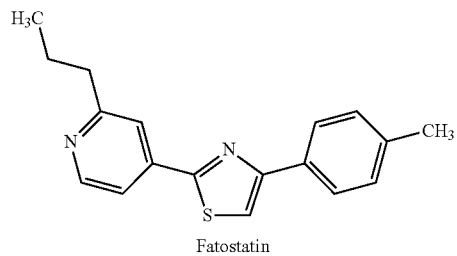

Fatostatin

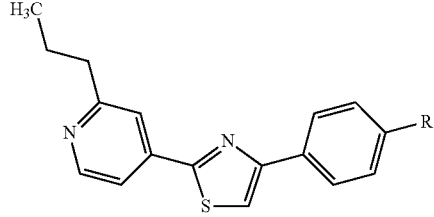

Formula X wherein R is H, F, Cl, Br, OBz, OH, OCH$_3$, OCH$_2$CO$_2$Me, OCH$_2$CO$_2$H, NH$_2$, NHiPr, NHCOCH$_3$, NHSO$_2$Me, NH[benzyl], NH[cyclopropyl], NH[tertbutyloxycarbonyl], NH[cyclohexyl], NH[tosyl], NH[quinolin-8-yl], and NH[thiophen-2-yl]. In particular, one compound (FGH10019), the methanesulfonamide derivative of fatostatin above wherein R is NHSO$_2$Me, has been described as a lead candidate [Kamisuki, et al. J. Med. Chem. (2011) 54:13, pp 4923-4927].

BRIEF SUMMARY

This disclosure provides compounds and methods of using those compounds to treat liver fibrosis, elevated cholesterol levels, and insulin resistance.

In some embodiments, compounds disclosed herein fall within formulae (Ia) or (Ib):

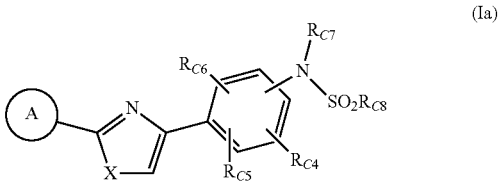

(Ia)

-continued

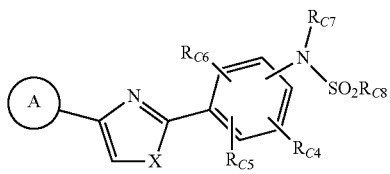
(Ib)

or a pharmaceutically acceptable salt thereof, wherein:
A is either:
i. an aryl or heteroaryl, each having only one ring, substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, $-(CH_2)_mCF_3$, $=O$, $-CH_2OCH_3$, $-OBn$, $-CO_2H$, $-CO_2$-Alkyl, $-NR10R11$, and $-CONR10R11$; or
ii. an aryl or heteroaryl, each having more than one ring, optionally substituted with 1, 2, or 3 substituents selected from the group consisting of halogen, CN, $CF_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, $-(CH_2)_mCF_3$, $=O$, $-CH_2OCH_3$, $-CH_2OH$, $-OBn$, $-CO_2H$, $-CO_2$-Alkyl, $-NR10R11$, and $-CONR10R11$;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, $-CO_2H$, $-CONR10R11$, or $-NHCONH_2$; or is taken with $R_{C7}$ to form the moiety

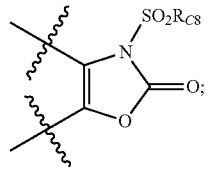

$R_{C7}$ is hydrogen, C1-C6 linear or branched alkyl, C1-C6 linear or branched hydroxyalkyl, $-(CR_{9a}R_{9b})_mNR10R11$, $-CO_2$-Alkyl, $-(CR_{9a}R_{9b})_mO$-Alkyl, $-(CR_{9a}R_{9b})_mOPO_3Na_2$, $-(CR_{9a}R_{9b})_mO(CR_{9a}R_{9b})_nO$-Alkyl, $-(CR_{9a}R_{9b})_mO(C=O)$-Alkyl, $-(CR_{9a}R_{9b})_mO(CR_{9a}R_{9b})_nO(C=O)$-Alkyl, $-(C=O)CH=CH_2$, $-SO_2R_{C8'}$;
or is taken with one of $R_{C4}$, $R_{C5}$ or $R_{C6}$ to form the moiety

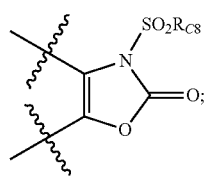

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;
R10 and R11 are independently hydrogen, $-SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;
X is a heteroatom selected from S, O; or $NR_B$ wherein $R_B$ is hydrogen, a C1-C6 linear or branched alkyl, or a C3-C6 cycloalkyl; and
Each m and n is 1, 2 or 3.

In some embodiments, compounds disclosed herein fall within formulae (IIa) or (IIb):

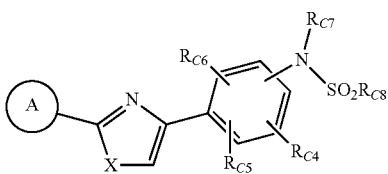
(IIa)

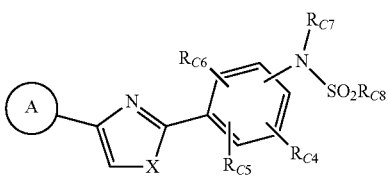
(IIb)

or a pharmaceutically acceptable salt thereof, wherein:
A is a moiety selected from the group consisting of:

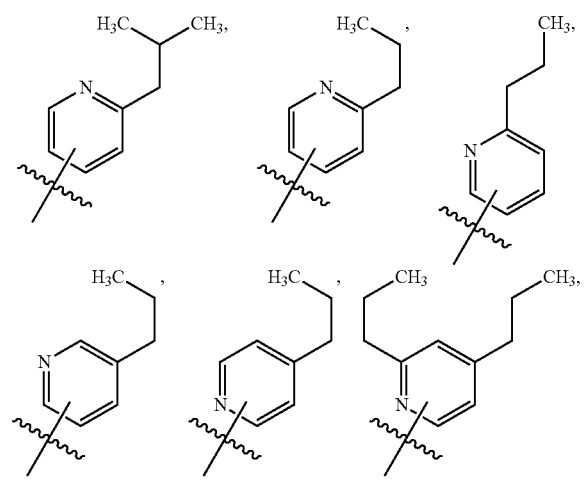

-continued
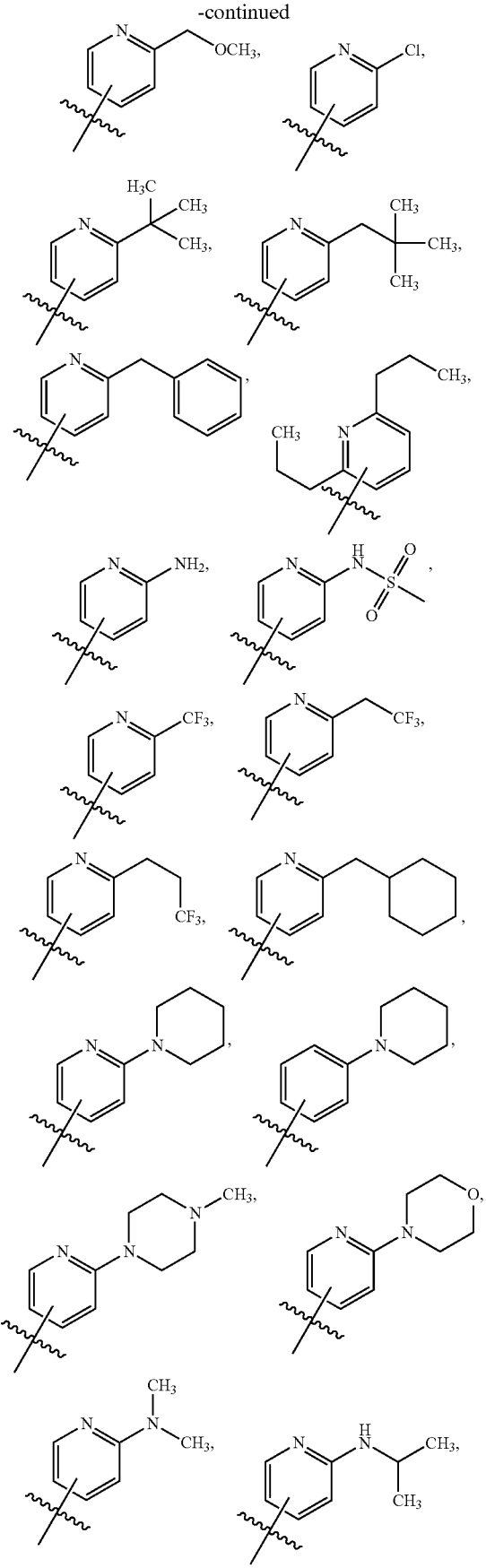
-continued
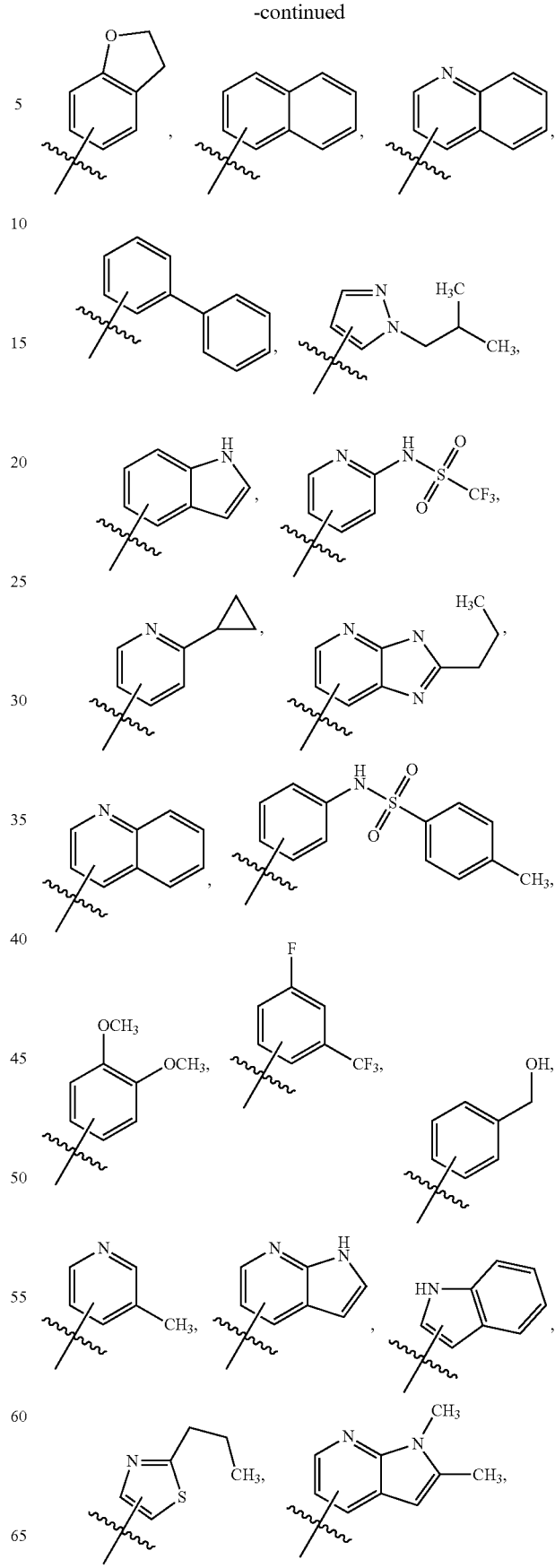

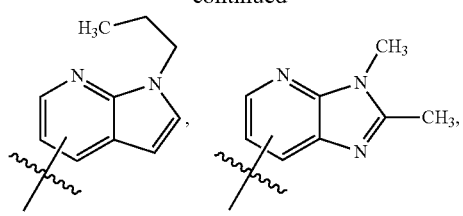
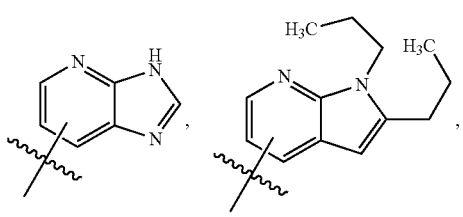
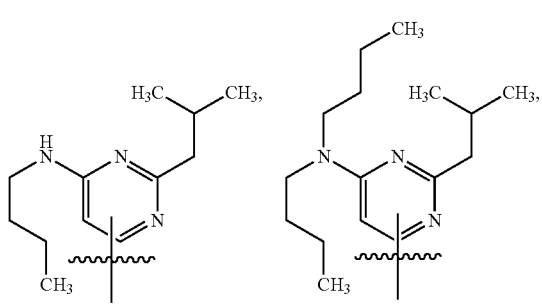
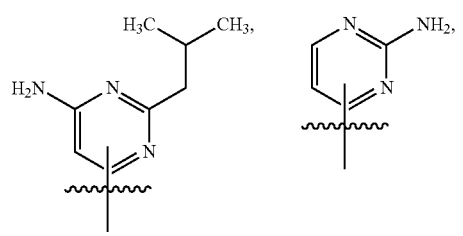
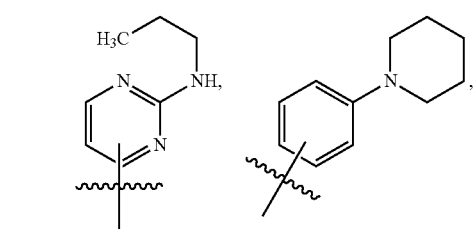
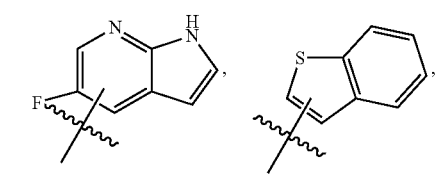
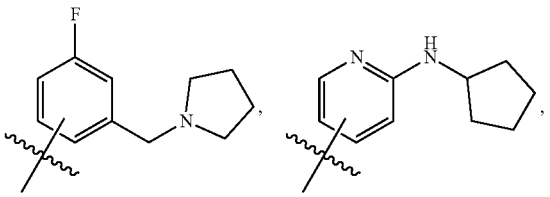
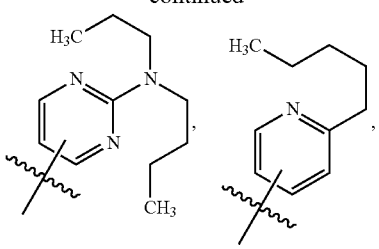
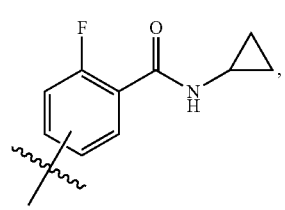
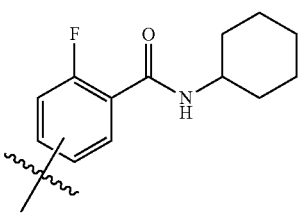
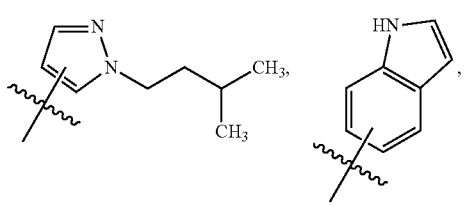
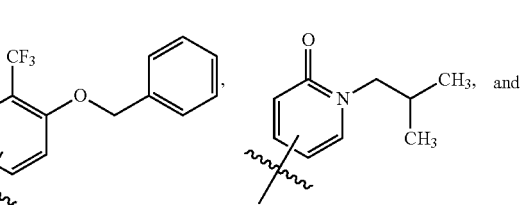
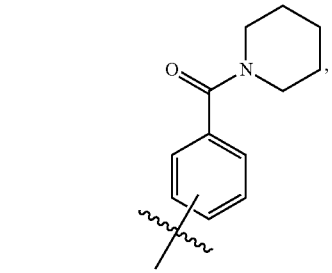
wherein the ring containing X is linked to ring A at any available position on ring A;
Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$; or is taken with $R_{C7}$ to form the moiety

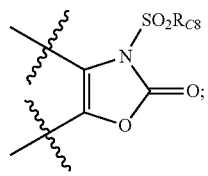

$R_{C7}$ is hydrogen, C1-C6 linear or branched alkyl, C1-C6 linear or branched hydroxyalkyl, —$(CR_{9a}R_{9b})_m NR10R11$, —$CO_2$-Alkyl, —$(CR_{9a}R_{9b})_m$O-Alkyl, —$(CR_{9a}R_{9b})_m OPO_3Na_2$, —$(CR_{9a}R_{9b})_m O(CR_{9a}R_{9b})_n$O-Alkyl, —$(CR_{9a}R_{9b})_m O(C=O)$-Alkyl, —$(CR_{9a}R_{9b})_m O(CR_{9a}R_{9b})_n O(C=O)$-Alkyl, —$(C=O)CH=CH_2$, —$SO_2R_{C8'}$; or is taken with one of $R_{C4}$, $R_{C5}$ or $R_{C6}$ to form the moiety

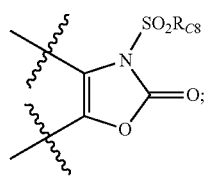

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6,2$-thiazolidine-1,1-dione, a $1,2\lambda^6,3$-oxathiazolidine-2,2-dione, or a $1\lambda^6,2,5$-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

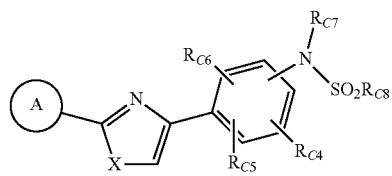
(IIa)

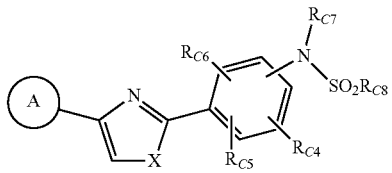
(IIb)

or a pharmaceutically acceptable salt thereof, wherein:

A is a moiety selected from the group consisting of:

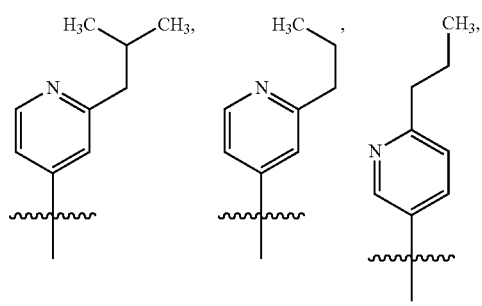

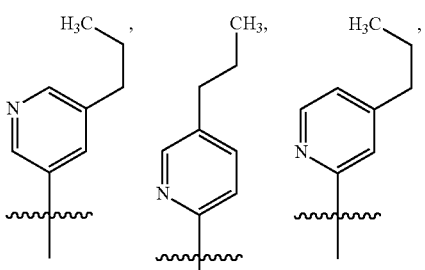

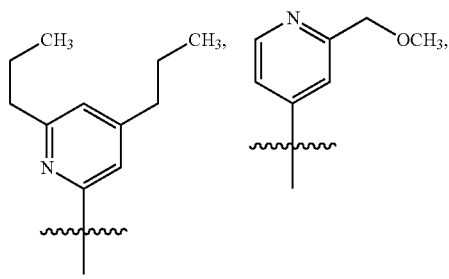

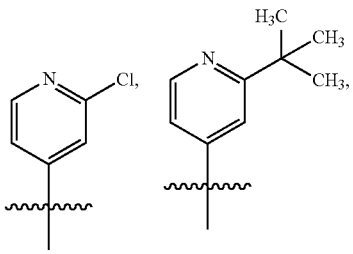

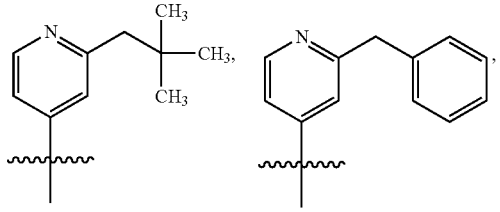

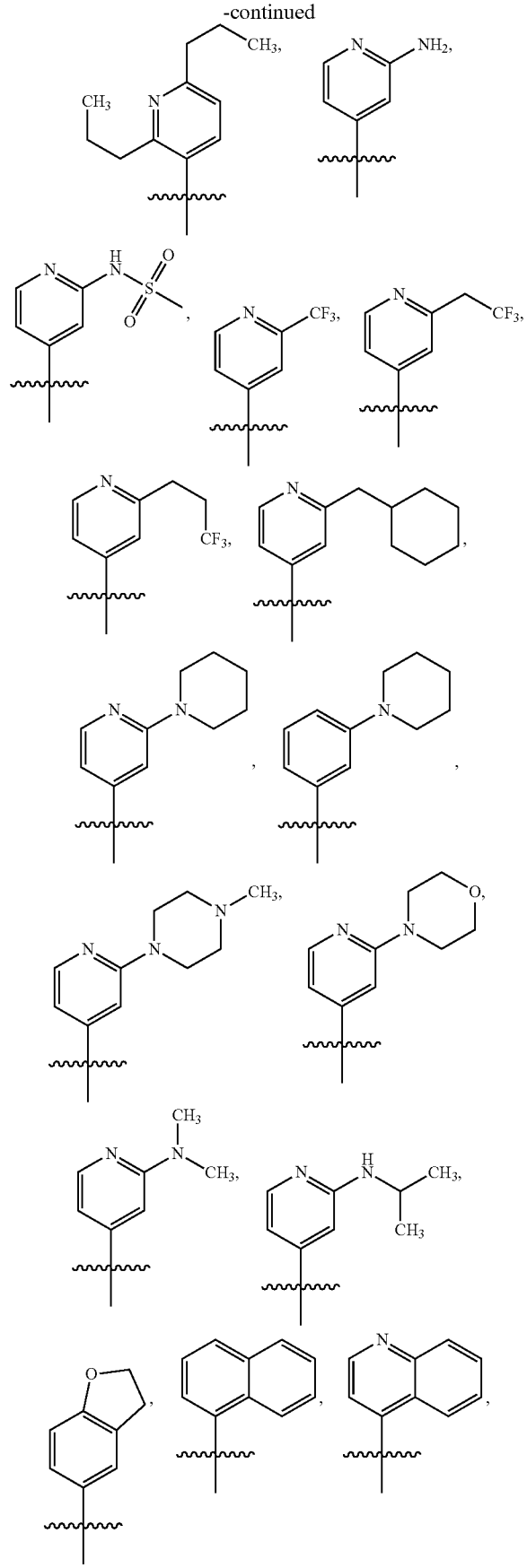
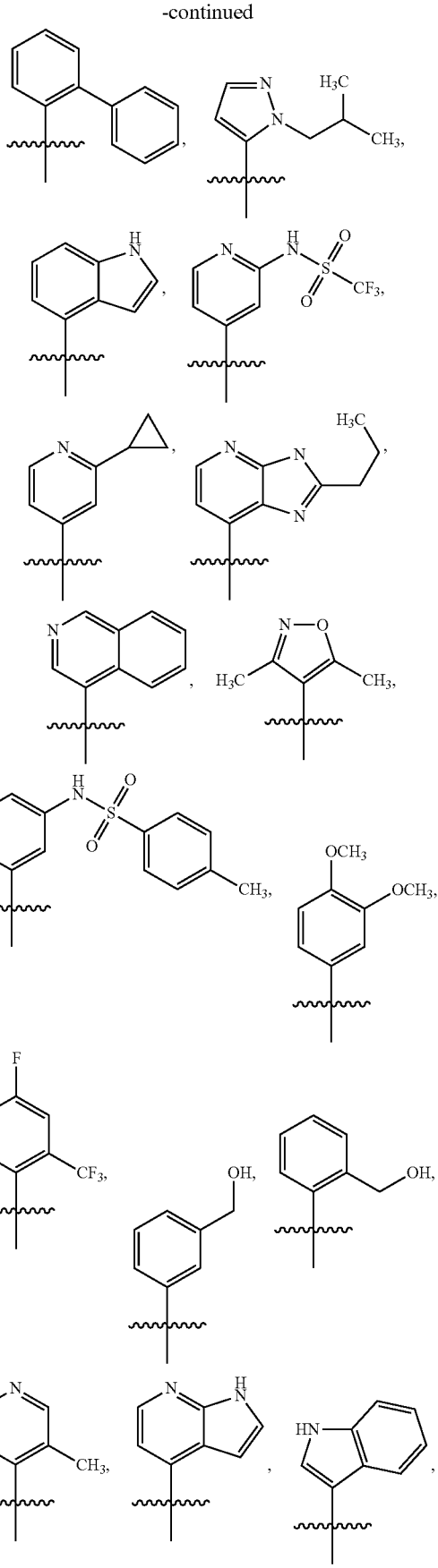

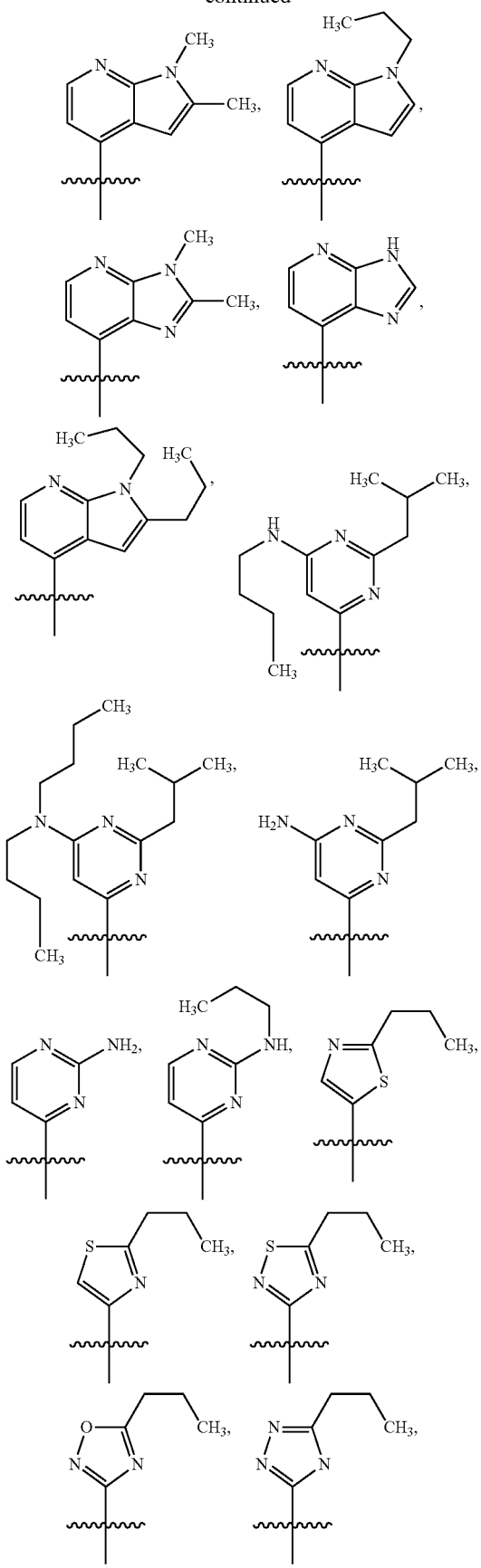
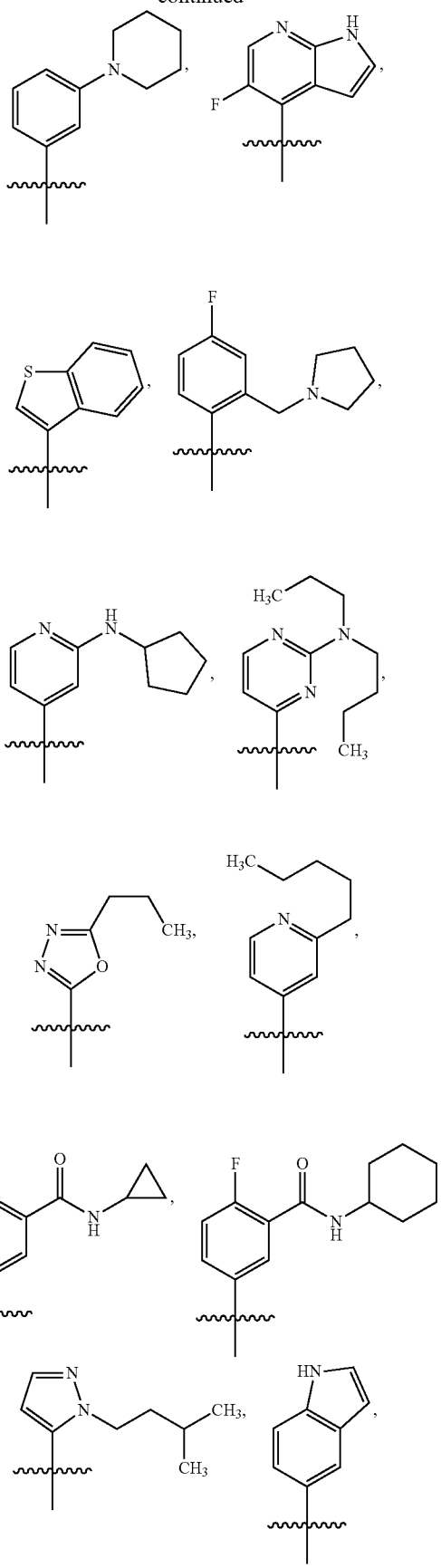

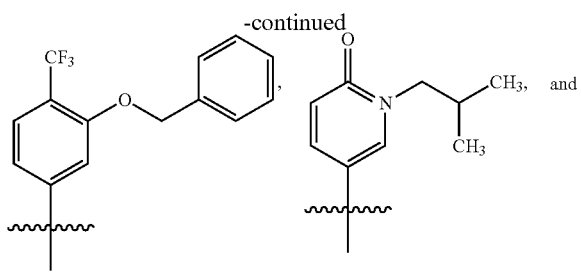

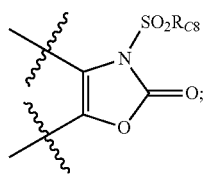

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —$CONR10R11$, or —$NHCONH_2$; or is taken with $R_{C7}$ to form the moiety

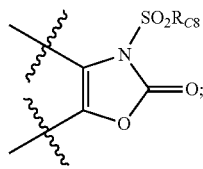

$R_{C7}$ is hydrogen, C1-C6 linear or branched alkyl, C1-C6 linear or branched hydroxyalkyl, —$(CR_{9a}R_{9b})_m NR10R11$, —$CO_2$-Alkyl, —$(CR_{9a}R_{9b})_m$O-Alkyl, —$(CR_{9a}R_{9b})_m OPO_3Na_2$, —$(CR_{9a}R_{9b})_m O(CR_{9a}R_{9b})_n$O-Alkyl, —$(CR_{9a}R_{9b})_m O(C=O)$-Alkyl, —$(CR_{9a}R_{9b})_m O(CR_{9a}R_{9b})_n O(C=O)$-Alkyl, —$(C=O)CH=CH_2$, —$SO_2R_{C8'}$; or is taken with one of $R_{C4}$, $R_{C5}$ or $R_{C6}$ to form the moiety $R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6$,2-thiazolidine-1,1-dione, a $1,2\lambda^6$,3-oxathiazolidine-2,2-dione, or a $1\lambda^6$,2,5-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

Examples of compounds falling within one or more of the formulae described above are provided in Table 1, such as a compound selected from the group consisting of Compound Nos. 1 to 152; or a pharmaceutically acceptable salt, solvate, prodrug, or N-oxide thereof.

Further provided is a pharmaceutical composition, comprising a compound of Formulae (Ia), (Ib), (IIa), or (IIb), or any variations described herein, or a salt thereof, and a pharmaceutically acceptable carrier or excipient.

Further provided is a kit, comprising a compound of Formulae (Ia), (Ib), (IIa) or (IIb), or any variations described herein, or a salt thereof, and instructions for use.

Further provided are methods of treating liver fibrosis, elevated cholesterol levels, and insulin resistance in individuals in need thereof, such as humans, comprising administering to an individual in need thereof a therapeutically effective amount of a compound of Formulae (Ia), (Ib), (IIa), or (IIb), or any variations described herein, or a pharmaceutically acceptable salt thereof. In some embodiments, the individuals are diagnosed with or are suspected of having non-alcoholic steatohepatitis (NASH).

BRIEF DESCRIPTION OF THE DRAWINGS

FIG. 2A. Pharmacokinetic parameters for Compound #37 (mouse).

FIG. 2-B. Pharmacokinetic parameters for Compound #37 (dog).

FIG. 5A, plasma glucose. FIG. 5B, insulin. FIG. 5C, calculated HOMA-IR scores. Error bars indicate ±SEM.

FIG. 8A, male dogs. FIG. 8B, female dogs. D-5, day 5 (pre-dose); D14, day 14; D27, day 27 (end of dosing, N=3); D57, day 57 (end of recovery, N=2).*, p<0.01;**, p<0.05.

FIG. 9A, male dogs. FIG. 9B, female dogs. D-5, day 5 (pre-dose); D14, day 14; D28, day 28 (end of dosing, N=3); D58, day 58 (end of recovery, N=2).

DETAILED DESCRIPTION

Definitions

Figure 1A:
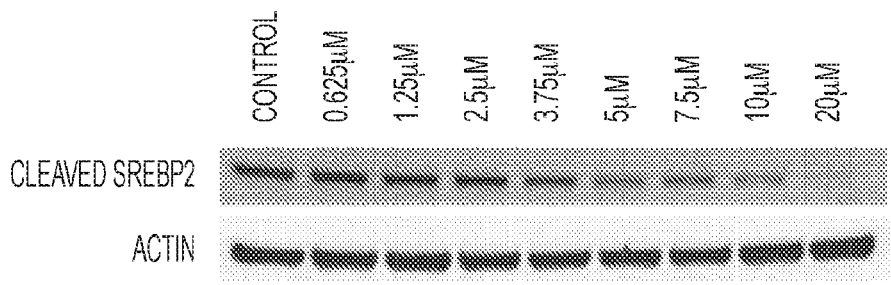
FIG. 1A. Western blot demonstrating inhibition of SREBP cleavage by Compound #37 in HepG2 Cells.

For use herein, unless clearly indicated otherwise, use of the terms "a," "an," and the like refers to one or more.

As used herein, reference to "about" a value or parameter herein includes (and describes) embodiments that are directed to that value or parameter per se. For example, description referring to "about X" includes description of "X."

"Alkyl" refers to and includes saturated linear or branched univalent hydrocarbon structures and combinations thereof. Particular alkyl groups are those having 1 to 6 carbon atoms (a "C1-C6 alkyl"). When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. This term is exemplified by groups such as methyl, t-butyl, n-heptyl, octyl, and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to ethenyl, —CH=CH$_2$, —CH$_2$—CH=CH—CH$_3$ and —CH=CH—CH=CH$_2$.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like. Examples of alkynyl include but are not limited to ethynyl, "—C≡CH," —CH$_2$—C≡C—CH$_3$ and —C≡C—C≡CH.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 6 annular carbon atoms (a "C3-C6 cycloalkyl"). Examples of cycloalkyl groups include adamantyl, decahydronaphthalenyl, cyclopropyl, cyclobutyl, cyclopentyl, cyclohexyl, and the like.

"Cycloalkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (a "C$_3$-C$_8$ cycloalkenyl"). Examples of cycloalkenyl groups include cyclopropenyl, cyclobutenyl, cyclopentenyl, cyclohexenyl, and the like.

"Heterocycle," "heterocyclic," or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Aryl" as used herein refers to an unsaturated aromatic carbocyclic group having a single ring (e.g., phenyl) or multiple condensed rings (e.g., naphthyl or anthryl) which condensed rings may or may not be aromatic. The aryl group may be optionally substituted independently with one or more substituents described herein. Particular aryl groups are those having from 6 to 14 annular (i.e., ring) carbon atoms (a "C6-C14 aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. The heteroaryl group may be optionally substituted independently with one or more substituents described herein. Particular heteroaryl groups are 5- to 14-membered rings having 1 to 12 annular (i.e., ring) carbon atoms and 1 to 6 annular (i.e., ring) heteroatoms independently selected from nitrogen, oxygen and sulfur; 5- to 10-membered rings having 1 to 8 annular carbon atoms and 1 to 4 annular heteroatoms independently selected from nitrogen, oxygen and sulfur; and 5-6- or 7-membered rings having 1 to 5 annular carbon atoms and 1 to 4 annular heteroatoms independently selected from nitrogen, oxygen and sulfur. In one variation, heteroaryl includes monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Alkoxy" refers to the group alkyl-O—, which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Hydroxyalkyl" refers to the group alkyl-OH, which includes, by way of example, hydroxymethyl, 1-hydroxyethyl, 2-hydroxyethyl, 1-hydroxyprop-1-yl, 2-hydroxyprop-2-yl, 3-hydroxypropyl, 4-hydroxybutyl, 5-hydroxypentyl, 6-hydroxyhexyl, and the like.

"Halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." An alkenyl group in which each H is replaced with a halo group is referred to as a "perhaloalkenyl." An alkynyl group in which each H is replaced with a halo group is referred to as a "perhaloalkynyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

Any and all stereoisomers, including geometric isomers (cis/trans or E/Z isomers), tautomers, salts, N-oxides, and solvates of the compounds described herein can be used in the disclosed methods. This disclosure also provides methods of making such compounds.

Compounds

In some embodiments, compounds disclosed herein fall within formulae (Ia) or (Ib):

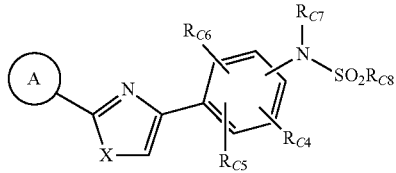

(Ia)

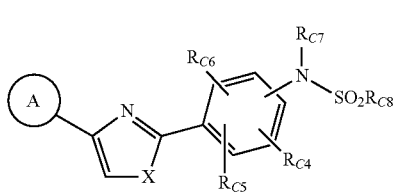

(Ib)

or a pharmaceutically acceptable salt thereof, wherein:
A is either:
i. an aryl or heteroaryl, each having only one ring, substituted with 1, 2, or 3 substituents selected from the group consisting of halogen, CN, CF$_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —(CH$_2$)$_m$CF$_3$, =O, —CH$_2$OCH$_3$, —OBn, —CO$_2$H, —CO$_2$-Alkyl, —NR10R11, and —CONR10R11; or
ii. an aryl or heteroaryl, each having more than one ring, optionally substituted with 1, 2, or 3 substituents selected from the group consisting of halogen, CN, CF$_3$, OH, C1-C6 linear or branched alkyl, C3-C6 cycloalkyl, C3-C6 cycloalkenyl, C1-C6 linear or branched hydroxyalkyl, C1-C3 linear or branched alkoxy, C3-C6 cycloalkylmethyl, —(CH$_2$)$_m$CF$_3$, =O, —CH$_2$OCH$_3$, —CH$_2$OH, —OBn, —CO$_2$H, —CO$_2$-Alkyl, —NR10R11, and —CONR10R11;

Each $R_{C4}$, $R_{C5}$, and $R_{C6}$, is independently hydrogen, halogen, CN, CF$_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —CO$_2$H, —CONR10R11, or —NHCONH$_2$; or is taken with $R_{C7}$ to form the moiety

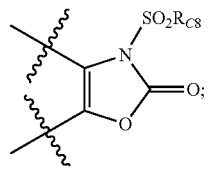

$R_{C7}$ is hydrogen, C1-C6 linear or branched alkyl, C1-C6 linear or branched hydroxyalkyl, —(CR$_{9a}$R$_{9b}$)$_m$NR10R11, —CO$_2$-Alkyl, —(CR$_{9a}$R$_{9b}$)$_m$O-Alkyl, —(CR$_{9a}$R$_{9b}$)$_m$OPO$_3$Na$_2$, —(CR$_{9a}$R$_{9b}$)$_m$O(CR$_{9a}$R$_{9b}$)$_n$O-Alkyl, —(CR$_{9a}$R$_{9b}$)$_m$O(C=O)-Alkyl, —(CR$_{9a}$R$_{9b}$)$_m$O(CR$_{9a}$R$_{9b}$)$_n$O(C=O)-Alkyl, —(C=O)CH=CH$_2$, —SO$_2$R$_{C8'}$; or is taken with one of $R_{C4}$, $R_{C5}$ or $R_{C6}$ to form the moiety

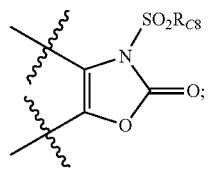

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —SO$_2$R$_{C8}$', C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a 1$\lambda^6$,2-thiazolidine-1,1-dione, a 1,2$\lambda^6$,3-oxathiazolidine-2,2-dione, or a 1$\lambda^6$,2,5-thiadiazolidine-1,1-dione;

X is a heteroatom selected from S, O; or NR$_B$ wherein R$_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

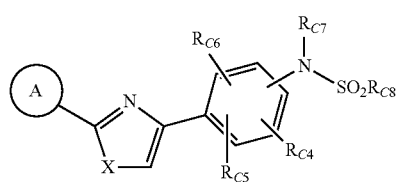
(IIa)

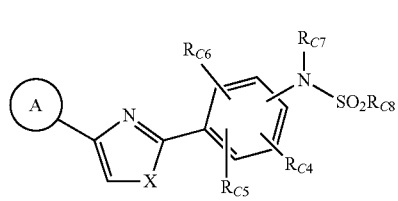
(IIb)

or a pharmaceutically acceptable salt thereof, wherein:

A is a moiety selected from the group consisting of:

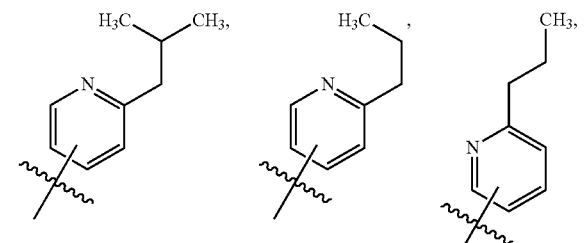

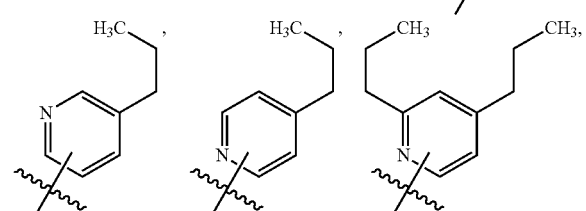

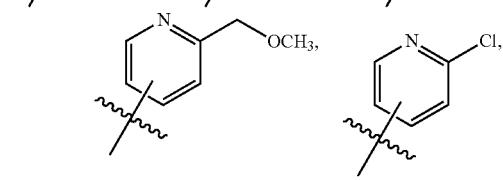

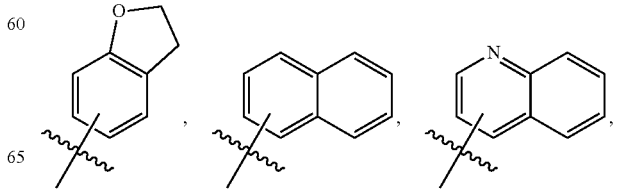

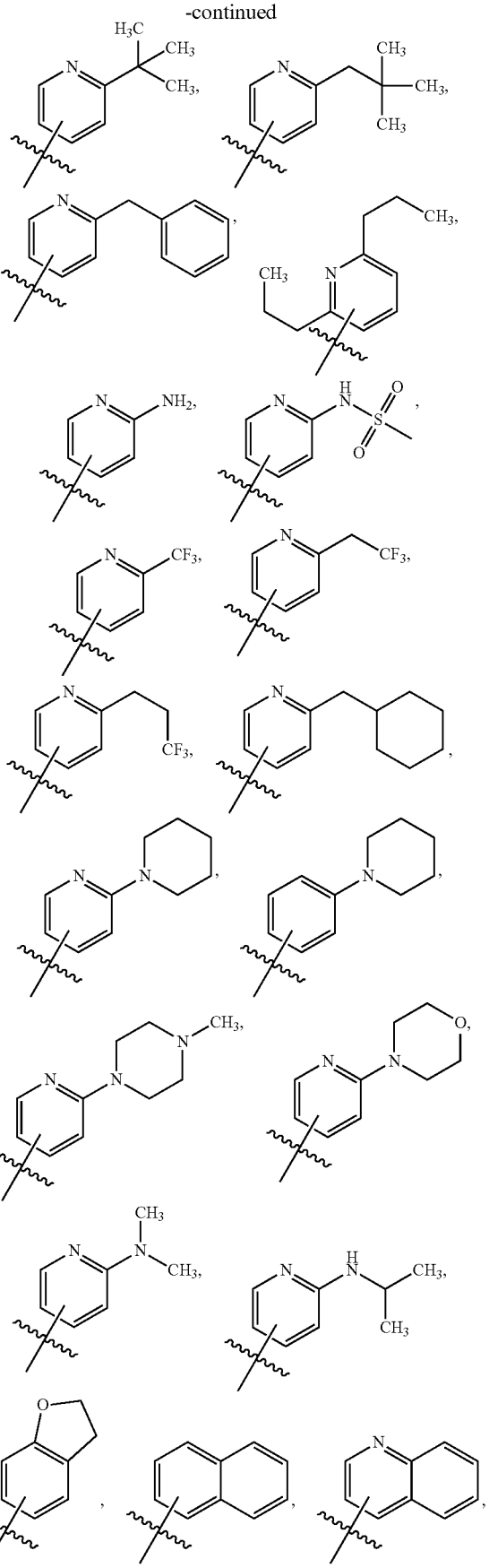

-continued
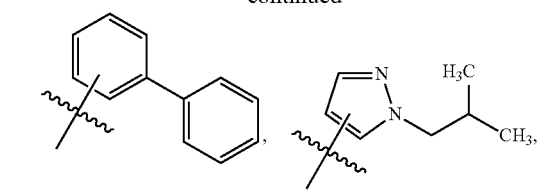
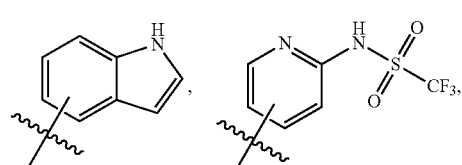
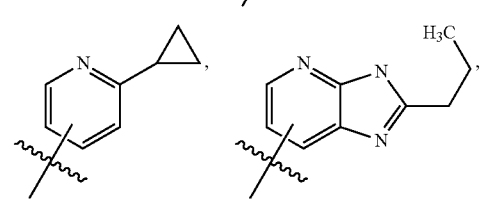
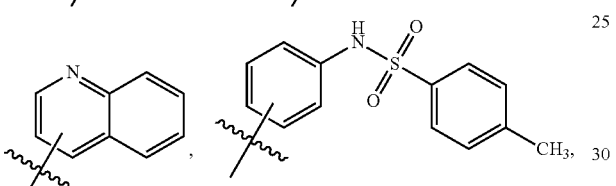
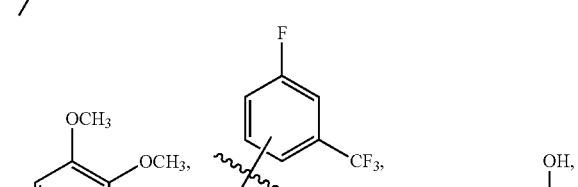
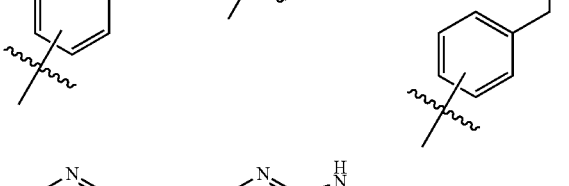
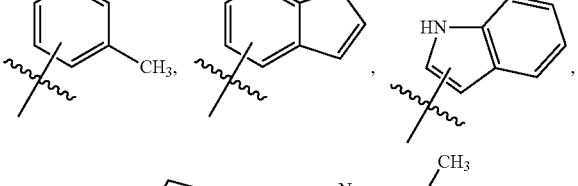
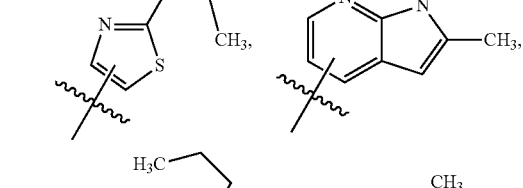
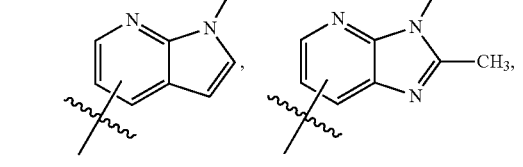
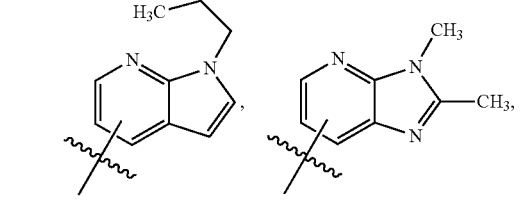
-continued
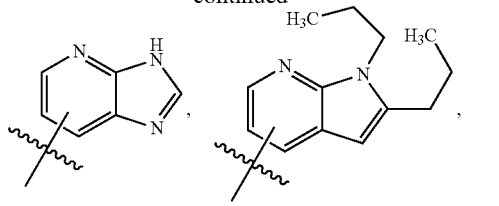
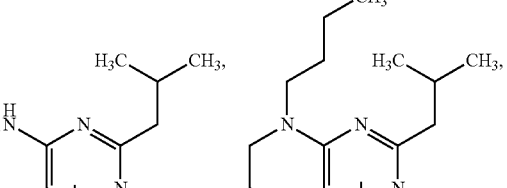
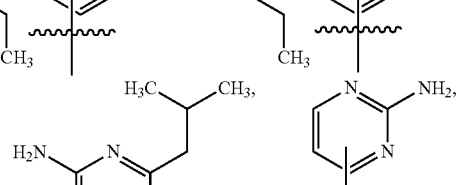
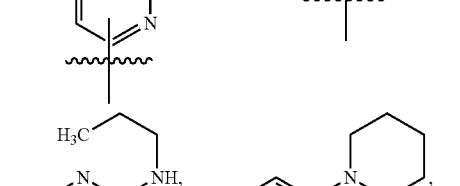
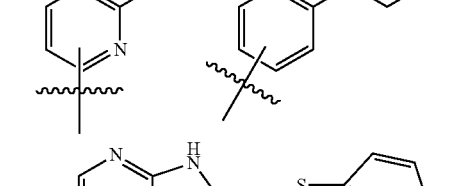
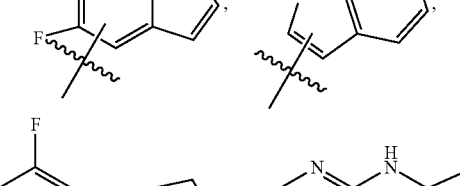
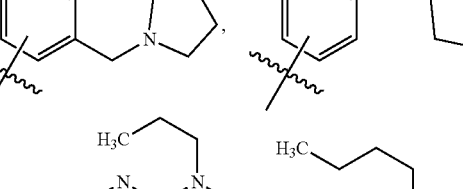
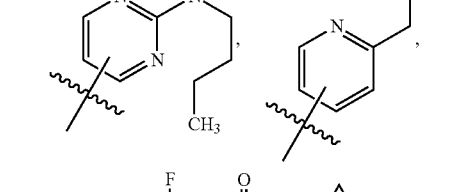
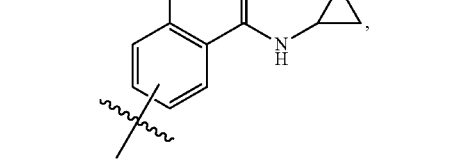
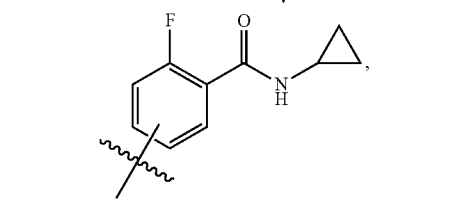

-continued

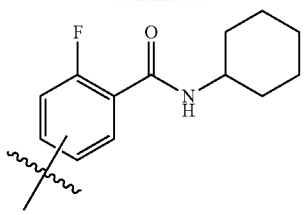

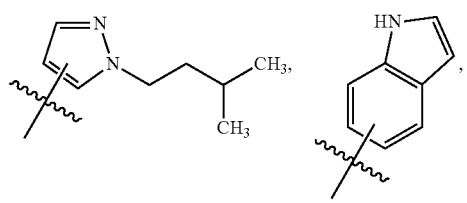

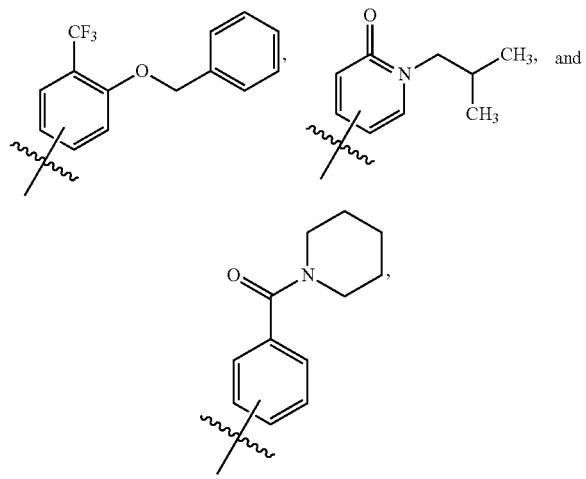

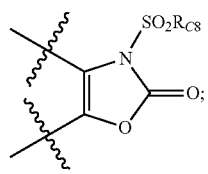

wherein the ring containing X is linked to ring A at any available position on ring A;

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$; or is taken with $R_{C7}$ to form the moiety

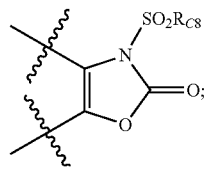

$R_{C7}$ is hydrogen, C1-C6 linear or branched alkyl, C1-C6 linear or branched hydroxyalkyl, —$(CR_{9a}R_{9b})_m NR10R11$, —$CO_2$-Alkyl, —$(CR_{9a}R_{9b})_m$O-Alkyl, —$(CR_{9a}R_{9b})_m$OPO$_3$Na$_2$, —$(CR_{9a}R_{9b})_m$O$(CR_{9a}R_{9b})_n$O-Alkyl, —$(CR_{9a}R_{9b})_m$O(C=O)-Alkyl, —$(CR_{9a}R_{9b})_m$O(C=O)O(C=O)-Alkyl, —(C=O)CH=CH$_2$, —SO$_2$R$_{C8'}$; or is taken with one of $R_{C4}$, $R_{C5}$ or $R_{C6}$ to form the moiety

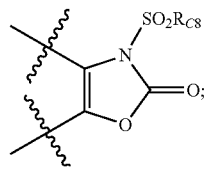

$R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —SO$_2$R$_{C8'}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a 1λ$^6$,2-thiazolidine-1,1-dione, a 1,2λ$^6$,3-oxathiazolidine-2,2-dione, or a 1λ$^6$,2,5-thiadiazolidine-1,1-dione;

X is a heteroatom selected from S, O; or NR$_B$ wherein R$_B$ is hydrogen, a C1-C6 linear or branched alkyl, or a C3-C6 cycloalkyl; and Each m and n is 1, 2 or 3.

In some embodiments, compounds disclosed herein fall within formulae (IIa) or (IIb):

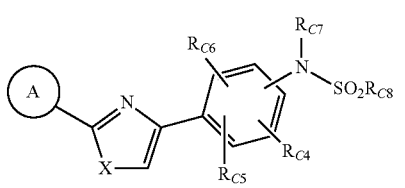

(IIa)

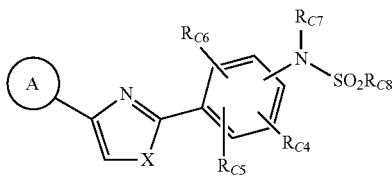

(IIb)

or a pharmaceutically acceptable salt thereof, wherein:
A is a moiety selected from the group consisting of:
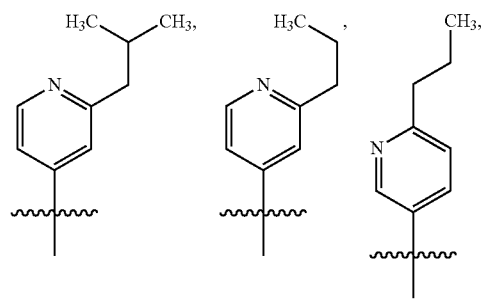
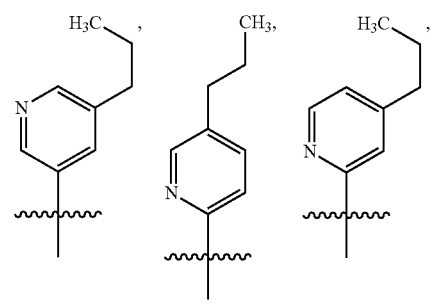
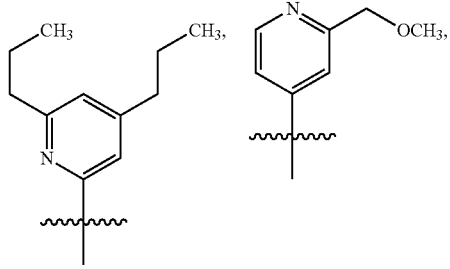
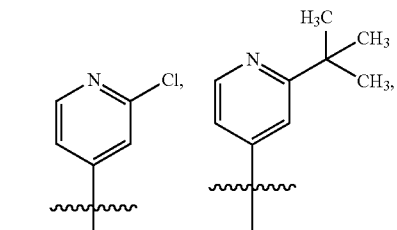
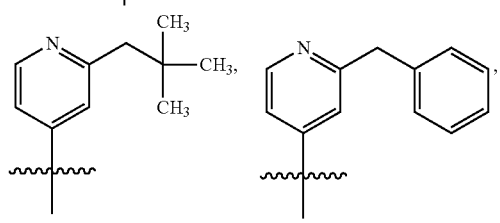
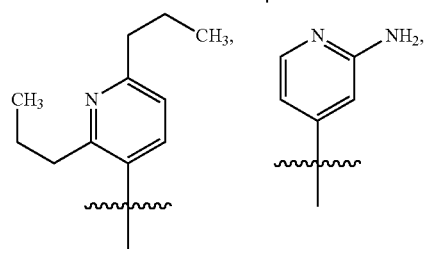
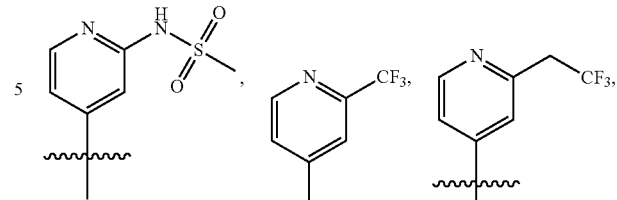
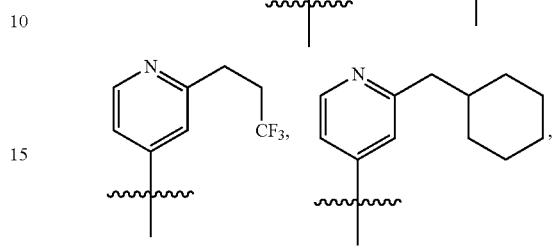
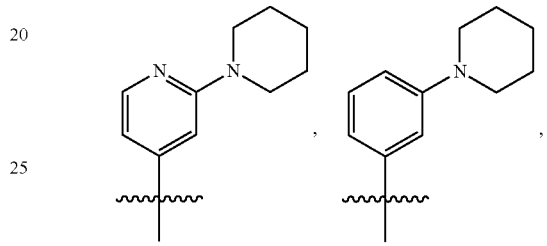
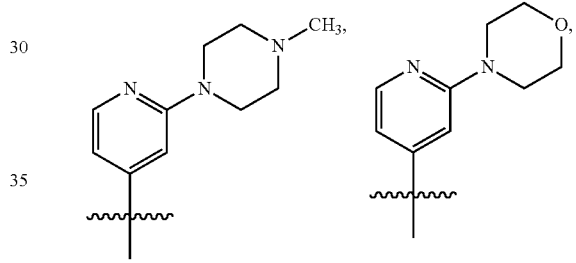
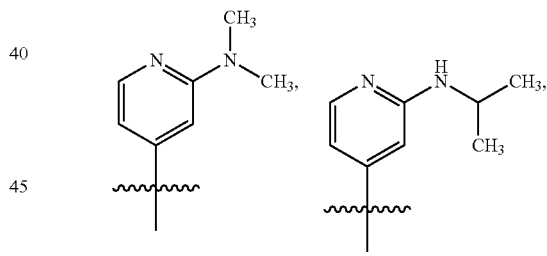
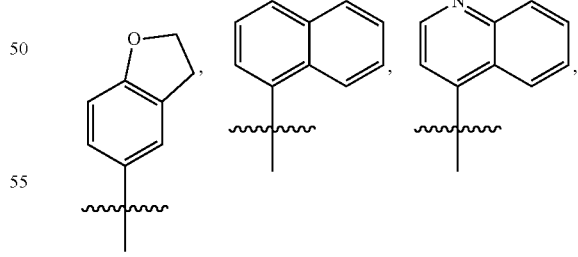
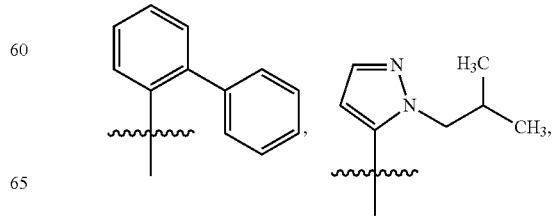

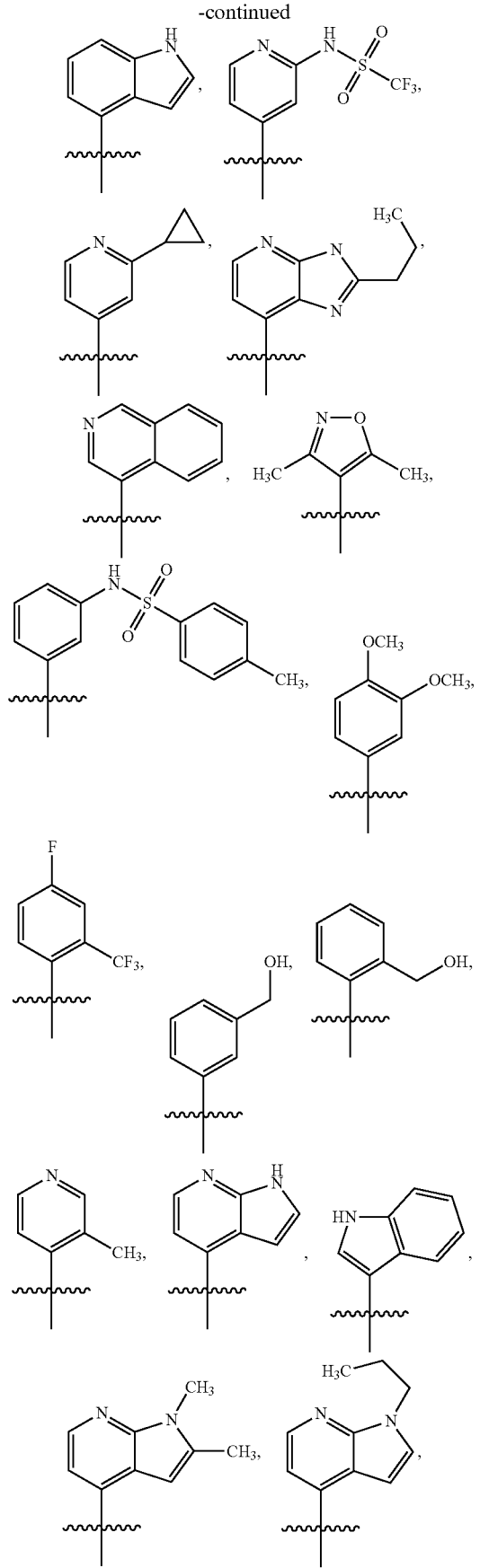
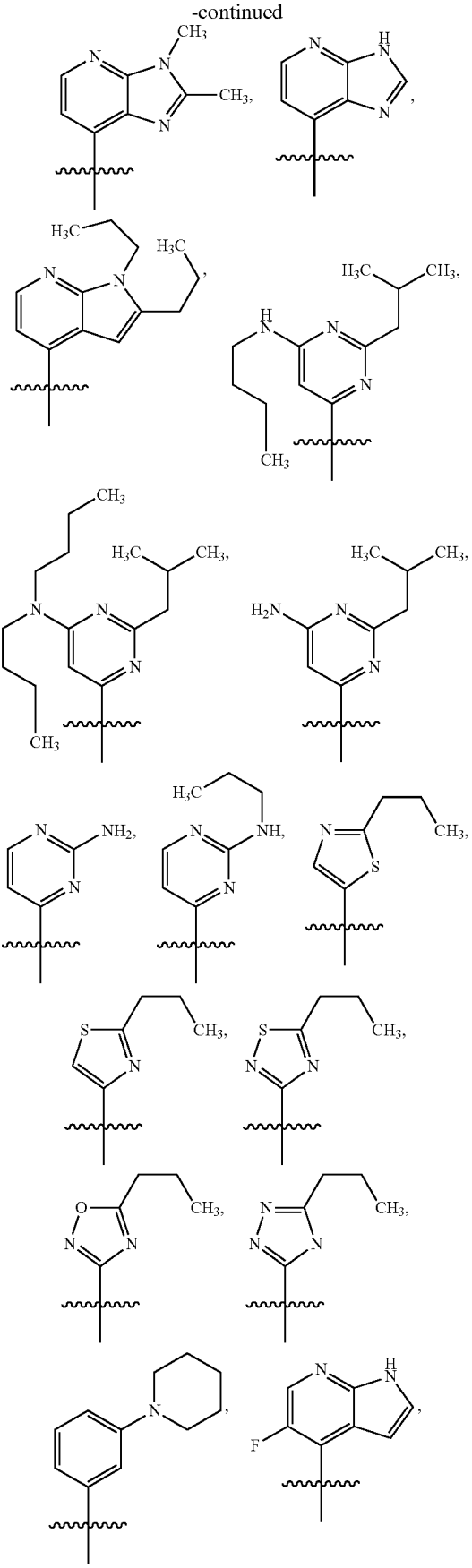

31
-continued

32
-continued

Each $R_{C4}$, $R_{C5}$, and $R_{C6}$, is independently hydrogen, halogen, CN, $CF_3$, OH, C1-C3 linear or branched alkyl, C2-C3 alkenyl, C2-C3 alkynyl, C3-C6 cycloalkyl, C3-C6 cycloalkenyl, C1-C3 linear or branched alkoxy, —$CO_2H$, —CONR10R11, or —$NHCONH_2$; or is taken with $R_{C7}$ to form the moiety

$R_{C7}$ is hydrogen, C1-C6 linear or branched alkyl, C1-C6 linear or branched hydroxyalkyl, —$(CR_{9a}R_{9b})_m$NR10R11, —$CO_2$-Alkyl, —$(CR_{9a}R_{9b})_m$O-Alkyl, —$(CR_{9a}R_{9b})_m$OPO$_3$Na$_2$, —$(CR_{9a}R_{9b})_m$O$(CR_{9a}R_{9b})_n$O-Alkyl, —$(CR_{9a}R_{9b})_m$O(C=O)-Alkyl, —$(CR_{9a}R_{9b})_m$O$(CR_{9a}R_{9b})_n$O(C=O)-Alkyl, —(C=O)CH=CH$_2$, —$SO_2R_{C8'}$; or is taken with one of $R_{C4}$, $R_{C5}$ or $R_{C6}$ to form the moiety $R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

$R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom;

Each $R_{9a}$ and $R_{9b}$, where present, is independently hydrogen or C1-C6 linear or branched alkyl;

R10 and R11 are independently hydrogen, —$SO_2R_{C8}$, C1-C6 linear or branched alkyl, C2-C6 linear or branched alkenyl, C3-C6 cycloalkyl, or C3-C6 cycloalkenyl; or are taken together with the N to which they are attached to form a C3-C6 heterocycle, pyrrolidinone, piperidinone, oxazolidinone, oxazinanone, imidazolidinone, tetrahydropyrimidin-2(1H)-one, a $1\lambda^6,2$-thiazolidine-1,1-dione, a $1,2\lambda^6,3$-oxathiazolidine-2,2-dione, or a $1\lambda^6,2,5$-thiadiazolidine-1,1-dione;

X is a heteroatom selected from S, O; or $NR_B$ wherein $R_B$ is hydrogen, a C1-C6 linear or branched alkyl, or a C3-C6 cycloalkyl; and Each m and n is 1, 2 or 3.

In some variations of Formulae (IIa) or (IIb), A is a moiety selected from the group consisting of:

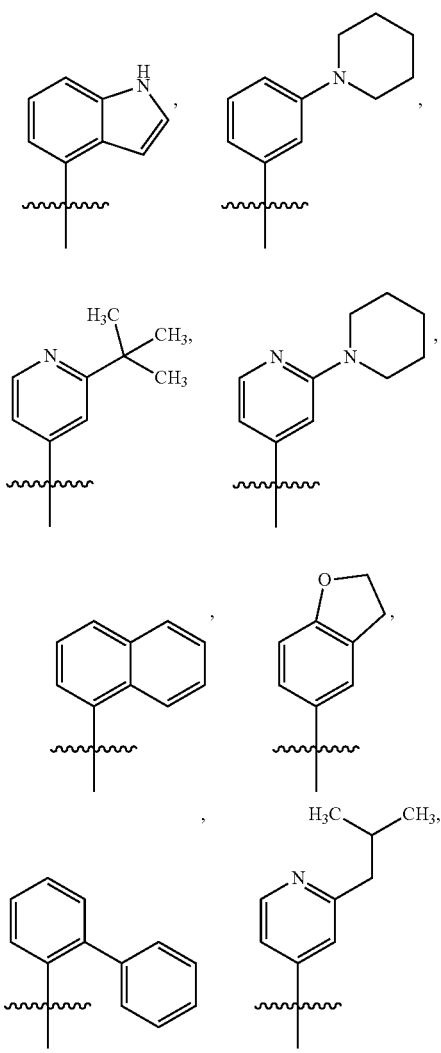

In some variations of Formulae (IIa) or (IIb), A is a moiety selected from the group consisting of:

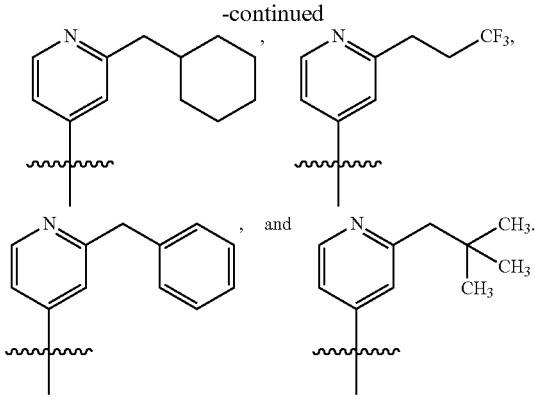

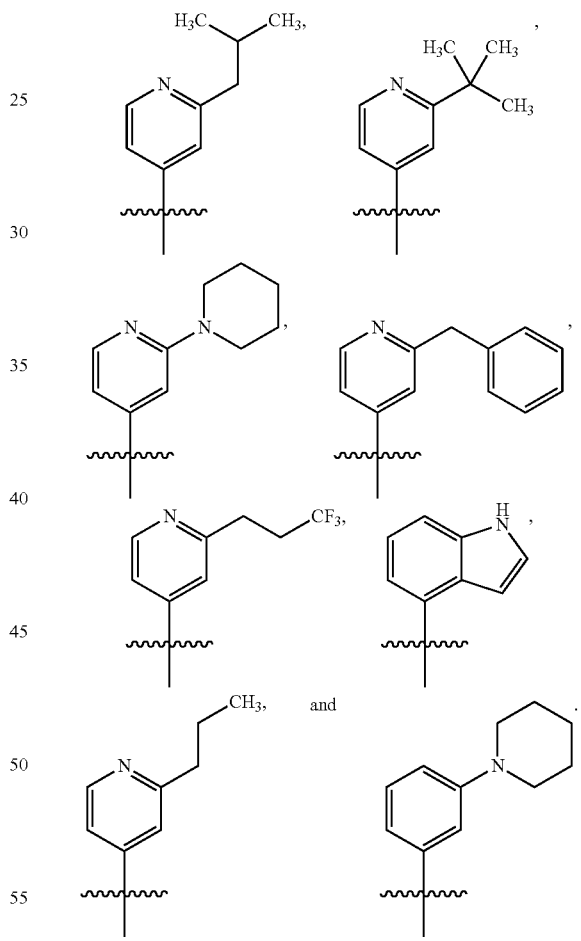

In some variations of Formulae (Ia), (Ib), (IIa) or (IIb), X is S. In some variations, X is O. In some variations, X is $NR_B$, wherein $R_B$ is hydrogen. In some variations, X is $NR_B$, wherein $R_B$ is a linear or branched C1-C6 alkyl. In these variations, $R_B$ is a linear C1-C6 alkyl selected from methyl, ethyl, n-propyl, n-butyl, n-pentyl or n-hexyl. In particular variations, $R_B$ is methyl. In some variations, $R_B$ is a branched C1-C6 alkyl selected from iso-propyl, iso-pentyl, and tert-butyl.

In some variations of Formulae (Ia), (Ib), (IIa) or (IIb), the phenyl ring containing the groups $R_{C4}$, $R_{C5}$, $R_{C6}$, and $-NR_{C7}SO_2R_{C8}$, is a moiety selected from:

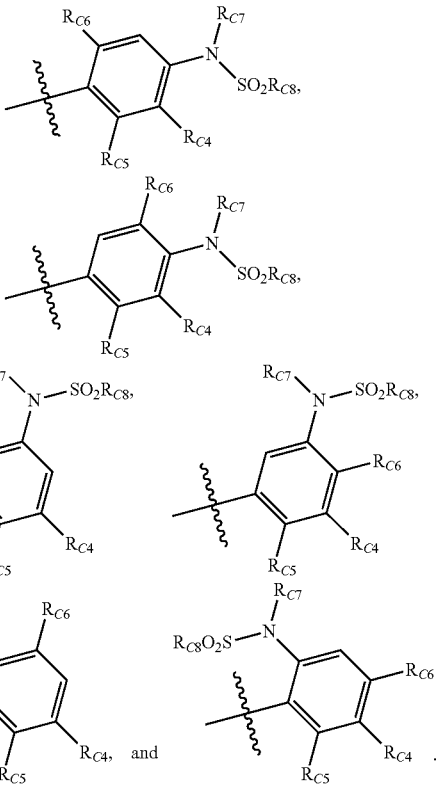

In particular variations of Formulae (Ia), (Ib), (IIa) or (IIb), the phenyl ring containing the groups $R_{C4}$, $R_{C5}$, $R_{C6}$, and $-NR_{C7}SO_2R_{C8}$, is a moiety selected from:

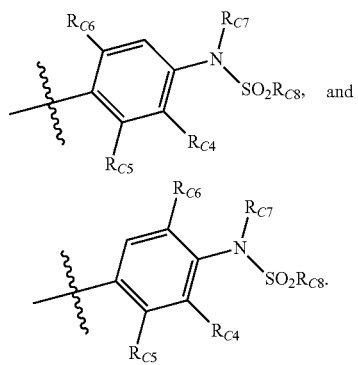

In some variations of Formulae (Ia), (Ib), (IIa) or (IIb), one or more of $R_{C4}$, $R_{C5}$ and $R_{C6}$, is hydrogen. In some variations, one or more of $R_{C4}$, $R_{C5}$ and $R_{C6}$, is halogen. In some variations, one or more of $R_{C4}$, $R_{C5}$ and $R_{C6}$, is CN. In some variations, one or more of $R_{C4}$, $R_{C5}$ and $R_{C6}$, is $CF_3$. In some variations, one or more of $R_{C4}$, $R_{C5}$ and $R_{C6}$, is OH. In some variations, one or more of $R_{C4}$, $R_{C5}$ and $R_{C6}$, is C1-C3 linear or branched alkyl. In some variations, one or more of $R_{C4}$, $R_{C5}$ and $R_{C6}$, is C2-C3 alkenyl. In some variations, one or more of $R_{C4}$, $R_{C5}$ and $R_{C6}$, is C2-C3 alkynyl. In some variations, one or more of $R_{C4}$, $R_{C5}$ and $R_{C6}$, is C3-C6 cycloalkyl. In some variations, one or more of $R_{C4}$, $R_{C5}$ and $R_{C6}$, is C3-C6 cycloalkenyl. In some variations, one or more of $R_{C4}$, $R_{C5}$ and $R_{C6}$, is C1-C3 linear or branched alkoxy. In some variations, one or more of $R_{C4}$, $R_{C5}$ and $R_{C6}$, is $-CON(CH_3)_2$. In some variations, one or more of $R_{C4}$, $R_{C5}$ and $R_{C6}$, is $-CO_2H$. In some variations, one or more of $R_{C4}$, $R_{C5}$ and $R_{C6}$, is $-CONH_2$. In some variations, one or more of $R_{C4}$, $R_{C5}$ and $R_{C6}$, is $-NHCONH_2$. In some variations, one or more of $R_{C4}$, $R_{C5}$ and $R_{C6}$, is $-CONHCH_3$. In some variations, one or more of $R_{C4}$, $R_{C5}$ and $R_{C6}$, is taken with $R_{C7}$ to form the moiety

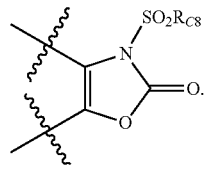

In some variations of Formulae (Ia), (Ib), (IIa) or (IIb), one of $R_{C4}$, $R_{C5}$ and $R_{C6}$ is hydrogen. In some variations, two of $R_{C4}$, $R_{C5}$ and $R_{C6}$ are hydrogen. In some variations, each $R_{C4}$, $R_{C5}$ and $R_{C6}$ is hydrogen. In some variations, one or more of $R_{C4}$, $R_{C5}$ and $R_{C6}$ is methoxy. In some variations, one or more of $R_{C4}$, $R_{C5}$ and $R_{C6}$ is OH.

In some variations of Formulae (Ia), (Ib), (IIa) or (IIb), one of $R_{C4}$, $R_{C5}$ and $R_{C6}$ is halogen. In some variations, two of $R_{C4}$, $R_{C5}$ and $R_{C6}$ are halogen. In some variations each $R_{C4}$, $R_{C5}$ and $R_{C6}$ is halogen. In some variations, one of $R_{C4}$, $R_{C5}$ and $R_{C6}$ is hydrogen, and the remaining two of $R_{C4}$, $R_{C5}$ and $R_{C6}$ are halogen. In some variations, two of $R_{C4}$, $R_{C5}$ and $R_{C6}$ are hydrogen, and the remaining one of $R_{C4}$, $R_{C5}$ and $R_{C6}$ is halogen. In some variations, $R_{C4}$, $R_{C5}$ and $R_{C6}$ are each halogen. In some embodiments, one of $R_{C4}$, $R_{C5}$ and $R_{C6}$ is fluoro, chloro or bromo. In some embodiments, two of $R_{C4}$, $R_{C5}$ and $R_{C6}$ are fluoro, chloro or bromo. In some embodiments, one of $R_{C4}$, $R_{C5}$ and $R_{C6}$ is chloro. In some embodiments, one of $R_{C4}$, $R_{C5}$ and $R_{C6}$ is chloro and one of $R_{C4}$, $R_{C5}$ and $R_{C6}$ is bromo. In some embodiments, $R_{C4}$ is chloro. In some embodiments, $R_{C5}$ is chloro. In some embodiments, $R_{C4}$ is bromo. In some embodiments, $R_{C5}$ is bromo.

In some variations of Formulae (Ia), (Ib), (IIa) or (IIb), $R_{C7}$ is hydrogen. In some variations, $R_{C7}$ is C1-C6 linear or branched alkyl. In some variations, $R_{C7}$ is C1-C6 linear or branched hydroxyalkyl. In some variations, $R_{C7}$ is $-(CR_{9a}R_{9b})_mNR10R11$. In some variations, $R_{C7}$ is $-CO_2$-Alkyl. In some variations, $R_{C7}$ is $-(CR_{9a}R_{9b})_mO$-Alkyl. In some variations, $R_{C7}$ is $-(CR_{9a}R_{9b})_mOPO_3Na_2$. In some variations, $R_{C7}$ is $-(CR_{9a}R_{9b})_mO(CR_{9a}R_{9b})_nO$-Alkyl. In some variations, $R_{C7}$ is $-(CR_{9a}R_{9b})_mO(C=O)$-Alkyl. In some variations, $R_{C7}$ is $-(CR_{9a}R_{9b})_mO(CR_{9a}R_{9b})_nO(C=O)$-Alkyl. In some variations, $R_{C7}$ is $-(C=O)CH=CH_2$. In some variations, $R_{C7}$ is $-SO_2R_{C8}$. In some variations, $R_{C7}$ is taken with one of $R_{C4}$, $R_{C5}$ or $R_{C6}$ to form the moiety

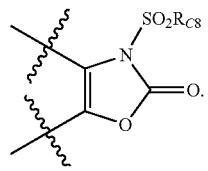

In all embodiments, $R_{C8}$ is a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom. In some embodiments, $R_{C8}$ is a linear or branched C1-C6 perhaloalkyl. In some embodiments, the C1-C6 perhaloalkyl is a C1-C6 perfluoroalkyl. In some embodiments, the C1-C6 perfluoroalkyl is selected from

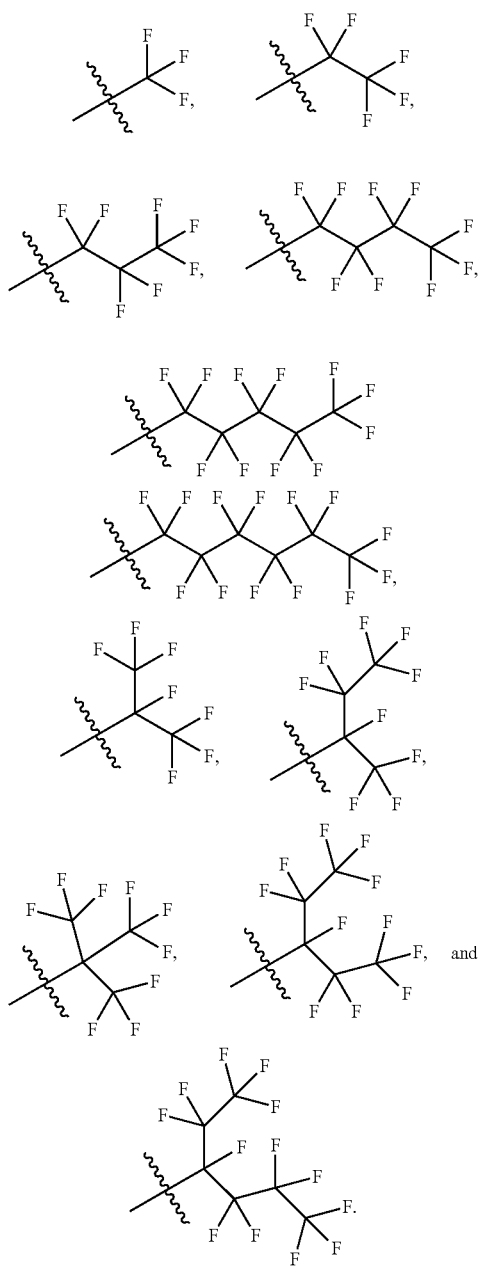

In preferred embodiments, the C1-C6 perfluoroalkyl is —CF$_3$. In some embodiments, $R_{C8}$ is a linear or branched C1-C6 alkyl having at least two halogen atoms. In some embodiments, $R_{C8}$ is selected from:

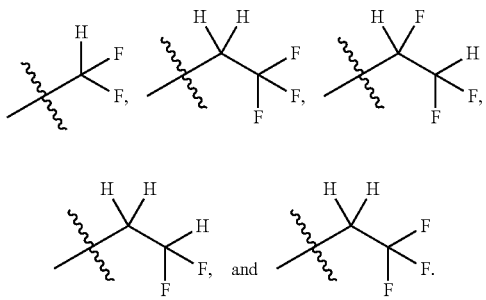

In some embodiments, $R_{C8}$ is a linear or branched C2-C6 perhaloalkenyl. In some embodiments, $R_{C8}$ is a linear or branched C2-C6 perhaloalkynyl. In some embodiments, $R_{C8}$ is a linear or branched C1-C6 alkyl having at least one halogen atom. In some embodiments, $R_{C8}$ is a linear or branched C2-C6 alkenyl having at least one halogen atom. In some embodiments, $R_{C8}$ is or a linear or branched C2-C6 alkynyl having at least one halogen atom.

In some embodiments, $R_{C8'}$ is a linear or branched C1-C6 alkyl, a linear or branched C1-C6 perhaloalkyl, a linear or branched C2-C6 perhaloalkenyl, a linear or branched C2-C6 perhaloalkynyl, a linear or branched C1-C6 alkyl having at least one halogen atom, a linear or branched C2-C6 alkenyl having at least one halogen atom, or a linear or branched C2-C6 alkynyl having at least one halogen atom. In some embodiments, $R_{C8'}$ is a linear or branched C1-C6 perhaloalkyl. In some embodiments, the C1-C6 perhaloalkyl is a C1-C6 perfluoroalkyl. In some embodiments, the C1-C6 perfluoroalkyl is selected from

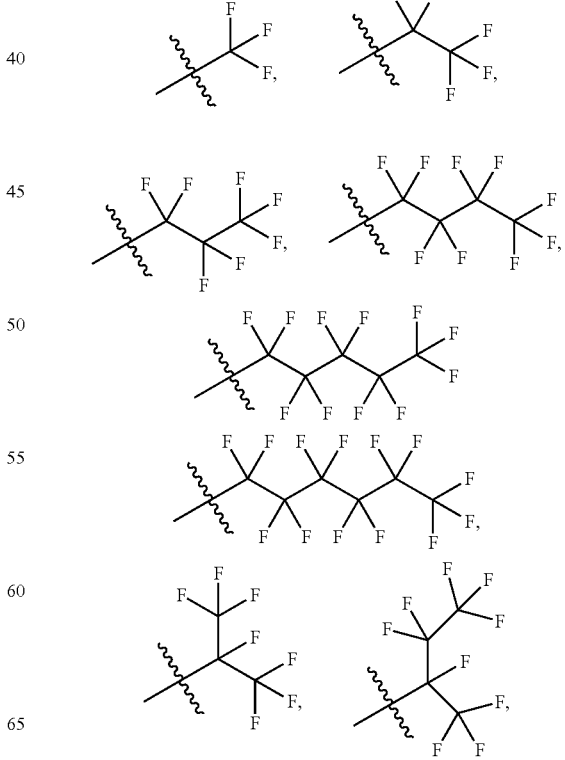

-continued

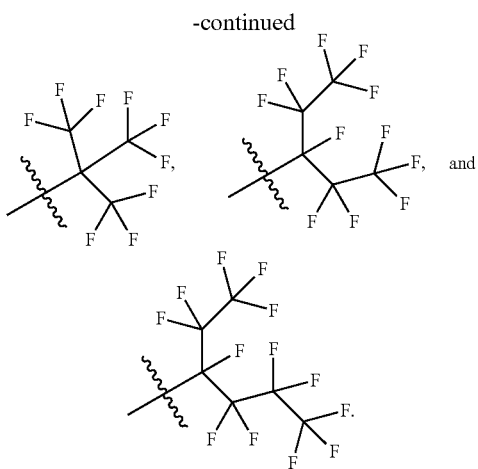

In preferred embodiments, the C1-C6 perfluoroalkyl is —CF$_3$. In some embodiments, R$_{C8'}$ is a linear or branched C1-C6 alkyl having at least two halogen atoms. In some embodiments, R$_{C8'}$ is selected from:

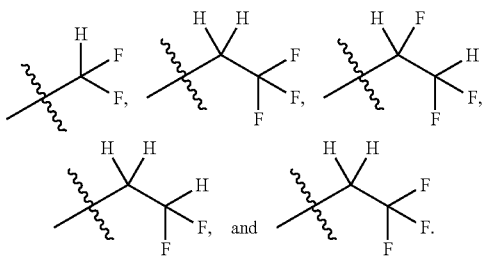

In some embodiments, R$_{C8'}$ is a linear or branched C2-C6 perhaloalkenyl. In some embodiments, R$_{C8'}$ is a linear or branched C2-C6 perhaloalkynyl. In some embodiments, R$_{C8'}$ is a linear or branched C1-C6 alkyl having at least one halogen atom. In some embodiments, R$_{C8'}$ is a linear or branched C2-C6 alkenyl having at least one halogen atom. In some embodiments, R$_{C8'}$ is or a linear or branched C2-C6 alkynyl having at least one halogen atom.

In some variations of Formulae (Ia), (Ib), (IIa) or (IIb), both R$_{9a}$ and R$_{9b}$ are hydrogen. In some embodiments, R$_{9a}$ is hydrogen, and R$_{9b}$ is C1-C6 linear or branched alkyl. In some embodiments, both R$_{9a}$ and R$_{9b}$ are C1-C6 linear or branched alkyl. In some embodiments, R$_{9a}$ is hydrogen, and R$_{9b}$ is methyl.

In some variations of Formulae (Ia), (Ib), (IIa) or (IIb), one or both of R10 and R11 are hydrogen. In some variations, one or both of R10 and R11 are —SO$_2$R$_{C8'}$. In some variations, one or both of R10 and R11 are C1-C6 linear or branched alkyl. In some variations, one or both of R10 and R11 are C2-C6 linear or branched alkenyl. In some variations, one or both of R10 and R11 are C3-C6 cycloalkyl. In some variations, one or both of R10 and R11 are C3-C6 cycloalkenyl.

In some variations of Formulae (Ia), (Ib), (IIa) or (IIb), R10 and R11 are taken together with the N to which they are attached to form a C3-C6 heterocycle. In some variations, R10 and R11 are taken together with the N to which they are attached to form a pyrrolidin-2-one or pyrrolidin-3-one. In some variations, R10 and R11 are taken together with the N to which they are attached to form a piperidin-2-one. In some variations, R10 and R11 are taken together with the N to which they are attached to form a piperidin-3-one. In some variations, R10 and R11 are taken together with the N to which they are attached to form a piperidin-4-one. In some variations, R10 and R11 are taken together with the N to which they are attached to form an oxazolidinone. In some variations, R10 and R11 are taken together with the N to which they are attached to form an oxazinanone. In some variations, R10 and R11 are taken together with the N to which they are attached to form an imidazolidinone. In some variations, R10 and R11 are taken together with the N to which they are attached to form a tetrahydropyrimidin-2(1H)-one. In some variations, R10 and R11 are taken together with the N to which they are attached to form a 1$\lambda^6$,2-thiazolidine-1,1-dione. In some variations, R10 and R11 are taken together with the N to which they are attached to form a 1,2$\lambda^6$,3-oxathiazolidine-2,2-dione. In some variations, R10 and R11 are taken together with the N to which they are attached to form a 1$\lambda^6$,2,5-thiadiazolidine-1,1-dione In some variations, the compound is of formula (Ia) or (IIa), wherein X is a heteroatom selected from S, O; or NR$_B$ wherein R$_B$ is hydrogen, a C1-C6 linear or branched alkyl, or a C3-C6 cycloalkyl. In some variations, X is S. In some variations, X is O. In some variations, X is NR$_B$ wherein R$_B$ is hydrogen, a C1-C6 linear or branched alkyl, or a C3-C6 cycloalkyl. In some variations, X is NR$_B$ wherein R$_B$ is a C1-C6 linear or branched alkyl. In some variations, X is NR$_B$ wherein R$_B$ is C3-C6 cycloalkyl.

In some variations, the compound is of formula (Ib) or (IIb), wherein X is a heteroatom selected from S, O; or NR$_B$ wherein R$_B$ is hydrogen, a C1-C6 linear or branched alkyl, or a C3-C6 cycloalkyl. In some variations, X is S. In some variations, X is O. In some variations, X is NR$_B$ wherein R$_B$ is hydrogen, a C1-C6 linear or branched alkyl, or a C3-C6 cycloalkyl. In some variations, X is NR$_B$ wherein R$_B$ is a C1-C6 linear or branched alkyl. In some variations, X is NR$_B$ wherein R$_B$ is C3-C6 cycloalkyl.

In some variations of Formulae (Ia), (Ib), (IIa) or (IIb), both m and n are 1. In some variations, m is 1 and n is 2. In some variations, m is 1 and n is 3. In some variations, m is 2 and n is 1. In some variations, both m and n are 2. In some variations, m is 2 and n is 3. In some variations, m is 3 and n is 1. In some variations, m is 3 and n is 2. In some variations, both m and n are 3.

In some variations of Formulae (Ia), (Ib), (IIa) or (IIb), A is a moiety selected from

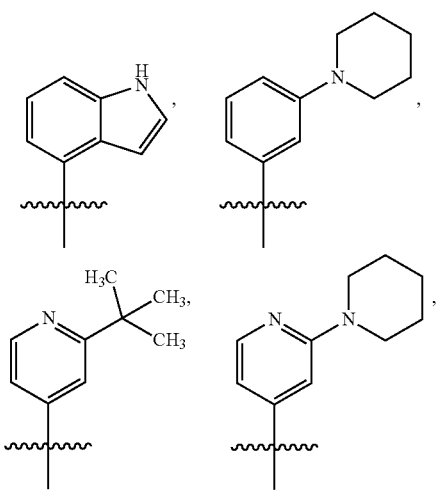

-continued

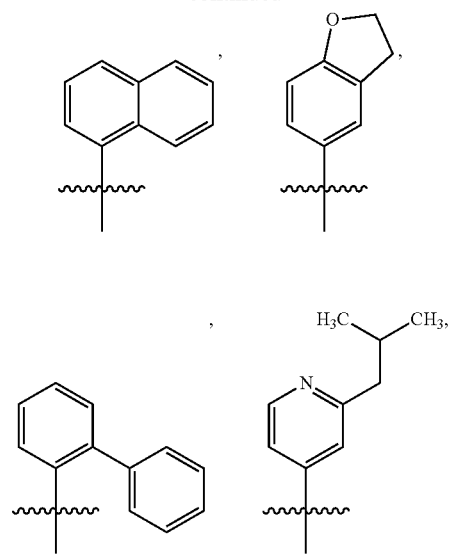

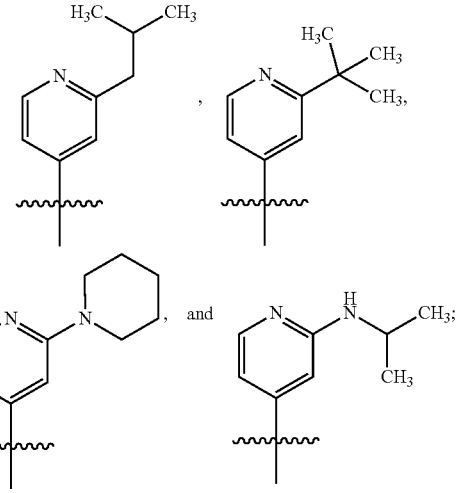

X is S, and the phenyl ring containing the groups $R_{C4}$, $R_{C5}$, $R_{C6}$, and —$NR_{C7}SO_2R_{C8}$, is a moiety selected from

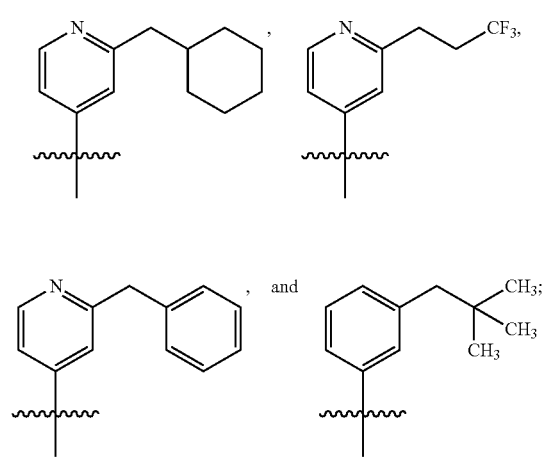

X is S, and the phenyl ring containing the groups $R_{C4}$, $R_{C5}$, $R_{C6}$, and —$NR_{C7}SO_2R_{C8}$, is a moiety selected from:

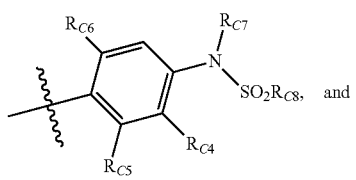

In some variations of Formulae (Ia), (Ib), (IIa) or (IIb), A is a moiety selected from

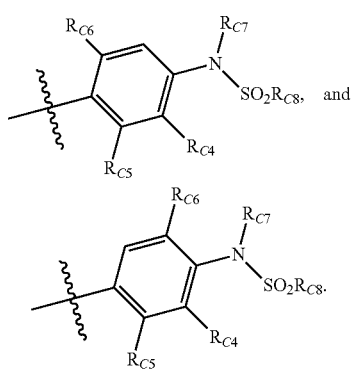

In some variations of Formulae (Ia), (Ib), (IIa) or (IIb), A is

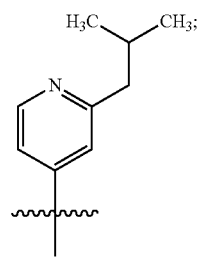 [SMILES: *c1ccnc(CC(C)C)c1]

X is S; the phenyl ring containing the groups $R_{C4}$, $R_{C5}$, $R_{C6}$, and —$NR_{C7}SO_2R_{C8}$, is selected from

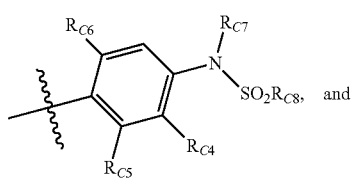

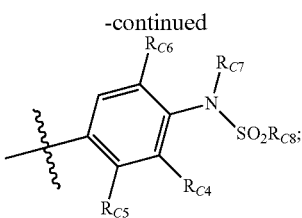
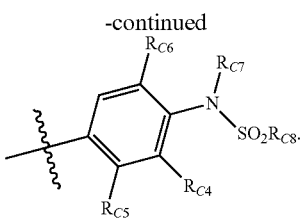

wherein $R_{C4}$, $R_{C5}$, and $R_{C6}$ are hydrogen or halogen; $R_{C7}$ is hydrogen; and $R_{C8}$ is perfluoroalkyl. In some variations $R_{C8}$ is —$CF_3$.

In some variations, the compound is of Formula (Ia), wherein A is a moiety selected from In particular variations, the compound is of Formula (Ia), wherein A is

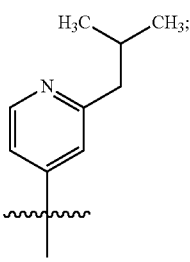 [SMILES: *c1ccnc(CC(C)C)c1]

X is S; the phenyl ring containing the groups $R_{C4}$, $R_{C5}$, $R_{C6}$, and —$NR_{C7}SO_2R_{C8}$, is selected from

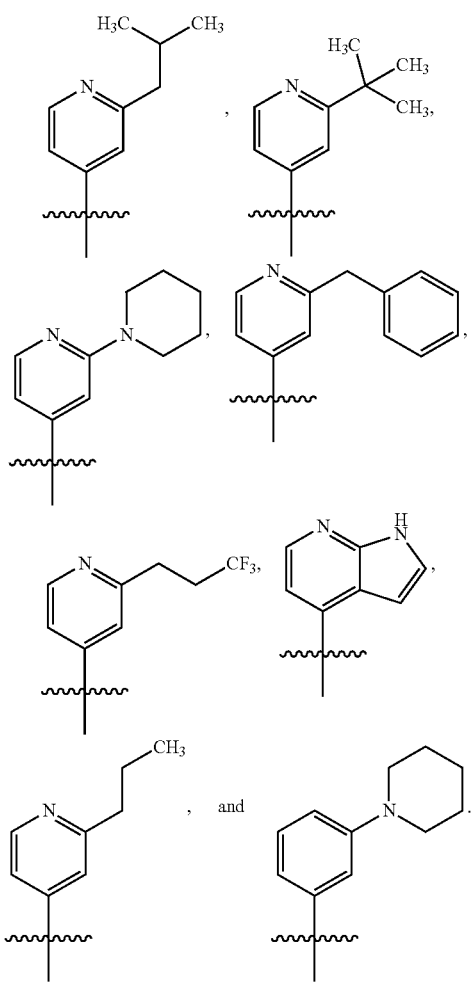

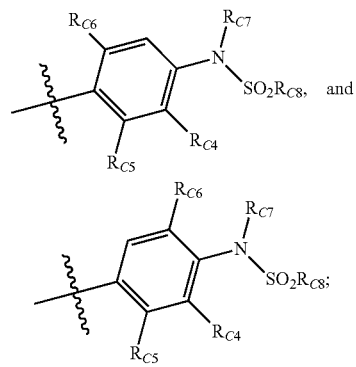

wherein $R_{C4}$, $R_{C5}$, and $R_{C6}$ are hydrogen or halogen; $R_{C7}$ is hydrogen and $R_{C8}$ is perfluoroalkyl. In some variations, $R_{C8}$ is —$CF_3$.

It is intended and understood that each and every variation of A, $R_{C4}$, $R_{C5}$, $R_{C6}$, $R_{C7}$, $R_{C8}$, $R_{C8'}$, $R_{9a}$, $R_{9b}$, R10, R11, X, m, and n, where present, described for formulae (Ia) and (Ib), may be combined with each and every variation of A, $R_{C4}$, $R_{C5}$, $R_{C6}$, $R_{C7}$, $R_{C8}$, $R_{C8'}$, $R_{9a}$, $R_{9b}$, R10, R11, X, m, and n, as if each and every combination is individually described.

In some embodiments, the compound is selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-5-yl)thiazol-4-yl)phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(1,2-dimethyl-1H-pyrrolo[2,3-b]pyridin-4-yl)thiazol-4-yl)phenyl)-1,1,1-trifluoromethanesulfonamide;

X is S, and the phenyl ring containing the groups $R_{C4}$, $R_{C5}$, $R_{C6}$, and —$NR_{C7}SO_2R_{C8}$, is a moiety selected from

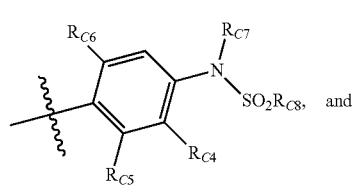

N-(3-chloro-4-(2-(1-propyl-1H-pyrrolo[2,3-b]pyridin-4-yl) thiazol-4-yl)phenyl)-1,1,1-trifluoromethanesulfonamide;
N-(3-chloro-4-(2-(2,3-dimethyl-3H-imidazo[4,5-b]pyridin-7-yl)thiazol-4-yl)phenyl)-1,1,1-trifluoromethanesulfonamide;
N-(3-chloro-4-(2-(3-propyl-3H-imidazo[4,5-b]pyridin-7-yl) thiazol-4-yl)phenyl)-1,1,1-trifluoromethanesulfonamide;
N-(4-(2-(3H-imidazo[4,5-b]pyridin-7-yl)thiazol-4-yl)-3-chlorophenyl)-1,1,1-trifluoromethanesulfonamide;
N-(3-chloro-4-(2-(1,2-dipropyl-1H-pyrrolo[2,3-b]pyridin-4-yl)thiazol-4-yl)phenyl)-1,1,1-trifluoromethanesulfonamide;
N-(4-(2-(6-(butylamino)-2-isobutylpyrimidin-4-yl)thiazol-4-yl)-3-chlorophenyl)-1,1,1-trifluoromethanesulfonamide;
N-(3-chloro-4-(2-(6-(dibutylamino)-2-isobutylpyrimidin-4-yl)thiazol-4-yl)phenyl)-1,1,1-trifluoromethanesulfonamide;
N-(4-(2-(6-amino-2-isobutylpyrimidin-4-yl)thiazol-4-yl)-3-chlorophenyl)-1,1,1-trifluoromethanesulfonamide;
N-(4-(2-(2-aminopyrimidin-4-yl)thiazol-4-yl)-3-chlorophenyl)-1,1,1-trifluoromethanesulfonamide;
N-(3-chloro-4-(2-(2-(propylamino)pyrimidin-4-yl)thiazol-4-yl)phenyl)-1,1,1-trifluoromethanesulfonamide;
N-(3-chloro-4-(2-(2-(dibutylamino)pyrimidin-4-yl)thiazol-4-yl)phenyl)-1,1,1-trifluoromethanesulfonamide;
N-(3-chloro-4-(2'-propyl-2,4'-bithiazol-4-yl)phenyl)-1,1,1-trifluoromethanesulfonamide;
N-(3-chloro-4-(2-(5-propyl-1,2,4-thiadiazol-3-yl)thiazol-4-yl)phenyl)-1,1,1-trifluoromethanesulfonamide;
N-(3-chloro-4-(2-(5-propyl-1,2,4-oxadiazol-3-yl)thiazol-4-yl)phenyl)-1,1,1-trifluoromethanesulfonamide;
N-(3-chloro-4-(2'-propyl-2,5'-bithiazol-4-yl)phenyl)-1,1,1-trifluoromethanesulfonamide;
N-(3-chloro-4-(2-(5-propyl-1,3,4-thiadiazol-2-yl)thiazol-4-yl)phenyl)-1,1,1-trifluoromethanesulfonamide;
N-(3-chloro-4-(2-(5-propyl-1,3,4-oxadiazol-2-yl)thiazol-4-yl)phenyl)-1,1,1-trifluoromethanesulfonamide;
N-(3-chloro-4-(2-(1-isobutyl-6-oxo-1,6-dihydropyridin-3-yl)thiazol-4-yl)phenyl)-1,1,1-trifluoromethanesulfonamide;
N-(3-chloro-4-(2-(4-fluoro-3-isobutylphenyl)thiazol-4-yl) phenyl)-1,1,1-trifluoromethanesulfonamide;
N-(2-bromo-3-chloro-4-(2-(2-isobutylpyridin-4-yl)thiazol-4-yl)phenyl)-1,1,1-trifluoromethanesulfonamide;
N-(3,5-dichloro-4-(2-(2-isobutylpyridin-4-yl)thiazol-4-yl) phenyl)-1,1,1-trifluoromethanesulfonamide;
1,1,1-trifluoro-N-(4-(2-(2-isobutylpyridin-4-yl)thiazol-4-yl)-2-(trifluoromethyl) phenyl)methanesulfonamide;
N-(2-cyclopropyl-4-(2-(2-isobutylpyridin-4-yl)thiazol-4-yl) phenyl)-1,1,1-trifluoromethanesulfonamide;
1,1,1-trifluoro-N-(4-(2-(2-isobutylpyridin-4-yl)thiazol-4-yl)-2-methylphenyl) methanesulfonamide;
1,1,1-trifluoro-N-(4-(2-(2-isobutylpyridin-4-yl)thiazol-4-yl)-2-isopropylphenyl) methanesulfonamide;
N-(2-ethynyl-4-(2-(2-isobutylpyridin-4-yl)thiazol-4-yl)phenyl)-1,1,1-trifluoromethanesulfonamide;
N-(2-bromo-3-ethynyl-4-(2-(2-isobutylpyridin-4-yl)thiazol-4-yl)phenyl)-1,1,1-trifluoromethanesulfonamide;
N-(2-bromo-6-chloro-4-(2-(2-isobutylpyridin-4-yl)thiazol-4-yl)phenyl)-1,1,1-trifluoromethanesulfonamide;
N-(2-chloro-4-(2-(2-isobutylpyridin-4-yl)thiazol-4-yl)-6-methylphenyl)-1,1,1-trifluoromethanesulfonamide;
N-(4-(4-(2-tert-butylpyridin-4-yl)-1-methyl-1H-imidazol-2-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
N-(2-bromo-4-(1-methyl-2-(2-propylpyridin-4-yl)-1H-imidazol-4-yl)phenyl)-1,1,1-trifluoromethanesulfonamide;
N-(2-bromo-3-chloro-4-(2-(2-propylpyridin-4-yl)-1H-imidazol-4-yl)phenyl)-1,1,1-trifluoromethanesulfonamide;
N-(2-bromo-5-chloro-4-(1-methyl-2-(2-propylpyridin-4-yl)-1H-imidazol-4-yl) phenyl)-1,1,1-trifluoromethanesulfonamide;
N-(4-(4-(2-tert-butylpyridin-4-yl)oxazol-2-yl)-3-chlorophenyl)-1,1,1-trifluoromethanesulfonamide;
N-(4-(2-(2-tert-butylpyridin-4-yl)oxazol-4-yl)-3-chlorophenyl)-1,1,1-trifluoromethanesulfonamide;
N-(3-chloro-4-(2-(2-(dimethylamino)pyridin-4-yl)thiazol-4-yl)phenyl)-1,1,1-trifluoromethanesulfonamide;
N-(3-chloro-4-(2-(2-propylpyridin-4-yl)thiazol-4-yl)phenyl)-N-(trifluoromethylsulfonyl) acrylamide;
N-(3-chloro-4-(2-(2-(methylsulfonamido)pyridin-4-yl)thiazol-4-yl)phenyl)-1,1,1-trifluoromethanesulfonamide;
N-(3-chloro-4-(2-(2-(3,3,3-trifluoropropyl)pyridin-4-yl)thiazol-4-yl)phenyl)-1,1,1-trifluoromethanesulfonamide;
1,1,1-trifluoro-N-(2-hydroxy-4-(2-(2-isobutylpyridin-4-yl) thiazol-4-yl) phenyl)methanesulfonamide;
1,1,1-trifluoro-N-(2-hydroxy-4-(2-(2-propylpyridin-4-yl) thiazol-4-yl) phenyl)methanesulfonamide;
N-(4-(2-(2-tert-butylpyridin-4-yl)thiazol-4-yl)-2-hydroxyphenyl)-1,1,1-trifluoromethanesulfonamide;
1,1,1-trifluoro-N-(2-methoxy-4-(2-(2-propylpyridin-4-yl) thiazol-4-yl) phenyl)methanesulfonamide;
1,1,1-trifluoro-N-(4-(2-(2-isobutylpyridin-4-yl)thiazol-4-yl)-2-methoxyphenyl) methanesulfonamide;
N-(4-(2-(2-tert-butylpyridin-4-yl)thiazol-4-yl)-2-methoxyphenyl)-1,1,1-trifluoromethanesulfonamide;
1,1,1-trifluoro-N-(4-(2-(2-isobutylpyridin-4-yl)thiazol-4-yl)-3-(trifluoromethyl) phenyl)methanesulfonamide;
N-(3-chloro-4-(2-(2-neopentylpyridin-4-yl)thiazol-4-yl) phenyl)-1,1,1-trifluoromethanesulfonamide;
6-(2-(2-isobutylpyridin-4-yl)thiazol-4-yl)-3-(trifluoromethylsulfonyl)benzo[d]oxazol-2(3H)-one;
N-(3-chloro-4-(2-(2-isobutylpyridin-4-yl)thiazol-4-yl)phenyl)-1,1,2,2,2-pentafluoroethanesulfonamide;
1,1,1-trifluoro-N-(2-methoxy-4-{2-[2-(2-methylpropyl) pyridin-4-yl]-1,3-thiazol-4-yl}phenyl) methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;

N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;
N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethanesulfonamide;
N-{3-chloro-4-[2-(2-phenylphenyl)-1,3-thiazol-4-yl]phenyl}-1,1,1-trifluoromethanesulfonamide;
N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide;
N-{3-chloro-4-[2-(3-methylpyridin-4-yl)-1,3-thiazol-4-yl]phenyl}-1,1,1-trifluoromethanesulfonamide;
N-[3-chloro-4-(2-{1H-pyrrolo[2,3-b]pyridin-4-yl}-1,3-thiazol-4-yl)phenyl]-1,1,1-trifluoromethanesulfonamide;
N-(3-chloro-4-{2-[3-(piperidin-1-yl)phenyl]-1,3-thiazol-4-yl}phenyl)-1,1,1-trifluoromethanesulfonamide;
N-[3-chloro-4-(2-{5-fluoro-1H-pyrrolo[2,3-b]pyridin-4-yl}-1,3-thiazol-4-yl)phenyl]-1,1,1-trifluoromethanesulfonamide;
N-{4-[2-(1-benzothiophen-3-yl)-1,3-thiazol-4-yl]-3-chlorophenyl}-1,1,1-trifluoromethanesulfonamide;
N-(3-chloro-4-{2-[4-fluoro-2-(pyrrolidin-1-ylmethyl)phenyl]-1,3-thiazol-4-yl}phenyl)-1,1,1-trifluoromethanesulfonamide;
N-(3-chloro-4-{2-[2-(cyclopentylamino)pyridin-4-yl]-1,3-thiazol-4-yl}phenyl)-1,1,1-trifluoromethanesulfonamide;
N-{3-chloro-4-[2-(1H-indol-3-yl)-1,3-thiazol-4-yl]phenyl}-1,1,1-trifluoromethanesulfonamide;
N-(3-chloro-4-(2-(quinolin-4-yl)thiazol-4-yl)phenyl)-1,1,1-trifluoromethanesulfonamide;
N-(3-chloro-4-(2-(2-chloropyridin-4-yl)thiazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoromethanesulfonamide;
N-(2-bromo-4-(2-(2-propylpyridin-4-yl)-1H-imidazol-4-yl)phenyl)-1,1,1-trifluoromethanesulfonamide;
N-(2-bromo-4-(2-(2-tert-butylpyridin-4-yl)thiazol-4-yl)-3-chlorophenyl)-1,1,1-trifluoro-N-(2-hydroxyethyl)methanesulfonamide;
N-(4-(2-(2-tert-butylpyridin-4-yl)thiazol-4-yl)-3-chlorophenyl)-1,1,1-trifluoro-N-(2-(2-oxopyrrolidin-1-yl)ethyl)methanesulfonamide;
N-(4-(2-(2-tert-butylpyridin-4-yl)thiazol-4-yl)-3-chlorophenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-(2-oxoimidazolidin-1-yl)ethyl)methanesulfonamide;
N-(2-bromo-4-(2-(2-(piperidin-1-yl)pyridin-4-yl)-1H-imidazol-4-yl)phenyl)-1,1,1-trifluoromethanesulfonamide;
2-(N-(4-(2-(2-tert-butylpyridin-4-yl)thiazol-4-yl)-3-chlorophenyl)-1,1,1-trifluoromethylsulfonamido) ethyl acetate;
(2-(N-(4-(2-(2-tert-butylpyridin-4-yl)thiazol-4-yl)-3-chlorophenyl)-1,1,1-trifluoromethylsulfonamido) ethoxy) methyl acetate;
N-{4-[2-(2-tert-butylpyridin-4-yl)-1,3-thiazol-4-yl]-3-chlorophenyl}-N-(2-{[4-(3-chlorophenyl)-2-oxo-1,3,2$\lambda^5$-dioxaphosphinan-2-yl]oxy}ethyl)-1,1,1-trifluoromethanesulfonamide;
(N-(4-(2-(2-tert-butylpyridin-4-yl)thiazol-4-yl)-3-chlorophenyl)-1,1,1-trifluoromethylsulfonamido) methyl acetate;
N-(4-(2-(2-tert-butylpyridin-4-yl)thiazol-4-yl)-3-chlorophenyl)-1,1,1-trifluoro-N-(methoxymethyl) methanesulfonamide;
N-{4-[2-(2-tert-butylpyridin-4-yl)-1,3-thiazol-4-yl]-3-chlorophenyl}-N-({[4-(3-chloro phenyl)-2-oxo-1,3,2$\lambda^5$-dioxaphosphinan-2-yl]oxy}methyl)-1,1,1-trifluoromethanesulfonamide;
methyl 4-(2-(2-tert-butylpyridin-4-yl)thiazol-4-yl)-3-chlorophenyl (trifluoromethylsulfonyl)carbamate;
sodium (N-(4-(2-(2-tert-butylpyridin-4-yl)thiazol-4-yl)-3-chlorophenyl)-1,1,1-trifluoromethylsulfonamido) methyl phosphate;
1-(N-(3-chloro-4-(2-(2-isobutylpyridin-4-yl)thiazol-4-yl)phenyl)-1,1,1-trifluoromethylsulfonamido) ethyl isobutyrate;
N-(3-chloro-4-(2-(2-isobutylpyridin-4-yl)thiazol-4-yl)phenyl)-1,1,1-trifluoro-N-(2-(2-oxooxazolidin-3-yl)ethyl)methanesulfonamide;
N-(4-(2-(2-tert-butylpyridin-4-yl)thiazol-4-yl)-3-chlorophenyl)-1,1,1-trifluoro-N-(2-hydroxyethyl) methanesulfonamide;
N-(3-chloro-4-(2-(2-isobutylpyridin-4-yl)thiazol-4-yl)phenyl)-1,1,1-trifluoro-N-(2-(pyrrolidin-1-yl)ethyl)methanesulfonamide;
N-(3-chloro-4-(2-(2-isobutylpyridin-4-yl)thiazol-4-yl)phenyl)-N-(2-(diethylamino) ethyl)-1,1,1-trifluoromethanesulfonamide;
N-(3-chloro-4-(2-(2-isobutylpyridin-4-yl)thiazol-4-yl)phenyl)-N-(2-(dimethylamino) ethyl)-1,1,1-trifluoromethanesulfonamide;
1,1,1-trifluoro-N-(3-fluoro-4-(2-(2-propylpyridin-4-yl)thiazol-4-yl) phenyl)methanesulfonamide;
N-(3-chloro-4-(2-(2-isobutylpyridin-4-yl)-1H-imidazol-4-yl)phenyl)-1,1,1-trifluoromethanesulfonamide;
N-(3-chloro-4-(2-(2-isobutylpyridin-4-yl)thiazol-4-yl)phenyl)-1,1,1-trifluoro-N-(2-hydroxyethyl) methanesulfonamide;
N-(3-chloro-4-(2-(2-propylpyridin-4-yl)thiazol-4-yl)phenyl)-1,1,1-trifluoro-N-methylmethanesulfonamide;
1,1,1-trifluoro-N-(3-(2-(2-isobutylpyridin-4-yl)thiazol-4-yl) phenyl)methanesulfonamide;
N-(2-bromo-4-(2-(2-isobutylpyridin-4-yl)thiazol-4-yl)phenyl)-1,1,1-trifluoromethanesulfonamide;

1,1,1-trifluoro-N-methyl-N-(4-(2-(2-propylpyridin-4-yl)thiazol-4-yl) phenyl)methanesulfonamide;
N-(4-(2-(2-butylpyridin-4-yl)thiazol-4-yl)phenyl)-1,1,1-trifluoromethanesulfonamide
1,1,1-trifluoro-N-(4-(2-(2-(methoxymethyl)pyridin-4-yl)thiazol-4-yl) phenyl)methanesulfonamide;
N-(4-(2-(4,6-dipropylpyridin-2-yl)thiazol-4-yl)phenyl)-1,1,1-trifluoromethanesulfonamide;
1,1,1-trifluoro-N-(4-(2-(4-propylpyridin-2-yl)thiazol-4-yl)phenyl)methanesulfonamide;
N-(4-(2-(2,6-dipropylpyridin-3-yl)thiazol-4-yl)phenyl)-1,1,1-trifluoromethanesulfonamide;
N-(4-(2-(2-(cyclohexylmethyl)pyridin-4-yl)thiazol-4-yl)phenyl)-1,1,1-trifluoromethanesulfonamide;
1,1,1-trifluoro-N-(4-(2-(2-isobutylpyridin-4-yl)thiazol-4-yl)-3-methoxyphenyl) methanesulfonamide;
N-(3-chloro-4-(2-(2-((trifluoromethylsulfonyl)methyl)pyridin-4-yl)thiazol-4-yl) phenyl)-1,1,1-trifluoromethanesulfonamide;
N-(4-(2-(1H-pyrrolo[2,3-b]pyridin-4-yl)thiazol-4-yl)-3-chlorophenyl)-1,1,1-trifluoromethanesulfonamide;
N-(3-chloro-4-(2-(2-propyl-3H-imidazo[4,5-b]pyridin-7-yl)thiazol-4-yl)phenyl)-1,1,1-trifluoromethanesulfonamide;
5-(4-(2-chloro-4-(trifluoromethylsulfonamido)phenyl)thiazol-2-yl)-N-cyclopropyl-2-fluorobenzamide;
5-(4-(2-chloro-4-(trifluoromethylsulfonamido)phenyl)thiazol-2-yl)-N-cyclohexyl-2-fluorobenzamide;
N-(4-(2-(1H-indol-4-yl)thiazol-4-yl)-3-chlorophenyl)-1,1,1-trifluoromethanesulfonamide;
N-(3-chloro-4-(2-(3-(piperidin-1-yl)phenyl)thiazol-4-yl) phenyl)-1,1,1-trifluoromethanesulfonamide;
N-(3-chloro-4-(2-(2-(piperidin-1-yl)pyridin-4-yl)thiazol-4-yl)phenyl)-1,1,1-trifluoromethanesulfonamide;
N-(2-bromo-4-(2-(2-tert-butylpyridin-4-yl)-1H-imidazol-4-yl)phenyl)-1,1,1-trifluoromethanesulfonamide;
N-(2-chloro-4-(2-(2-propylpyridin-4-yl)-1H-imidazol-4-yl)phenyl)-1,1,1-trifluoromethanesulfonamide;
N-(2-bromo-5-chloro-4-(2-(2-propylpyridin-4-yl)-1H-imidazol-4-yl)phenyl)-1,1,1-trifluoromethanesulfonamide; and
N-(2-bromo-4-(2-(2-propylpyridin-4-yl)thiazol-4-yl)phenyl)-1,1,1-trifluoromethanesulfonamide.

In some embodiments, the compound is selected from the group consisting of:
1,1,1-trifluoro-N-(4-(2-(2-propylpyridin-4-yl)thiazol-4-yl)phenyl)methanesulfonamide;
1,1,1-trifluoro-N-(3-(2-(2-propylpyridin-4-yl)thiazol-4-yl)phenyl)methanesulfonamide;
N-(3-chloro-4-(2-(1-isobutyl-1H-pyrazol-5-yl)thiazol-4-yl) phenyl)-1,1,1-trifluoromethanesulfonamide;
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
1,1,1-trifluoro-N-(2-methoxy-4-{2-[2-(2-methylpropyl)pyridin-4-yl]-1,3-thiazol-4-yl}phenyl) methanesulfonamide;
1,1,1-trifluoro-N-{2-methoxy-4-[2-(2-propylpyridin-4-yl)-1,3-thiazol-4-yl]phenyl}methanesulfonamide;
N-{4-[2-(2-tert-butylpyridin-4-yl)-1,3-thiazol-4-yl]-2-methoxyphenyl}-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-{4-[2-(2-aminopyridin-4-yl)-1,3-thiazol-4-yl]-3-chlorophenyl}-1,1,1-trifluoromethanesulfonamide;
N-{3-chloro-4-[2-(2-methanesulfonamidopyridin-4-yl)-1,3-thiazol-4-yl]phenyl}-1,1,1-trifluoromethanesulfonamide;
1,1,1-trifluoro-N-{2-hydroxy-4-[2-(2-propylpyridin-4-yl)-1,3-thiazol-4-yl]phenyl}methanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-(4-{2-[2-(2,2-dimethylpropyl)pyridin-4-yl]-1,3-thiazol-4-yl}-2-methoxyphenyl)-1,1,1-trifluoromethanesulfonamide;
N-{3-chloro-4-[2-(2-trifluoromethanesulfonamidopyridin-4-yl)-1,3-thiazol-4-yl]phenyl}-1,1,1-trifluoromethanesulfonamide;
N-(3-chloro-4-(2-(4-(piperidine-1-carbonyl)phenyl)thiazol-4-yl)phenyl)-1,1,1-trifluoromethanesulfonamide;
N-(3-chloro-4-{2-[1-(3-methylbutyl)-1H-pyrazol-5-yl]-1,3-thiazol-4-yl}phenyl)-1,1,1-trifluoromethanesulfonamide;
N-{4-[5-(2-tert-butylpyridin-4-yl)thiophen-3-yl]-3-chlorophenyl}methanesulfonamide;
N-(3-chloro-4-{2-[2-(cyclohexylmethyl)pyridin-4-yl]-1,3-thiazol-4-yl}phenyl)-1,1,1-trifluoromethanesulfonamide;
N-{3-chloro-4-[2-(naphthalen-1-yl)-1,3-thiazol-4-yl]phenyl}-1,1,1-trifluoromethanesulfonamide;
N-{3-chloro-4-[2-(1H-indol-6-yl)-1,3-thiazol-4-yl]phenyl}-1,1,1-trifluoromethanesulfonamide;
N-(4-{2-[3-(benzyloxy)-4-(trifluoromethyl)phenyl]-1,3-thiazol-4-yl}-3-chlorophenyl)-1,1,1-trifluoromethanesulfonamide;
N-{3-chloro-4-[2-(2-phenylphenyl)-1,3-thiazol-4-yl]phenyl}-1,1,1-trifluoromethanesulfonamide;
N-{3-chloro-4-[2-(isoquinolin-4-yl)-1,3-thiazol-4-yl]phenyl}-1,1,1-trifluoromethanesulfonamide;
N-(3-chloro-4-{2-[2-(4-methylpiperazin-1-yl)pyridin-4-yl]-1,3-thiazol-4-yl}phenyl)-1,1,1-trifluoromethanesulfonamide;
N-{3-chloro-4-[2-(dimethyl-1,2-oxazol-4-yl)-1,3-thiazol-4-yl]phenyl}-1,1,1-trifluoromethanesulfonamide;
N-{3-[4-(2-chloro-4-trifluoromethanesulfonamidophenyl)-1,3-thiazol-2-yl]phenyl}-4-methylbenzene-1-sulfonamide;
N-{3-chloro-4-[2-(3,4-dimethoxyphenyl)-1,3-thiazol-4-yl]phenyl}-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[4-fluoro-2-(trifluoromethyl)phenyl]-1,3-thiazol-4-yl}phenyl)-1,1,1-trifluoromethanesulfonamide;
N-{3-chloro-4-[2-(2,3-dihydro-1-benzofuran-5-yl)-1,3-thiazol-4-yl]phenyl}-1,1,1-trifluoromethanesulfonamide;
N-(3-chloro-4-{2-[3-(hydroxymethyl)phenyl]-1,3-thiazol-4-yl}phenyl)-1,1,1-trifluoromethanesulfonamide;
N-(3-chloro-4-{2-[2-(hydroxymethyl)phenyl]-1,3-thiazol-4-yl}phenyl)-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide;
N-{3-chloro-4-[2-(3-methylpyridin-4-yl)-1,3-thiazol-4-yl]phenyl}-1,1,1-trifluoromethanesulfonamide;
N-[3-chloro-4-(2-{1H-pyrrolo[2,3-b]pyridin-4-yl}-1,3-thiazol-4-yl)phenyl]-1,1,1-trifluoromethanesulfonamide;
N-(3-chloro-4-{2-[3-(piperidin-1-yl)phenyl]-1,3-thiazol-4-yl}phenyl)-1,1,1-trifluoromethanesulfonamide;
N-[3-chloro-4-(2-{5-fluoro-1H-pyrrolo[2,3-b]pyridin-4-yl}-1,3-thiazol-4-yl)phenyl]-1,1,1-trifluoromethanesulfonamide;
N-{4-[2-(1-benzothiophen-3-yl)-1,3-thiazol-4-yl]-3-chlorophenyl}-1,1,1-trifluoromethanesulfonamide;

N-(3-chloro-4-{2-[4-fluoro-2-(pyrrolidin-1-ylmethyl)phenyl]-1,3-thiazol-4-yl}phenyl)-1,1,1-trifluoromethanesulfonamide;
N-(3-chloro-4-{2-[2-(cyclopentylamino)pyridin-4-yl]-1,3-thiazol-4-yl}phenyl)-1,1,1-trifluoromethanesulfonamide;
N-{3-chloro-4-[2-(1H-indol-3-yl)-1,3-thiazol-4-yl]phenyl}-1,1,1-trifluoromethanesulfonamide; and
N-(3-chloro-4-(2-(quinolin-4-yl)thiazol-4-yl)phenyl)-1,1,1-trifluoromethanesulfonamide.

In some embodiments, the compound is selected from the group consisting of:
N-(3-chloro-4-(2-(2-propylpyridin-4-yl)thiazol-4-yl)phenyl)-1,1,1-trifluoromethanesulfonamide;
N-(4-(2-(2-tert-butylpyridin-4-yl)thiazol-4-yl)-3-chlorophenyl)-1,1,1-trifluoromethanesulfonamide;
N-(3-chloro-4-(2-(2-isobutylpyridin-4-yl)thiazol-4-yl)phenyl)-1,1,1-trifluoromethanesulfonamide;
N-{4-[2-(2-benzylpyridin-4-yl)-1,3-thiazol-4-yl]-3-chlorophenyl}-1,1,1-trifluoromethanesulfonamide;
N-(3-chloro-4-{2-[2-(3,3,3-trifluoropropyl)pyridin-4-yl]-1,3-thiazol-4-yl}phenyl)-1,1,1-trifluoromethanesulfonamide;
N-{3-chloro-4-[2-(1H-indol-4-yl)-1,3-thiazol-4-yl]phenyl}-1,1,1-trifluoromethanesulfonamide;
N-(3-chloro-4-{2-[2-(piperidin-1-yl)pyridin-4-yl]-1,3-thiazol-4-yl}phenyl)-1,1,1-trifluoromethanesulfonamide; and
N-(3-chloro-4-{2-[3-(piperidin-1-yl)phenyl]-1,3-thiazol-4-yl}phenyl)-1,1,1-trifluoromethanesulfonamide.

In some embodiments, the compound is compound #37: N-(3-chloro-4-(2-(2-isobutylpyridin-4-yl)thiazol-4-yl)phenyl)-1,1,1-trifluoromethanesulfonamide.

The compounds described below are not intended to be limiting; rather, these embodiments and variations are intended to provide examples of compounds within the scope of Formulae (Ia), (Ib), (IIa) or (IIb).

Representative compounds are presented in Table 1.

TABLE 1

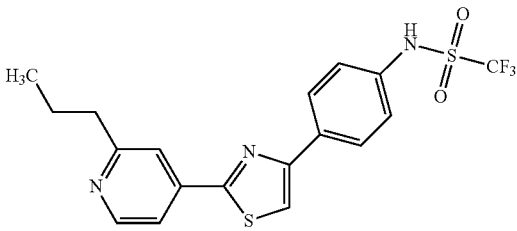 [SMILES: CCCc1cc(-c2nc(-c3ccc(NS(=O)(=O)C(F)(F)F)cc3)cs2)ccn1]

1

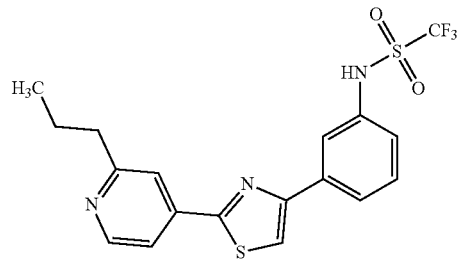 [SMILES: CCCc1cc(-c2nc(-c3cccc(NS(=O)(=O)C(F)(F)F)c3)cs2)ccn1]

2

3

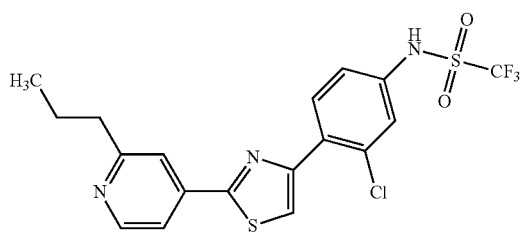 [SMILES: CCCc1cc(-c2nc(-c3ccc(NS(=O)(=O)C(F)(F)F)cc3Cl)cs2)ccn1]

4

TABLE 1-continued
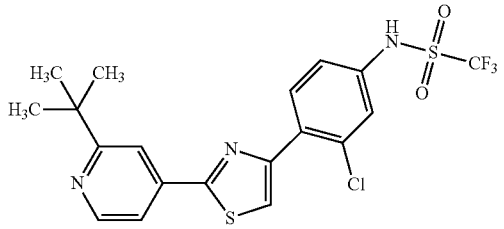 [SMILES: CC(C)(C)c1cc(-c2nc(-c3ccc(NS(=O)(=O)C(F)(F)F)cc3Cl)cs2)ccn1]
5
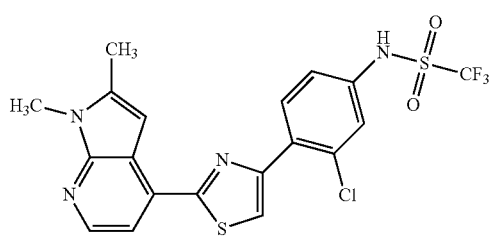 [SMILES: Cc1cc2c(-c3nc(-c4ccc(NS(=O)(=O)C(F)(F)F)cc4Cl)cs3)ccnc2n1C]
6
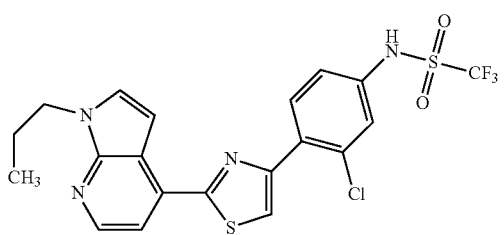 [SMILES: CCCn1ccc2c(-c3nc(-c4ccc(NS(=O)(=O)C(F)(F)F)cc4Cl)cs3)ccnc21]
7
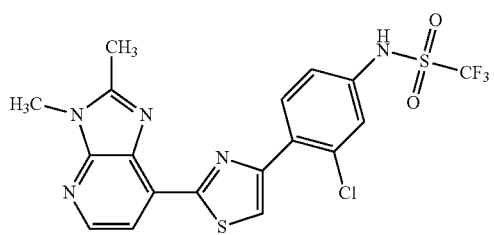 [SMILES: Cc1nc2c(-c3nc(-c4ccc(NS(=O)(=O)C(F)(F)F)cc4Cl)cs3)ccnc2n1C]
8
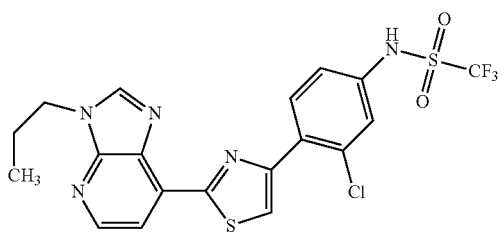 [SMILES: CCCn1cnc2c(-c3nc(-c4ccc(NS(=O)(=O)C(F)(F)F)cc4Cl)cs3)ccnc21]
9
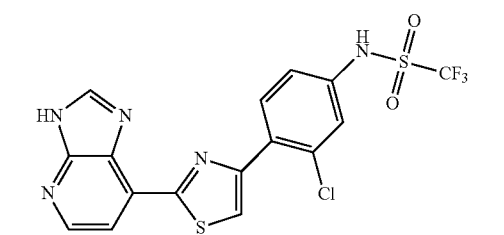 [SMILES: O=S(=O)(Nc1ccc(-c2csc(-c3ccnc4[nH]cnc34)n2)c(Cl)c1)C(F)(F)F]
10

TABLE 1-continued
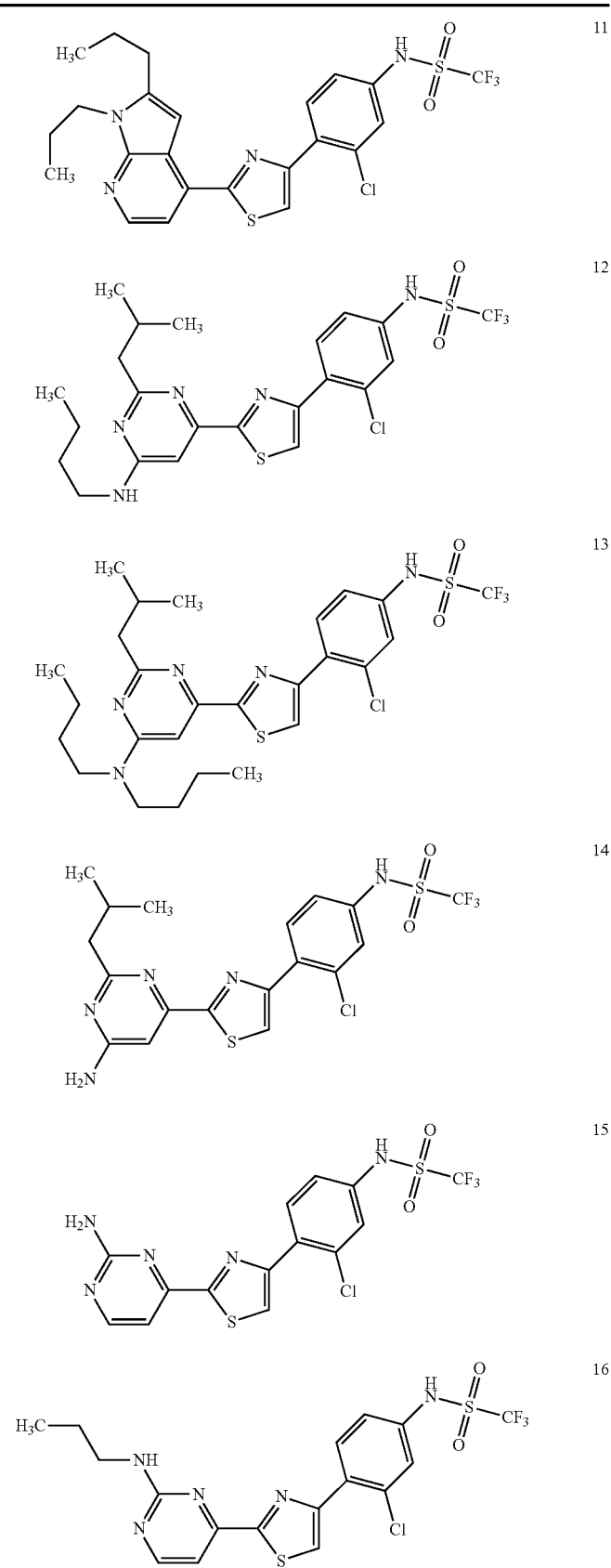

TABLE 1-continued
| | |
|---|---|
| 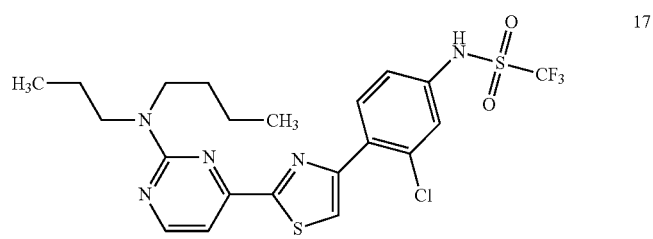 | 17 |
| 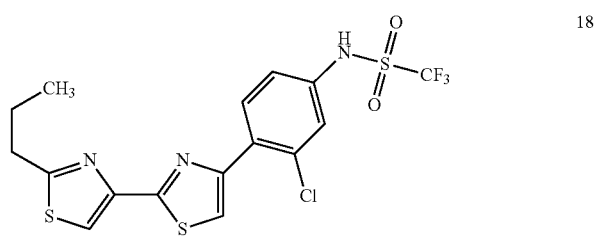 | 18 |
| 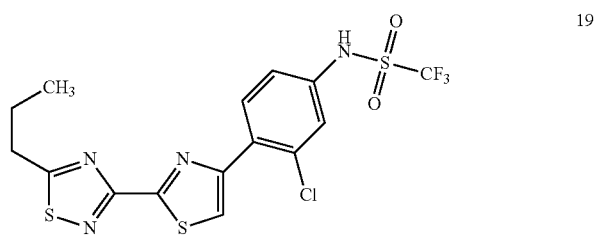 | 19 |
| 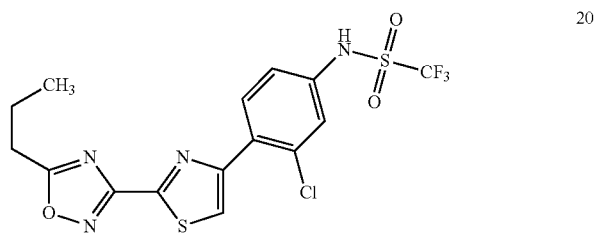 | 20 |
| 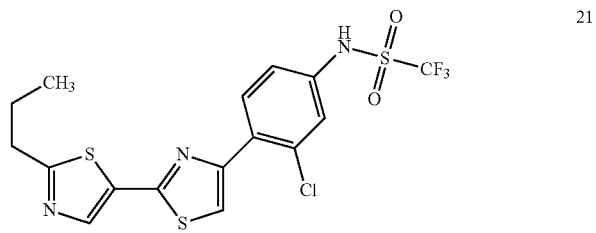 | 21 |
| 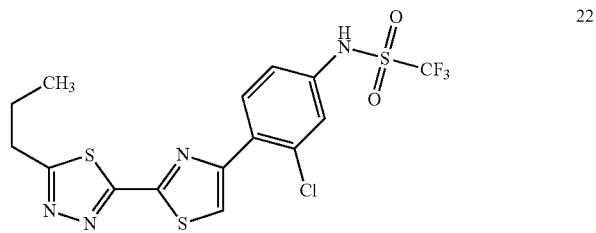 | 22 |

TABLE 1-continued
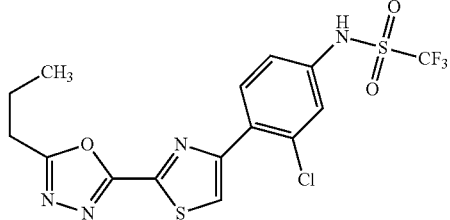 [SMILES: CCCc1nnc(-c2nc(-c3ccc(NS(=O)(=O)C(F)(F)F)cc3Cl)cs2)o1] 23
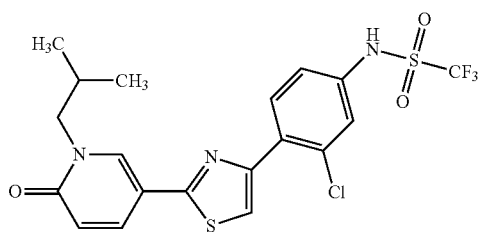 [SMILES: CC(C)Cn1cc(-c2nc(-c3ccc(NS(=O)(=O)C(F)(F)F)cc3Cl)cs2)ccc1=O] 24
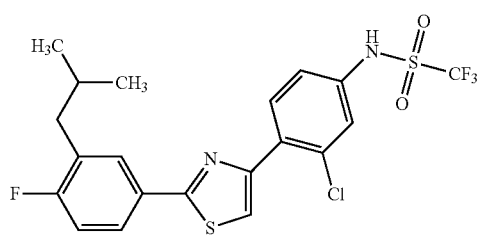 [SMILES: CC(C)Cc1cc(-c2nc(-c3ccc(NS(=O)(=O)C(F)(F)F)cc3Cl)cs2)ccc1F] 25
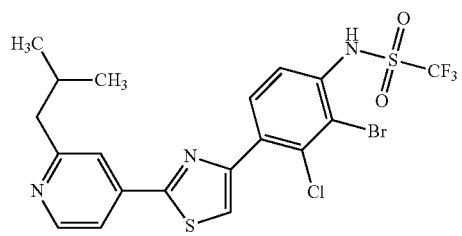 [SMILES: CC(C)Cc1cc(-c2nc(-c3ccc(NS(=O)(=O)C(F)(F)F)c(Br)c3Cl)cs2)ccn1] 26
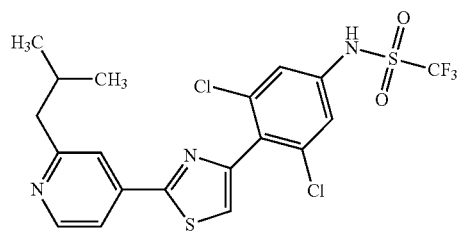 [SMILES: CC(C)Cc1cc(-c2nc(-c3c(Cl)cc(NS(=O)(=O)C(F)(F)F)cc3Cl)cs2)ccn1] 27
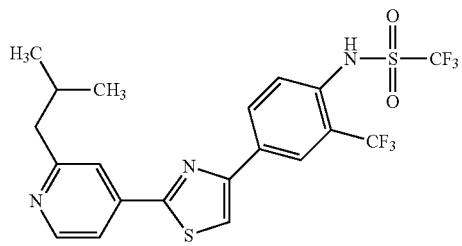 [SMILES: CC(C)Cc1cc(-c2nc(-c3ccc(NS(=O)(=O)C(F)(F)F)c(C(F)(F)F)c3)cs2)ccn1] 28

TABLE 1-continued
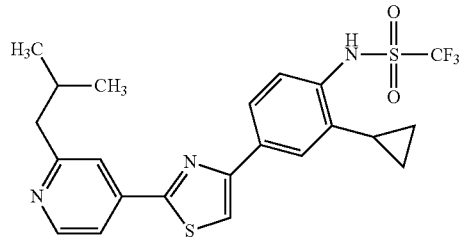 [SMILES: CC(C)Cc1cc(-c2nc(-c3ccc(NS(=O)(=O)C(F)(F)F)c(C4CC4)c3)cs2)ccn1]
29
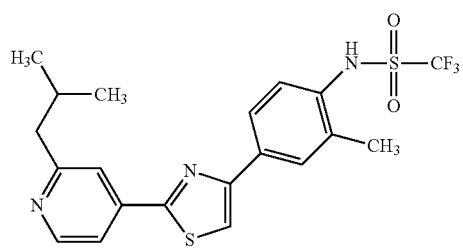
30
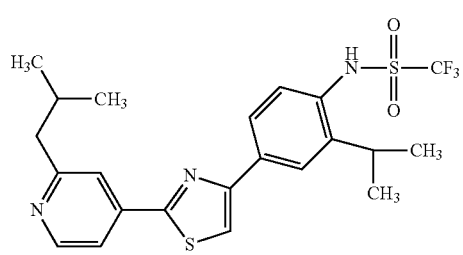 [SMILES: CC(C)Cc1cc(-c2nc(-c3ccc(NS(=O)(=O)C(F)(F)F)c(C(C)C)c3)cs2)ccn1]
31
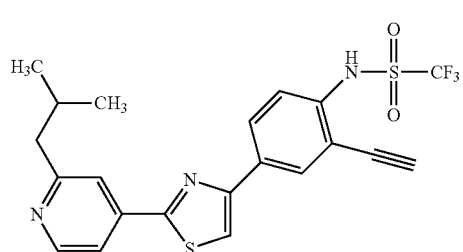
32
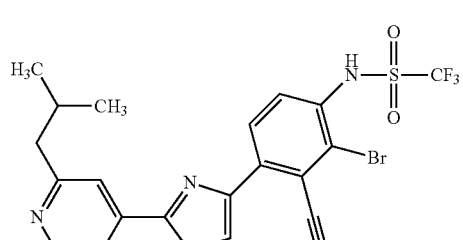
33
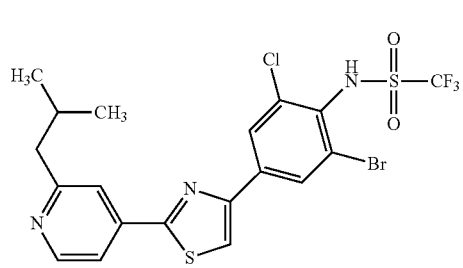 [SMILES: CC(C)Cc1cc(-c2nc(-c3cc(Cl)c(NS(=O)(=O)C(F)(F)F)c(Br)c3)cs2)ccn1]
34

TABLE 1-continued
| | |
|---|---|
| 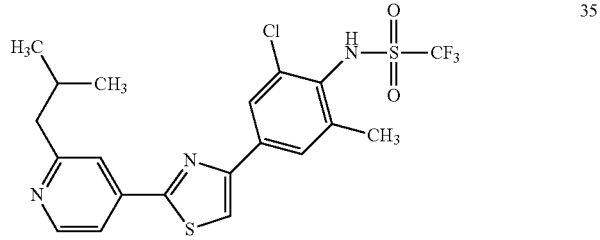 | 35 |
| 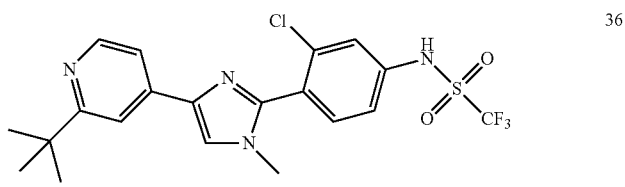 | 36 |
| 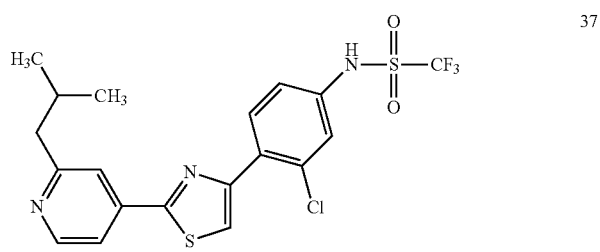 | 37 |
| 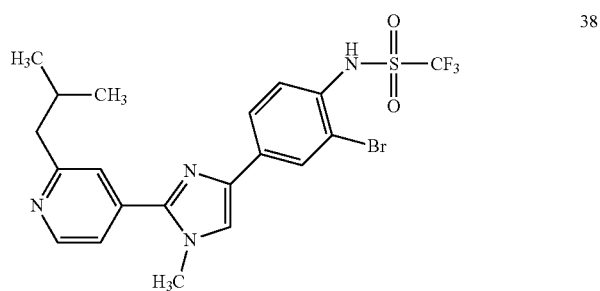 | 38 |
| 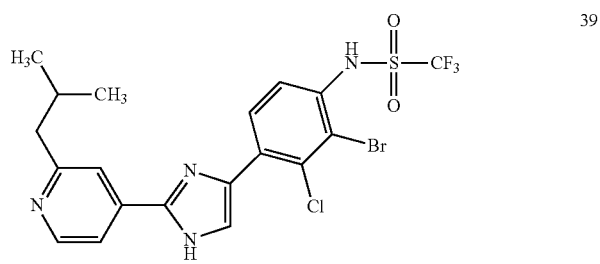 | 39 |
| 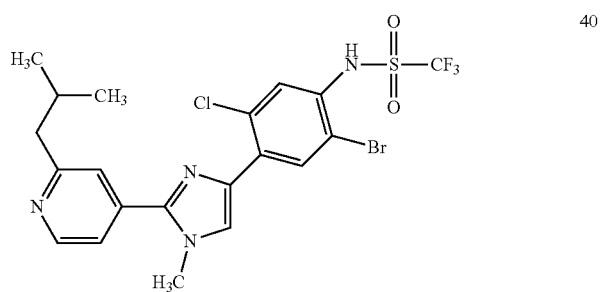 | 40 |

TABLE 1-continued

| Structure | # |
|---|---|
| (structure) | 41 |
| (structure) | 42 |
| (structure) | 43 |
| (structure) | 44 |
| (structure) | 45 |
| (structure) | 46 |
| (structure) | 47 |
| (structure) | 48 |

TABLE 1-continued
| | |
|---|---|
| 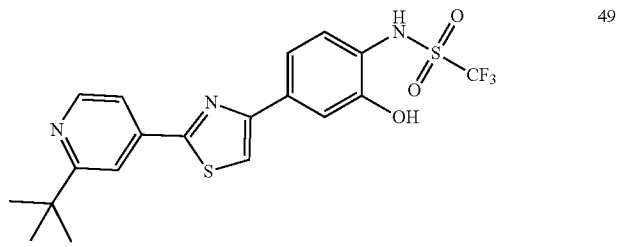 | 49 |
| 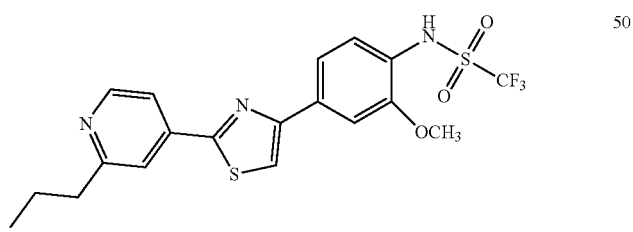 | 50 |
| 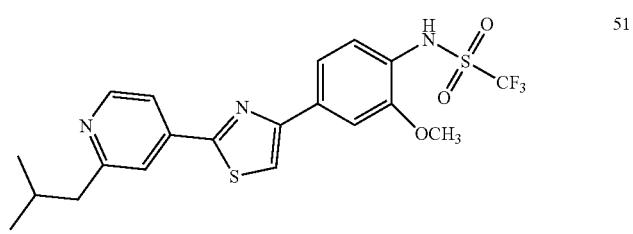 | 51 |
| 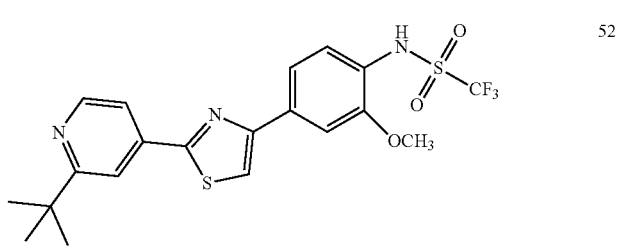 | 52 |
| 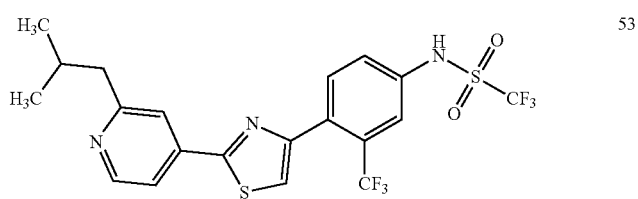 | 53 |
| 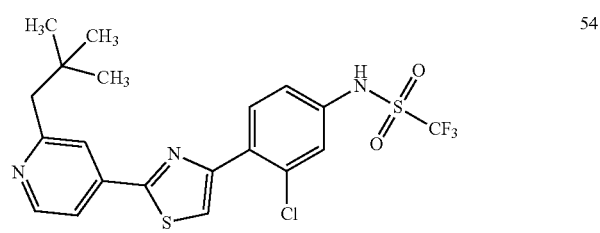 | 54 |
| 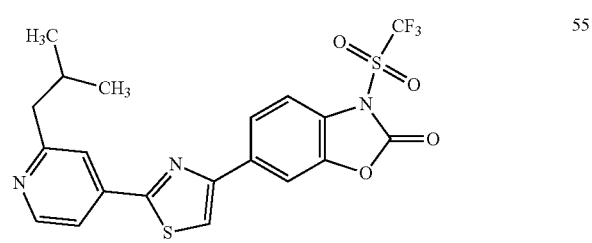 | 55 |

TABLE 1-continued
| | |
|---|---|
| 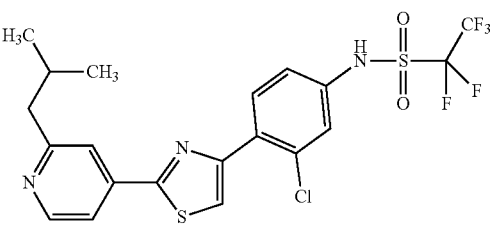 [SMILES: CC(C)Cc1cc(-c2nc(-c3ccc(NS(=O)(=O)C(F)(F)C(F)(F)F)cc3Cl)cs2)ccn1] | 56 |
| 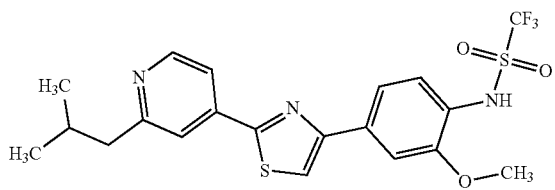 [SMILES: COc1cc(-c2csc(-c3ccnc(CC(C)C)c3)n2)ccc1NS(=O)(=O)C(F)(F)F] | 57 |
| 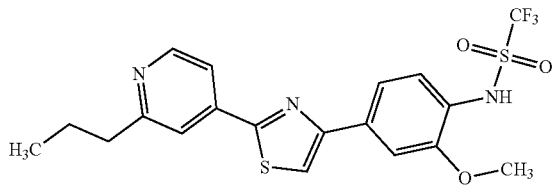 [SMILES: CCCc1cc(-c2nc(-c3ccc(NS(=O)(=O)C(F)(F)F)c(OC)c3)cs2)ccn1] | 58 |
| 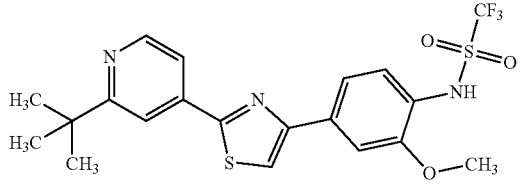 [SMILES: COc1cc(-c2csc(-c3ccnc(C(C)(C)C)c3)n2)ccc1NS(=O)(=O)C(F)(F)F] | 59 |
| 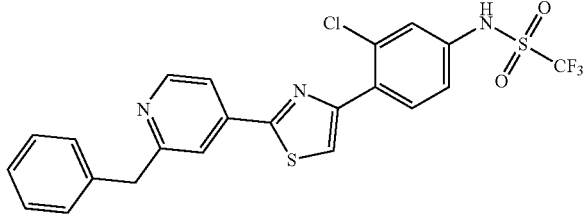 [SMILES: O=S(=O)(Nc1ccc(-c2csc(-c3ccnc(Cc4ccccc4)c3)n2)c(Cl)c1)C(F)(F)F] | 60 |
| 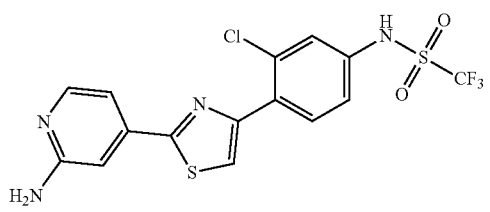 [SMILES: Nc1cc(-c2nc(-c3ccc(NS(=O)(=O)C(F)(F)F)cc3Cl)cs2)ccn1] | 61 |
| 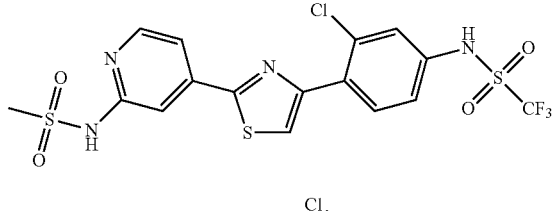 | 62 |
| 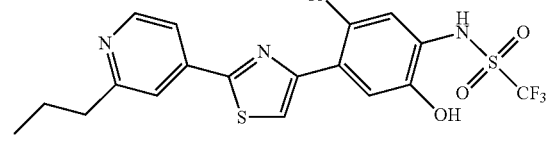 | 63 |

TABLE 1-continued
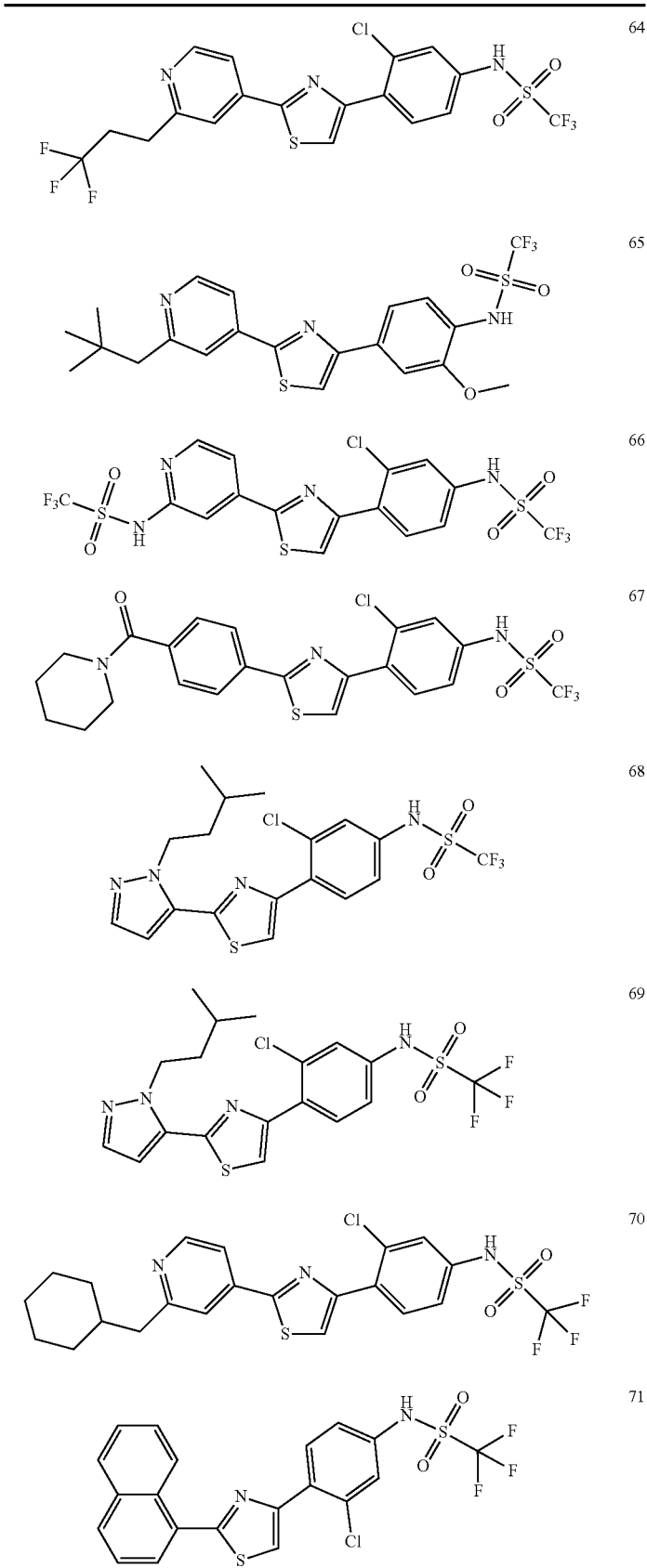

TABLE 1-continued
| | |
|---|---|
| 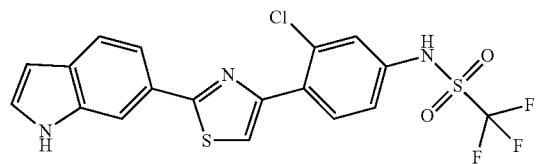 [SMILES: O=S(=O)(Nc1ccc(-c2csc(-c3ccc4cc[nH]c4c3)n2)c(Cl)c1)C(F)(F)F] | 72 |
| 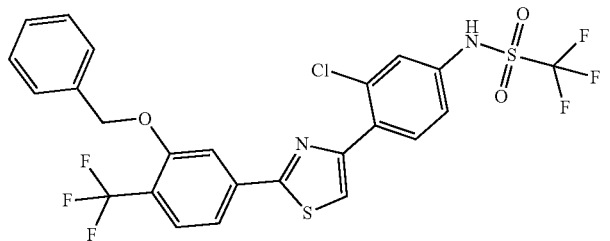 [SMILES: O=S(=O)(Nc1ccc(-c2csc(-c3ccc(C(F)(F)F)c(OCc4ccccc4)c3)n2)c(Cl)c1)C(F)(F)F] | 73 |
| 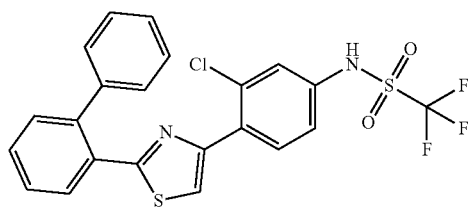 [SMILES: O=S(=O)(Nc1ccc(-c2csc(-c3ccccc3-c3ccccc3)n2)c(Cl)c1)C(F)(F)F] | 74 |
| 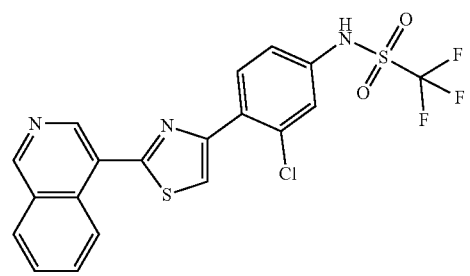 [SMILES: O=S(=O)(Nc1ccc(-c2csc(-c3cncc4ccccc34)n2)c(Cl)c1)C(F)(F)F] | 75 |
| 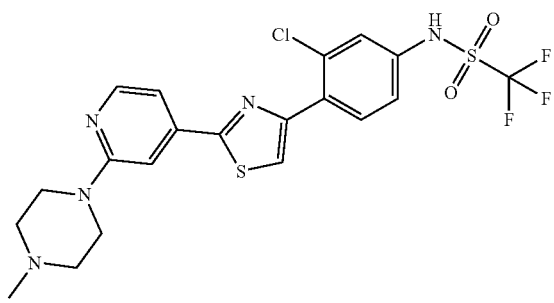 [SMILES: CN1CCN(c2cc(-c3nc(-c4ccc(NS(=O)(=O)C(F)(F)F)cc4Cl)cs3)ccn2)CC1] | 76 |
|  | 77 |
| 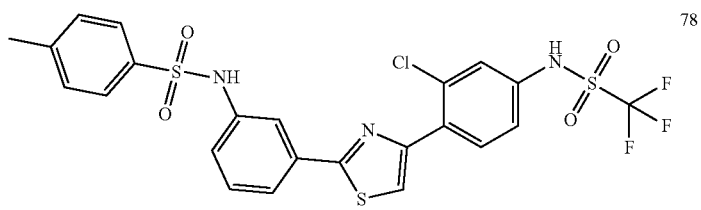 | 78 |

TABLE 1-continued
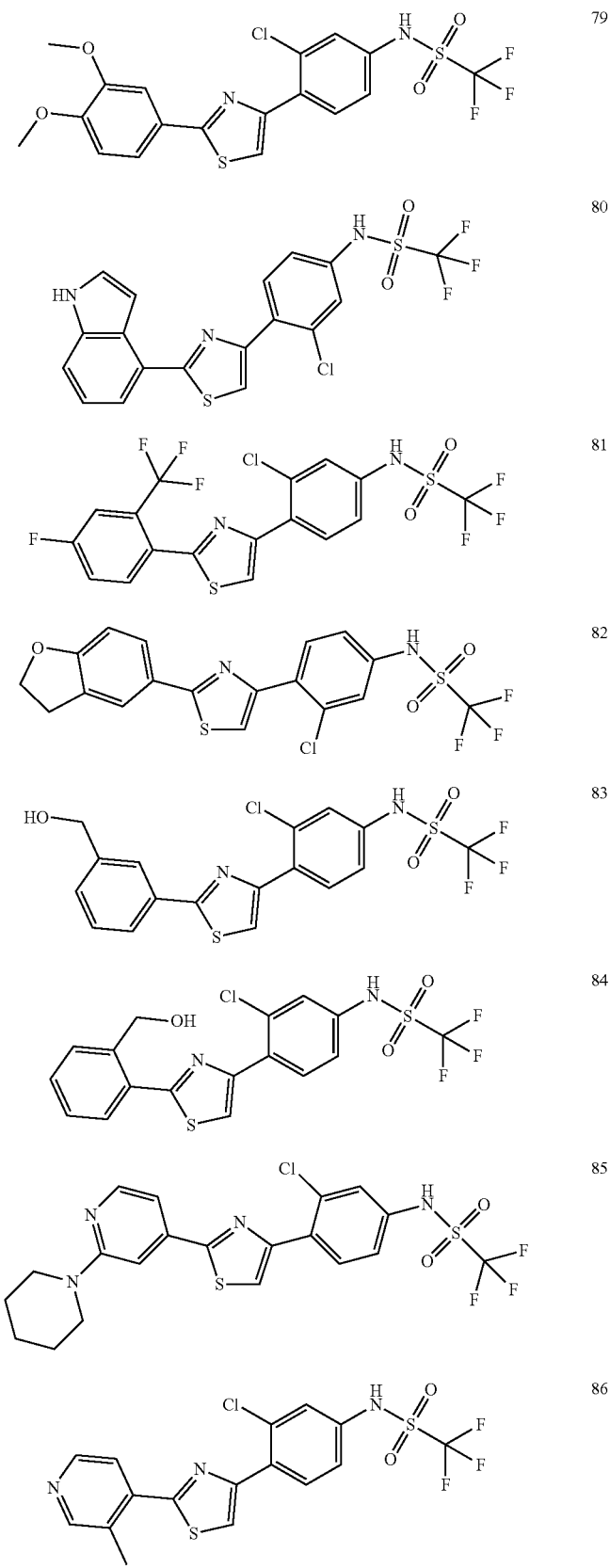

TABLE 1-continued
| | |
|---|---|
| 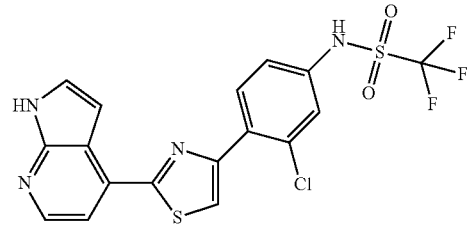 [SMILES: O=S(=O)(Nc1ccc(-c2csc(-c3ccnc4[nH]ccc34)n2)c(Cl)c1)C(F)(F)F] | 87 |
| 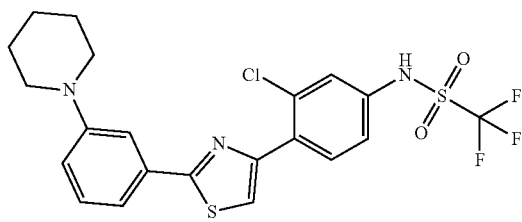 [SMILES: O=S(=O)(Nc1ccc(-c2csc(-c3cccc(N4CCCCC4)c3)n2)c(Cl)c1)C(F)(F)F] | 88 |
| 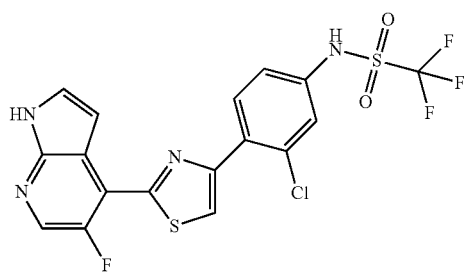 [SMILES: O=S(=O)(Nc1ccc(-c2csc(-c3c(F)cnc4[nH]ccc34)n2)c(Cl)c1)C(F)(F)F] | 89 |
| 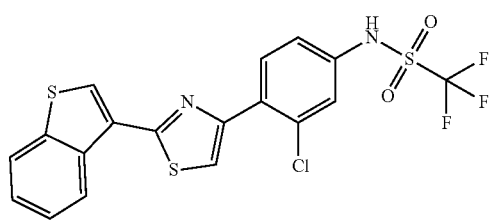 [SMILES: O=S(=O)(Nc1ccc(-c2csc(-c3csc4ccccc34)n2)c(Cl)c1)C(F)(F)F] | 90 |
| 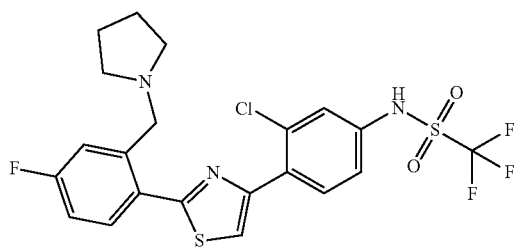 [SMILES: O=S(=O)(Nc1ccc(-c2csc(-c3ccc(F)cc3CN3CCCC3)n2)c(Cl)c1)C(F)(F)F] | 91 |
| 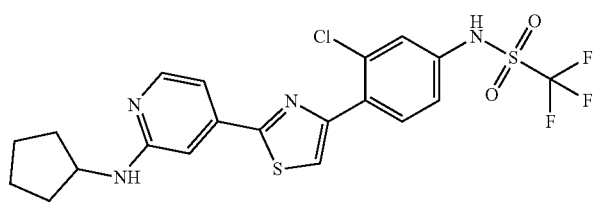 [SMILES: O=S(=O)(Nc1ccc(-c2csc(-c3ccnc(NC4CCCC4)c3)n2)c(Cl)c1)C(F)(F)F] | 92 |
| 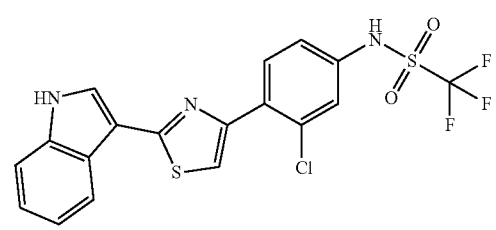 [SMILES: O=S(=O)(Nc1ccc(-c2csc(-c3c[nH]c4ccccc34)n2)c(Cl)c1)C(F)(F)F] | 93 |

TABLE 1-continued
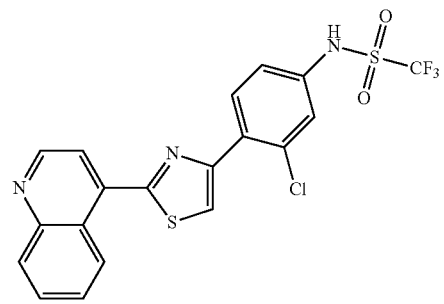 [SMILES: O=S(=O)(Nc1ccc(-c2csc(-c3ccnc4ccccc34)n2)c(Cl)c1)C(F)(F)F]
94
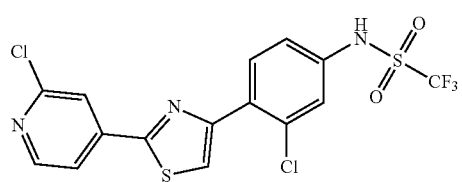 [SMILES: O=S(=O)(Nc1ccc(-c2csc(-c3ccnc(Cl)c3)n2)c(Cl)c1)C(F)(F)F]
95
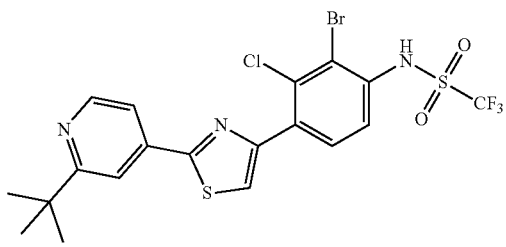 [SMILES: CC(C)(C)c1cc(-c2nc(-c3ccc(NS(=O)(=O)C(F)(F)F)c(Br)c3Cl)cs2)ccn1]
96
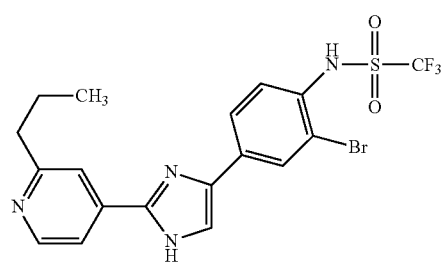 [SMILES: CCCc1cc(-c2nc(-c3ccc(NS(=O)(=O)C(F)(F)F)c(Br)c3)c[nH]2)ccn1]
97
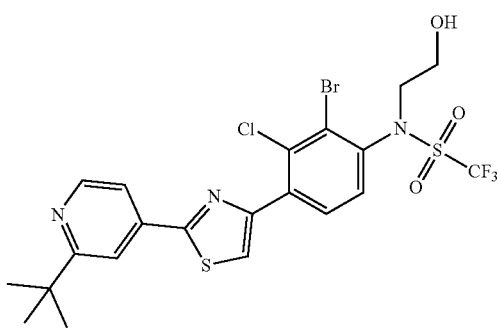 [SMILES: CC(C)(C)c1cc(-c2nc(-c3ccc(N(CCO)S(=O)(=O)C(F)(F)F)c(Br)c3Cl)cs2)ccn1]
98

TABLE 1-continued
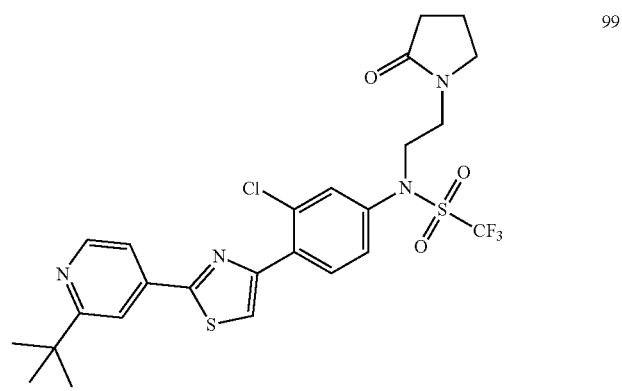
99
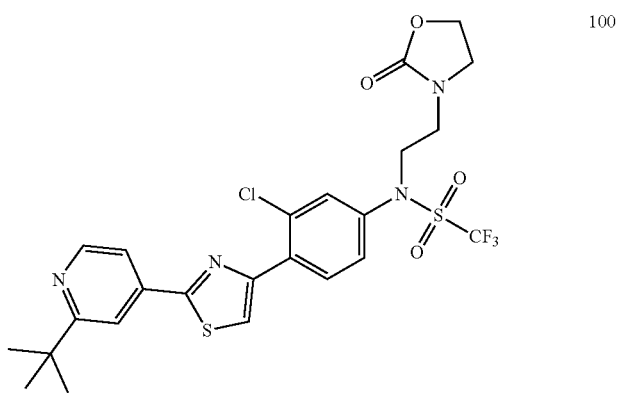
100
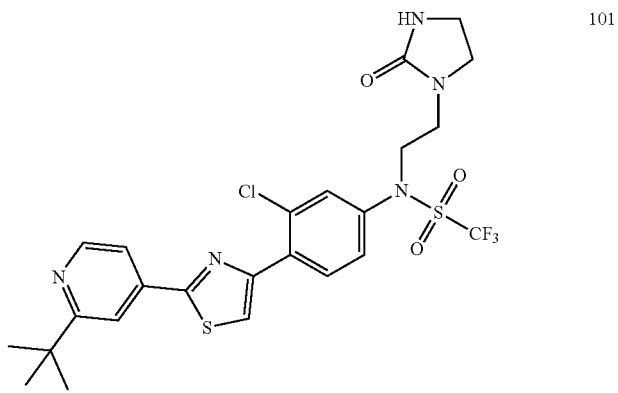
101
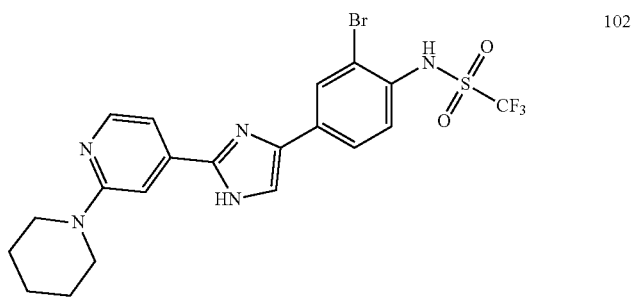
102

TABLE 1-continued
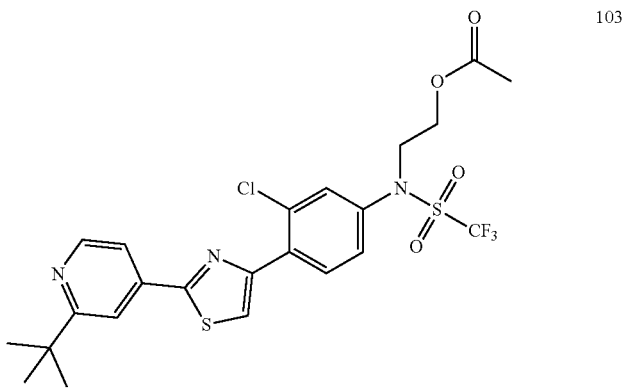
103
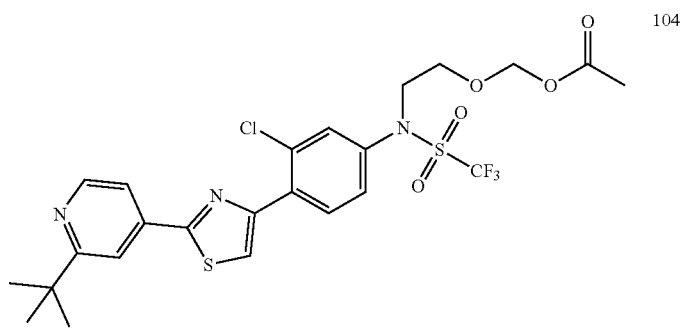
104
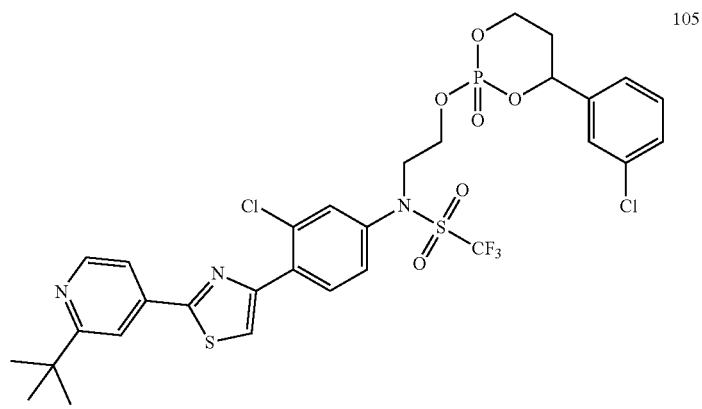
105
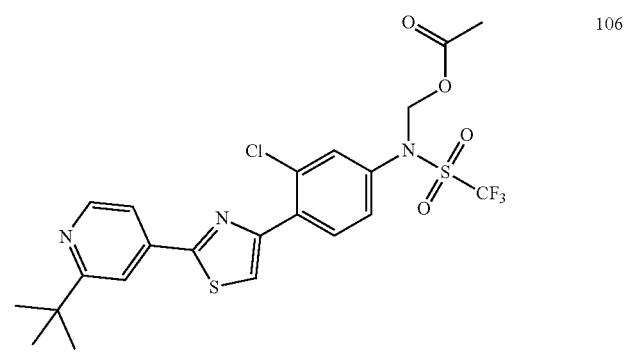
106

TABLE 1-continued
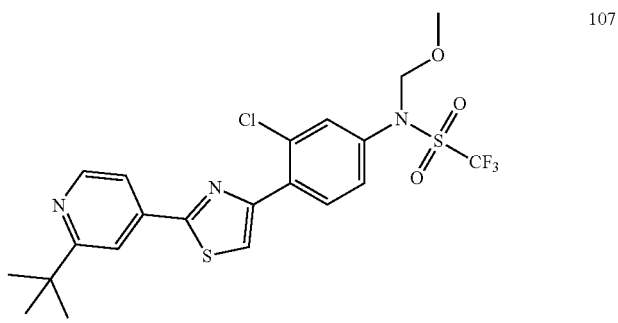
107
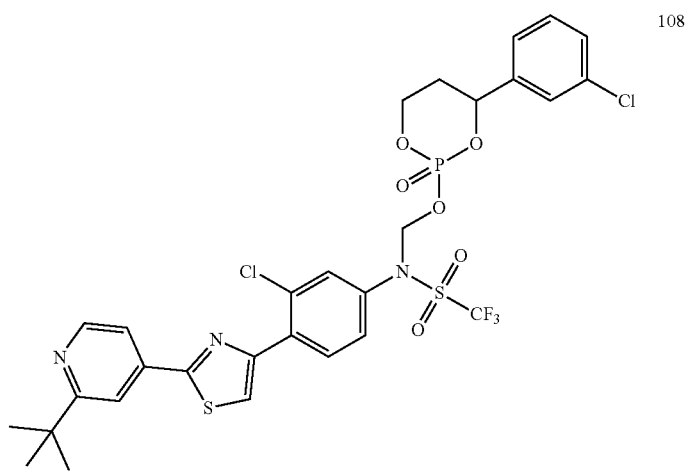
108
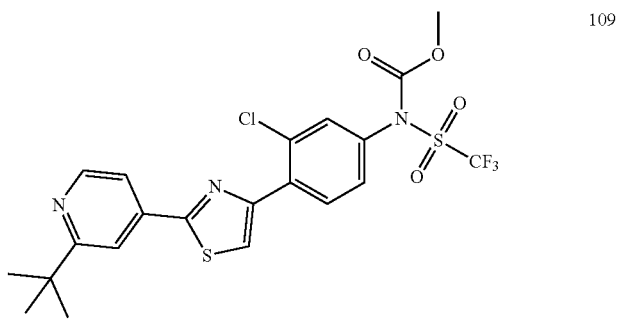
109
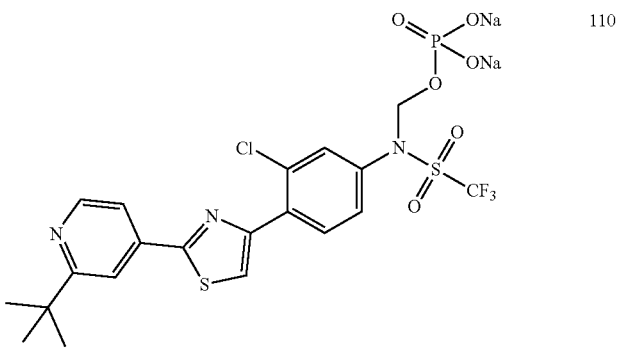
110

TABLE 1-continued
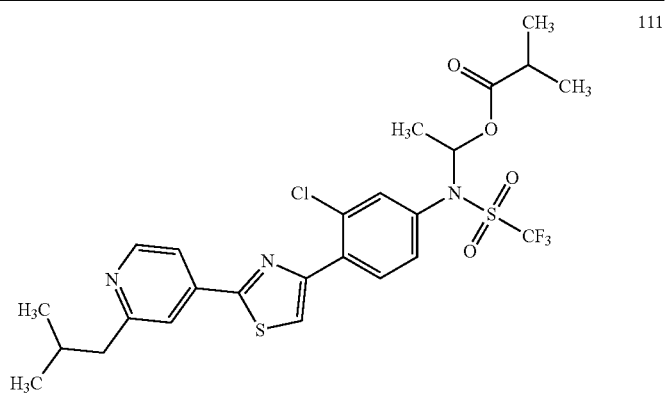
111
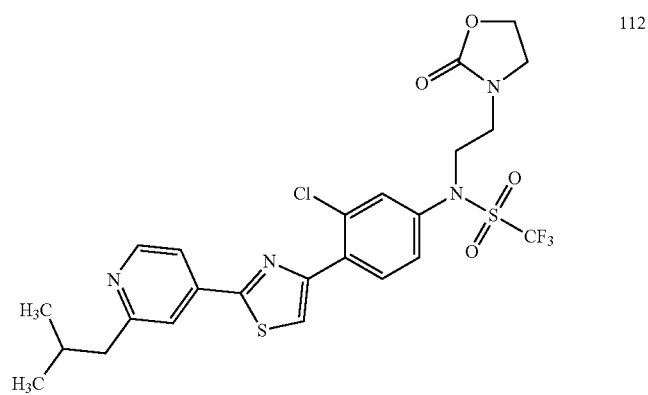
112
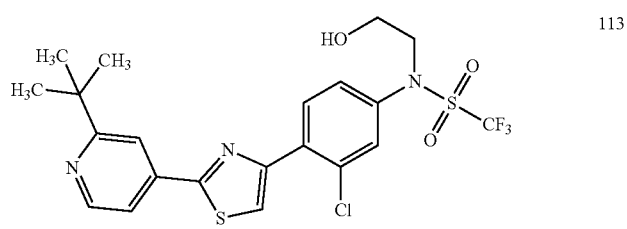
113
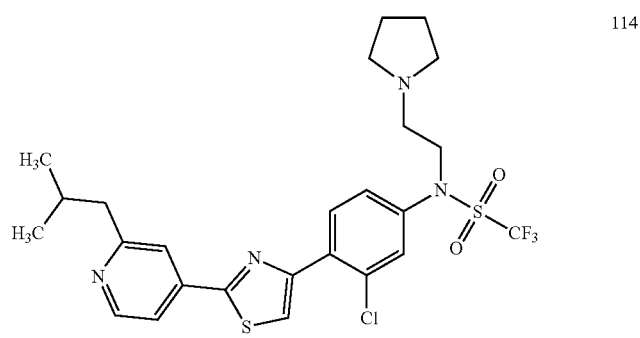
114

TABLE 1-continued
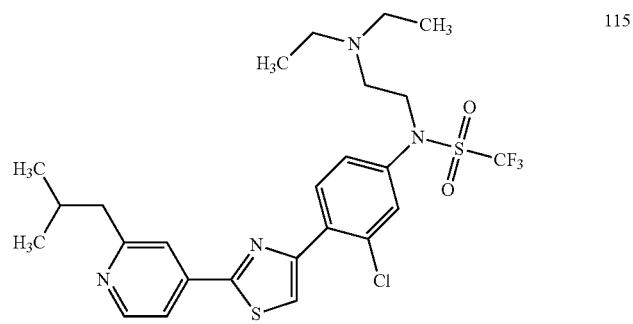 115
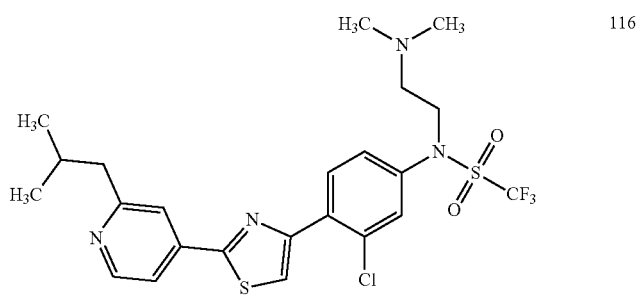 116
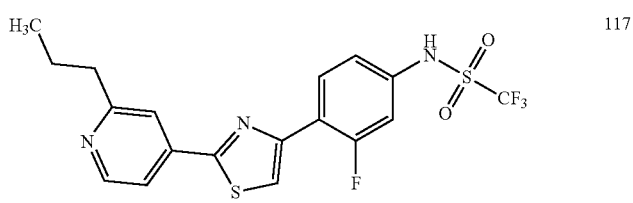 117
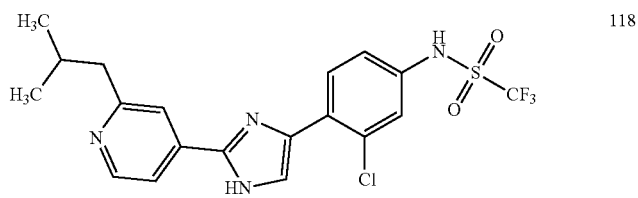 118
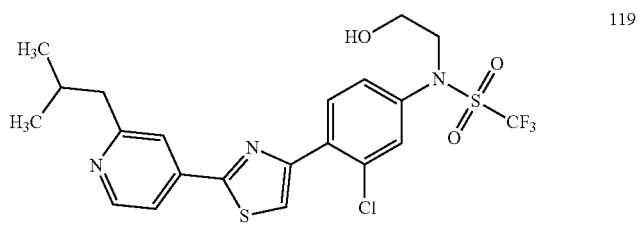 119
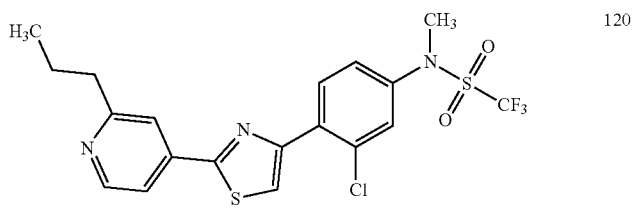 120

TABLE 1-continued
| | |
|---|---|
| 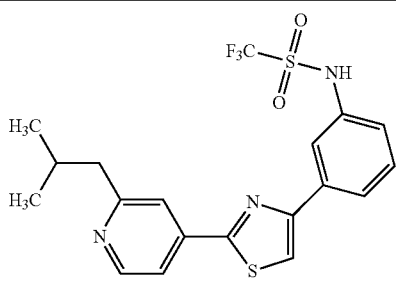 | 121 |
| 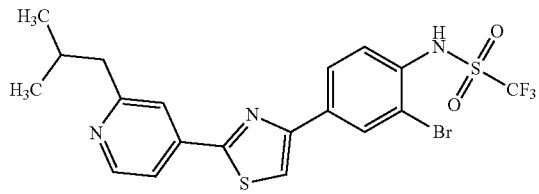 [SMILES: CC(C)Cc1cc(-c2nc(-c3ccc(NS(=O)(=O)C(F)(F)F)c(Br)c3)cs2)ccn1] | 122 |
| 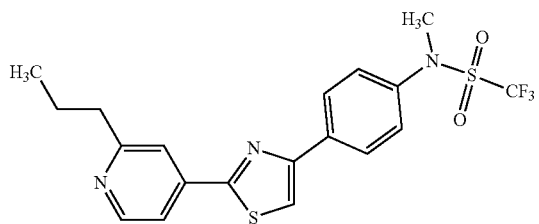 [SMILES: CCCc1cc(-c2nc(-c3ccc(N(C)S(=O)(=O)C(F)(F)F)cc3)cs2)ccn1] | 123 |
| 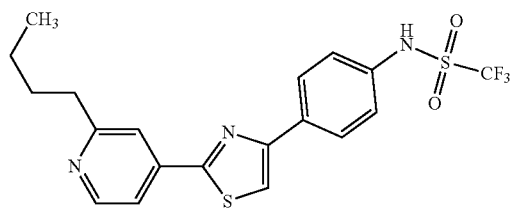 [SMILES: CCCCc1cc(-c2nc(-c3ccc(NS(=O)(=O)C(F)(F)F)cc3)cs2)ccn1] | 124 |
| 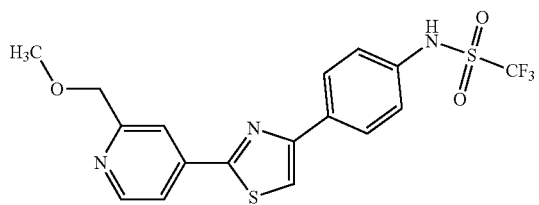 [SMILES: COCc1cc(-c2nc(-c3ccc(NS(=O)(=O)C(F)(F)F)cc3)cs2)ccn1] | 125 |
| 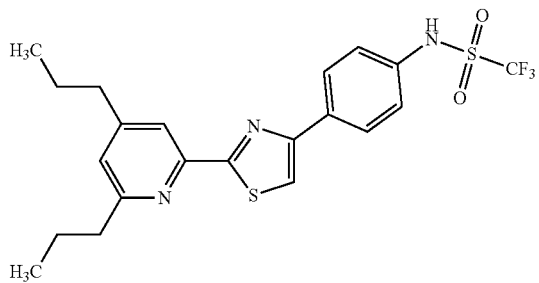 [SMILES: CCCc1cc(CCC)nc(-c2nc(-c3ccc(NS(=O)(=O)C(F)(F)F)cc3)cs2)c1] | 126 |
| 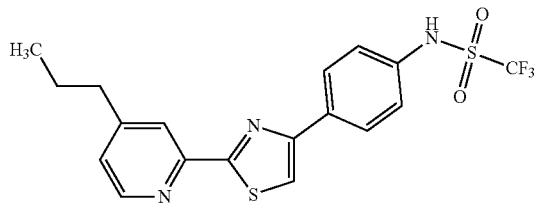 [SMILES: CCCc1ccnc(-c2nc(-c3ccc(NS(=O)(=O)C(F)(F)F)cc3)cs2)c1] | 127 |

TABLE 1-continued
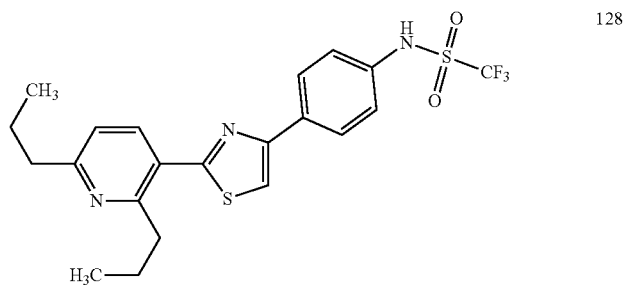 128
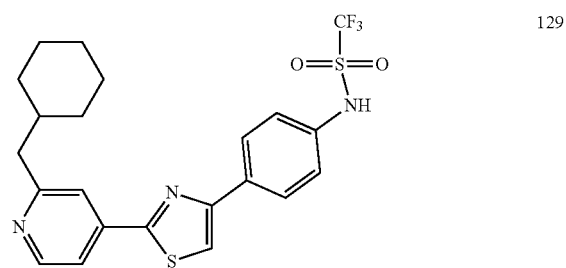 129
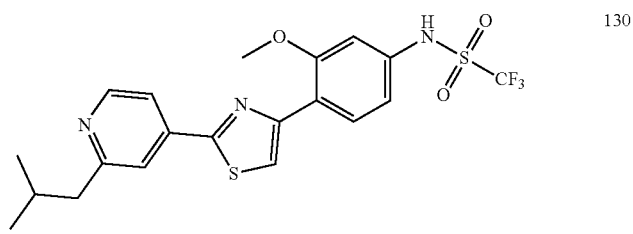 130
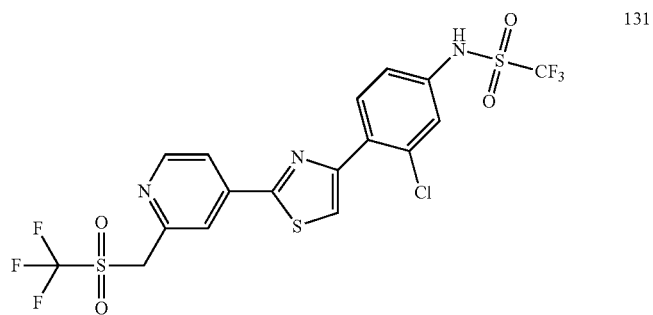 131
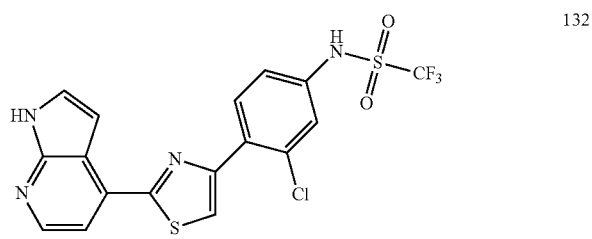 132

TABLE 1-continued
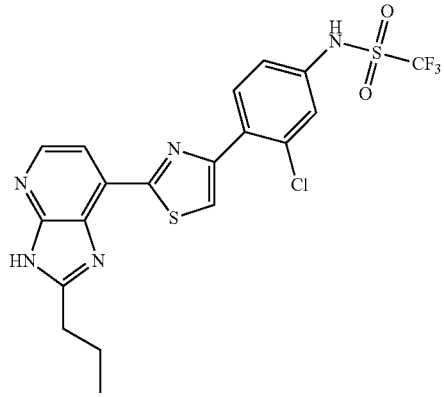 [SMILES: CCCc1nc2c(-c3nc(-c4ccc(NS(=O)(=O)C(F)(F)F)cc4Cl)cs3)ccnc2[nH]1] 133
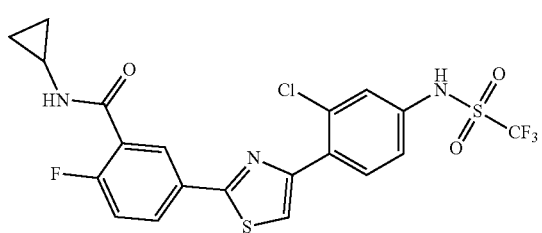 [SMILES: O=C(NC1CC1)c1cc(-c2nc(-c3ccc(NS(=O)(=O)C(F)(F)F)cc3Cl)cs2)ccc1F] 134
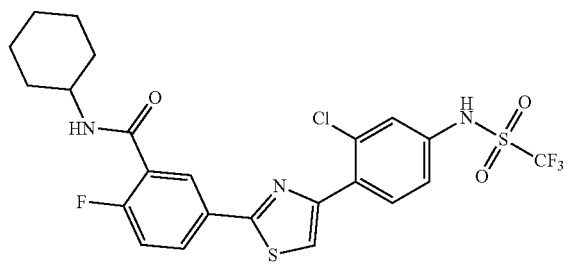 [SMILES: O=C(NC1CCCCC1)c1cc(-c2nc(-c3ccc(NS(=O)(=O)C(F)(F)F)cc3Cl)cs2)ccc1F] 135
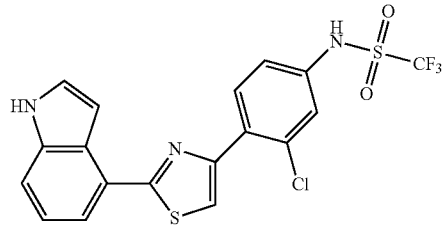 [SMILES: O=S(=O)(Nc1ccc(-c2csc(-c3cccc4[nH]ccc34)n2)c(Cl)c1)C(F)(F)F] 136
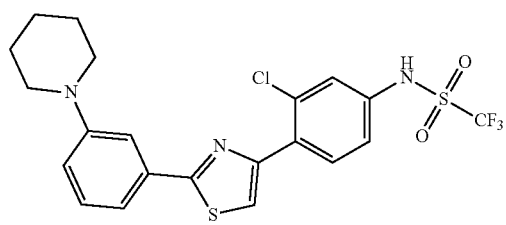 [SMILES: O=S(=O)(Nc1ccc(-c2csc(-c3cccc(N4CCCCC4)c3)n2)c(Cl)c1)C(F)(F)F] 137
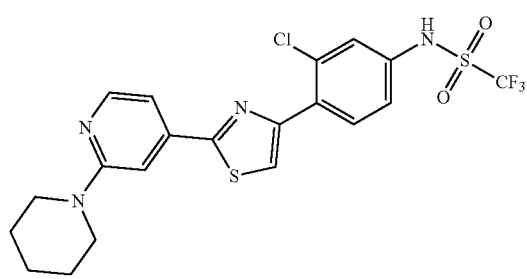 [SMILES: O=S(=O)(Nc1ccc(-c2csc(-c3ccnc(N4CCCCC4)c3)n2)c(Cl)c1)C(F)(F)F] 138

TABLE 1-continued
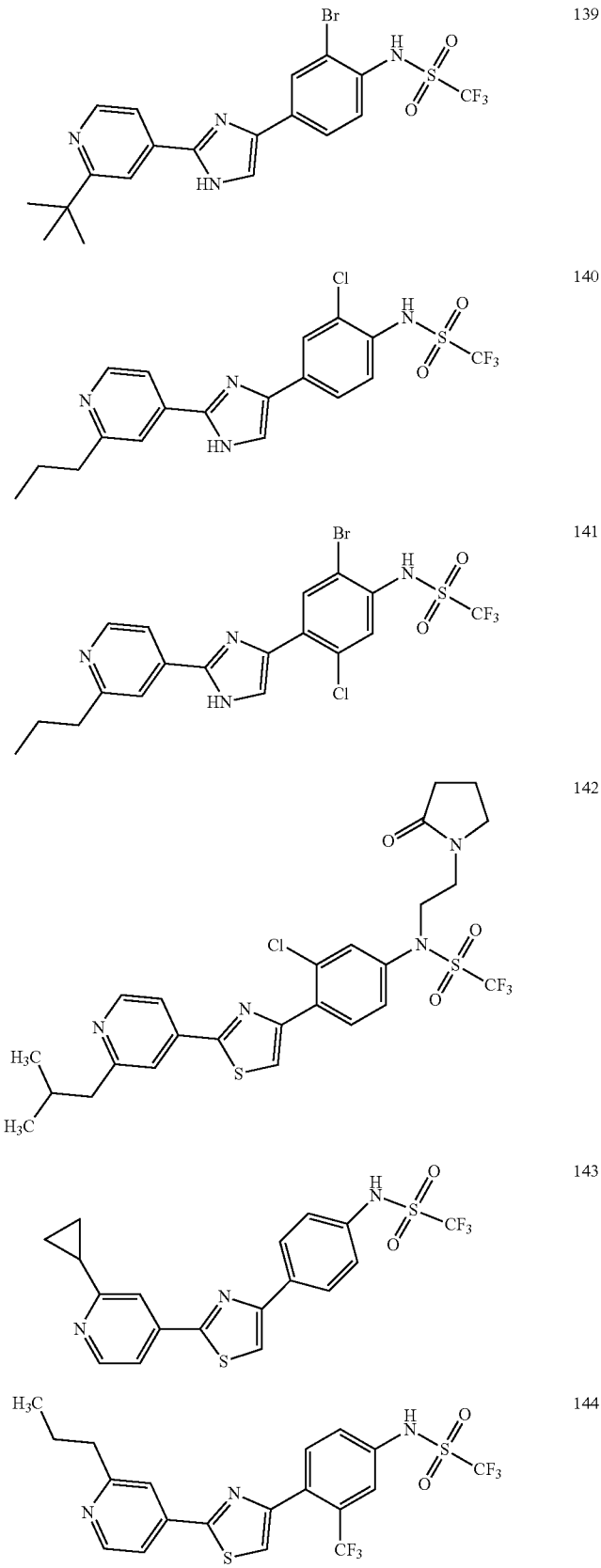

TABLE 1-continued
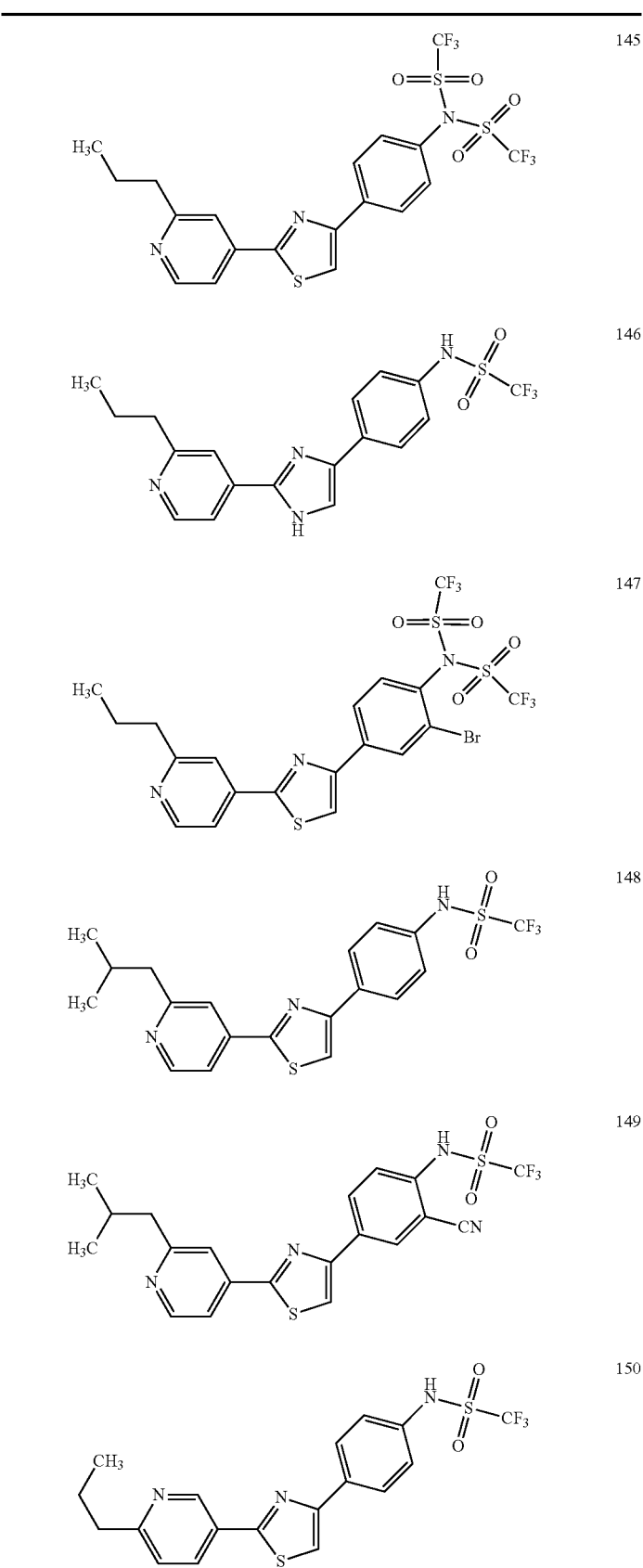

TABLE 1-continued

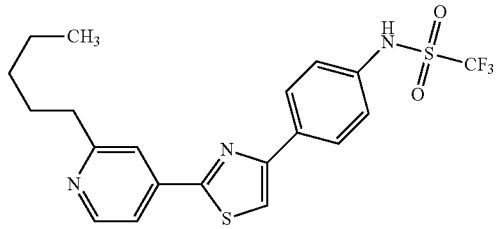 [SMILES: CCCCCc1cc(-c2nc(-c3ccc(NS(=O)(=O)C(F)(F)F)cc3)cs2)ccn1]

151

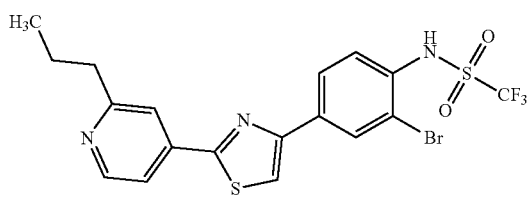 [SMILES: CCCc1cc(-c2nc(-c3ccc(NS(=O)(=O)C(F)(F)F)c(Br)c3)cs2)ccn1]

152

In some embodiments, the compound is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152.

In some embodiments, the compound is 1, 2, 3, 4, 5, 37, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94.

Representative examples of compounds detailed herein, including intermediates and final compounds, are depicted in Table 1 and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one embodiment, the compound is a pharmaceutically acceptable salt of a compound of Formulae (Ia), (Ib), (IIa) or (IIb), or any variation presented herein, or a pharmaceutically acceptable salt thereof.

In some embodiments, certain compounds presented herein are considered to be "prodrug" forms of other compounds herein. Prodrugs are precursor derivatives that, upon administration to a patient, undergo metabolism in-vivo such as, for example, hydrolysis to release the active form of the compound—the 'parent' compound. The prodrug form itself is either inactive or less active than the parent. Prodrugs are designed to improve bioavailability or to improve selective administration to particular organs, such as the liver [see, for example, Erion, et al. PNAS (2007) 104:39, pp 15490-15495; Erion, et al. J. Pharmacol. Exp. Ther. (2005) 312:2, pp 554-560; Meyer, et al. Patent Publication US 2006-0281695A1]. Compounds provided herein such as, for example, compound nos. 106-111 can be considered prodrug forms of the 'parent' compound no. 5. In some embodiments, prodrug forms of compounds presented herein are provided. Conventional procedures for the selection and preparation of suitable prodrug derivatives are described, for example, in "Design of Prodrugs"," ed. H. Bundgaard, Elsevier, 1985; Beaumont; K. et al. Curr. Drug Metab. (2003) 4, pp 461-485; Mizen, L, et al. Pharm. Biotechnol. (1998) 11, pp 345-365. In addition to prodrugs, this disclosure provides the salts, esters, amides, and other protected or derivatized forms of the described compounds.

As has been described above, the inherent pKa(s) of molecules can be assessed by potentiometric methods known to the skilled artisan, typically UV spectrophotometry [see, for example, Julémont, et al. J. Med. Chem. (2002), 45, pp 5182-5185]. In-silico methods can be used as a predictive tool, and software is commercially available from, for example, ACD/Labs, Molecular Discovery, ChemAxon, and other vendors. Without being bound by theory, it is presented that compounds provided herein possess unexpected physicochemical properties presumed to arise from the presence of the trifluoromethylsulfonamide moiety and its effect on the acidity of the remaining structure of the provided compounds as a whole. The compounds provided herein contain several ionizable centers including, for example, the trifluoromethylsulfonamide nitrogen atom; the thiazole ring nitrogen atom; the "ring A" pyridine nitrogen atom, etc.

As one example to describe the theory, compound #37 could exist in the following forms:

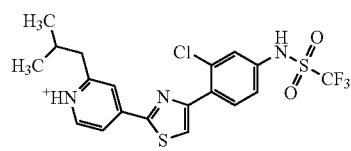 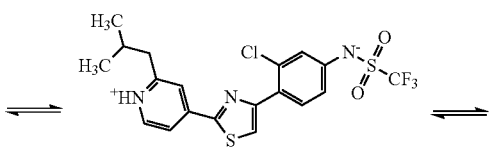 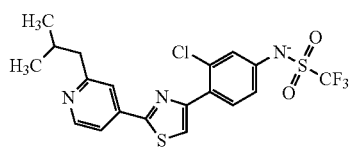

Other ionized forms are conceivable, but those presented here are a protonated form; a neutral or internal zwitterionic form; and an anionic form. Which form would exist is dependent upon the pH of the aqueous or physiological solution in which the compound is placed. Calculated pKa values of compound #37 [provided by I-Lab 2.0 (ACD/Labs, Inc.)] give two values of 3.4 and 5.4. These values are similar to those experimentally obtained under potentiometric and spectrophotometric methods [courtesy of Pion, Inc.], found to be 3.09 and 5.27. When the $CF_3$ group is replaced by a $CH_3$ group, the calculated pKa values become 5.1 and 7.5—both notably higher. It is postulated that the more electronegative nature of the $CF_3$ group results in a more highly acidic nature of the compound. Based on the calculated/measured pKa values of the trifluoromethylsulfonamide containing compounds claimed herein, it is likely that at a pH of 6-8, these compounds will predominantly exist in the anionic form, with the above equilibrium lying to the right at higher pH values. The anionic form renders the compound more aqueous soluble and therefore better absorbed. A solubility study [courtesy of Pion, Inc.] showed average solubilities of 13 μg/mL @ pH 6.0, 104 μg/mL @ pH 7.0, and >130 μg/mL @ pH 8.0. When a compound is dosed orally, most of the absorption occurs in the intestines where the pH ranges from 6-8. Therefore it is likely that the trifluoromethylsulfonamide containing compounds claimed herein will have significantly better solubility and absorption when dose orally relative to the methylsulfonamides which the anionic form would be present to a significantly lower extent at pH 6-8, compared to its neutral/zwitterionic form).

Examples of perhaloalkylsulfonamide groups are presented hereinabove. In some embodiments, also provided are compounds bearing perhaloalkenylsulfonamide groups, perhaloalkynylsulfonamide groups, or alkylsulfonamide groups bearing 1 or more halogen atoms. Such compounds can include, for example, the following:

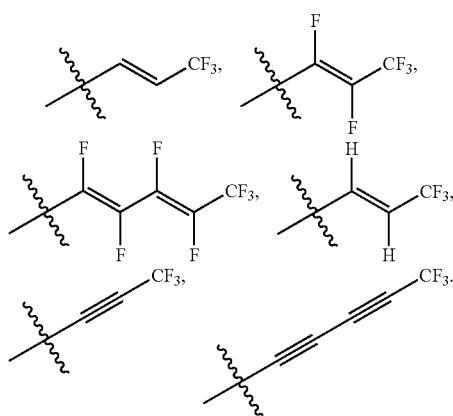

Without being bound by theory, it is expected that each of these particular groups, and variations therein, has varying degrees of electronegativity, affording subtle changes in pKa, and allowing a tuning of the acidity of the disclosed compounds, where required by the skilled artisan.

Pharmaceutically Acceptable Salts

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound disclosed herein in its free acid or base form with a suitable organic or inorganic base or acid, respectively, and isolating the salt thus formed during subsequent purification. In one embodiment, a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Pharmaceutical Compositions

A compound of Formulae (Ia), (Ib), (IIa) or (IIb), or any variation presented herein, typically is provided in a pharmaceutical composition comprising a pharmaceutically acceptable carrier and/or excipient. A "pharmaceutically acceptable" carrier or excipient is a material that is not biologically or otherwise undesirable, e.g., the material may be incorporated into a pharmaceutical composition administered to an individual without causing significant undesirable biological effects or interacting in a deleterious manner with any of the other components of the composition, wherein it is contained. Pharmaceutically acceptable carriers or excipients meet the required standards of toxicological and manufacturing testing and/or are included on the Inactive Ingredient Guide prepared by the U.S. Food and Drug administration.

A pharmaceutical composition can comprise one or more compounds of Formulae (Ia), (Ib), (IIa) or (IIb), or any variation presented herein. In some embodiments, a pharmaceutical composition further comprises chemotherapeutic agent, as described below.

Preferably a compound of Formulae (Ia), (Ib), (IIa) or (IIb), or any variation presented herein, is bioavailable orally. However, the compounds may also be formulated for parenteral (e.g., intravenous) administration.

A compound of Formulae (Ia), (Ib), (IIa) or (IIb), or any variation presented herein, can be used in the preparation of a medicament by combining the compound or compounds as an active ingredient with a pharmacologically acceptable carrier, which is known in the art. Depending on the therapeutic form of the medication, the carrier may be in various forms. In one variation, the manufacture of a medicament is for use in any of the methods disclosed herein.

Methods as provided herein may comprise administering to an individual a pharmacological composition that contains an effective amount of a compound of Formulae (Ia), (Ib), (IIa) or (IIb), or any variation presented herein, and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound of Formulae (Ia), (Ib), (IIa) or (IIb), or any variation presented herein, can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20*th* ed. (2000), which is incorporated herein by reference.

A compound of Formulae (Ia), (Ib), (IIa) or (IIb), or any variation presented herein, may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

A compound of Formulae (Ia), (Ib), (IIa) or (IIb), or any variation presented herein, can be formulated in a tablet in any dosage form described, for example, a compound as described herein or a pharmaceutically acceptable salt thereof can be formulated as a 10 mg tablet.

A compound of Formulae (Ia), (Ib), (IIa) or (IIb), or any variation presented herein, may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, a compound of Formulae (Ia), (Ib), (IIa) or (IIb), or any variation presented herein, is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

In some embodiments, a pharmaceutical composition is provided as a unit dosage form, such as a tablet, capsule, or individually packaged container (e.g., an ampoule, syringe, or vial).

In some embodiments, the unit dosage form contains a daily dose of a compound of Formulae (Ia), (Ib), (IIa) or (IIb), or any variation presented herein. In some embodiments, the unit dosage form contains a daily sub-dose of the compound.

In some embodiments, the unit dosage form contains a daily dose of each of two or more compounds of Formulae (Ia), (Ib), (IIa) or (IIb), or any variation presented herein. In some embodiments, the unit dosage form contains a daily sub-dose of each of two or more compounds.

In some embodiments, the unit dosage form contains a daily dose of compound of Formulae (Ia), (Ib), (IIa) or (IIb), or any variation presented herein, and a daily dose of each of one or more chemotherapeutic agents. In some embodiments, the unit dosage form contains a daily sub-dose of the compound and a daily sub-dose of each of one or more chemotherapeutic agents.

In some embodiments, the unit dosage form contains a daily dose of each of two or more compounds of Formulae (Ia), (Ib), (IIa) or (IIb), or any variation presented herein, and a daily dose of each of one or more chemotherapeutic agents. In some embodiments, the unit dosage form contains a daily sub-dose of each of two or more compounds and a daily dose of each of one or more chemotherapeutic agents.

Kits and Articles of Manufacture

This disclosure also provides kits and articles of manufacture comprising one or more compounds of Formulae (Ia), (Ib), (IIa) or (IIb), or any variation presented herein, or a pharmacological composition comprising a compound of Formulae (Ia), (Ib), (IIa) or (IIb), or any variation presented herein. The kits may employ any of the compounds disclosed herein. In one variation, the kit employs a compound described herein or a pharmaceutically acceptable salt thereof.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the disclosed methods. The instructions included with the kit generally include information as to the components and their administration to an individual.

Therapeutic Uses

Compounds of Formulae (Ia), (Ib), (IIa) or (IIb), or any variation presented herein, can be used to treat liver fibrosis, elevated cholesterol levels, and insulin resistance. Unless otherwise defined, "treat," as used herein, refers to the reduction of one or more symptoms associated with a disorder or to slowing the progression of one or more such symptoms.

a. Liver Fibrosis

Compounds disclosed herein can be administered to an individual to treat liver fibrosis. In some embodiments, the liver fibrosis is secondary to chronic hepatitis C virus infection. In some embodiments, the liver fibrosis is secondary to alcohol abuse. In some embodiments, the liver fibrosis is a precursor to, is concurrent with, is associated with, or is secondary to nonalcoholic steatohepatitis (NASH).

In some embodiments in which the liver fibrosis is a precursor to, is concurrent with, is associated with, or is secondary to NASH, the individual has been diagnosed with NASH following a liver biopsy in which one or more of steatosis, hepatocyte ballooning, lobular inflammation, Mallory hyaline bodies, mixed inflammatory infiltrate, pericellular fibrosis, and perisinusoidal fibrosis is detected.

In other embodiments in which the liver fibrosis is a precursor to, is concurrent with, is associated with, or is secondary to NASH, the individual is suspected of having or developing NASH based on one or more symptoms such as such as elevated serum levels of liver enzymes (e.g., alanine aminotransferase (ALT), aspartate aminotransferase (AST), γ-glutamyltransferase, alkaline phosphatase); focal or diffuse accumulation of lipid as detected by imaging techniques such as magnetic resonance spectroscopy, ultrasonography, computed tomography; abdominal discomfort, acanthosis nigricans, bowel dismotility, coma, constipation, disseminated intravascular coagulopathy, epigastric pain, fatigue, fluid retention, hepatomegaly, hypoglycemia, intestinal bleeding, jaundice, lipomatosis, lipoatrophy, lipodystrophy, muscle wasting, nausea, neurological defects, Palmer erythema, panniculitis, periumbilical pain, small bowel bacterial overgrowth, spider angiomata, splenomegaly, subacute liver failure, or vomiting.

In some embodiments, the individual is overweight or obese. In some embodiments, the individual has symptoms of insulin resistance, as described below; i.e., the individual is pre-diabetic or has type II diabetes.

In some embodiments, administration of one or more disclosed compounds prevents or slows the histologic progression of liver fibrosis and the clinical progression to cirrhosis in patients who have NASH or who are suspected of having NASH.

In some embodiments, administration of one or more disclosed compounds reduces the patient's risk of developing NASH.

Treatment or prevention can be assessed by one or more of the following:
reduction in average liver fat concentration (measured, e.g., by NMRS or MRI);
reduction of serum ALT;
reduction of serum AST;
reduction of serum γ-glutamyltransferase;
reduction of serum alkaline phosphatase;
increased in plasma concentrations of the cholesterol synthesis intermediate lathosterol;
improved NASH activity index or NAFLD activity score (NAS) (Kleiner et al., Hepatology 41, 1313-21, 2005);
improved SAF score (Bedossa et al., Hepatology 56, 1751-59, 2012;
changes in insulin resistance (measured, e.g., by Homeostatis Model Assessment of Insulin Resistance (HOMA-IR);
reduced hemoglobin A1c levels;
adiponectin level;
leptin:adiponectin ratio (LAR);
reduction in one or more markers of inflammation or fibrosis such as fibrinogen, CK-18, C-reactive protein (CRP), TNFα, IL-6;
reduction in body weight; or
reduced histological features such as cholestasis, fat cysts, fibrosis, granular iron, hepatocellular ballooning, increased numbers of eosinophils, inflammation, lobular disarray, lobular inflammation, macrovesicular steatosis, Mallory bodies, megamitochondria, necrosis, periodic acid-Schiff stained globulines, portal inflammation, microvesicular steatosis, or steatosis.

b. Elevated Cholesterol Levels

Compounds disclosed herein can be administered to an individual to treat elevated cholesterol levels, e.g., cholesterol levels above 200 mg/dL (5.2 mmol/L), such as 200-239 mg/dL (5.2-6.2 mmol/L) or 240 mg/dL (6.2 mmol/L) and above. In some embodiments, the individual has LDL cholesterol levels in the range of 130-159 mg/dL (3.4-4.1 mmol/L). In some embodiments, the individual has LDL cholesterol levels in the range of 160-189 mg/dL (4.1-4.9 mmol/L). In some embodiments, the individual has LDL cholesterol levels in the range of 190 mg/dL (4.9 mmol/L) and above. In some embodiments, the individual has HDL cholesterol levels below 40 mg/dL (1 mmol/L; men) or below 50 mg/dL (1.3 mmol/L; women). In some embodiments, the individual has HDL cholesterol levels in the range of 50-59 mg/dL (1.3-1.5 mmol/L). In some embodiments, the individual has triglyceride levels in the range of 150-199 mg/dL (1.7-2.2 mmol/L). In some embodiments, the individual has triglyceride levels in the range of 200-499 mg/dL (2.3-5.6 mmol/L). In some embodiments, the individual has triglyceride levels in the range of 500 mg/dL (5.6 mmol/L) and above.

In some embodiments, the elevated cholesterol levels are a precursor to NASH or the individual has NASH or is suspected of having NASH, as described above.

In some embodiments, the individual has symptoms of insulin resistance, as described below.

c. Insulin Resistance

Compounds disclosed herein can be administered to an individual to treat insulin resistance. In some embodiments, the individual has pre-diabetes, e.g., the individual has a hemoglobin A1C level between 5.7 and 6.4 percent and/or a fasting blood sugar level from 100-125 mg/dL (5.6-6.9 mmol/L). In some embodiments, the individual has type II diabetes e.g., the individual has a hemoglobin A1C level of 6.5 percent or higher and/or a fasting blood sugar level of 126 mg/dL (7 mmol/L) or higher.

In some embodiments, the individual has one or more of the following symptoms, which may improve upon treatment with one or more compounds disclosed herein: increased thirst and frequent urination, increased hunger; weight loss; fatigue; blurred vision; slow-healing sores or frequent infections; and acanthosis nigricans.

In some embodiments, the insulin resistance is a precursor to NASH or the individual has NASH or is suspected of having NASH, as described above.

d. Combination Therapies

Compounds of Formulae (Ia), (Ib), (IIa) or (IIb), or any variation presented herein, can be administered in combination with other therapeutic interventions for treating elevated cholesterol levels, liver fibrosis, or insulin resistance. Unless otherwise defined, "in combination" includes any coordinated administration of such therapeutic interventions with one or more therapeutic compounds disclosed herein, including sequential administration, alternating administration, and substantially simultaneous administration.

Therapeutic interventions for treating elevated cholesterol levels include, but are not limited to, statins, such as atorvastatin (e.g., LIPITOR®), fluvastatin (e.g., LESCOL®), lovastatin (e.g., ALTOPREV®, MEVACOR®), pitavastatin (E.G., LIVALO®), pravastatin (e.g., PRAVACHOL®), rosuvastatin (e.g., CRESTOR®), and SIMVASTATIN (e.g., ZOCOR®); bile acid binding resins, such as cholestyramine (e.g., PREVALITE®), colesevelam (e.g., WELCHOL®), and colestipol (e.g., COLESTID®); and cholesterol absorption inhibitors such as ezetimibe (e.g., ZETIA®).

Therapeutic interventions for treating liver fibrosis include, but are not limited to, angiotensin inhibitors, colchicine, corticosteroids, endothelin inhibitors, interferon-α, interleukin 10, pentoxifylline or oxpentifylline (e.g., TRENTAL®), phosphatidylcholine, PPAR antagonists, S-adenosyl-methionine, TGF-β inhibitors, and tocopherol.

Therapeutic interventions for treating insulin resistance include, but are not limited to, insulin-sensitizing agents such as metformin (e.g., GLUCOPHAGE®), thiazolidinediones such as pioglitazone (e.g., ACTOS®) and rosiglitazone (e.g., AVANDIA®); and leptin); α-glucosidase inhibitors such as miglitol (e.g., GIYSET®); insulin; meglitinides such as repaglinide (e.g., PRANDIN®) and nateglinide (e.g., STARLIX®); sulfonylureas such as glyburide (e.g., ORINASE®, TOLINASE®, MICRONASE®, GLYNASE®, DIABETA®, AMARYL®) and chlorpropamide (e.g., DIABINASE®, GLUTROL®, GLUCOTROL XL®; and combinations such as AVANDAMET® (metformin and rosiglitazone).

Dosing and Method of Administration

The dose of a compound administered to an individual (such as a human) may vary with the particular compound or salt thereof, the method of administration, and the particular stage of the disorder being treated. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by blocking of SREBP function. The amount should be sufficient to produce a desirable response, such as a therapeutic or prophylactic response against the disorder. In some embodiments, the amount of the compound or salt thereof is a therapeutically effective amount. In some embodiments, the amount of the compound or salt thereof is a prophylactically effective amount. In some embodiments, the amount of compound or salt thereof is below the level that induces a toxicological effect (e.g., an effect above a clinically acceptable level of toxicity) or is at a level where a potential side effect can be controlled or tolerated when the composition is administered to the individual.

The effective amount of the compound may in one aspect be a dose of between about 0.01 and about 100 mg/kg.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal.

In one aspect, provided is a method of treating one or more of liver fibrosis, elevated cholesterol levels, and insulin resistance in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal. e.g. Also provided are articles of manufacture, comprising a compound provided herein or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

General Synthetic Methods

The compounds may be prepared by a number of processes as generally described below in the General Synthetic Schemes and more specifically in the Examples hereinafter. In the following process descriptions, the symbols when used in the formulae depicted are to be understood to represent those groups described above in relation to the formulae herein.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

The following General Synthetic Schemes and Examples are provided to illustrate and not to be limiting. Those skilled in the art will be familiar with many of the reaction steps described. Particular publications are presented to assist with certain steps of the synthetic route.

General Synthetic Scheme 1

General Synthetic Scheme 1 provides methods to prepare compounds with a thiazole or imidazole B-ring as presented herein. Substituents $R_1$-$R_6$ are as exemplified in the Examples below. Syntheses of tricyclic substituted thiazoles, oxazoles and imidazoles, such as those presented herein, will be familiar to those skilled in the art. An example to illustrate a synthesis of a substituted thiazole is presented below. Complete details for syntheses of the compounds presented herein are provided in the Examples.

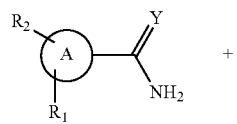

+

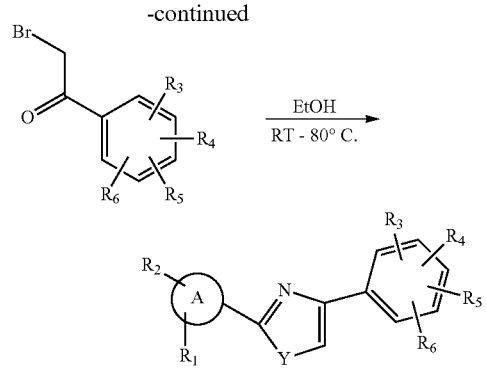

A = aromatic or heteroaromatic ring
Y = O, S, NH

General Procedure:

The corresponding substituted pyridine-4-carbothioamide or isonicotinamide and the corresponding substituted 2-bromoacetylbenzene are dissolved in EtOH. The resultant reaction mixture is stirred at between RT and 70° C. for between 30 min and 2 h. The progress of the reaction is monitored by TLC and LCMS. The reaction mixture is cooled to RT, basified with aq. sodium bicarbonate solution and the mixture extracted with EtOAc. The organic layer is dried over sodium sulfate and concentrated to obtain the crude product, which is purified by silica gel (100-200 mesh) column chromatography/by HPLC to obtain the desired product.

EXAMPLES

Example 1. Preparation of Compound No. 1

Pyridine (0.02 mL, 0.248 mmol) was added to a solution of triflic anhydride (0.05 mL, 0.297 mmol) at 0° C. under nitrogen in DCM (2 mL). After 15 min, 4-(2-(2-propylpyridin-4-yl)thiazol-4-yl)aniline (70 mg, 0.236 mmol) was added dropwise at 0° C. in DCM (3 mL). The reaction was allowed to stir at RT for additional 30 min, monitored by TLC. After completion, the reaction mixture was diluted with water (10 mL) and the mixture extracted with EtOAc (2×20 mL). The combined organic layer was dried over anhydrous sodium sulfate and concentrated under reduced pressure to afford the crude product, which was purified by reverse phase preparative HPLC to obtain 17 mg of 1,1,1-trifluoro-N-(4-(2-(2-propylpyridin-4-yl)thiazol-4-yl)phenyl)methanesulfonamide (yellow solid). This was treated with 2N aq. HCl for salt formation. $^1$H NMR (400 MHz, CD$_3$OD) δ (ppm): 8.77 (d, J=6.2 Hz, 1H), 8.54 (s, 1H), 8.48 (d, J=6.2 Hz, 1H), 8.36 (s, 1H), 8.13 (d, J=8.2 Hz, 2H), 7.42 (d, J=8.4 Hz, 2H), 3.18-2.98 (m, 2H), 1.91 (p, J=7.7 Hz, 2H), 1.10 (t, J=7.4 Hz, 3H).

Example 2. Preparation of Compound No. 2

2-Propylpyridine-4-carbothioamide (50 mg, 0.118 mmol) and N-(3-(2,2-dibromoacetyl)phenyl)-1,1,1-trifluoromethanesulfonamide (16.9 mg, 0.09 mmol) were charged in acetic acid (1 mL) and the reaction mixture was stirred at 80° C. for 30 min. The reaction was monitored by LCMS and acetic acid was evaporated under vacuum. The crude reaction mixture was purified using reverse phase chromatography to get 2.4 mg of 1,1,1-trifluoro-N-(3-(2-(2-propylpyridin-4-yl)thiazol-4-yl)phenyl)methanesulfonamide. $^1$H NMR (CD$_3$OD) δ (ppm): 8.59 (d, J=5.3 Hz, 1H), 8.08 (s, 1H), 8.00

(s, 1H), 7.94 (m, 2H), 7.49 (m, 1H), 7.33 (d, J=8.1 Hz, 1H), 2.99-2.77 (m, 3H), 1.83 (m, 2H), 1.03 (t, J=7.3 Hz, 3H).

Example 3. Preparation of Compound No. 4

N-(4-(2-Bromoacetyl)-3-chlorophenyl)-1,1,1-trifluoromethanesulfonamide (50 mg, 0.132 mmol) and 2-propylpyridine-4-carbothioamide (23.8 mg, 0.132 mmol) were charged in EtOH (10 mL) and the reaction mixture was heated at 80° C. for 1 h. The reaction mixture was concentrated and purified through reverse phase HPLC. Yield: 17 mg TFA salt. $^1$H NMR (TFA salt, CD$_3$OD) δ (ppm): 8.72 (d, J=6.0 Hz, 1H), 8.38 (d, J=7.6 Hz, 1H), 8.31 (d, J=6.0 Hz, 2H), 8.07 (d, J=8.5 Hz, 1H), 7.49 (s, 1H), 3.04 (t, J=7.8 Hz, 3H), 1.88 (m, 2H), 1.07 (s, J=7.3 Hz, 3H).

Example 4. Preparation of Compound No. 5

2-tert-Butylpyridine-4-carbothioamide (100 mg, 0.26 mmol) and N-(4-(2-bromoacetyl)-3-chlorophenyl)-1,1,1-trifluoromethanesulfonamide (51 mg, 0.26 mmol) were charged in EtOH (5 mL) and the reaction mixture was stirred at 80° C. for 30 min. The reaction was monitored by LCMS, and then the EtOH was evaporated under vacuum. The reaction mixture was purified using reverse phase chromatography to get 43 mg of N-(4-(2-(2-tert-butylpyridin-4-yl)thiazol-4-yl)-3-chlorophenyl)-1,1,1-trifluoromethanesulfonamide. $^1$H NMR (HCl salt, CD$_3$OD) δ (ppm): 8.76 (d, J=6.1 Hz, 1H), 8.50 (s, 1H), 8.43 (m, 2H), 8.06 (d, J=8.5 Hz, 1H), 7.50 (d, J=2.2 Hz, 1H), 7.4 (m, 1H), 1.58 (s, 9H).

Example 5. Preparation of Compound No. 57

Synthesis of 1,1,1-trifluoro-N-(2-methoxy-4-{2-[2-(2-methylpropyl)pyridin-4-yl]-1,3-thiazol-4-yl}phenyl)methanesulfonamide Step-1: Synthesis of 3-methoxy-4-nitrobenzoyl chloride 3-Methoxy-4-nitrobenzoicacid (5) (3 g) and thionyl chloride (10 mL) were added dropwise at 0° C. The reaction mixture was allowed to come to RT and heated to reflux overnight. Thionyl chloride was evaporated and ice was added to the reaction mixture. The organic layer was extracted in ethyl acetate (2×50 mL). The combined organic layer was dried over anhydrous sodium sulfate and concentrated to get 6 g of 3-methoxy-4-nitrobenzoyl chloride.

Step-2: Synthesis of 1-(3-methoxy-4-nitrophenyl)ethanone

A suspension of anhydrous magnesium chloride (932 mg, 9.8 mmol) in toluene (13 mL) was treated with triethylamine (4.7 mL, 33.4 mmol) and diethylmalonate (2.7 mL, 16.74 mmol). The reaction mixture was stirred at RT for 1.5 h. Finally, 3-methoxy-4-nitrobenzoyl chloride (6) (3 g, 13.9 mmol) was added and the reaction mixture was stirred at RT for 18 h. Concentrated hydrochloric acid (10 mL) was added and the organic layer was separated. DMSO (11.5 mL) and water (0.5 mL) were added and the mixture was heated to reflux for 2 h. The reaction mixture was allowed to come to RT and partitioned between water and EtOAc. The organic phase was washed subsequently with saturated sodium bicarbonate solution and brine and concentrated to get 2.5 g of 1-(3-methoxy-4-nitrophenyl)ethanone.

Step-3: Synthesis of 1-(4-amino-3-methoxyphenyl)ethanone 1-(3-Methoxy-4-nitrophenyl)ethanone (2 g, 10.25 mmol) was charged in MeOH (30 mL). Iron powder (1.72 g, 30.76 mmol) was added and concentrated HCl (10 mL) was added dropwise with constant stirring. The reaction mixture was heated at 60° C. for 1 h. The iron powder was filtered off and MeOH was concentrated. Water (10 mL) was added and the organic layer was extracted in EtOAc (3×50 mL). The combined organic layer was dried over anhydrous sodium sulfate and concentrated to get 1.2 g of 1-(4-amino-3-methoxyphenyl) ethanone.

Step-4: Synthesis of N-(4-acetyl-2-methoxyphenyl)-1,1,1-trifluoromethanesulfonamide Triflic anhydride (0.6 ml 13.6 mmol) was charged in DCM (20 mL). The reaction mixture was cooled to 0° C. and pyridine was added dropwise with constant stirring. After 15 min, 1-(4-amino-3-methoxyphenyl)ethanone (500 mg, 3.03 mmol) was dissolved in DCM (10 mL) and added slowly to the reaction mixture. The reaction mixture was allowed to come to RT and the reaction mixture was stirred at RT for 1 h. The reaction was monitored by TLC. Water (15 mL) was added and the organic layer was extracted in DCM (3×100 mL). The combined organic layer was dried over anhydrous sodium sulfate and concentrated to get 700 mg of N-(4-acetyl-2-methoxyphenyl)-1,1,1-trifluoromethanesulfonamide.

Step-5: Synthesis of N-(4-(2-bromoacetyl)-2-methoxyphenyl)-1,1,1-trifluoromethanesulfonamide N-(4-Acetyl-2-methoxyphenyl)-1,1,1-trifluoromethanesulfonamide (700 mg, 2.35 mmol) was charged in chloroform (50 mL) and the reaction mixture was cooled to 0° C. Liquid bromine (0.125 mL, 2.35 mmol) was added dropwise and the reaction mixture was stirred at RT for 18 h. A saturated solution of sodium thiosulfate (20 mL) was added and the chloroform layer was isolated and concentrated under reduced pressure to get 525 mg of N-(4-(2-bromoacetyl)-2-methoxyphenyl)-1,1,1-trifluoromethanesulfonamide.

Step-6: Synthesis of 1,1,1-trifluoro-N-(4-(2-(2-isobutylpyridin-4-yl)thiazol-4-yl)-2-methoxyphenyl) methanesulfonamide N-(4-(2-Bromoacetyl)-3-chlorophenyl)methanesulfonamide (50 mg, 0.133 mmol) and 2-isobutylpyridine-4-carbothioamide compound (20.6 mg, 0.10 mmol) were charged in ethanol (5 mL) and the reaction mixture was heated at 80° C. for 1 h. The reaction mixture was concentrated under reduced pressure and purified through reverse phase HPLC to get 16 mg of 1,1,1-trifluoro-N-(2-methoxy-4-{2-[2-(2-methylpropyl)pyridin-4-yl]-1,3-thiazol-4-yl}phenyl) methanesulfonamide. $^1$H NMR (400 MHz, Methanol-d4): δ (ppm): 8.56 (d, J=5.2 Hz, 1H), 7.96-7.70 (m, 3H), 7.58 (d, J=1.9 Hz, 1H), 7.48 (dd, J=8.3, 1.9 Hz, 1H), 7.33 (dd, J=8.3, 2.1 Hz, 2H), 3.92 (s, 3H), 2.76 (d, J=7.3 Hz, 2H), 2.12 (td, J=14.0, 7.2 Hz, 1H), 0.98 (d, J=6.6 Hz, 6H). LCMS: 473.2 (M+1).

Example 6. Preparation of Compound No. 58

Steps 1-5: Synthesis of N-(4-(2-bromoacetyl)-2-methoxyphenyl)-1,1,1-trifluoromethanesulfonamide See Example 6.

Step-6: Synthesis of N-(2-methoxy-4-(2-(2-propylpyridin-4-yl)thiazol-4 yl)phenyl)methanesulfonamide N-(4-(2-Bromoacetyl)-3-chlorophenyl)methanesulfonamide (50 mg, 0.133 mmol) and 2-propylpyridine-4-carbothioamide (18 mg, 0.1 mmol) were charged in ethanol (10 mL) and the reaction mixture was heated at 80° C. for 1 h. The reaction mixture was concentrated under reduced pressure and purified through reverse phase HPLC to get 17 mg of N-(2-methoxy-4-(2-(2-propylpyridin-4-yl)thiazol-4yl)phenyl)methanesulfonamide. $^1$H NMR (400 MHz, Methanol-d4): δ (ppm): 8.68 (d, J=5.8 Hz, 1H), 8.28 (d, J=5.9 Hz, 1H), 8.22 (d, J=5.6 Hz, 1H), 7.77 (d, J=1.8 Hz, 1H), 7.68 (dd, J=8.4, 1.8 Hz, 1H), 7.47 (d, J=8.2 Hz, 2H), 4.02 (s, 3H), 3.01 (m, 2H), 1.87 (m, 2H), 1.07 (t, J=7.4 Hz, 3H). LCMS: (M+1) 458.3.

Example 7. Preparation of Compound No. 59

Steps 1-5: Synthesis of N-(4-(2-bromoacetyl)-2-methoxyphenyl)-1,1,1-trifluoromethanesulfonamide See Example 6.

Step-6: Synthesis of N-(4-(2-(2-tert-butylpyridin-4-yl)thiazol-4-yl)-2-methoxyphenyl)-1,1,1-trifluoromethanesulfonamide N-(4-(2-Bromoacetyl)-3-chlorophenyl)methanesulfonamide (50 mg, 0.133 mmol) and 2-tert-butylpyridine-4-carbothioamide (20.6 mg, 0.10 mmol) were charged in ethanol (5 mL) and the reaction mixture was heated at 80° C. for 1 h. The reaction mixture was concentrated under reduced pressure and purified through reverse phase HPLC to get 15 mg of N-(4-(2-(2-tert-butylpyridin-4-yl)thiazol-4-yl)-2-methoxyphenyl)-1,1,1-trifluoromethanesulfonamide. $^1$H NMR (400 MHz, Methanol-d4): δ (ppm): 8.61 (d, J=5.1 Hz, 1H), 8.03 (d, J=3.3 Hz, 2H), 7.82 (dd, J=5.2, 1.6 Hz, 1H), 7.70 (d, J=1.8 Hz, 1H), 7.60 (dd, J=8.3, 1.9 Hz, 1H), 7.41 (d, J=8.2 Hz, 1H), 3.98 (s, 3H), 1.45 (s, 9H). LCMS: (M+1) 472.5.

Example 8. Preparation of Compound No. 60

N-(4-(2-Bromoacetyl)-3-chlorophenyl)-1,1,1-trifluoromethane sulfonamide (100 mg, 0.263 mol) and 2-benzylpyridine-4-carbothioamide (54.1 mg, 0.237 mol) were charged in ethanol (5 mL) and the reaction mixture was heated at 80° C. for 1 h. A yellow solid reaction mixture was obtained, which was filtered and the residue was washed with diethyl ether (15 mL) to get N-{4-[2-(2-benzylpyridin-4-yl)-1,3-thiazol-4-yl]-3-chlorophenyl}-1,1,1-trifluoromethanesulfonamide (33 mg) as a brown solid. $^1$H NMR (400 MHz, Methanol-d4) δ (ppm): 8.85-8.68 (d, J=6.2 Hz, 1H), 8.55-8.39 (m, 2H), 8.03 (d, J=8.5 Hz, 1H), 7.49 (d, J=2.3 Hz, 1H), 7.48-7.31 (m, 7H), 4.51 (s, 2H). LCMS (M+1): 510.1.

Example 9. Preparation of Compound No. 61

Step-1: Synthesis of 2-aminopyridine-4-carbothioamide

To a solution of 2-aminoisonicotinamide (100 mg, 0.0729 mol, 1 eq.) in pyridine (3 mL), phosphorus pentasulfide (83 mg, 0.0365 mol, 0.5 eq.) was added. The reaction was heated at 100° C. for 3 h. The reaction was monitored by LCMS. After completion, pyridine was concentrated under reduced pressure and residue was dissolved in water (5 mL) and the mixture extracted with EtOAc (3×15 mL). The EtOAc extracts were combined, dried over anhydrous sodium sulfate and concentrated under reduced pressure to get 33 mg of 2-aminopyridine-4-carbothioamide as a yellow solid.

Step-2: Synthesis of 2-chloro-4-nitrobenzoyl chloride

To a two neck RBF (1 liter) placed in ice bath, 2-chloro-4-nitrobenzoic acid (50 g, 0.248 mol, 1 eq.) was charged. Thionyl chloride (110 mL, 1.51 mol, 6.1 eq.) was added dropwise at 0° C. The reaction mixture was allowed to come to RT and then heated to reflux. The reflux was continued overnight. Thionyl chloride was evaporated and ice (approx. 150 g) was added into the reaction mixture. The aqueous reaction mass was extracted with DCM (2×200 mL). The DCM extracts were combined dried over anhydrous sodium sulfate and concentrated under vacuum to get 50 g (91.7%) of 2-chloro-4-nitrobenzoyl chloride as a light yellow liquid.

Step-3: Synthesis of 1-(2-chloro-4-nitrophenyl) ethanone

A suspension of anhydrous magnesium chloride (47 g, 0.214 mol, 0.7 eq.) in toluene (300 mL) was treated with triethylamine (75.04 mL, 0.535 mol, 2.5 eq.) and diethylmalonate (41.09 g, 0.257 mol, 1.2 eq.). The reaction mixture was stirred at RT for 1.5 h. To this was added 2-chloro-4-nitrobenzoyl chloride (4) (47 g, 0.214 mol, 1 eq.) was added dropwise (an exothermic reaction up to 50° C. was observed during addition). Toluene (50 mL) was used for complete transfer of 2-chloro-4-nitrobenzoyl chloride to the reaction mixture. The reaction mixture was stirred at RT for 18 h. The reaction was monitored by TLC and NMR. After complete consumption of starting material, concentrated hydrochloric acid (35% solution) (300 mL) was added and the upper toluene layer was separated. Toluene was evaporated under reduced pressure below 50° C. To the residue after concentration, DMSO (200 mL) and water (10 mL) were added and the mixture was heated at 160° C. for 12 h. The reaction was monitored by TLC and NMR. The reaction mixture was allowed to come to RT and water (40 mL) was added to the reaction mixture. The reaction mixture was extracted with EtOAc (3×200 mL). The EtOAc extracts were combined was washed brine solution (3×300 mL) and dried over anhydrous sodium sulfate. The EtOAc layer was concentrated to get 43 g (100%) of 1-(2-chloro-4-nitrophenyl) ethanone as a yellow liquid which solidified upon refrigeration.

Step-4: Synthesis of 1-(4-amino-2-chlorophenyl) ethanone 1-(2-Chloro-4-nitrophenyl) ethanone (126 g, 0.63 mole 1 eq.) was dissolved in MeOH (600 mL). Iron powder (105.8 g, 1.89 mol, 3 eq.) was added to the solution. Concentrated HCl (130 mL, 1.89 mol, 3 eq.) was added dropwise with constant stirring. The reaction mixture was then heated at 70° C. for 12 h. The reaction was monitored by TLC and NMR. The reaction mixture showed presence of starting material. The same quantity of iron powder and concentrated HCl were added again at 70° C. and the heating was continued at 70° C. for 4 h. The reaction mixture was again monitored by TLC and NMR. After completion of reaction, Iron powder was filtered through a celite bed and the MeOH filtrate was concentrated. Water (100 mL) was added and the reaction mixture was extracted in EtOAc (5×300 mL). The EtOAc extracts were combined, dried over anhydrous sodium sulfate and concentrated to get 100 g of crude product. 71 g of the crude product was purified through silica column (#100-200) using 0-20% EtOAc: hexane as eluant to get 38.6 g (52.5%) of 1-(4-amino-3-methoxyphenyl) ethanone (6) as pink solid. $^1$H NMR (400 MHz, Chloroform-d): δ (ppm): 7.62 (d, J=8.5 Hz, 1H), 6.66 (d, J=2.3 Hz, 1H), 6.54 (dd, J=8.5, 2.3 Hz, 1H), 4.07 (s, 2H), 2.61 (s, 3H).

Step-5: Synthesis of N-(4-acetyl-3-chlorophenyl)-1, 1,1-trifluoromethanesulfonamide A solution of triflic anhydride (75.1 g, 0.266 mol, 1.5 eq.) in DCM (600 mL) was cooled to 0° C. Pyridine (21.4 mL, 0.266 mol, 1.5 eq.) was added dropwise with constant stirring over 30 min. The reaction mixture was stirred at same temperature for 1 h. A solution of 1-(4-amino-2-chlorophenyl)ethanone (30 g, 0.177 mol, 1 eq.) in DCM (400 mL) was added dropwise maintaining the temperature 0° C. with constant stirring over a period of 45 min. The reaction mixture was then allowed to come to RT and stirred for 1 h at RT. The reaction was monitored by TLC and NMR. Upon completion, ice water (500 mL) was added and the DCM layer was separated. The aqueous layer was again extracted with DCM (2×100 mL). The DCM extracts were combined washed with ice water (2×500 mL). The DCM layer was dried over anhydrous sodium sulfate and concentrated under reduced pressure below 40° C. to obtain the crude product. Diethyl ether (200 mL) and pentane (600 mL) were added into the reaction mixture and stirred for 30 min. The reaction mixture was filtered and the mother liquor was concentrated and triturated in pentane to get 28 g (52.8%) of N-(4-acetyl-3-chlorophenyl)-1,1,1-trifluoromethanesulfonamide as a light pink solid.

Step-6: Synthesis of N-(4-(2-bromoacetyl)-3-chlorophenyl)-1,1,1-trifluoromethanesulfonamide A solution of N-(4-acetyl-3-chlorophenyl)-1,1,1-trifluoromethanesulfonamide (21 g, 0.07 mol, 1 eq.) in chloroform (600 mL) was cooled to 0° C. Liquid bromine (2.9 mL, 0.004 mol, 0.8 eq.) dissolved in chloroform (400 mL) was added dropwise over a period of 40 min, maintaining the temperature between 0-10° C. The reaction mixture was allowed to come to RT and was stirred at RT for 18 h. The reaction was monitored by TLC and NMR, which indicated the presence of starting material and desired compound along with some amount of N-(3-chloro-4-(2,2-dibromoacetyl)phenyl)-1,1,1-trifluoromethanesulfonamide (dibromo impurity). A saturated solution of sodium thiosulfate (200 mL) was added and the chloroform layer was separated. The aqueous layer was extracted with chloroform (2×100 mL). The main chloroform layer and the chloroform extracts were combined, dried over anhydrous sodium sulfate and concentrated under reduced pressure. A clear liquid was obtained as a residue. To this were added diethylether (50 mL) and pentane (250 mL) and the mixture stirred for 10 min. The reaction mixture was filtered off and mother liquor was concentrated. The crude product obtained was triturated with pentane (~50 mL) to obtain a white solid. The white solid obtained was filtered off and dried under vacuum to get 20 g of N-(4-(2-bromoacetyl)-3-chlorophenyl)-1,1,1-trifluoromethanesulfonamide with contained approximately 35% of starting material i.e. N-(4-acetyl-3-chlorophenyl)-1,1,1-trifluoromethanesulfonamide by NMR. The mixture of both was directly used in the next step.

Step-7: Synthesis of N-(4-(2-(2-aminopyridin-4-yl) thiazol-5-yl)-3-chlorophenyl)-1,1,1-trifluoromethanesulfonamide N-(4-(2-Bromoacetyl)-3-chlorophenyl)-1,1,1-trifluoromethanesulfonamide (50 mg, 0. 132 mmol, 1 eq.) and 2-aminopyridine-4-carbothioamide (32.8 mg, 0.132 mmol, 1 eq.) were charged in ethanol (5 mL) and the reaction mixture was heated at 80° C. for 12 h. The reaction mixture was concentrated and purified by reverse phase chromatography to get 6.8 mg of N-(4-(2-(2-aminopyridin-4-yl) thiazol-5-yl)-3-chlorophenyl)-1,1,1-trifluoromethanesulfonamide. $^1$H NMR (400 MHz, Methanol-d4): δ (ppm): 8.25 (s, 1H), 8.01-7.89 (m, 2H), 7.55 (d, J=1.6 Hz, 1H), 7.46-7.40 (m, 1H), 7.33 (dd, J=8.5, 2.2 Hz, 1H). LCMS: (M+1) 435.1.

Example 10. Preparation of Compound No. 62

Steps 1-7: Synthesis of N-{3-chloro-4-[2-(2-methanesulfonamidopyridin-4-yl)-1,3-thiazol-4-yl]phenyl}-1,1,1-trifluoromethanesulfonamide See Example 10.

Step-8: Synthesis of N-(3-chloro-4-(2-(2-(methylsulfonamido)pyridin-4-yl)thiazol-5-yl)phenyl)-1,1,1-trifluoromethanesulfonamide N-(4-(2-(2-Aminopyridin-4-yl)thiazol-5-yl)-3-chlorophenyl)-1,1,1-trifluoro methanesulfonamide (50 mg, 0.115 mmol, 1 eq.) was charged in pyridine (3 mL). The reaction mixture was cooled to 0° C. and methane sulfonyl chloride (0.01 mL, 0.115 mol, 1 eq.) was added dropwise with constant stirring. The reaction mixture was allowed to come to RT and the reaction mixture was stirred at RT for 1 h. Pyridine was evaporated and water was added and the mixture extracted in EtOAc (3×100 mL). The combined organic layer was concentrated and purified using reverse phase chromatography to get 1.3 mg of N-(3-chloro-4-(2-(2-(methylsulfonamido)pyridin-4-yl)thiazol-5-yl)phenyl)-1, 1,1-trifluoromethanesulfonamide. $^1$H NMR (400 MHz, Methanol-d4): δ (ppm): 8.32 (d, J=5.6 Hz, 1H), 8.17 (s, 1H), 8.02 (d, J=8.5 Hz, 1H), 7.66 (s, 1H), 7.59 (dd, J=5.6, 1.6 Hz, 1H), 7.47 (d, J=2.3 Hz, 1H), 7.35 (dd, J=8.6, 2.3 Hz, 1H), 3.2 (s, 1H). LCMS: 513 (M+1).

Example 11. Preparation of Compound No. 63

Steps 1-6: Synthesis of N-(2-methoxy-4-(2-(2-propylpyridin-4-yl)thiazol-4 yl)phenyl)methanesulfonamide See Example 7.

Step-7: Synthesis of 1,1,1-trifluoro-N-(2-hydroxy-4-(2-(2-propylpyridin-4-yl)thiazol-4-yl) phenyl)methanesulfonamide 1,1,1-Trifluoro-N-(2-methoxy-4-(2-(2-propylpyridin-4-yl)thiazol-4-yl) phenyl)methanesulfonamide (17 mg, 0.037 mmol, 1 eq.) charged in DCM (5 mL) and the reaction mixture was cooled at 0° C. A 1M solution of boron tribromide (0.12 mL, 0.11 mmol) was added dropwise. The reaction mixture was allowed to come to RT and stirred at RT for 12 h. The reaction was monitored by LCMS. A saturated sodium bicarbonate was added and the mixture extracted in EtOAc (3×25 mL). The combined organic layer was dried over anhydrous sodium sulfate and concentrated under reduced pressure and the crude reaction mixture was purified using reverse phase HPLC to get (1.5 mg) of 1,1,1-trifluoro-N-(2-hydroxy-4-(2-(2-propylpyridin-4-yl) thiazol-4-yl)phenyl)methanesulfonamide as the TFA salt. $^1$H NMR (400 MHz, Methanol-d4): δ (ppm): 8.63 (d, J=5.6 Hz, 1H), 8.13-8.00 (m, 2H), 7.63 (d, J=1.9 Hz, 1H), 7.53-7.38 (m, 2H), 2.94 (t, J=7.7 Hz, 2H), 1.84 (p, J=7.5 Hz, 2H), 1.05 (t, J=7.4 Hz, 3H) LCMS (M+1): 444.4.

Example 12. Preparation of Compound No. 64

N-(4-(2-Bromoacetyl)-3-chlorophenyl)1,1,1-trifluoro methane sulfonamide (100 mg, 0.263 mol) and 2-(3,3,3-trifluoropropyl) pyridine-4-carbothioamide (55.5 mg, 0.237 mol) were charged in ethanol (5 mL) and the reaction mixture was heated at 80° C. for 1h. The resultant reaction mixture was concentrated under reduced pressure and purified by reverse phase HPLC to afford N-(3-chloro-4-{2-[2-(3,3,3-trifluoropropyl)pyridin-4-yl]-1,3-thiazol-4-yl}phenyl)-1,1,1-trifluoromethanesulfonamide (27 mg) as a yellow solid. $^1$H NMR (400 MHz, Methanol-d4) δ (ppm): 8.84 (d, J=6.2 Hz, 1H), 8.63 (d, J=2.0 Hz, 1H), 8.52 (d, J=6.1 Hz, 1H), 8.42 (s, 1H), 8.09 (d, J=8.5 Hz, 1H), 7.50 (d, J=2.3 Hz, 1H), 7.40 (d, J=8.5 Hz, 1H), 3.42 (m 2H), 2.87 (m, 2H). LCMS (M+1): 516.1.

Example 13. Preparation of Compound No. 65

Steps 1-5: Synthesis of N-(4-(2-bromoacetyl)-2-methoxyphenyl)-1,1,1-trifluoromethanesulfonamide See Example 6

Step-6: Synthesis of 1,1,1-trifluoro-N-(2-methoxy-4-(2-(2-neopentylpyridin-4-yl)thiazol-4-yl) phenyl) methanesulfonamide N-(4-(2-Bromoacetyl)-3-chlorophenyl)methanesulfonamide (50 mg, 0.133 mmol) and 2-neopentylpyridine-4-carbothioamide (50 mg, 0.10 mmol) was charged in ethanol (5 mL) and the reaction mixture was heated at 80° C. for 1 h. The reaction mixture was concentrated under reduced pressure and purified through reverse phase HPLC to get 14 mg of 1,1,1-trifluoro-N-(2-methoxy-4-(2-(2-neopentylpyridin-4-yl)thiazol-4-yl) phenyl)methanesulfonamide. $^1$H NMR (400 MHz, Methanol-d4): δ (ppm): 8.71 (d, J=5.8 Hz, 1H), 8.33-8.14 (m, 2H), 7.76 (d, J=1.9 Hz, 1H), 7.68 (dd, J=8.4, 1.9 Hz, 1H), 7.47 (d, J=8.3 Hz, 1H), 4.01 (s, 3H), 2.95 (s, 2H), 1.06 (s, 9H). LCMS: 486 (M+1).

Example 14. Preparation of Compound No. 66

A solution of triflic anhydride (0.03 ml, 0.17 mmol, 1.5 eq.) in DCM (8 mL) was cooled to 0° C. Pyridine (0.01 mL, 0.17 mmol, 1.5 eq.) was added dropwise with constant stirring over 30 min. A solution of N-(4-(2-(2-aminopyridin-4-yl)thiazol-4-yl)-3-chlorophenyl)-1,1,1-trifluoromethanesulfonamide (50 mg, 0.115 mmol, 1 eq.) in DCM (2 mL) was added dropwise maintaining the temperature at 0° C. with constant stirring over a period of 5 min. The reaction mixture was then allowed to come to RT and stirred for 1 h at RT. The reaction was monitored by LCMS and NMR. Upon completion, ice water (10 mL) was added and the DCM layer was separated. The aqueous layer was again extracted with DCM (2×20 mL). The DCM layer was dried over anhydrous sodium sulfate and concentrated under reduced pressure and purified using reverse phase chromatography to get 9.26 mg of N-{3-chloro-4-[2-(2-trifluoromethanesulfonamidopyridin-4-yl)-1,3-thiazol-4-yl]phenyl}-1,1,1-trifluoromethanesulfonamide. $^1$H NMR (400 MHz, Methanol-d4): δ (ppm): 8.40-8.22 (m, 2H), 8.06 (dd, J=7.6, 3.6 Hz, 2H), 7.72 (dd, J=6.6, 1.7 Hz, 1H), 7.49 (d, J=2.3 Hz, 1H), 7.37 (dd, J=8.6, 2.3 Hz, 1H). LCMS (M+1): 566.8.

Example 15. Preparation of Compound No. 67

N-[4-(2-Bromothiazol-4-yl)-3-chloro-phenyl]-1,1,1-trifluoro-methanesulfonamide (300 mg, 0.71 mmol, 1 eq.), [4-(piperidine-1-carbonyl)phenyl]boronic acid (233 mg, 1.4 eq.) and sodium carbonate (189 mg, 2.5 eq. in 1 mL water) were charged in 5 mL of DMF in a 25 mL glass bottle and aerated with nitrogen gas for 7 min. After adding Pd(PPh$_3$)$_4$ (82.5 mg, 0.1 mmol) the mixture was further purged for 3 min and was heated to 100° C. overnight. The reaction was monitored by LCMS. The reaction mixture was allowed to cool to RT; water (10 mL) was added and the mixture extracted with EtOAc (3×50 mL). The combined organic layer was washed with water (4×50 mL), dried over anhydrous sodium sulfate and concentrated under reduced pressure to obtain a crude product, which was purified by reverse phase HPLC to afford N-(3-chloro-4-{2-[4-(piperidine-1-carbonyl)phenyl]-1,3-thiazol-4-yl}phenyl)-1,1,1-trifluoromethanesulfonamide (207 mg) as a white solid as the free base. $^1$H NMR (400 MHz, Chloroform-d) δ (ppm): 7.98 (d, J=8.5 Hz, 1H), 7.89 (d, J=7.9 Hz, 2H), 7.82 (s, 1H), 7.36 (d, J=7.9 Hz, 2H), 7.18 (d, J=2.2 Hz, 1H), 6.98 (dd, J=8.5, 2.3 Hz, 1H), 3.78 (s, 2H), 3.37 (s, 2H), 1.72 (s, 4H), 1.55 (s, 2H). LCMS (M+1): 530.1.

Example 16. Preparation of Compound No. 68

N-(4-(2-Bromothiazol-4-yl)-3-chlorophenyl)-1,1,1-trifluoromethane sulfonamide (200 mg, 0.4761 mmol) and 1-isopentyl-5-(4,4,5,5-tetramethyl-1,3,2-dioxaborolan-2-yl) pyrazole (150.9 mg, 0.5714 mmol), sodium carbonate (100 mg, 0.952 mmol), dimethyl formamide (5 mL), water (0.5 mL) were charged in a 2 neck round bottom flask and aerated with nitrogen gas for 5 min. After adding Pd(PPh$_3$)$_4$ (55 mg, 0.0476 mmol), the mixture was heated to 100° C. for 18 h. The reaction was monitored by LCMS. The reaction mixture was allowed to cool to RT; water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-(3-chloro-4-{2-[1-(3-methylbutyl)-1H-pyrazol-5-yl]-1,3-thiazol-4-yl}phenyl)-1,1,1-trifluoromethanesulfonamide (135 mg) as a white solid. $^1$H NMR (400 MHz, Methanol-d4) δ (ppm): 8.05 (s, 1H), 7.96 (d, J=8.6 Hz, 1H), 7.55 (d, J=2.1 Hz, 1H), 7.47 (d, J=2.2 Hz, 1H), 7.33 (d, J=8.5 Hz, 1H), 6.82 (d, J=2.1 Hz, 1H), 4.75 (m, 2H), 1.77 (m, J=9.4 Hz, 2H), 1.60 (m, 1H), 0.91 (d, J=6.6 Hz, 6H). LCMS (M+1): 479.1.

Example 17. Preparation of Compound No. 69

Step-1: Synthesis of N-[3-chloro-4-(4,4,5,5-tetramethyl-1,3,2-dioxaborolan-2-yl)phenyl]methanesulfonamide 3-Chloro-4-(4,4,5,5-tetramethyl-1,3,2-dioxaborolan-2-yl) aniline (506 mg, 1 mmol, 1 eq.) was suspended in DCM (18 mL) then TEA (808 mg, 4 eq.) added and stirred for 5 min at RT. The mixture was maintained at ice-bath condition and mesyl chloride (458 mg, 2 eq.) was added dropwise and stirred for 2 h at the same temperature. The reaction was monitored by 1H-NMR. After completion of the reaction, the solvent was evaporated to get the desired product as a solid which was used for next step without any further purification.

Step-2: Synthesis of 4-(4-bromo-2-thienyl)-2-tert-butyl-pyridine 2,4-Dibromothiophene (150 mg, 0.62 mmol), 2-tert-butyl-4-(4,4,5,5-tetramethyl-1,3,2-dioxaborolan-2-yl)pyridine (242 mg, 1.5 equiv) and sodium carbonate (164 mg, 1.54 mmol, 2.5 eq. in 1.0 mL water) in dimethyl formamide (5 mL) were charged in a 25 mL glass bottle and aerated with nitrogen gas for 8 min. After adding Pd(PPh$_3$)$_4$ (35 mg, 0.05 mmol) and Xantphos (35.8 mg, 0.1 eq.), the mixture was further purged for 3 min, and was heated to 100° C. overnight. The reaction was monitored by LCMS. The reaction mixture was allowed to cool to RT; water (10 mL) was added and the mixture extracted with EtOAc (3×25 mL). The combined organic layer was washed with water (4×30 mL), dried over anhydrous sodium sulfate and concentrated under reduced pressure to obtain crude 4-(4-bromo-2-thienyl)-2-tert-butyl-pyridine, which was used as such for the next step of synthesis without any further purification.

Step-3: Synthesis of N-[4-[5-(2-tert-butyl-4-pyridyl)-3-thienyl]-3-chloro-phenyl]methanesulfonamide 4-(4-Bromo-2-thienyl)-2-tert-butyl-pyridine (170 mg, 0.576 mmol, 1 eq.), N-[3-chloro-4-(4,4,5,5-tetramethyl-1,3,2-dioxaborolan-2-yl)phenyl]methanesulfonamide (286 mg, 1.5 eq.) and sodium carbonate (152 mg, 2.5 equiv) were charged in DMF (5 mL) in a 25 mL glass bottle and aerated with nitrogen gas for 7 min. After adding Pd(PPh$_3$)$_4$ (66 mg, 0.1 mmol) the mixture was further purged for 3 min and was heated to 100° C. overnight. The reaction was monitored by LCMS. The reaction mixture was allowed to come to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-{4-[5-(2-tert-butylpyridin-4-yl)thiophen-3-yl]-3-chlorophenyl}methanesulfonamide (64 mg) as a light yellow solid as the formate salt. $^1$H NMR (400 MHz, DMSO-d6) δ (ppm): 8.53 (d, J=5.2 Hz, 1H), 7.99 (s, 1H), 7.82 (s, 1H), 7.65 (s, 1H), 7.57 (d, J=8.4 Hz, 1H), 7.47 (d, J=5.2 Hz, 1H), 7.36 (d, J=2.2 Hz, 1H), 7.24 (dd, J=8.2, 2.1 Hz, 1H), 3.07 (s, 3H), 1.36 (s, 9H). LCMS (M+1): 421.1.

Example 19. Preparation of Compound No. 70

N-(4-(2-Bromoacetyl)-3-chlorophenyl) 1,1,1-trifluoromethane sulfonamide (200 mg, 0.527 mol) and 2-(cyclohexylmethyl) pyridine-4-carbothioamide (111.2 mg, 0.475 mol) were charged in ethanol (10 mL) and the reaction mixture was heated at 80° C. for 1h. The resultant reaction mixture was concentrated under reduced pressure and purified by reverse phase HPLC to afford N-(3-chloro-4-{2-[2-(cyclohexylmethyl)pyridin-4-yl]-1,3-thiazol-4-yl}phenyl)-1,1,1-trifluoromethanesulfonamide (45 mg) as a white solid. $^1$H NMR (400 MHz, Methanol-d4) δ (ppm): 8.75 (d, J=6.2 Hz, 1H), 8.46-8.36 (m, 3H), 8.07 (d, j=8.5 Hz, 1H), 7.49 (d, J=2.3 Hz, 1H), 7.40 (d, J=8.5 Hz, 1H), 2.98 (d, J=7.3 Hz, 2H), 1.88 (m, J=10.9 Hz, 1H), 1.76 (m 5H), 1.35 (m, 5H). LCMS (M+1): 516.1.

Example 19. Preparation of Compound No. 71

N-(4-(2-Bromothiazol-4-yl)-3-chlorophenyl)-1,1,1-trifluoromethane sulfonamide (100 mg, 0.2380 mmol) and naphthalene-1-yl-boronic acid (61.3 mg, 0.3571 mmol), cesium carbonate (155 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(naphthalen-1-yl)-1,3-thiazol-4-yl]phenyl}-1,1,1-trifluoromethanesulfonamide (40 mg) as a yellow solid. $^1$H NMR (400 MHz, Methanol-d4) δ (ppm): 8.69-8.60 (d, J=6.2 Hz, 1H), 8.18 (s, 1H), 8.10 (d, J=8.1 Hz, 1H), 8.04-7.96 (m, 2H), 7.92 (d, J=7.2 Hz, 1H), 7.6 (m, 3H), 7.53 (d, J=2.2 Hz, 1H), 7.39 (d, J=8.4 Hz, 1H). LCMS (M+1): 469.0.

Example 20. Preparation of Compound No. 72

N-(4-(2-Bromothiazol-4-yl)-3-chlorophenyl)-1,1,1-trifluoromethane sulfonamide (100 mg, 0.2380 mmol) and 1H-indole-6-yl-boronic acid (57.4 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol) the reaction mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(1H-indol-6-yl)-1,3-thiazol-4-yl]phenyl}-1,1,1- trifluoromethanesulfonamide (43 mg) as a yellow solid. $^1$H NMR (400 MHz, Methanol-d4) δ (ppm): 8.10 (d, J=6.2 Hz, 1H), 8.04 (d, J=1.9 Hz, 1H), 7.88 (s, 1H), 7.65 (m, 2H), 7.48 (d, J=2.2 Hz, 1H), 7.39 (m, 2H), 6.52 (d, J=7.2 Hz, 1H). LCMS (M+1): 457.9.

Example 21. Preparation of Compound No. 73

N-(4-(2-Bromothiazol-4-yl)-3-chlorophenyl)-1,1,1-trifluoromethane sulfonamide (100 mg, 0.2380 mmol) and 3-(benzyloxy)-4-(trifluoromethyl)phenylboronic acid (105.7 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-(4-{2-[3-(benzyloxy)-4-(trifluoromethyl)phenyl]-1,3-thiazol-4-yl}-3-chlorophenyl)-1,1,1-trifluoromethanesulfonamide (10 mg) as a yellow solid. $^1$H NMR (400 MHz, Methanol-d4) δ (ppm): 8.06-7.94 (m, 2H), 7.91-7.80 (d, J=1.9 Hz, 1H), 7.71-7.67 (d, J=1.9 Hz, 1H), 7.65-7.60 (m, 1H), 7.48-7.40 (m, 3H), 7.38-7.27 (m, 4H), 3.33 (d, J=15.4 Hz, 2H). LCMS (M+1): 593.2.

Example 22. Preparation of Compound No. 74

N-(4-(2-Bromothiazol-4-yl)-3-chlorophenyl)-1,1,1-trifluoromethane sulfonamide (100 mg, 0.2380 mmol) and biphenyl-2-ylboronic acid (70 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.238 mol), the mixture was heated to 100° C. for 18h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(2-phenylphenyl)-1,3-thiazol-4-yl]phenyl}-1,1,1-trifluoromethanesulfonamide (18 mg) as a yellow solid. $^1$H NMR (400 MHz, Methanol-d4) δ (ppm): 7.92 (d, J=7.8 Hz, 2H), 7.72-7.59 (m, 2H), 7.57-7.47 (m, 2H), 7.43 (d, J=2.2 Hz 1H), 7.43-7.35 (m, 3H), 7.28 (m, 3H). LCMS (M+1): 495.

Example 23. Preparation of Compound No. 75

N-(4-(2-Bromothiazol-4-yl)-3-chlorophenyl)-1,1,1-trifluoromethane sulfonamide (100 mg, 0.2380 mmol) and isoquinolin-4-ylboronic acid (61.7 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(isoquinolin-4-yl)-1,3-thiazol-4-yl]phenyl}-1,1,1-trifluoromethanesulfonamide (18 mg) as a yellow solid. $^1$H NMR (400 MHz, Methanol-d4) δ (ppm): 9.41 (s, 1H), 9.08 (d, J=8.5 Hz, 1H) 8.95 (s, 1H), 8.38 (d, J=2.3 Hz, 1H), 8.28 (s, 1H), 7.98-8.12 (m, 2H), 7.88 (m, 1H)), 7.58 (s, 1H), 7.39 (d, J=5.5 Hz, 1H). LCMS (M+1): 469.9.

Example 24. Preparation of Compound No. 76

N-(4-(2-Bromothiazol-4-yl)-3-chlorophenyl)-1,1,1-trifluoromethane sulfonamide (100 mg, 0.2380 mmol) and 1-methyl-4-(4-(4,4,5,5-tetramethyl-1,3,2-dioxaborolan-2-yl)pyridine-2-yl)piperazine (108 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-(3-chloro-4-{2-[2-(4-methylpiperazin-1-yl)pyridin-4-yl]-1,3-thiazol-4-yl}phenyl)-1,1,1-trifluoromethanesulfonamide (54.2 mg) as a yellow solid. $^1$H NMR (400 MHz, Methanol-d4) δ (ppm): 8.28 (d, J=5.6 Hz, 1H), 8.19 (s, 1H), 8.02 (d, J=8.6 Hz, 1H), 7.67 (s, 1H), 7.52-7.43 (m, 2H), 7.38 (d, J=8.4, Hz, 1H), 4.60 (d, J=14.5 Hz, 2H), 3.67 (d, J=12.5 Hz, 2H), 3.42 (s, 2H), 3.22 (d, J=10.5 Hz, 2H), 2.99 (s, 3H). LCMS (M+1): 518.06.

Example 25. Preparation of Compound No. 77

N-(4-(2-Bromothiazol-4-yl)-3-chlorophenyl)-1,1,1-trifluoromethane sulfonamide (100 mg, 0.2380 mmol) and 3,5-dimethyl-4-(4,4,5,5-tetramethyl-1,3,2-dioxaborolan-2-yl) isoxazole (79.6 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-chloro-4-[2-(dimethyl-1,2-oxazol-4-yl)-1,3-thiazol-4-yl]phenyl}-1,1,1-trifluoromethanesulfonamide (3.2 mg) as a yellow solid. $^1$H NMR (400 MHz, DMSO-d6) δ (ppm): 8.20 (s, 1H), 7.97 (d, J=8.5 Hz, 1H), 7.41 (d, J=2.2 Hz, 1H), 7.32 (d, J=8.5 Hz, 1H), 2.73 (s, 3H), 2.52 (s, 3H). LCMS (M+1): 437.9.

Example 26. Preparation of Compound No. 78

N-(4-(2-Bromothiazol-4-yl)-3-chlorophenyl)-1,1,1-trifluoromethane sulfonamide (100 mg, 0.2380 mmol) and 4-methyl-N-(3-(4,4,5,5-tetramethyl-1,3,2-dioxaborolan-2-yl) phenyl)benzenesulfonamide (133 mg, 0.357 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was cooled to RT, water (10 mL) was added and the mixture extracted with EtOAc (3×25 mL). The combined organic layer was washed with water (30 mL), dried over sodium sulfate and concentrated under reduced pressure to obtain the crude product, which was purified by reverse phase HPLC to afford N-{3-[4-(2-chloro-4-trifluoromethanesulfonamidophenyl)-1,3-thiazol-2-yl]phenyl}-4-methylbenzene-1-sulfonamide (35.2 mg) as a white solid. $^1$H NMR (400 MHz, DMSO-d6) δ (ppm): 10.48 (s, 1H), 8.11 (s, 1H), 7.91 (d, J=8.5 Hz, 1H), 7.78-7.66 (m, 3H), 7.62 (d, J=7.8 Hz, 1H), 7.43-7.34 (m, 2H), 7.37-7.27 (m, 2H), 7.23 (d, J=8.0 Hz, 1H), 2.32 (s, 3H). LCMS (M+1): 588.

Example 27. Preparation of Compound No. 79

N-(4-(2-Bromothiazol-4-yl)-3-chlorophenyl)-1,1,1-trifluoromethane sulfonamide (100 mg, 0.2380 mmol) and (3,4-dimethoxy phenyl) boronic acid (64.9 mg, 0.3571 mmol), cesium carbonate (155 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(3,4-dimethoxyphenyl)-1,3-thiazol-4-yl]phenyl}-1,1,1-trifluoromethanesulfonamide (11 mg) as a white solid. $^1$H NMR (400 MHz, Methanol-d4) δ (ppm): 7.70 (d, J=8.6 Hz, 2H), 7.63 (d, J=2.1 Hz, 1H), 7.54 (d, J=8.4 Hz, 1H), 7.31 (d, J=2.1 Hz, 1H), 7.16 (d, J=8.4 Hz, 1H), 7.05 (d, J=8.4 Hz, 1H), 3.93 (s, 3H), 3.90 (s, 3H). LCMS (M+1): 479.0.

Example 28. Preparation of Compound No. 80

N-(4-(2-Bromothiazol-4-yl)-3-chlorophenyl)-1,1,1-trifluoromethane sulfonamide (100 mg, 0.2380 mmol) and 1H-indole-4-yl-boronic acid (57.5 mg, 0.3571 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(1H-indol-4-yl)-1,3-thiazol-4-yl]phenyl}-1,1,1-trifluoromethanesulfonamide (30 mg) as a white solid. $^1$H NMR (400 MHz, Methanol-d4) δ (ppm): 8.10 (d, J=8.5 Hz, 1H), 7.98 (s, 1H), 7.72 (d, J=7.4 Hz, 1H), 7.55 (d, J=8.1 Hz, 1H), 7.48 (d, J=2.3 Hz, 1H), 7.43 (t, J=2.8 Hz, 1H), 7.37 (d, J=8.6 Hz, 1H), 7.25 (d, J=5.4 Hz, 1H), 7.22 (d, J=7.8 Hz, 1H). LCMS (M+1): 457.7.

Example 29. Preparation of Compound No. 81

Step-1: Synthesis of
4-fluoro-2-(trifluoromethyl)benzamide

A solution of 4-fluoro-2-(trifluoromethyl)benzonitrile (100 mg, 0.528 mmol) in conc. sulfuric acid (1.2 mL) and glacial acetic acid (0.8 mL) was heated at 120° C. for 0.5h, monitored by TLC. The reaction was diluted with water and the mixture extracted with EtOAc (2×30 mL). The organic layer was dried over anhydrous sodium sulfate and concentrated under reduced pressure to afford 80 mg of 4-fluoro-2-(trifluoromethyl) benzamide as an off-white solid.

Step-2: Synthesis of
4-fluoro-2-(trifluoromethyl)benzenecarbothioamide

A solution of 4-fluoro-2-(trifluoromethyl)benzamide (500 mg, 2.414 mmol) and Lawesson's Reagent (1.95 g, 4.821 mmol) in toluene (30 mL) was heated at 80° C. for 1h. The progress of the reaction was monitored by TLC. The reaction was diluted with water (30 mL) and the mixture extracted with EtOAc (2×50 mL). The organic layer was dried over anhydrous sodium sulfate and concentrated under reduced pressure to afford a crude product, which was purified by column chromatography (silica-gel, 230-400 mesh) using 10% EtOAc in hexane as eluent to obtain 100 mg of 4-fluoro-2-(trifluoromethyl)benzenecarbothioamide as a yellow sticky compound.

Step-3: Synthesis of N-[3-chloro-4-[2-[4-fluoro-2-(trifluoromethyl)phenyl]thiazol-4-yl]phenyl]-1,1,1-trifluoro-methanesulfonamide A solution of 4-fluoro-2-(trifluoromethyl)benzenecarbothioamide (50 mg, 0224 mmol) and N-[4-(2-bromoacetyl)-3-chloro-phenyl]-1,1,1-trifluoro-methanesulfonamide (170 mg, 0.446 mmol) in ethanol (10 mL) was heated at 70° C. for 40 min, monitored by TLC. The reaction was diluted with aqueous saturated NaHCO$_3$ solution (25 mL) and the mixture extracted with EtOAc (2×50 mL). The combined organic layer was dried over anhydrous sodium sulfate and concentrated under reduced pressure to afford a crude product, which was purified by reverse phase preparative HPLC to obtain N-[3-chloro-4-[2-[4-fluoro-2-(trifluoromethyl)phenyl]thiazol-4-yl]phenyl]-1,1,1-trifluoro-methanesulfonamide (22 mg) as an off-white solid. $^1$H NMR (400 MHz, Methanol-d4): δ (ppm): 7.98 (s, 1H), 7.81 (dd, J=8.6, 5.4 Hz, 1H), 7.68 (dd, J=8.9, 3.0 Hz, 2H), 7.53 (td, J=8.4, 2.6 Hz 1H), 7.30 (d, J=2.2 Hz, 1H), 7.11 (dd, J=8.4, 2.1 Hz, 1H).

Example 30. Preparation of Compound No. 82

N-(4-(2-Bromothiazol-4-yl)-3-chlorophenyl)-1,1,1-trifluoromethane sulfonamide (100 mg, 0.2380 mmol) and 2,3-dihydrobenzofuran-5-boronic acid (58.5 mg, 0.3571 mmol), potassium carbonate (65 mg, 0.476 mmol), dimethyl formamide (5 mL), water (0.5 mL) were charged in a 2 neck round bottom flask and aerated with nitrogen gas for 5 min. After adding Pd(PPh$_3$)$_4$ (27.4 mg, 0.0238 mmol), the mixture was heated to 100° C. for 18 h. The reaction was monitored by LCMS. The reaction mixture was allowed to cool to RT; water (10 mL) was added and the mixture extracted with EtOAc (3×25 mL). The combined organic layer was washed with water (30 mL), dried over anhydrous sodium sulfate and concentrated under reduced pressure to obtain a crude product, which was purified by reverse phase HPLC to afford N-{3-chloro-4-[2-(2,3-dihydro-1-benzofuran-5-yl)-1,3-thiazol-4-yl]phenyl}-1,1,1-trifluoromethanesulfonamide (15 mg) as a white solid. $^1$H NMR (400 MHz, Methanol-d4) δ (ppm): 7.97 (d, J=8.5 Hz, 1H), 7.88 (s, 1H), 7.82 (s, 1H), 7.77 (d, J=8.3 Hz, 1H), 7.44 (s, 1H), 7.32 (d, J=8.5 Hz, 1H), 6.83 (d, J=8.3 Hz, 1H), 4.63 (t, J=8.7 Hz, 2H), 2.17 (t, J=9.3 Hz, 2H). LCMS (M+1): 460.6.

Example 31. Preparation of Compound No. 83

N-(4-(2-Bromothiazol-4-yl)-3-chlorophenyl)-1,1,1-trifluoromethane sulfonamide (100 mg, 0.2380 mmol) and [3-(bromomethyl)phenyl]boronic acid (61.3 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol), the mixture was further purged for 2 min and was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-(3-chloro-4-{2-[3-(hydroxymethyl)phenyl]-1,3-thiazol-4-yl}phenyl)-1,1,1-trifluoromethanesulfonamide (9 mg) as a white solid. $^1$H NMR (400 MHz, DMSO-d6) δ (ppm): 8.13 (s, 1H), 8.00 (d, J=8.5 Hz, 2H), 7.97-7.79 (m, 1H), 7.51-7.43 (m, 2H), 7.41 (d, J=2.2 Hz, 1H), 7.33 (dd, J=8.6, 2.2 Hz, 1H), 4.59 (s, 2H). LCMS (M+1): 448.9.

Example 32. Preparation of Compound No. 84

N-(4-(2-Bromothiazol-4-yl)-3-chlorophenyl)-1,1,1-trifluoromethane sulfonamide (100 mg, 0.2380 mmol) and [2-(bromomethyl)phenyl]boronic acid (56 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(hydroxymethyl)phenyl]-1,3-thiazol-4-yl}phenyl)-1,1,1-trifluoromethanesulfonamide (25 mg) as a white solid. $^1$H NMR (400 MHz, DMSO-d6) δ (ppm): 8.20 (s, 1H), 7.95 (d, J=8.5 Hz, 1H), 7.81-7.79 (m, 1H), 7.79-7.71 (m, 1H), 7.54 (dd, J=7.5, 1.3 Hz, 1H), 7.43 (dt, J=3.7, 1.9 Hz, 2H), 7.35 (dd, J=8.5, 2.3 Hz, 1H), 4.87 (s, 2H). LCMS (M+1): 449.1.

Example 33. Preparation of Compound No. 85

N-(4-(2-Bromothiazol-4-yl)-3-chlorophenyl)-1,1,1-trifluoromethane sulfonamide (100 mg, 0.2380 mmol) and [2-(1-piperidyl)-4-pyridyl]boronic acid (53 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(piperidin-1-yl)pyridin-4-yl]-1,3-thiazol-4-yl}phenyl)-1,1,1-trifluoromethanesulfonamide (56 mg) as a yellow solid. $^1$H NMR (400 MHz, DMSO-d6) δ (ppm): 8.23-8.07 (m, 2H), 7.38 (s, 1H) 7.83 (d, J=8.5 Hz, 1H), 7.35 (s, 1H), 7.19-7.09 (m, 2H), 3.62 (t, J=5.1 Hz, 4H), 3.17 (s, 2H), 1.60 (dt, J=9.7, 5.7 Hz, 4H). LCMS (M+1): 504.0.

Example 34. Preparation of Compound No. 86

N-(4-(2-Bromothiazol-4-yl)-3-chlorophenyl)-1,1,1-trifluoromethane sulfonamide (100 mg, 0.2380 mmol) and (3-methyl-4-pyridyl)boronic acid (35 mg, 0. 0.0261 mmol), sodium carbonate (63 mg, 0. 0.0595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{3-chloro-4-[2-(3-methylpyridin-4-yl)-1,3-thiazol-4-yl]phenyl}-1,1,1-trifluoromethanesulfonamide (13 mg) as a white solid. $^1$H NMR (400 MHz, Methanol-d4) δ (ppm): 8.80 (s, 1H), 8.70 (s, 1H), 8.41 (s, 2H), 8.04 (d, J=8.5 Hz, 1H), 7.49 (d, J=2.3 Hz, 1H), 7.38 (dd, J=8.5, 2.3 Hz, 1H), 2.86 (s, 3H). LCMS (M+1): 434.4.

Example 35. Preparation of Compound No. 87

N-(4-(2-Bromothiazol-4-yl)-3-chlorophenyl)-1,1,1-trifluoromethane sulfonamide (100 mg, 0.2380 mmol) and 4-(4,4,5,5-tetramethyl-1,3,2-dioxaborolan-2-yl)-1H-pyrrolo[2,3-b]pyridine (63 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-[3-chloro-4-(2-{1H-pyrrolo[2,3-b]pyridin-4-yl}-1,3-thiazol-4-yl)phenyl]-1,1,1-trifluoromethanesulfonamide (37 mg) as a white solid. $^1$H NMR (400 MHz, Methanol-d4) δ (ppm): 8.39 (d, J=5.6 Hz, 1H), 8.29 (s, 1H), 8.11 (d, J=8.5 Hz, 1H), 7.92 (d, J=5.6 Hz, 1H), 7.69 (d, J=3.5 Hz, 1H), 7.50 (d, J=2.3 Hz, 1H), 7.43-7.33 (m, 2H). LCMS (M+1): 459.5.

Example 36. Preparation of Compound No. 37

N-(4-(2-Bromoacetyl)-3-chlorophenyl)-1,1,1-trifluoromethanesulfonamide (50 mg, 0.132 mmol) and 2-isobutylpyridine-4-carbothioamide (25.34 mg, 0.132 mmol) were charged in EtOH (10 mL) and the reaction mixture was heated at 80° C. for 1 h. The reaction mixture was concentrated and purified through reverse phase HPLC. (Yield: 17 mg TFA salt). $^1$H NMR (TFA salt, CD$_3$OD) δ (ppm): 8.73 (d, J=5.9 Hz, 1H), 8.38 (d, J=2.9 Hz, 1H), 8.31 (d, J=6.2 Hz, 1H), 8.07 (d, J=8.5 Hz, 1H), 7.49 (s, 1H), 7.39 (d, J=8.2 Hz, 1H), 2.94 (d, J=7.3 Hz, 2H), 2.19 (m, 2H), 1.07 (d, J=6.6 Hz, 6H).
Complete Synthesis of Compound No. 37
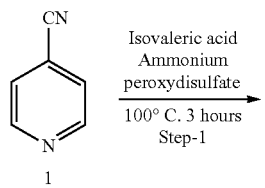
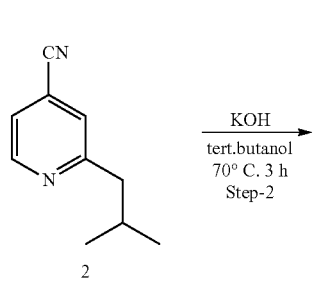
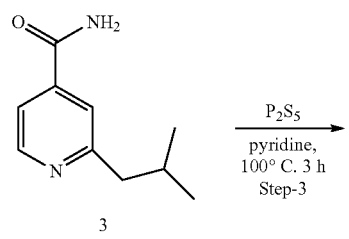
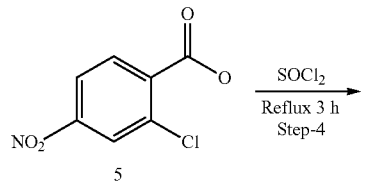
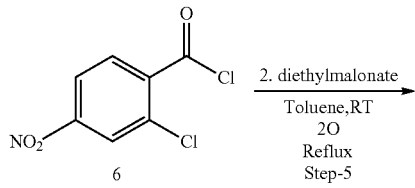
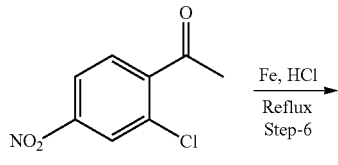
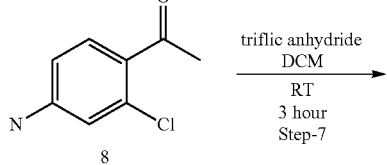
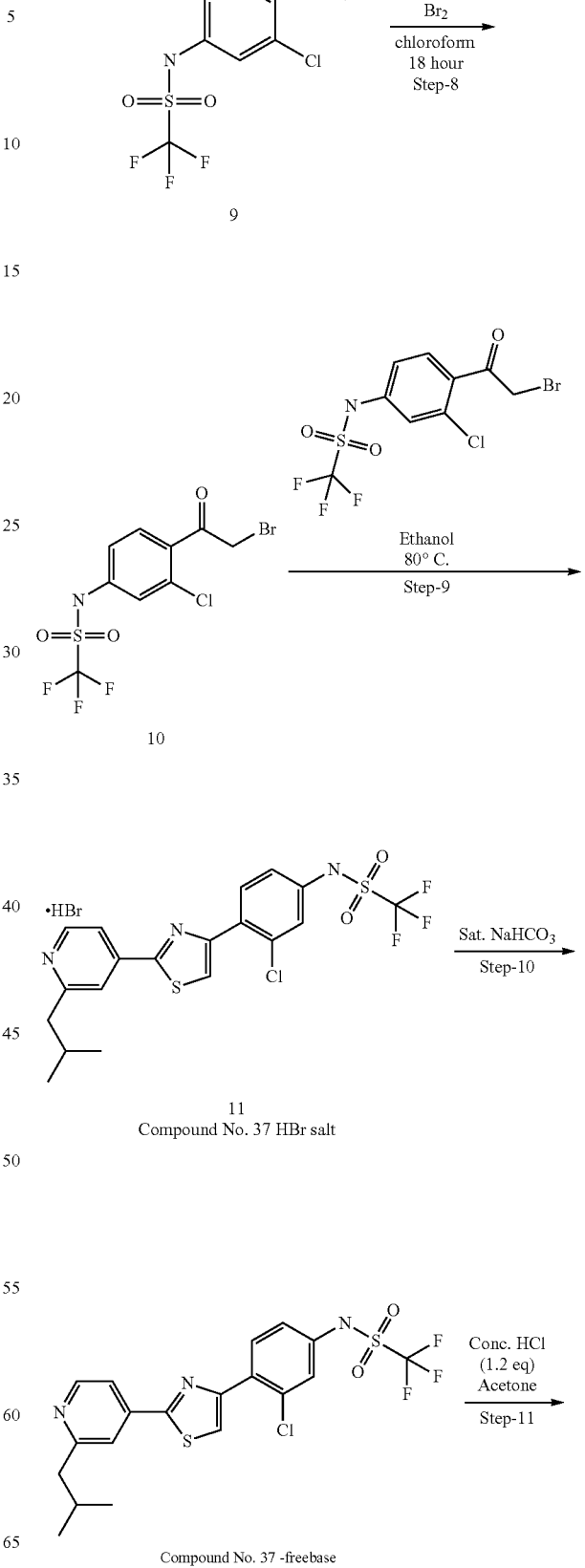

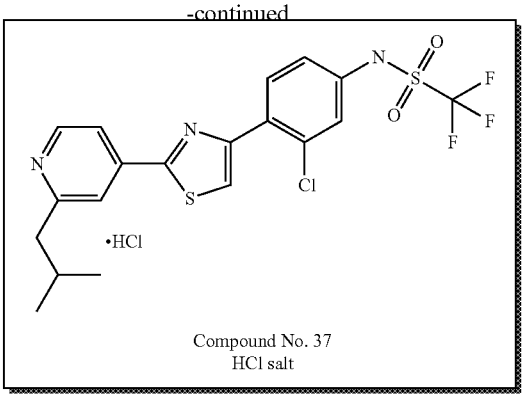

Compound No. 37
HCl salt

Step 1: Synthesis of 2-isobutylpyridine-4-carbonitrile (2)

To a suspension of 4-cyano pyridine (1) (30 g, 0.288 mol, 1 equiv.) in water (210 mL), concentrated sulfuric acid (15.3 mL, 0.288 mol, 1 equiv.) was added dropwise maintaining the temperature at 20-25° C. After formation of a clear solution, $AgNO_3$ (4.9 g, 0.028 mmol, 0.0001 equiv.) followed by isovaleric acid (160 mL, 1.47 mol, 5 equiv.) were added in to the reaction mixture. A white hazy solution formed. Ammonium peroxydisulfate (66 g, 0.288 mol, 1 equiv.) dissolved in water (90 mL) was then added. A black clear solution formed. The reaction mixture was then heated to reflux at 100° C. for 3 h. The reaction was monitored by TLC. After completion, the reaction mixture was basified (pH=7-8) using a saturated solution of sodium bicarbonate, and extracted with EtOAc (3×750 mL). The extracts were combined and were washed with brine (3×300 mL) and dried over anhydrous sodium sulfate. The solution was concentrated under reduced pressure and the crude product was purified by column chromatography (silica gel: #100-200) using 0-6% EtOAc in hexane as eluant to afford 2-isobutylpyridine-4-carbonitrile (2) (15 g (32.5% yield)) as a pale yellow liquid. $^1$H NMR (400 MHz, Chloroform-d): δ (ppm): 8.78-8.63 (m, 1H), 7.41-7.27 (m, 2H), 2.72 (d, J=7.2 Hz, 2H), 1.35-1.23 (m, 1H), 0.94 (d, J=6.6 Hz, 6H).

Step 2: Synthesis of 2-isobutylpyridine-4-carboxamide (3)

2-Isobutylpyridine-4-carbonitrile (2) (15 g, 0.093 mol, 1 equiv.) and KOH (15.7 g, 0.281 mol, 3 equiv.) was dissolved in tert-butanol (160 mL). The reaction mixture was stirred at 70° C. for 90 min. The reaction was monitored by TLC. After completion, the tert-butanol was removed under reduced pressure; the residue was dissolved in water and extracted with EtOAc (3×275 mL). The extracts were combined, dried over anhydrous sodium sulfate and concentrated under reduced pressure. The crude product was triturated with n-hexane (3×200 mL). To the residue was added diethyl ether (50 mL) and then concentrated under reduced pressure to afford 2-isobutylpyridine-4-carboxamide (3) (13.5 g (81.3% yield)) as a white solid. $^1$H NMR (400 MHz, Chloroform-d): δ (ppm): 8.68 (d, J=5.1 Hz, 1H), 7.49 (s, 1H), 7.42 (d, J=5.1 Hz, 1H), 6.14 (s, 1H), 5.81 (s, 1H), 2.73 (d, J=7.3 Hz, 2H), 2.13 (m, 1H), 0.94 (d, J=6.7 Hz, 6H).

Step 3: Synthesis of 2-isobutylpyridine-4-carbothioamide (4)

To a solution of 2-isobutylpyridine-4-carboxamide (3) (13.5 g, 0.075 mol, 1 equiv.) in pyridine (135 ml), was added $P_2S_5$ (8.45 g, 0.037 mol, 0.5 equiv.). The reaction was heated at 100° C. for 3 h. The progress of the reaction was monitored by TLC. After completion, the pyridine was evaporated under reduced pressure; the residue was dissolved in water (100 mL) and extracted with EtOAc (3×250 mL). The EtOAc extracts were combined, dried over anhydrous sodium sulfate and concentrated under reduced pressure. The crude product obtained was triturated with n-hexane (3×200 mL) to afford 2-isobutylpyridine-4-carbothioamide (4) (8 g (54.4% yield)) as a yellow solid. $^1$H NMR (400 MHz, Chloroform-d): δ (ppm): 8.62 (d, J=5.1 Hz, 1H), 7.73-7.64 (broad, 1H), 7.52-7.40 (m, 2H), 7.32-7.25 (m, 1H), 2.72 (d, J=7.2 Hz, 2H), 2.13 (m, 1H), 0.95 (d, J=6.6 Hz, 6H).

Step 4: Synthesis of 2-chloro-4-nitrobenzoyl chloride (6)

To a two neck flask (1 L) placed in ice bath was placed 2-chloro-4-nitrobenzoic acid (5) (50 g, 0.248 mol, 1 equiv.). Thionyl chloride (110 ml, 1.51 mol, 6.1 equiv.) was added dropwise at 0° C. The reaction mixture was allowed to come to RT and then heated to reflux. The heating was continued overnight. The thionyl chloride was evaporated and ice (approx. 150 g) was added to the reaction mixture. The aqueous reaction mixture was extracted with DCM (2×200 mL). The DCM extracts were combined dried over anhydrous sodium sulfate and concentrated under vacuum to get 2-chloro-4-nitrobenzoyl chloride (6) (50 g (91.7% yield)) as a light yellow liquid. $^1$H NMR (400 MHz, Chloroform-d): δ (ppm): 8.37 (d, J=2.2 Hz, 1H), 8.25 (dd, J=8.6, 2.2 Hz, 1H), 8.15 (d, J=8.7 Hz, 1H).

Step 5: Synthesis of 1-(2-chloro-4-nitrophenyl)ethanone (7)

A suspension of anhydrous magnesium chloride (47 g, 0.214 mol, 0.7 equiv.) in toluene (300 mL) was treated with triethylamine (75.04 mL, 0.535 mol, 2.5 equiv.) and diethylmalonate (41.09 g, 0.257 mol, 1.2 equiv.). The reaction mixture was stirred at RT for 1.5 h. To this was added 2-chloro-4-nitrobenzoyl chloride (6) (47 g, 0.214 mol, 1 equiv.) dropwise (an exothermic reaction up to 50° C. was observed during addition). Toluene (50 mL) was used for complete transfer of 2-chloro-4-nitrobenzoyl chloride to the reaction mixture. The reaction mixture was stirred at RT for 18 h. The reaction was monitored by TLC and NMR. After complete consumption of starting material, concentrated hydrochloric acid (35% solution) (300 mL) was added and the upper toluene layer was separated. The toluene was evaporated under reduced pressure below 50° C. To the residue were added DMSO (200 mL) and water (10 mL), and the mixture heated at 160° C. for 12 h. The reaction was monitored by TLC and NMR. The reaction mixture was allowed to come to RT and water (40 mL) was added. The reaction mixture was extracted with EtOAc (3×200 mL). The EtOAc extracts were combined and washed with brine solution (3×300 mL) and dried over anhydrous sodium sulfate. The EtOAc layer was concentrated to get 1-(2-chloro-4-nitrophenyl) ethanone (7) (43 g (84% yield)) as a yellow liquid which solidified upon refrigeration. $^1$H NMR (400 MHz, Chloroform-d): δ (ppm): 8.29 (d, J=2.2 Hz, 1H), 8.17 (dd, J=8.5, 2.1 Hz, 1H), 7.65 (d, J=8.4 Hz, 1H), 2.66 (s, 3H).

Step 6: Synthesis of 1-(4-amino-2-chlorophenyl) ethanone (8)

1-(2-Chloro-4-nitrophenyl) ethanone (87.8 g, 0.43 mol, 1 equiv.) was charged in methanol (600 mL). The reaction mixture was heated to 70° C. and concentrated HCl (131 mL, 1.29 mol, 3 equiv.) was added dropwise with constant stirring. After the completion of addition, iron powder (98.2 g, 1.75 mol, 4 equiv.) was added in four parts at 5 minute intervals. The reaction mixture was heated at 70° C. for 7 h and the reaction monitored by TLC and NMR. After completion of reaction, the mixture was allowed to come to RT and then filtered through a celite bed. The filtrate was concentrated under reduced pressure and celite bed was washed with EtOAc to obtain further crude product. Both portions were combined and water (200 mL) was added. The EtOAc layer was separated and aqueous layer was extracted with EtOAc (2×500 mL). The combined organic layer was dried over anhydrous sodium sulfate and concentrated to get crude product (57 g). This crude product was precipitated in pentane to get 1-(4-amino-3-methoxyphenyl) ethanone (8) (50 g (67% yield)) as a pink solid. $^1$H NMR (400 MHz, Chloroform-d): δ (ppm): 7.62 (d, J=8.5 Hz, 1H), 6.66 (d, J=2.3 Hz, 1H), 6.54 (dd, J=8.5, 2.3 Hz, 1H), 4.07 (s, 2H), 2.61 (s, 3H).

Step 7: Synthesis of N-(4-acetyl-3-chlorophenyl)-1,1,1-trifluoromethanesulfonamide (9)

A solution of triflic anhydride (75.1 g, 0.266 mol, 1.5 equiv.) in DCM (600 mL) was cooled to 0° C. Pyridine (23.4 mL, 0.266 mol, 1.5 equiv.) was added dropwise with constant stirring over 30 min. The reaction mixture was stirred at the same temperature for 1 h. A solution of 1-(4-amino-2-chlorophenyl)ethanone (8) (30 g, 0.177 mol, 1 equiv.) in DCM (400 mL) was added dropwise maintaining the temperature at 0° C. with constant stirring over a period of 45 min. The reaction mixture was then allowed to come to RT and stirred for 1 h at RT. The reaction was monitored by TLC and NMR. Upon completion, ice cold water (500 mL) was added and the DCM layer was separated. The aqueous layer was again extracted with DCM (2×100 mL). The DCM extracts were combined washed with ice cold water (2×500 mL). The DCM layer was dried over anhydrous sodium sulfate and concentrated under reduced pressure below 40° C. to obtain the crude product. Diethyl ether (200 mL) and pentane (600 mL) were added to the mixture which was then stirred for 30 min. The mixture was filtered and the filtrate concentrated and triturated in pentane to get N-(4-acetyl-3-chlorophenyl)-1,1,1-trifluoromethanesulfonamide (9) (28 g (52.8% yield)) as a light pink solid. $^1$H NMR (400 MHz, Chloroform-d): δ (ppm): 7.63 (d, J=8.4 Hz, 1H), 7.36 (d, J=2.2 Hz, 1H), 7.28-7.21 (m, 1H), 2.66 (s, 3H).

Step 8: Synthesis of N-(4-(2-bromoacetyl)-3-chlorophenyl)-1,1,1-trifluoromethanesulfonamide (10)

A solution of N-(4-acetyl-3-chlorophenyl)-1,1,1-trifluoromethanesulfonamide (9) (21 g, 0.07 mol, 1 equiv.) in chloroform (600 mL) was cooled to 0° C. Liquid bromine (2.9 mL, 0.004 mol, 0.8 equiv.) dissolved in chloroform (400 mL) was added dropwise over a period of 40 min, maintaining the reaction temperature between 0-10° C. The mixture was allowed to come to RT and then stirred at RT for 18 h. The reaction was monitored by TLC and NMR. There was an indication of the presence of starting material and desired compound along with some amount of N-(3-chloro-4-(2,2-dibromoacetyl)phenyl)-1,1,1-trifluoromethanesulfonamide (dibromo impurity). A saturated solution of sodium thiosulfate (200 mL) was added and the chloroform layer was separated. The aqueous layer was extracted with chloroform (2×100 mL). The main chloroform layer and the chloroform extracts were combined, dried over anhydrous sodium sulfate and concentrated under reduced pressure. A clear liquid was obtained as the residue. To this were added diethylether (50 mL) and pentane (250 mL) and the mixture stirred for 10 min. The reaction mixture was filtered and the filtrate concentrated. The crude product obtained was triturated with pentane (~50 mL) to obtain a white solid. This white solid was filtered and dried under vacuum to get N-(4-(2-bromoacetyl)-3-chlorophenyl)-1,1,1-trifluoromethanesulfonamide (10) (20 g) which contained approximately 35% of starting material i.e. N-(4-acetyl-3-chlorophenyl)-1,1,1-trifluoromethanesulfonamide (9) by NMR. The mixture of products was directly used for the next step without any further purification. $^1$H NMR (400 MHz, Chloroform-d): δ (ppm): 7.64 (d, J=8.4 Hz, 1H), 7.38 (d, J=2.2 Hz, 1H), 7.30-7.27 (m, 1H), 4.51 (s, 2H).

Step 9: Synthesis of N-(3-chloro-4-(2-(2-isobutylpyridin-4-yl) thiazol-4-yl) phenyl)-1,1,1-trifluoromethanesulfonamide (11)

N-(4-(2-Bromoacetyl)-3-chlorophenyl)-1,1,1-trifluoromethanesulfonamide (10) (15.5 g, 0.041 mol, 1 equiv.) and 2-isobutylpyridine-4-carbothioamide (5.2 g, 0.027 mol, 0.65 equiv.) were charged in ethanol (40 mL) and the reaction mixture was heated at 80° C. for 30 min. The reaction mixture was cooled in an ice bath and stirred at 0° C. for 30 min. The solid obtained was isolated by filtration and washed with cold ethanol (2×5 mL). The solid obtained was dried under vacuum to get N-(3-chloro-4-(2-(2-isobutylpyridin-4-yl) thiazol-4-yl) phenyl)-1,1,1-trifluoromethanesulfonamide (11) (10.2 g (53.6% yield)) as the hydrobromide salt. $^1$H NMR (400 MHz, Methanol-d4): δ (ppm): 8.80 (d, J=6.3 Hz, 1H), 8.57-8.45 (m, 3H), 8.08 (d, J=8.5 Hz, 1H), 7.50 (d, J=2.2 Hz, 1H), 7.40 (dd, J=8.6, 2.3 Hz, 1H), 3.01 (d, J=7.4 Hz, 2H), 2.21 (m, 1H), 1.06 (d, J=6.6 Hz, 6H). UPLC: In method, Column Type: ACQUITY BEH SHIELD C18, Column ID: 2.1*50 mm, 1.7μ; Flow Rate—0.35 mL/min, Mobile Phase A: 0.05% TFA; Mobile Phase B: acetonitrile. Gradient: 10% B To 50% B in 1 min., hold for 0.5 min, 50% B to 90% B in 0.1 min, hold for 1 min, 90% B to 10% B in 0.4 min compound eluted at a retention time of 2.66 min.

Step 10: Synthesis of N-(3-chloro-4-(2-(2-isobutylpyridin-4-yl) thiazol-4-yl) phenyl)-1,1,1-trifluoromethanesulfonamide—free base (12)

N-(3-Chloro-4-(2-(2-isobutylpyridin-4-yl) thiazol-4-yl) phenyl)-1,1,1-trifluoromethanesulfonamide hydrobromide salt (11) (88.5. g) was charged in a flask and a saturated solution of sodium bicarbonate (300 mL) was added so that the pH became slightly basic (pH=7-8). EtOAc (3×500 mL) was added and the reaction mixture was stirred at RT until the mixture became clear. The organic layer was separated and washed with water (50 mL). The EtOAc layer was dried over anhydrous sodium sulfate and concentrated to get N-(3-chloro-4-(2-(2-isobutylpyridin-4-yl) thiazol-4-yl) phenyl)-1,1,1-trifluoromethanesulfonamide (12) (46.3 g (61% yield)) as the free base. $^1$H NMR (400 MHz, Methanol-d): δ (ppm): 8.56 (d, J=5.3 Hz, 1H), 8.10 (s, 1H), 7.99 (d, J=8.6 Hz, 1H), 7.92-7.80 (m, 2H), 7.44 (d, J=2.2 Hz, 1H), 7.31 (dd, J=8.5, 2.3 Hz, 1H), 3.06 (s, 3H), 2.86 (dd, J=8.6, 6.7 Hz, 2H), 1.88-1.74 (m, 2H), 1.01 (t, J=7.4 Hz, 3H).

Step 11: Synthesis of N-(3-chloro-4-(2-(2-isobutylpyridin-4-yl) thiazol-4-yl) phenyl)-1,1,1-trifluoromethanesulfonamide Hydrochloride (13)

N-(3-chloro-4-(2-(2-isobutylpyridin-4-yl) thiazol-4-yl) phenyl)-1,1,1-trifluoromethanesulfonamide—free base (12)

(46.4 g, 0.097 mol, 1 equiv.) was charged in acetone (1.5 L) and stirred at RT for 5-10 min until a clear solution was obtained. A solution of concentrated hydrochloric acid [~35% v/v] (13.3 mL, 0.126 mol, 1.3 equiv.) in acetone (85 mL) was added dropwise with constant stirring. After addition, the pH of the reaction mixture was 1-2. The reaction mixture was stirred for 30 min at RT. The solid obtained was filtered under vacuum and washed with acetone (3×100 mL) (the washing was performed without vacuum and once acetone was absorbed by the solid, the solvent was removed by vacuum filtration). The washing was repeated until the filtrate was colorless. The light yellow solid obtained was dried at 50° C. under reduced pressure for 2 h to get N-(3-chloro-4-(2-(2-isobutylpyridin-4-yl) thiazol-4-yl) phenyl)-1,1,1-trifluoromethanesulfonamide-hydrochloride salt (13) (44 g (88% yield)). $^1$H NMR (400 MHz, Methanol-d4): δ (ppm): 8.81 (d, J=6.3 Hz, 1H), 8.58-8.45 (m, 3H), 8.08 (d, J=8.5 Hz, 1H), 7.49 (t, J=2.8 Hz, 1H), 7.40 (dd, J=8.5, 2.4 Hz, 1H), 3.02 (d, J=7.3 Hz, 2H), 2.22 (m, 1H), 1.06 (d, J=6.6 Hz, 6H). Melting point: 165° C.-173° C. (FB). LCMS—(M+1):475.9 (99.5%). In method, Column type: HYPERSILGOLD,C18, Column_ID: 4.6*50 mm, 5 μu; Mobile Phase A: 0.05% formic acid in H$_2$O; Mobile Phase B: 0.01% formic acid in acetonitrile. Gradient: 10% B to 90% B From 0.2 to 2 min, hold for 2.5 min, 10% B in 0.1 min. Flow: 0.7 mL/min. The desired compound has RT of 4.514 min. UPLC—In method, Column Type: ACQUITY BEH C18; Column ID: 2.1*50 mm, 1.7μ; Flow Rate: 0.35 mL/min. Mobile phase A: 0.05% TFA Mobile phase B: Acetonitrile, Gradient: 10% B to 90% B in 2.5 min, hold for 1 min, 90% B to 10% B in 0.3 min. The desired compound had RT of 2.793 min. Melting point: 220° C.-227° C. (Hydrochloride salt).

Example 37. Preparation of Compound No. 88

N-(4-(2-Bromothiazol-4-yl)-3-chlorophenyl)-1,1,1-trifluoromethane sulfonamide (100 mg, 0.2380 mmol) and [3-(1-piperidyl)phenyl]boronic acid (53 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd-acetate (8 mg, 0.035 mmol) and xantphos (27.5 mg, 0.0476 mmol), the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[3-(piperidin-1-yl)phenyl]-1,3-thiazol-4-yl}phenyl)-1,1,1-trifluoromethanesulfonamide (25 mg) as a yellow solid. $^1$H NMR (400 MHz, Methanol-d4) δ (ppm): 8.23 (s, 1H), 8.11-7.94 (m, 3H), 7.71-7.59 (m, 2H), 7.47 (d, J=2.2 Hz, 1H), 7.37 (dd, J=8.6, 2.2 Hz, 1H), 3.63 (t, J=5.5 Hz, 4H), 2.01 (q, J=6.2 Hz, 4H), 1.80 (q, J=6.0 Hz, 2H). LCMS (M+1): 502.5.

Example 38. Preparation of Compound No. 89

N-(4-(2-Bromothiazol-4-yl)-3-chlorophenyl)-1,1,1-trifluoromethane sulfonamide (100 mg, 0.2380 mmol) and [5-fluoro-4-(4,4,5,5-tetramethyl-1,3,2-dioxaborolan-2-yl) pyrrolo[2,3-b]pyridin-1-yl]-triisopropyl-silane (109 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-[3-chloro-4-(2-{5-fluoro-1H-pyrrolo[2,3-b]pyridin-4-yl}-1,3-thiazol-4-yl)phenyl]-1,1,1-trifluoromethanesulfonamide (35 mg) as a white color solid. $^1$H NMR (400 MHz, DMSO-d6) δ (ppm): 12.10 (s, 1H), 8.43 (d, J=2.2 Hz, 2H), 8.08 (d, J=8.5 Hz, 1H), 7.74 (t, J=3.0 Hz, 1H), 7.47 (d, J=2.2 Hz, 1H), 7.45-7.36 (m, 2H). LCMS (M+1): 477.1.

Example 39. Preparation of Compound No. 90

N-(4-(2-Bromothiazol-4-yl)-3-chlorophenyl)-1,1,1-trifluoromethane sulfonamide (100 mg, 0.2380 mmol) and benzothiophen-3-ylboronic acid (47 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{4-[2-(1-benzothiophen-3-yl)-1,3-thiazol-4-yl]-3-chlorophenyl}-1,1,1-trifluoromethanesulfonamide (59 mg) as a white solid. $^1$H NMR (400 MHz, Methanol-d4) δ (ppm): 8.80 (d, J=8.0 Hz, 1H), 8.26 (s, 1H), 8.08 (d, J=8.5 Hz, 1H), 7.99 (s, 1H), 7.98 (d, J=8.1 Hz, 1H), 7.57-7.51 (m, 1H), 7.51-7.43 (m, 2H), 7.38 (dd, J=8.6, 2.3 Hz, 1H). LCMS (M+1): 475.

Example 40. Preparation of Compound No. 91

N-(4-(2-Bromothiazol-4-yl)-3-chlorophenyl)-1,1,1-trifluoromethane sulfonamide (100 mg, 0.2380 mmol) and 1-[[5-fluoro-2-(4,4,5,5-tetramethyl-1,3,2-dioxaborolan-2-yl) phenyl]methyl]pyrrolidine (80 mg, 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[4-fluoro-2-(pyrrolidin-1-ylmethyl)phenyl]-1,3-thiazol-4-yl}phenyl)-1,1,1-trifluoromethanesulfonamide (80 mg) as a pale red solid. $^1$H NMR (400 MHz, Methanol-d4) δ (ppm): 8.11 (dd, J=8.7, 5.4 Hz, 1H), 7.98 (s, 1H), 7.72 (d, J=8.4 Hz, 1H), 7.56 (dd, J=9.0, 2.7 Hz, 1H), 7.51-7.43 (m, 2H), 7.33 (dd, J=8.4, 2.2 Hz, 1H), 4.61 (s, 2H), 3.43 (t, 2H), 3.25 (t, 2H), 2.17 (m, 2H), 1.97 (m, 2H). LCMS (M+1): 521.4.

Example 41. Preparation of Compound No. 92

N-(4-(2-Bromothiazol-4-yl)-3-chlorophenyl)-1,1,1-trifluoromethane sulfonamide (100 mg, 0.2380 mmol) and N-cyclopentyl-4-(4,4,5,5-tetramethyl-1,3,2-dioxaborolan-2-yl) pyridin-3-amine (76 mg, 0. 0.261 mmol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT; water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-(3-chloro-4-{2-[2-(cyclopentylamino) pyridin-4-yl]-1,3-thiazol-4-yl}phenyl)-1,1,1-trifluoromethanesulfonamide (96 mg) as a yellow solid. $^1$H NMR (400 MHz, Methanol-d4) δ (ppm): 8.25 (s, 1H), 7.94 (dd, J=14.6, 7.6 Hz, 2H), 7.57 (d, J=1.6 Hz, 1H), 7.44 (d, J=2.3 Hz, 1H), 7.40 (d, J=1.7 Hz, 1H), 7.38-7.29 (m, 1H), 4.11 (q, J=6.1 Hz, 1H), 2.14 (dt, J=13.2, 6.4 Hz, 2H), 1.84 (dt, J=6.6 Hz, 2H), 1.71 (tt, J=24.6, 11.7, 6.0 Hz, 4H). LCMS (M+1): 503.8.

Example 42. Preparation of Compound No. 93

N-(4-(2-Bromothiazol-4-yl)-3-chlorophenyl)-1,1,1-trifluoromethane sulfonamide (100 mg, 0.2380 mmol) and 3-(4,4,5,5-tetramethyl-1,3,2-dioxaborolan-2-yl)-1H-indole (64 mg, 0.261 mmol), sodium carbonate (63 mg, 0.595), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) the mixture was further purged for 2 min and was heated to 100° C. for 18 h. The reaction was monitored by LCMS. The reaction mixture was cooled to RT, water (10 mL) was added and the mixture extracted with EtOAc (3×25 mL). The combined organic layer was washed with water (4×30 mL), dried over sodium sulfate and concentrated under reduced pressure to obtain the crude product, which was purified by reverse phase HPLC to afford N-{3-chloro-4-[2-(1H-indol-3-yl)-1,3-thiazol-4-yl]phenyl}-1,1,1-trifluoromethanesulfonamide (42 mg) as a white solid. $^1$H NMR (400 MHz, Methanol-d4) δ (ppm): 8.24-8.19 (m, 1H), 8.03 (d, J=8.5 Hz, 1H), 7.98 (s, 1H), 7.77 (s, 1H), 7.50-7.45 (m, 2H), 7.36 (dd, J=8.5, 2.3 Hz, 1H), 7.26-7.20 (m, 2H). LCMS (M+1): 458.3.

Example 43. Preparation of Compound No. 94

N-(4-(2-Bromothiazol-4-yl)-3-chlorophenyl)-1,1,1-trifluoromethane sulfonamide (100 mg, 0.2380 mmol) and 4-quinolyl boronic acid (61.7 mg, 0.3571 mol), sodium carbonate (63 mg, 0.595 mmol), dimethyl formamide (4 mL), water (1.0 mL) were charged in a 25 mL glass bottle and aerated with nitrogen gas for 5 min. After adding Pd(PPh$_3$)$_4$ (27.4 mg, 0.0238 mmol) re-purged the mixture for 2 min and was heated to 100° C. for 18 h. The reaction was monitored by LCMS. The reaction mixture was allowed to cool to RT, water (10 mL) was added and the mixture extracted with EtOAc (3×25 mL). The combined organic layer was washed with water (4×30 mL), dried over anhydrous sodium sulfate and concentrated under reduced pressure to obtain a crude product, which was purified by reverse phase HPLC to afford N-[3-chloro-4-[2-(4-quinolyl)thiazol-4-yl]phenyl]-1,1,1-trifluoro-methanesulfonamide (37 mg) as a white solid. $^1$H NMR (400 MHz, Methanol-d4) δ (ppm): 7.94 (s, 1H), 7.89 (d, J=8.5 Hz, 1H), 7.57-7.48 (m, 1H), 7.46-7.38 (m, 4H), 7.31 (dd, J=8.5, 2.3 Hz, 2H), 6.16 (s, 1H), 5.64 (s, 1H). LCMS (M+1): 445.3.

Example 44. Preparation of Compound Nos. 6-36, 38-56, and 95-152

Compound nos. 6-36, 38-56, and 95-152 can be prepared using conditions analogous to those in both the General Methods and Examples provided above.

Example B1A. Effect of Compounds on SREBP2 Cleavage and Cell Viability in HepG2 Cells Cancer cells such as HepG2 cells depend on SREBP activation and de novo lipogenesis to survive, particularly in low serum or serum-free conditions. Using this model, compounds were screened over 24 hours for the ability to block cleavage of SREBP to its active form and over 72 hours for an effect on cell viability under serum-free conditions.

Average SREBP2 cleavage in HepG2 cells was measured in the presence of compounds disclosed in Table 1. HepG2 cells were seeded at 500,000 cells per well in 6-well plates in DMEM supplemented with 10% FBS. After 2 days, cells were treated with compounds (20 µM) for 1 day in DMEM without FBS. Western blots were normalized with respect to actin.

For viability measurements, HepG2 cells were seeded at 5,000 cells per well in 96-well plates in DMEM supplemented with 10% FBS. After 1 day in culture, cells were treated with compounds (20 µM & 5 µM) for 3 days in DMEM without FBS. Viability was measured by MTS (3-(4,5-dimethylthiazol-2-yl)-2,5-diphenyltetrazolium bromide). Treatment with compounds (20 µM & 5 µM) was carried out in medium without FBS, and viability was measured by MTS.

The results are shown in Table 2 as percent inhibition @ 20 µM, and in Table 3 as percent inhibition @ 5 µM.

TABLE 2

| | (20 µM) | |
|---|---|---|
| Compound No. | Average SREBP2 cleavage (% Inhibition, n = 3) | Average Viability (% Inhibition, n = 3) |
| 1 | 73.7 | 92.07 |
| 2 | 73 | 80.5 |
| 4 | 96.07 | 94.38 |
| 5 | 81.7 | 99.2 |
| 37 | 94.59 | 95.03 |
| 57 | 46.9 | 56.4 |
| 58 | 29.4 | 67.9 |
| 59 | 60.6 | 99.8 |
| 60 | 99.0 | 100.0 |
| 61 | 2.0 | 43.0 |
| 62 | 0.0 | 0.0 |
| 63 | 39.0 | 47.0 |
| 64 | 97.0 | 100.0 |
| 66 | 0.0 | 11.0 |
| 67 | 3.0 | 20.0 |

TABLE 3

| Compound No. | Average SREBP2 cleavage (% Inhibition, n = 3) | Average Viability (% Inhibition, n = 3) |
|---|---|---|
| | (5 µM) | |
| 37 | 75 | 94 |
| 70 | 73 | 100 |
| 71 | 77 | 97 |
| 72 | 61 | 94 |
| 73 | 64 | 99 |
| 74 | 76 | 97 |
| 75 | 55 | 88 |
| 76 | 7 | 3 |
| 77 | 56 | 41 |
| 78 | 38 | 87 |
| 79 | 65 | 74 |
| 80 | 90 | 86 |
| 81 | 44 | 88 |
| 82 | 77 | 82 |
| 83 | 2 | 0 |
| 84 | 20 | 18 |
| 85 | 82 | 93 |
| 86 | 54 | 27 |
| 87 | 50 | 9 |
| 88 | 90 | 19 |
| 89 | 53 | 5100 |
| 90 | 64 | 99 |
| 91 | 16 | 4 |
| 92 | 59 | 94 |
| 93 | 28 | 82 |
| 94 | 35 | 84 |
| 95 | 39 | 86 |

Figure 1B:
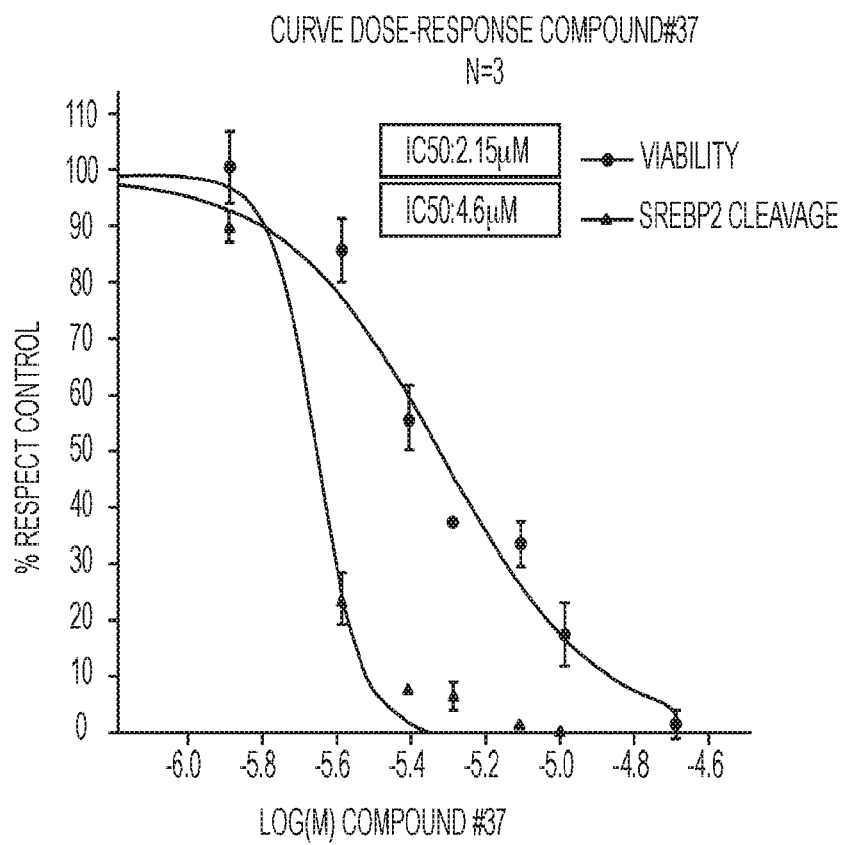
FIG. 1B. Dose-response curves for $IC_{50}$ of Compound #37 for SREBP cleavage in HepG2 cells determined by Western blot and $IC_{50}$ of Compound #37 for effect on HepG2 cell viability. Error bars are ±SEM.

Compound #37 reduces SREBP cleavage in a concentration-dependent manner with an $IC_{50}$ of 4.6 µM in HepG2 cells when analyzed by Western blot following 24 hours of treatment (FIG. 1A and FIG. 1B).

Figure 1C:
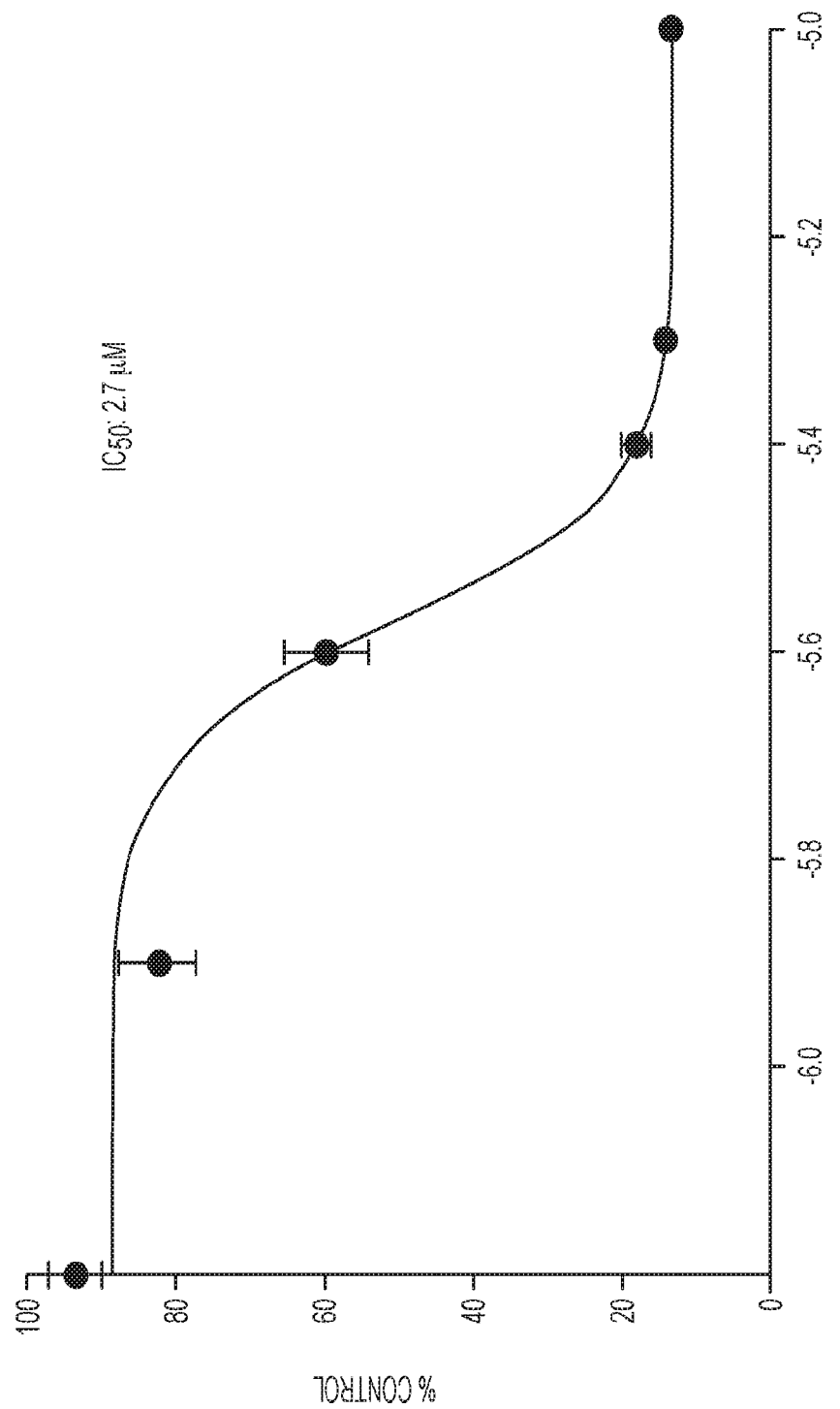
FIG. 1C. Dose-response curve for $IC_{50}$ of Compound #37 for SREBP cleavage in HepG2 cells determined by luciferase expression. Error bars are ±SEM.

Inhibition of SREBP activity by Compound #37 was further demonstrated in a HepG2 reporter cell line with luciferase synthesis driven by an SREBP-responsive promoter (HepG2_LSSprom). HepG2_LSSprom cells were cultured in DMEM with 10% fetal bovine serum and 1% penicillin/streptomycin for 24 hours. Cells were then treated with increasing concentrations of Compound #37 or an equal volume of DMSO in culture medium without serum. Luciferase expression was measured and compared after 6 hours of treatment. The results are shown in FIG. 1C. Similar to the results shown by Western blot, Compound #37 reduced luciferase expression in a dose-dependent manner with an $IC_{50}$ of 2.7 µM In these complementary SREBP cell-based activity assays, Compound #37 consistently exhibited an $IC_{50}$ between 2 and 5 µM for inhibiting SREBP activation. Consistent with the dependence on de novo lipogenesis, inhibition of SREBP activation by Compound #37 in this cell-based model led to decreased viability of HepG2 cells with an $IC_{50}$ of 2.1 µM, as shown in FIG. 1B.

Example B1B

Effect of Compound #37 on Gene Expression in HepG2 Cells

Figure 3:
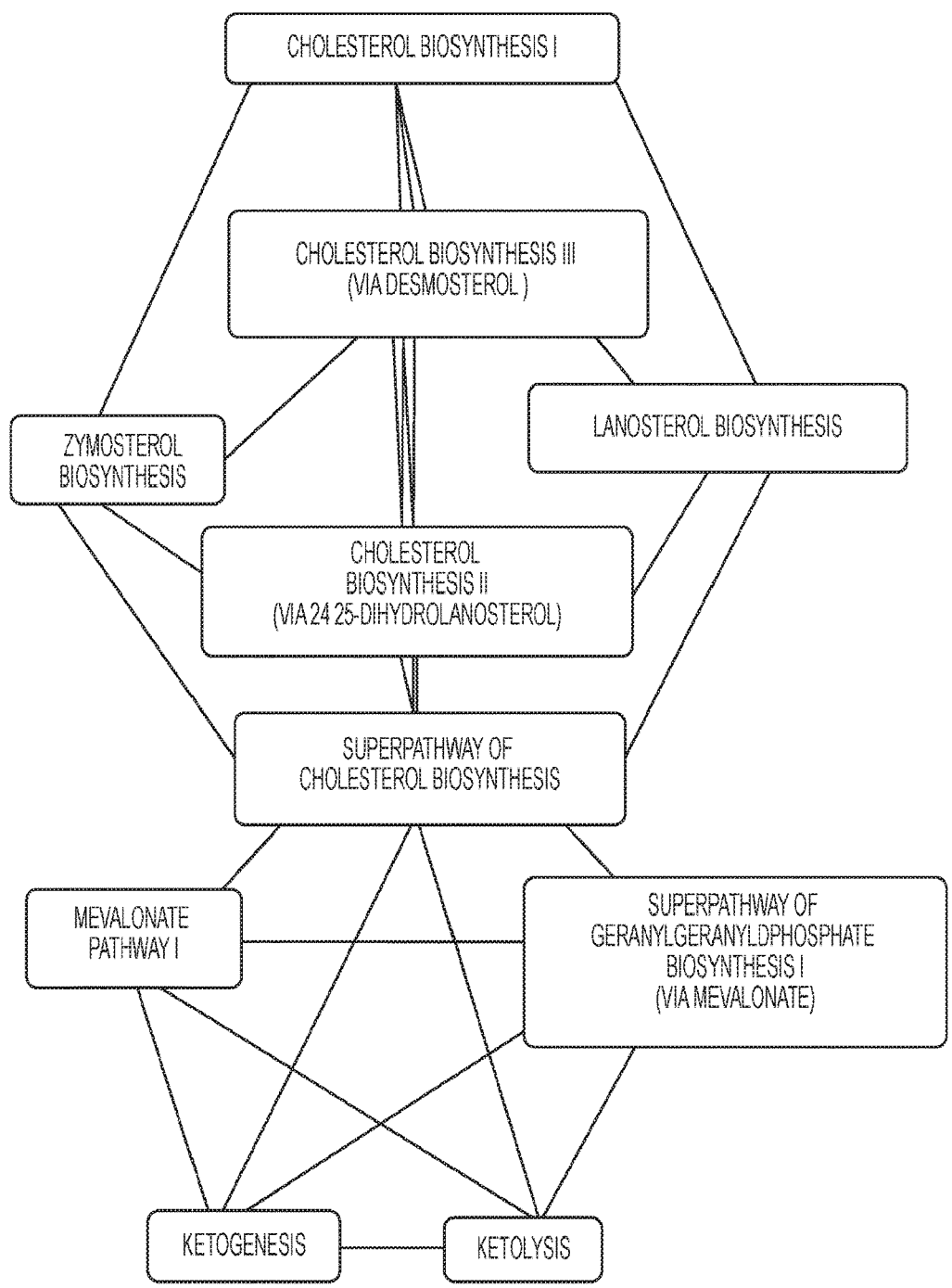
FIG. 3. Summary of lipid and cholesterol pathways down-regulated by Compound #37 based on total transcriptome mRNA levels determined by microarray. Degree of pathway down-regulation is indicated by the shading, with darker shading indicating greater inhibition.

HepG2 cells were incubated with 10 µM Compound #37 in DMSO in serum-free conditions for 16 hours followed by microarray analysis of SREBP-driven gene expression performed with Ingenuity Pathway Analysis software. This analysis revealed that the major SREBP pathways involved in lipid and cholesterol biosynthesis were down-regulated in Compound #37-treated cells. Many of the genes altered are direct transcriptional targets of SREBP, indicating that inhibition of SREBP cleavage by Compound #37 is sufficient to reduce expression of SREBP target genes. A summary of lipid and cholesterol pathways down-regulated by Compound #37 is presented in FIG. 3.

Overall, the in vitro studies in Examples B1A and B1B demonstrate that Compound #37 prevents SREBP cleavage activation, and as a consequence, down-regulates SREBP target gene expression. These data are consistent with the inhibition of SREBP activation demonstrated by fatostatin (Kamisuki et al, 2009).

Example B2

PK Data for Representative Compounds

Standard PK parameters were collected in Mouse and Dog for Compound #37 in mouse (FIG. 2A) and dog (FIG. 2B). Data for additional compounds was collected and is presented in Table 4:

TABLE 4

PK parameters for representative compounds

| | i.v. @ 2 mg/kg | | | | | p.o. @ 10 mg/kg | | | | |
|---|---|---|---|---|---|---|---|---|---|---|
| Cpd No. | Cmax (µM) | $AUC_{last}$ (µM*h) | Terminal $t_{1/2}$ (h) | CL (L/h/kg) | $V_d$ (L/kg) | $C_{max}$ (µM) | $T_{max}$ (h) | $AUC_{last}$ (µM*h) | Terminal $t_{1/2}$ (h) | Bioavailability |
| 5 | 10.2 | 41 | 2.51 | 0.095 | 0.345 | 20.3 | 1 | 302 | 6.96 | 149.0% |
| 60 | 3.38 | 12.6 | 3.08 | 0.288 | 1.28 | 6.58 | 4 | 57.1 | >8 hrs | 90.20% |
| 64 | 7.13 | 38.5 | | 0.055 | 1.95 | 32.1 | 24 | 526 | >8 hrs | 273% |
| 70 | 4 | 2.2 | 1.1 | 3.28 | 5.22 | 2.2 | 0.5 | 5.19 | 1.04 | 46.4% |
| 71 | 3.57 | 13.6 | 3.5 | 0.251 | 1.27 | 7.57 | 4 | 51.5 | >8 hrs | 75.9% |
| 80 | 3.63 | 8.94 | 2.8 | 4.25 | 1.72 | 20.6 | 4 | 130 | >8 hrs | 291.0% |
| 82 | 12.6 | 25.4 | 3.64 | 0.137 | 0.719 | 25.8 | 4 | 175 | >8 hrs | 138.0% |
| 85 | 0.241 | 0.655 | 4.08 | 4.63 | 27.3 | 0.45 | 2 | 2.27 | >8 hrs | 69.3% |
| 88 | 3.44 | 10.6 | 3.35 | 0.3 | 1.45 | 8.41 | 2 | 51.5 | >8 hrs | 96.8% |

Example B3

Effects of Compound #37 on Liver Injuries in a Short-Term (21 day) Induced NASH Mouse Model This example demonstrates the effects of Compound #37 on liver injuries in a short-term (21 day) induced NASH mouse model generated using a 60% high fat Paigen diet.

C57BL/6J mice who are fed an atherogenic Paigen diet, a high-fat (60% fat), high-cholesterol (1.25%) diet supplemented with cholate (0.5%) have been shown to have acute liver damage with significant, predominantly mononuclear, leukocyte infiltration in the liver, severe hepatic steatosis, elevated hepatic expression of inflammatory cytokines (MCP-1, RANTES, and MIP-2), increased serum liver transaminase concentrations, and increased molecular markers of fibrosis (Desai et al, 2008; Vergnes et al, 2003; Nishina et al, 1993).

To investigate whether Compound #37 prevents the development of pathology associated with NASH and steatosis in an acute exploratory disease model, a study was conducted using a diet-induced acute liver steatosis model in mice. As described below, in this study, C57BL/6J mice were initiated on the Paigen diet and simultaneously treated with Compound #37 (5, 20, and 40 mg/kg/day) or vehicle control (20% HPβCD 10 mL/kg/day) by oral gavage for 21 days.

After acclimation, 8-week old male C57Bl/6J mice (Charles River) weighing about 25 g were randomized in 4 groups according their body weight and treated once daily around noon by oral gavage with vehicle, or Compound #37 at various for 21 days as follows: Group 1: vehicle-20% (2-hydroxypropyl)-β-cyclodextrin (HP-β-CD) (n=10); Group 2: Compound #37, 5 mg/kg (n=10) Group 3: Compound #37, 20 mg/kg (n=10) Group 4: Compound #37, 40 mg/kg (n=10). During the treatment period, body weight and food intake (measured over 24h) were measured 3 times per week and once a week, respectively. During the acclimation, all mice were fed a standard diet (Special Diets Services RM1 (E), product no. 801492) and tap water ad libitum. After the acclimation period, mice were fed until the end of the experiment with a 60% high fat Paigen diet (60 kcal % fat, 1.25% cholesterol, and 0.5% cholate; D11061901, Research Diet) and tap water ad libitum.

After 21 days of treatment, mice were 4-hour fasted (9 am to 1 pm). One hour after the last dosing (noon), blood was collected by retro-orbital bleeding (maximal volume on EDTA) under isoflurane anesthesia to measure plasma triglycerides, total cholesterol, non-esterified fatty acid, ALT and AST. Mice were then sacrificed by cervical dislocation, and livers were harvested and weighed. Liver samples from the same lobe were dissected, frozen, and analyzed as described below.

Data Analysis. Values are presented as mean±standard error of the mean (sem). To assess the compound effect, treated groups were compared to vehicle with a 1-way ANOVA+Dunnett's post-test. When variances were significantly different a Kruskall-Wallis test was performed. For RT-qPCR and score Kruskall-Wallis test was performed with Dunns post-test. For body weight evolution the treated groups were compared to vehicle with a 2-way ANOVA with Bonferroni post-test. For each test, a p<0.05 was considered significant.

Results. The day following the start of diet and treatment, Compound #37 at 20 mg/kg and at 40 mg/kg induced a body weight decrease and death in some mice. Treatment with Compound #37 at 40 mg/kg was stopped after 4 administrations. Mice were maintained on specific diet and were sacrificed after 9 days of diet. The treatment with Compound #37 at 20 mg/kg was maintained, and the mice that were still alive recovered. Body weight evolution of Compound #37-treated groups was similar to vehicle and was associated with similar food intake.

After 21 days of diet, treatment with Compound #37 at 5 mg/kg and 20 mg/kg tended to prevent plasma ALT and AST increase. Mice treated with Compound #37 at 40 mg/kg displayed very high ALT and AST levels at day 9, which may be related to an acute effect of the diet or the potential liver toxicity effect of Compound #37 at 40 mg/kg in combination with the diet. After 21 days, treatment with Compound #37 at 20 mg/kg significantly decreased free fatty acids and tended to prevent triglyceride plasma levels. Plasma cholesterol levels were unchanged. See Tables 5A and 5B.

TABLE 5A

Plasma levels of cholesterol, triglycerides, and free fatty acids after 21 days of diet and treatment

| Group | animal # | ALT (U/L) | AST (U/L) | AST/ALT ratio |
|---|---|---|---|---|
| vehicle | 7 | 960 | 1415 | 1.47 |
| | 15 | 1800 | 1260 | 0.7 |
| | 17 | 507 | 615 | 1.21 |
| | 20 | 344 | 416 | 1.21 |
| | 24 | 309 | 425 | 1.38 |
| | 26 | 634 | 619 | 0.98 |
| | 27 | 372 | 480 | 1.29 |
| | 31 | 200 | 221 | 1.11 |
| | 35 | 278 | 434 | 1.56 |
| | 39 | 359 | 439 | 1.22 |
| | mean | 576.3 | 632.4 | 1.2 |
| | SD | 482.8 | 389.6 | 0.2 |
| | sem | 152.7 | 123.2 | 0.1 |
| | n | 10 | 10 | 10 |
| 5 mg/kg | 2 | 382 | 350 | 0.92 |
| | 5 | 620 | ND | ND |
| | 6 | 346 | 416 | 1.20 |
| | 8 | 825 | 710 | 0.86 |
| | 12 | 267 | 405 | 1.52 |
| | 19 | 246 | 286 | 1.16 |
| | 23 | 255 | 392 | 1.54 |
| | 36 | 447 | 481 | 1.08 |
| | 37 | 435 | 528 | 1.21 |
| | 38 | 370 | 477 | 1.29 |
| | mean | 419.3 | 449.4 | 1.2 |
| | sd | 181.1 | 121.9 | 0.2 |
| | sem | 57.3 | 40.6 | 0.1 |
| | n | 10 | 9 | 9 |
| 20 mg/kg | 3 | 266 | 362 | 1.36 |
| | 16 | 587 | 467 | 0.80 |
| | 21 | 432 | 344 | 0.80 |
| | 28 | 413 | 615 | 1.49 |
| | 32 | 385 | 424 | 1.10 |
| | 40 | 338 | 375 | 1.11 |
| | mean | 403.5 | 431.2 | 1.1 |
| | sd | 107.8 | 100.7 | 0.3 |
| | sem | 44.0 | 41.1 | 0.1 |
| | n | 6 | 6 | 6 |

TABLE 5B

Plasma levels of cholesterol, triglycerides, and free fatty acids after 9 days of diet and treatment

| Group | animal # | ALT (U/L) | AST (U/L) | AST/ALT ratio |
|---|---|---|---|---|
| 40 mg/kg | 25 | 1095 | 1165 | 1.1 |
| | 30 | 1160 | 1555 | 1.3 |
| | 33 | 12560 | 3900 | 0.3 |
| | 34 | 13360 | 4120 | 0.3 |
| | mean | 7043.8 | 2685.0 | 0.8 |
| | sd | 6839.4 | 1540.9 | 0.5 |
| | sem | 3419.7 | 770.4 | 0.3 |
| | n | 4 | 4 | 4 |

At the end of the treatment period, livers were weighed, and their lipid content was analyzed. The liver weights were unchanged by the treatment. An increase of liver cholesterol and fatty acid levels were observed in the group treated with Compound #37 at 20 mg/kg. An increase in liver triglycerides tended to be prevented in the groups treated with Compound #37. See Tables 6A and 6B.

TABLE 6A

Liver cholesterol, triglycerides, and fatty acid levels at 21 days of diet and treatment.

| Group | animal # | cholesterol (μg/mg tissue) | triglycerides (μg/mg tissue) | fatty acids (nmol/mg tissue) |
|---|---|---|---|---|
| vehicle | 7 | 35.43 | 8.85 | 56.5 |
|  | 15 | 27.12 | 20.11 | 46.3 |
|  | 17 | 24.55 | 7.29 | 44.7 |
|  | 20 | 25.59 | 6.90 | 46.5 |
|  | 24 | 32.85 | 4.42 | 56.9 |
|  | 26 | 27.78 | 5.39 | 47.5 |
|  | 27 | 27.03 | 5.47 | 41.4 |
|  | 31 | 28.57 | 6.24 | 45.1 |
|  | 35 | 32.61 | 4.04 | 53.2 |
|  | 39 | 36.99 | 7.26 | 70.8 |
|  | mean | 29.9 | 7.6 | 50.9 |
|  | sd | 4.3 | 4.6 | 8.7 |
|  | sem | 1.4 | 1.5 | 2.8 |
|  | n | 10 | 10 | 10 |
| 5 mg/kg | 2 | 42.24 | 6.91 | 65.4 |
|  | 5 | 37.91 | 7.18 | 66.6 |
|  | 6 | 31.39 | 4.64 | 53.5 |
|  | 8 | 23.12 | 9.62 | 47.5 |
|  | 12 | 31.47 | 6.13 | 55.2 |
|  | 19 | 25.31 | 5.69 | 35.5 |
|  | 23 | 29.76 | 5.49 | 55.0 |
|  | 36 | 37.34 | 6.13 | 55.2 |
|  | 37 | 49.15 | 3.62 | 77.4 |
|  | 38 | 36.57 | 6.16 | 65.2 |
|  | mean | 34.4 | 6.2 | 57.6 |
|  | sd | 7.8 | 1.6 | 11.6 |
|  | sem | 2.5 | 0.5 | 3.7 |
|  | n | 10 | 10 | 10 |
| 20 mg/kg | 3 | 38.32 | 6.75 | 63.4 |
|  | 16 | 42.07 | 2.65 | 66.5 |
|  | 21 | 39.38 | 2.83 | 65.0 |
|  | 28 | 32.61 | 3.72 | 50.0 |
|  | 32 | 40.02 | 9.84 | 62.7 |
|  | 40 | 42.44 | 6.82 | 72.5 |
|  | mean | 39.1 | 5.4 | 63.3 |
|  | sd | 3.6 | 2.8 | 7.4 |
|  | sem | 1.5 | 1.2 | 3.0 |
|  | n | 6 | 6 | 6 |

TABLE 6B

Liver cholesterol, triglycerides, and fatty acid levels at 9 days of diet and treatment.

| Group | animal # | cholesterol (μg/mg tissue) | triglycerides (μg/mg tissue) | fatty acids (nmol/mg tissue) |
|---|---|---|---|---|
| 40 mg/kg | 25 | 20.18 | 11.15 | 43.1 |
|  | 30 | 20.88 | 14.68 | 43.5 |
|  | 33 | 17.60 | 11.77 | 41.8 |
|  | 34 | 22.40 | 9.11 | 43.6 |
|  | mean | 20.3 | 11.7 | 43.0 |
|  | sd | 2.0 | 2.3 | 0.8 |
|  | sem | 1.0 | 1.2 | 0.4 |
|  | n | 4 | 4 | 4 |

Oil Red O staining.

One 0.5 cm³ piece of liver was frozen in OCT in isopentane and stored at −80° C. for neutral lipid coloration with quantification to evaluate accumulation of neutral lipids in the liver. One section (thickness 5-7 μm) per block was deposited on superfrost+slides for Red Oil staining. Red Oil-stained slides were digitalized at ×20 with the Nanozoomer 2.0 HT. Red Oil labeling was quantified (surface, density): the stained slides were analyzed using an image. All the samples were analyzed within the same range of labeling intensity (0-130), allowing comparison between animals. The intensity scale ranged from 0 to 255 grey levels, in which 0 is the value of a black pixel, and 255 is the value of a white pixel. The staining intensity was calculated as the mean intensity of each pixel composing the labeling signal. For each slide, the percentage (%) of labeling was also calculated: %=(Surface of labeling*100)/section area.

There were deposits in the OCT, which contributed to the red oil signal from the lipids. A high variability of response in the vehicle group was observed, due in part to one animal. However, treatment with Compound #37 tended to prevent the accumulation of neutral lipids, which was correlated with the tendency of liver triglycerides to decrease. Liver lipids and cholesterol metabolism genes were analyzed by RT-qPCR and were unchanged by the treatment except for the ACC1 gene. Compound #37 decreased ACC1 liver gene expression in a dose-dependent manner. See Tables 7A and 7B.

TABLE 7A

Liver O red Oil staining at 21 days of diet and treatment.

| group | animal # | % labeling |
|---|---|---|
| vehicle | 7 | 3.05 |
|  | 15 | 11.17 |
|  | 17 | 2.91 |
|  | 20 | 4.61 |
|  | 24 | 0.50 |
|  | 26 | 0.36 |
|  | 27 | 0.76 |
|  | 31 | 0.67 |
|  | 35 | 0.09* |
|  | 39 | 1.90 |
|  | mean | 2.88 |
|  | sd | 3.43 |
|  | sem | 1.14 |
|  | n | 9 |
| 5 mg/kg | 2 | 2.08 |
|  | 5 | 2.02 |
|  | 6 | 1.19 |
|  | 8 | 2.18 |
|  | 12 | 1.64 |
|  | 19 | 1.09 |
|  | 23 | 1.16 |
|  | 36 | 1.50 |
|  | 37 | 0.70 |
|  | 38 | 1.39 |
|  | mean | 1.50 |
|  | sd | 0.48 |
|  | sem | 0.15 |
|  | n | 10 |
| 20 mg/kg | 3 | 1.53 |
|  | 16 | 0.81 |
|  | 21 | 0.29 |
|  | 28 | 1.11 |
|  | 32 | 0.92 |
|  | 40 | 0.92 |
|  | mean | 0.93 |
|  | sd | 0.40 |
|  | sem | 0.16 |
|  | n | 6 |

TABLE 7B

Liver O red Oil staining at 9 days of diet and treatment

| Group | animal # | % labeling |
|---|---|---|
| 40 mg//kg | 25 | 2.53 |
|  | 30 | 2.54 |
|  | 33 | 1.12 |
|  | 34 | 1.28 |
|  | mean | 1.87 |
|  | sd | 0.77 |
|  | sem | 0.39 |
|  | n | 4 |

Gene expression analysis. Hepatic expression levels of genes involved in lipid metabolism (FAS, SREBP1, ACC1, SCD1), cholesterol metabolism (HMG-CoAR, LDLR), SREBP proteolysis (SCAP, INSIG1), ER stress (PERK), oxidative stress (NRF2), inflammation (MCP-1), and fibrosis (collagen 1α1) were quantified by RTqPCR. Expression level was normalized to 18S gene expression and relative expression to vehicle group was calculated with the 2-t method.

The 60% high fat Paigen diet induced accumulation of liver lipids, inflammation, oxidative stress, and then fibrosis. Compound #37 at 5 mg/kg tended to decrease in a non-significant manner some gene expression markers of inflammation and oxidative stress, but no clear modifications were observed. Expression of these genes was unchanged in the group treated with Compound #37 at 20 mg/kg, but a tendency to prevent increase in liver IL-6 levels was observed. Compound #37 treatment tended to decrease expression of the collagen 1α1 gene in a dose-dependent manner. The results are shown in Tables 8-13.

TABLE 8A

Lipid metabolism gene expression (21 days): FAS

| Group | No | 18S | FAS | Dct | DDct | 2DDct |
|---|---|---|---|---|---|---|
| Vehicle | 7 | 12.96 | 22.25 | 9.29 | −0.62 | 1.54 |
| | 15 | 11.15 | 21.28 | 10.13 | 0.22 | 0.86 |
| | 17 | 11.14 | 20.72 | 9.58 | −0.33 | 1.26 |
| | 20 | 13.25 | 22.42 | 9.17 | −0.74 | 1.67 |
| | 24 | 11.65 | 22.16 | 10.51 | 0.6 | 0.66 |
| | 26 | 12.41 | 23.01 | 10.6 | 0.69 | 0.62 |
| | 27 | 13.25 | 21.37 | 8.12 | −1.79 | 3.46 |
| | 31 | 11.38 | 21.57 | 10.19 | 0.28 | 0.82 |
| | 35 | 11.26 | 22 | 10.74 | 0.83 | 0.56 |
| | 39 | 11.5 | 22.26 | 10.76 | 0.85 | 0.55 |
| | mean | 12 | 21.9 | 9.9 | 0 | 1.2 |
| | sd | 0.9 | 0.7 | 0.9 | 0.86 | 0.89 |
| | sem | 0.3 | 0.2 | 0.3 | 0.27 | 0.28 |
| | n | 10 | 10 | 10 | 10 | 10 |
| 5 mg/kg | 2 | 13.46 | 22.23 | 8.77 | −1.14 | 2.2 |
| | 5 | 13.11 | 22.4 | 9.29 | −0.62 | 1.54 |
| | 6 | 11.61 | 20.89 | 9.28 | −0.63 | 1.55 |
| | 8 | 13.35 | 22.03 | 8.68 | −1.23 | 2.34 |
| | 12 | 12.03 | 22.49 | 10.46 | 0.55 | 0.68 |
| | 19 | 13.35 | 24.63 | 11.28 | 1.37 | 0.39 |
| | 23 | 11.6 | 21.65 | 10.05 | 0.14 | 0.91 |
| | 36 | 11.79 | 22.31 | 10.52 | 0.61 | 0.65 |
| | 37 | 11.14 | 22.66 | 11.52 | 1.61 | 0.33 |
| | 38 | 11.12 | 21.79 | 10.67 | 0.76 | 0.59 |
| | mean | 12.3 | 22.3 | 10.1 | 0.14 | 1.12 |
| | sd | 1 | 1 | 1 | 1.01 | 0.74 |
| | sem | 0.3 | 0.3 | 0.3 | 0.32 | 0.23 |
| | n | 10 | 10 | 10 | 10 | 10 |
| 20 mg/kg | 3 | 12.91 | 22.25 | 9.34 | −0.57 | 1.48 |
| | 16 | 12.29 | 23.04 | 10.75 | 0.84 | 0.56 |
| | 21 | 12.2 | 22.78 | 10.58 | 0.67 | 0.63 |
| | 28 | 13.03 | 22.22 | 9.19 | −0.72 | 1.65 |
| | 32 | 11.49 | 21.55 | 10.06 | 0.15 | 0.9 |
| | 40 | 11.26 | 20.26 | 9 | −0.91 | 1.88 |
| | mean | 12.2 | 22 | 9.8 | −0.09 | 1.18 |
| | sd | 0.7 | 1 | 0.7 | 0.75 | 0.56 |
| | sem | 0.3 | 0.4 | 0.3 | 0.31 | 0.23 |
| | n | 6 | 6 | 6 | 6 | 6 |

TABLE 8B

Lipid metabolism gene expression (21 days): SCD1

| Group | No | 18S | SCD1 | Dct | DDct | 2DDct |
|---|---|---|---|---|---|---|
| Vehicle | 7 | 12.96 | 19.94 | 6.98 | 1.16 | 0.45 |
| | 15 | 11.15 | 16.71 | 5.56 | −0.26 | 1.19 |

TABLE 8B-continued

Lipid metabolism gene expression (21 days): SCD1

| Group | No | 18S | SCD1 | Dct | DDct | 2DDct |
|---|---|---|---|---|---|---|
| | 17 | 11.14 | 17.76 | 6.62 | 0.8 | 0.57 |
| | 20 | 13.25 | 17.23 | 3.98 | −1.84 | 3.57 |
| | 24 | 11.65 | 17.71 | 6.06 | 0.24 | 0.84 |
| | 26 | 12.41 | 18.17 | 5.76 | −0.06 | 1.04 |
| | 27 | 13.25 | 17.58 | 4.33 | −1.49 | 2.8 |
| | 31 | 11.38 | 18.1 | 6.72 | 0.9 | 0.53 |
| | 35 | 11.26 | 17.62 | 6.36 | 0.54 | 0.69 |
| | 39 | 11.5 | 17.3 | 5.8 | −0.02 | 1.01 |
| | mean | 12 | 17.8 | 5.8 | 0 | 1.27 |
| | sd | 0.9 | 0.9 | 1 | 0.99 | 1.05 |
| | sem | 0.3 | 0.3 | 0.3 | 0.31 | 0.33 |
| | n | 10 | 10 | 10 | 10 | 10 |
| 5 mg/kg | 2 | 13.46 | 17.71 | 4.25 | −1.57 | 2.96 |
| | 5 | 13.11 | 18.94 | 5.83 | 0.01 | 0.99 |
| | 6 | 11.61 | 18.03 | 6.42 | 0.6 | 0.66 |
| | 8 | 13.35 | 18.15 | 4.8 | −1.02 | 2.02 |
| | 12 | 12.03 | 18.23 | 6.2 | 0.38 | 0.77 |
| | 19 | 13.35 | 21.37 | 8.02 | 2.2 | 0.22 |
| | 23 | 11.6 | 17.52 | 5.92 | 0.1 | 0.93 |
| | 36 | 11.79 | 18.01 | 6.22 | 0.4 | 0.76 |
| | 37 | 11.14 | 17.69 | 6.55 | 0.73 | 0.6 |
| | 38 | 11.12 | 17.7 | 6.58 | 0.76 | 0.59 |
| | mean | 12.3 | 18.3 | 6.1 | 0.26 | 1.05 |
| | sd | 1 | 1.1 | 1 | 1.03 | 0.82 |
| | sem | 0.3 | 0.4 | 0.3 | 0.32 | 0.26 |
| | n | 10 | 10 | 10 | 10 | 10 |
| 20 mg/kg | 3 | 12.91 | 18.75 | 5.84 | 0.02 | 0.98 |
| | 16 | 12.29 | 19.21 | 6.92 | 1.1 | 0.47 |
| | 21 | 12.2 | 18.2 | 6 | 0.18 | 0.88 |
| | 28 | 13.03 | 17.66 | 4.63 | −1.19 | 2.28 |
| | 32 | 11.49 | 18.39 | 6.9 | 1.08 | 0.47 |
| | 40 | 11.26 | 16.08 | 4.82 | −1 | 2 |
| | mean | 12.2 | 18 | 5.9 | 0.03 | 1.18 |
| | sd | 0.7 | 1.1 | 1 | 0.98 | 0.78 |
| | sem | 0.3 | 0.4 | 0.4 | 0.4 | 0.32 |
| | n | 6 | 6 | 6 | 6 | 6 |

TABLE 8C

Lipid metabolism gene expression (21 days): SREBP1C

| Group | No | 18S | SREBP1C | Dct | DDct | 2DDct |
|---|---|---|---|---|---|---|
| Vehicle | 7 | 12.96 | 27.64 | 14.68 | 0.9 | 0.54 |
| | 15 | 11.15 | 24.42 | 13.27 | −0.51 | 1.43 |
| | 17 | 11.14 | 26.39 | 15.25 | 1.47 | 0.36 |
| | 20 | 13.25 | 26.73 | 13.48 | −0.3 | 1.23 |
| | 24 | 11.65 | 25.69 | 14.04 | 0.26 | 0.84 |
| | 26 | 12.41 | 26.37 | 13.96 | 0.18 | 0.88 |
| | 27 | 13.25 | 25.05 | 11.8 | −1.98 | 3.95 |
| | 31 | 11.38 | 25.31 | 13.93 | 0.15 | 0.9 |
| | 35 | 11.26 | 25.23 | 13.97 | 0.19 | 0.88 |
| | 39 | 11.5 | 24.95 | 13.45 | −0.33 | 1.26 |
| | mean | 12 | 25.8 | 13.8 | 0 | 1.23 |
| | sd | 0.9 | 1 | 0.9 | 0.91 | 1.01 |
| | sem | 0.3 | 0.3 | 0.3 | 0.29 | 0.32 |
| | n | 10 | 10 | 10 | 10 | 10 |
| 5 mg/kg | 2 | 13.46 | 27.03 | 13.57 | −0.21 | 1.16 |
| | 5 | 13.11 | 27.79 | 14.68 | 0.9 | 0.54 |
| | 6 | 11.61 | 25.45 | 13.84 | 0.06 | 0.96 |
| | 8 | 13.35 | 26.15 | 12.8 | −0.98 | 1.98 |
| | 12 | 12.03 | 27.27 | 15.24 | 1.46 | 0.36 |
| | 19 | 13.35 | 28.65 | 15.3 | 1.52 | 0.35 |
| | 23 | 11.6 | 25.29 | 13.69 | −0.09 | 1.07 |
| | 36 | 11.79 | 25.3 | 13.51 | −0.27 | 1.21 |
| | 37 | 11.14 | 25.09 | 13.95 | 0.17 | 0.89 |
| | 38 | 11.12 | 24.92 | 13.8 | 0.02 | 0.99 |
| | mean | 12.3 | 26.3 | 14 | 0.26 | 0.95 |
| | sd | 1 | 1.3 | 0.8 | 0.8 | 0.48 |
| | sem | 0.3 | 0.4 | 0.3 | 0.25 | 0.15 |
| | n | 10 | 10 | 10 | 10 | 10 |
| 20 mg/kg | 3 | 12.91 | 27.19 | 14.28 | 0.5 | 0.71 |
| | 16 | 12.29 | 26.45 | 14.16 | 0.38 | 0.77 |

TABLE 8C-continued

Lipid metabolism gene expression (21 days): SREBP1C

| Group | No | 18S | SREBP1C | Dct | DDct | 2DDct |
|---|---|---|---|---|---|---|
| | 21 | 12.2 | 26.09 | 13.89 | 0.11 | 0.93 |
| | 28 | 13.03 | 25.45 | 12.42 | −1.36 | 2.57 |
| | 32 | 11.49 | 25.93 | 14.44 | 0.66 | 0.63 |
| | 40 | 11.26 | 23.96 | 12.7 | −1.08 | 2.12 |
| | mean | 12.2 | 25.8 | 13.6 | −0.13 | 1.29 |
| | sd | 0.7 | 1.1 | 0.9 | 0.87 | 0.84 |
| | sem | 0.3 | 0.4 | 0.4 | 0.35 | 0.34 |
| | n | 6 | 6 | 6 | 6 | 6 |

TABLE 8D

Lipid metabolism gene expression (21 days): ACC1

| Group | No | 18S | ACC1 | Dct | DDct | 2DDct |
|---|---|---|---|---|---|---|
| Vehicle | 7 | 12.96 | 32.8 | 19.84 | 1.92 | 0.26 |
| | 15 | 11.15 | 28.48 | 17.33 | −0.59 | 1.51 |
| | 17 | 11.14 | 30.19 | 19.05 | 1.13 | 0.46 |
| | 20 | 13.25 | 30.61 | 17.36 | −0.56 | 1.47 |
| | 24 | 11.65 | 29.85 | 18.2 | 0.28 | 0.82 |
| | 26 | 12.41 | 29.78 | 17.37 | −0.55 | 1.46 |
| | 27 | 13.25 | 28.92 | 15.67 | −2.25 | 4.76 |
| | 31 | 11.38 | 25.26 | 13.88* | −3.64* | 12.43* |
| | 35 | 11.26 | 30.65 | 19.39 | 1.47 | 0.36 |
| | 39 | 11.5 | 28.57 | 17.07 | −0.85 | 1.8 |
| | mean | 12 | 29.5 | 17.9 | 0 | 1.43 |
| | sd | 0.9 | 2 | 1.3 | 1.32 | 1.37 |
| | sem | 0.3 | 0.6 | 0.4 | 0.44 | 0.46 |
| | n | 10 | 10 | 9 | 9 | 9 |
| 5 mg/kg | 2 | 13.46 | 32.46 | 19 | 1.08 | 0.47 |
| | 5 | 13.11 | 31.81 | 18.7 | 0.78 | 0.58 |
| | 6 | 11.61 | 31.41 | 19.8 | 1.88 | 0.27 |
| | 8 | 13.35 | 34.39 | 21.04 | 3.12 | 0.12 |
| | 12 | 12.03 | ND | ND | ND | ND |
| | 19 | 13.35 | ND | ND | ND | ND |
| | 23 | 11.6 | 28.99 | 17.39 | −0.53 | 1.44 |
| | 36 | 11.79 | 28.84 | 17.05 | −0.87 | 1.83 |
| | 37 | 11.14 | 30.07 | 18.93 | 1.01 | 0.5 |
| | 38 | 11.12 | 29.05 | 17.93 | 0.01 | 0.99 |
| | mean | 12.3 | 30.9 | 18.7 | 0.81 | 0.78 |
| | sd | 1 | 2 | 1.3 | 1.3 | 0.6 |
| | sem | 0.3 | 0.7 | 0.5 | 0.46 | 0.21 |
| | n | 10 | 8 | 8 | 8 | 8 |
| 20 mg/kg | 3 | 12.91 | 31.43 | 18.52 | 0.6 | 0.66 |
| | 16 | 12.29 | 37.36 | 25.07 | 7.15 | 0.01 |
| | 21 | 12.2 | 33.78 | 21.58 | 3.66 | 0.08 |
| | 28 | 13.03 | 31.41 | 18.38 | 0.46 | 0.73 |
| | 32 | 11.49 | 33.32 | 21.83 | 3.91 | 0.07 |
| | 40 | 11.26 | 29.63 | 18.37 | 0.45 | 0.73 |
| | mean | 12.2 | 32.8 | 20.6 | 2.71 | 0.38 |
| | sd | 0.7 | 2.7 | 2.7 | 2.71 | 0.36 |
| | sem | 0.3 | 1.1 | 1.1 | 1.11 | 0.15 |
| | n | 6 | 6 | 6 | 6 | 6 |

TABLE 8E

Lipid metabolism gene expression (21 days): SCAP

| Group | No | 18S | SCAP | Dct | DDct | 2DDct |
|---|---|---|---|---|---|---|
| Vehicle | 7 | 12.96 | 26.59 | 13.6 | 0.97 | 0.51 |
| | 15 | 11.15 | 23.78 | 12.63 | −0.03 | 1.02 |
| | 17 | 11.14 | 25.51 | 14.37 | 1.71 | 0.31 |
| | 20 | 13.25 | 25.19 | 11.94 | −0.72 | 1.65 |
| | 24 | 11.65 | 24.43 | 12.78 | 0.12 | 0.92 |
| | 26 | 12.41 | 25.13 | 12.72 | 0.06 | 0.96 |
| | 27 | 13.25 | 23.95 | 10.7 | −1.96 | 3.89 |
| | 31 | 11.38 | 24.59 | 13.21 | 0.55 | 0.68 |
| | 35 | 11.26 | 23.84 | 12.58 | −0.08 | 1.06 |
| | 39 | 11.5 | 23.53 | 12.03 | −0.63 | 1.55 |
| | mean | 12 | 24.7 | 12.7 | 0 | 1.25 |
| | sd | 0.9 | 1 | 1 | 1 | 1.01 |
| | sem | 0.3 | 0.3 | 0.3 | 0.32 | 0.32 |
| | n | 10 | 10 | 10 | 10 | 10 |
| 5 mg/kg | 2 | 13.46 | 25.42 | 11.96 | −0.7 | 1.62 |
| | 5 | 13.11 | 26.49 | 13.38 | 0.72 | 0.61 |
| | 6 | 11.61 | 24.17 | 12.56 | −0.1 | 1.07 |
| | 8 | 13.35 | 25.83 | 12.48 | −0.18 | 1.13 |
| | 12 | 12.03 | 25.9 | 13.87 | 1.21 | 0.43 |
| | 19 | 13.35 | 26.71 | 13.36 | 0.7 | 0.62 |
| | 23 | 11.6 | 24.53 | 12.93 | 0.27 | 0.83 |
| | 36 | 11.79 | 24.24 | 12.45 | −0.21 | 1.16 |
| | 37 | 11.14 | 23.78 | 12.64 | −0.02 | 1.01 |
| | 38 | 11.12 | 23.95 | 12.83 | 0.17 | 0.89 |
| | mean | 12.3 | 25.1 | 12.8 | 0.19 | 0.94 |
| | sd | 1 | 1.1 | 0.6 | 0.56 | 0.34 |
| | sem | 0.3 | 0.3 | 0.2 | 0.18 | 0.11 |
| | n | 10 | 10 | 10 | 10 | 10 |
| 20 mg/kg | 3 | 12.91 | 26.17 | 13.26 | 0.6 | 0.66 |
| | 16 | 12.29 | 25.78 | 13.49 | 0.83 | 0.56 |
| | 21 | 12.2 | 25.19 | 12.99 | 0.33 | 0.79 |
| | 28 | 13.03 | 24.4 | 11.37 | −1.29 | 2.44 |
| | 32 | 11.49 | 25.05 | 13.56 | 0.9 | 0.54 |
| | 40 | 11.26 | 22.98 | 11.72 | −0.94 | 1.92 |
| | mean | 12.2 | 24.9 | 12.7 | 0.07 | 1.15 |
| | sd | 0.7 | 1.1 | 0.9 | 0.95 | 0.82 |
| | sem | 0.3 | 0.5 | 0.4 | 0.39 | 0.33 |
| | n | 6 | 6 | 6 | 6 | 6 |

TABLE 8F

Lipid metabolism gene expression (21 days): INSIG1

| Group | No | 18S | INSIG1 | Dct | DDct | 2DDct |
|---|---|---|---|---|---|---|
| Vehicle | 7 | 12.96 | 25.29 | 12.33 | 0.65 | 0.64 |
| | 15 | 11.15 | 22.6 | 11.45 | −0.23 | 1.18 |
| | 17 | 11.14 | 23.06 | 11.92 | 0.24 | 0.85 |
| | 20 | 13.25 | 24.5 | 11.25 | −0.43 | 1.35 |
| | 24 | 11.65 | 23.76 | 12.11 | 0.43 | 0.74 |
| | 26 | 12.41 | 24.06 | 11.65 | −0.03 | 1.02 |
| | 27 | 13.25 | 24.05 | 10.8 | −0.88 | 1.85 |
| | 31 | 11.38 | 23.49 | 12.11 | 0.43 | 0.74 |
| | 35 | 11.26 | 23.08 | 11.82 | 0.14 | 0.91 |
| | 39 | 11.5 | 22.9 | 11.4 | −0.28 | 1.22 |
| | mean | 12 | 23.7 | 11.7 | 0 | 1.05 |
| | sd | 0.9 | 0.8 | 0.5 | 0.47 | 0.36 |
| | sem | 0.3 | 0.3 | 0.1 | 0.15 | 0.11 |
| | n | 10 | 10 | 10 | 10 | 10 |
| 5 mg/kg | 2 | 13.46 | 24.56 | 11.1 | −0.58 | 1.5 |
| | 5 | 13.11 | 25 | 11.89 | 0.21 | 0.87 |
| | 6 | 11.61 | 23.77 | 12.16 | 0.48 | 0.72 |
| | 8 | 13.35 | 25 | 11.65 | −0.03 | 1.02 |
| | 12 | 12.03 | 24.05 | 12.02 | 0.34 | 0.79 |
| | 19 | 13.35 | 26.48 | 13.13 | 1.45 | 0.37 |
| | 23 | 11.6 | 23.37 | 11.77 | 0.09 | 0.94 |
| | 36 | 11.79 | 23.99 | 12.2 | 0.52 | 0.7 |
| | 37 | 11.14 | 23.14 | 12 | 0.32 | 0.8 |
| | 38 | 11.12 | 22.85 | 11.73 | 0.05 | 0.97 |
| | mean | 12.3 | 24.2 | 12 | 0.28 | 0.87 |
| | sd | 1 | 1.1 | 0.5 | 0.52 | 0.29 |
| | sem | 0.3 | 0.3 | 0.2 | 0.16 | 0.09 |
| | n | 10 | 10 | 10 | 10 | 10 |
| 20 mg/kg | 3 | 12.91 | 25.09 | 12.18 | 0.5 | 0.71 |
| | 16 | 12.29 | 24.72 | 12.43 | 0.75 | 0.6 |
| | 21 | 12.2 | 24.39 | 12.19 | 0.51 | 0.7 |
| | 28 | 13.03 | 24.04 | 11.01 | −0.67 | 1.6 |
| | 32 | 11.49 | 23.79 | 12.3 | 0.62 | 0.65 |
| | 40 | 11.26 | 22.18 | 10.92 | −0.76 | 1.7 |
| | mean | 12.2 | 24 | 11.8 | 0.15 | 0.99 |
| | sd | 0.7 | 1 | 0.7 | 0.68 | 0.51 |
| | sem | 0.3 | 0.4 | 0.3 | 0.28 | 0.21 |
| | n | 6 | 6 | 6 | 6 | 6 |

TABLE 9A

Cholesterol metabolism genes expression: HMGCoA

| Group | No | 18S | HMGCoA | Dct | DDct | 2DDct |
|---|---|---|---|---|---|---|
| Vehicle | 7 | 12.96 | 26.27 | 13.31 | 0.44 | 0.74 |
|  | 15 | 11.15 | 23.46 | 12.31 | −0.56 | 1.47 |
|  | 17 | 11.14 | 24.5 | 13.36 | 0.49 | 0.71 |
|  | 20 | 13.25 | 26.15 | 12.9 | 0.03 | 0.98 |
|  | 24 | 11.65 | 24.92 | 13.27 | 0.40 | 0.76 |
|  | 26 | 12.41 | 25.17 | 12.76 | −0.11 | 1.08 |
|  | 27 | 13.25 | 25.14 | 11.89 | −0.98 | 1.97 |
|  | 31 | 11.38 | 24.76 | 13.38 | 0.51 | 0.70 |
|  | 35 | 11.26 | 24.19 | 12.93 | 0.06 | 0.96 |
|  | 39 | 11.5 | 24.05 | 12.55 | −0.32 | 1.24 |
|  | mean | 12.0 | 24.9 | 12.9 | 0.00 | 1.06 |
|  | sd | 0.9 | 0.9 | 0.5 | 0.50 | 0.41 |
|  | sem | 0.3 | 0.3 | 0.2 | 0.16 | 0.13 |
|  | n | 10 | 10 | 10 | 10 | 10 |
| 5 mg/kg | 2 | 13.46 | 25.94 | 12.48 | −0.39 | 1.31 |
|  | 5 | 13.11 | 26.3 | 13.19 | 0.32 | 0.80 |
|  | 6 | 11.61 | 24.57 | 12.96 | 0.09 | 0.94 |
|  | 8 | 13.35 | 26.14 | 12.79 | −0.08 | 1.05 |
|  | 12 | 12.03 | 25.77 | 13.74 | 0.87 | 0.55 |
|  | 19 | 13.35 | 26.85 | 13.5 | 0.63 | 0.64 |
|  | 23 | 11.6 | 24.44 | 12.84 | −0.03 | 1.02 |
|  | 36 | 11.79 | 24.76 | 12.97 | 0.10 | 0.93 |
|  | 37 | 11.14 | 24.36 | 13.22 | 0.35 | 0.78 |
|  | 38 | 11.12 | 24.19 | 13.07 | 0.20 | 0.87 |
|  | mean | 12.3 | 25.3 | 13.1 | 0.21 | 0.89 |
|  | sd | 1.0 | 1.0 | 0.4 | 0.36 | 0.22 |
|  | sem | 0.3 | 0.3 | 0.1 | 0.11 | 0.07 |
|  | n | 10 | 10 | 10 | 10 | 10 |
| 20 mg/kg | 3 | 12.91 | 26.35 | 13.44 | 0.57 | 0.67 |
|  | 16 | 12.29 | 26.22 | 13.93 | 1.06 | 0.48 |
|  | 21 | 12.2 | 25.65 | 13.45 | 0.58 | 0.67 |
|  | 28 | 13.03 | 25.5 | 12.47 | −0.40 | 1.32 |
|  | 32 | 11.49 | 25.13 | 13.64 | 0.77 | 0.58 |
|  | 40 | 11.26 | 23.49 | 12.23 | −0.64 | 1.55 |
|  | mean | 12.2 | 25.4 | 13.2 | 0.33 | 0.88 |
|  | sd | 0.7 | 1.0 | 0.7 | 0.68 | 0.44 |
|  | sem | 0.3 | 0.4 | 0.3 | 0.28 | 0.18 |
|  | n | 6 | 6 | 6 | 6 | 6 |

TABLE 9B

Cholesterol metabolism genes expression: LDLR

| Group | No | 18S | LDLR | Dct | DDct | 2DDct |
|---|---|---|---|---|---|---|
| Vehicle | 7 | 12.96 | 26.32 | 13.36 | 0.70 | 0.61 |
|  | 15 | 11.15 | 23.24 | 12.09 | −0.57 | 1.48 |
|  | 17 | 11.14 | 24.91 | 13.77 | 1.11 | 0.46 |
|  | 20 | 13.25 | 25.49 | 12.24 | −0.42 | 1.34 |
|  | 24 | 11.65 | 24.71 | 13.06 | 0.40 | 0.76 |
|  | 26 | 12.41 | 25.81 | 13.4 | 0.74 | 0.60 |
|  | 27 | 13.25 | 24.04 | 10.79 | −1.87 | 3.65 |
|  | 31 | 11.38 | 24.63 | 13.25 | 0.59 | 0.66 |
|  | 35 | 11.26 | 23.72 | 12.46 | −0.20 | 1.15 |
|  | 39 | 11.5 | 23.66 | 12.16 | −0.50 | 1.41 |
|  | mean | 12.0 | 24.7 | 12.7 | 0.00 | 1.21 |
|  | sd | 0.9 | 1.0 | 0.9 | 0.89 | 0.94 |
|  | sem | 0.3 | 0.3 | 0.3 | 0.28 | 0.30 |
|  | n | 10 | 10 | 10 | 10 | 10 |
| 5 mg/kg | 2 | 13.46 | 25.2 | 11.74 | −0.92 | 1.89 |
|  | 5 | 13.11 | 25.9 | 12.79 | 0.13 | 0.91 |
|  | 6 | 11.61 | 23.67 | 12.06 | −0.60 | 1.51 |
|  | 8 | 13.35 | 25.03 | 11.68 | −0.98 | 1.97 |
|  | 12 | 12.03 | 26.15 | 14.12 | 1.46 | 0.36 |
|  | 19 | 13.35 | 27.4 | 14.05 | 1.39 | 0.38 |
|  | 23 | 11.6 | 24.3 | 12.7 | 0.04 | 0.97 |
|  | 36 | 11.79 | 24.78 | 12.99 | 0.33 | 0.79 |
|  | 37 | 11.14 | 24.32 | 13.18 | 0.52 | 0.70 |
|  | 38 | 11.12 | 24.15 | 13.03 | 0.37 | 0.77 |
|  | mean | 12.3 | 25.1 | 12.8 | 0.18 | 1.03 |
|  | sd | 1.0 | 1.1 | 0.8 | 0.85 | 0.57 |
|  | sem | 0.3 | 0.4 | 0.3 | 0.27 | 0.18 |
|  | n | 10 | 10 | 10 | 10 | 10 |

TABLE 9B-continued

Cholesterol metabolism genes expression: LDLR

| Group | No | 18S | LDLR | Dct | DDct | 2DDct |
|---|---|---|---|---|---|---|
| 20 mg/kg | 3 | 12.91 | 25.95 | 13.04 | 0.38 | 0.77 |
|  | 16 | 12.29 | 25.86 | 13.57 | 0.91 | 0.53 |
|  | 21 | 12.2 | 25.18 | 12.98 | 0.32 | 0.80 |
|  | 28 | 13.03 | 24.47 | 11.44 | −1.22 | 2.33 |
|  | 32 | 11.49 | 24.57 | 13.08 | 0.42 | 0.75 |
|  | 40 | 11.26 | 22.55 | 11.29 | −1.37 | 2.58 |
|  | mean | 12.2 | 24.8 | 12.6 | −0.09 | 1.29 |
|  | sd | 0.7 | 1.2 | 1.0 | 0.96 | 0.91 |
|  | sem | 0.3 | 0.5 | 0.4 | 0.39 | 0.37 |
|  | n | 6 | 6 | 6 | 6 | 6 |

TABLE 10

MCP-1 gene expression (21 days)

| Group | No | 18S | MCP-1 | Dct | DDct | 2DDct |
|---|---|---|---|---|---|---|
| Vehicle | 7 | 12.96 | 25.15 | 12.19 | −1.14 | 2.2 |
|  | 15 | 11.15 | 25.35 | 14.2 | 0.87 | 0.55 |
|  | 17 | 11.14 | 23.92 | 12.78 | −0.55 | 1.46 |
|  | 20 | 13.25 | 25.1 | 11.85 | −1.48 | 2.79 |
|  | 24 | 11.65 | 25.61 | 13.96 | 0.63 | 0.65 |
|  | 26 | 12.41 | 25.96 | 13.55 | 0.22 | 0.86 |
|  | 27 | 13.25 | 24.49 | 11.24 | −2.09 | 4.25 |
|  | 31 | 11.38 | 26.59 | 15.21 | 1.88 | 0.27 |
|  | 35 | 11.26 | 25.64 | 14.38 | 1.05 | 0.48 |
|  | 39 | 11.5 | 25.43 | 13.93 | 0.6 | 0.66 |
|  | mean | 12 | 25.3 | 13.3 | 0 | 1.42 |
|  | sd | 0.9 | 0.7 | 1.3 | 1.26 | 1.29 |
|  | sem | 0.3 | 0.2 | 0.4 | 0.4 | 0.41 |
|  | n | 10 | 10 | 10 | 10 | 10 |
| 5 mg/kg | 2 | 13.46 | 26.68 | 13.2 | −0.11 | 1.08 |
|  | 5 | 13.11 | 26.47 | 13.36 | 0.03 | 0.98 |
|  | 6 | 11.61 | 26.76 | 15.15 | 1.82 | 0.28 |
|  | 8 | 13.35 | 26.19 | 12.84 | −0.49 | 1.4 |
|  | 12 | 12.03 | 26.35 | 14.32 | 0.99 | 0.5 |
|  | 19 | 13.35 | 27.79 | 14.44 | 1.11 | 0.46 |
|  | 23 | 11.6 | 25.17 | 13.57 | 0.24 | 0.85 |
|  | 36 | 11.79 | 25.06 | 13.27 | −0.06 | 1.04 |
|  | 37 | 11.14 | 25.54 | 14.4 | 1.07 | 0.48 |
|  | 38 | 11.12 | 26.04 | 14.92 | 1.59 | 0.33 |
|  | mean | 12.3 | 26.2 | 13.9 | 0.62 | 0.74 |
|  | sd | 1 | 0.8 | 0.8 | 0.79 | 0.38 |
|  | sem | 0.3 | 0.3 | 0.3 | 0.25 | 0.12 |
|  | n | 10 | 10 | 10 | 10 | 10 |
| 20 mg/kg | 3 | 12.91 | 25.89 | 12.98 | −0.35 | 1.27 |
|  | 16 | 12.29 | 24.04 | 11.75 | −1.58 | 2.99 |
|  | 21 | 12.2 | 23.5 | 11.3 | −2.03 | 4.08 |
|  | 28 | 13.03 | 24.46 | 11.43 | −1.9 | 3.73 |
|  | 32 | 11.49 | 25.7 | 14.21 | 0.88 | 0.54 |
|  | 40 | 11.26 | 26.54 | 15.28 | 1.95 | 0.26 |
|  | mean | 12.2 | 25 | 12.8 | −0.5 | 2.15 |
|  | sd | 0.7 | 1.2 | 1.6 | 1.64 | 1.66 |
|  | sem | 0.3 | 0.5 | 0.7 | 0.67 | 0.68 |
|  | n | 6 | 6 | 6 | 6 | 6 |

TABLE 11A

ER and oxidative stress gene expression (21 days): PERK

| Group | No | 18S | PERK | Dct | DDct | 2DDct |
|---|---|---|---|---|---|---|
| Vehicle | 7 | 12.96 | 28.22 | 15.26 | 0.22 | 0.86 |
|  | 15 | 11.15 | 25.95 | 14.8 | −0.24 | 1.18 |
|  | 17 | 11.14 | 27.09 | 15.95 | 0.91 | 0.53 |
|  | 20 | 13.25 | 27.67 | 14.42 | −0.62 | 1.54 |
|  | 24 | 11.65 | 27.17 | 15.52 | 0.48 | 0.72 |
|  | 26 | 12.41 | 27.67 | 15.26 | 0.22 | 0.86 |
|  | 27 | 13.25 | 26.37 | 13.12 | −1.92 | 3.79 |
|  | 31 | 11.38 | 27.17 | 15.79 | 0.75 | 0.6 |
|  | 35 | 11.26 | 26.93 | 15.67 | 0.63 | 0.65 |

TABLE 11A-continued

ER and oxidative stress gene expression (21 days): PERK

| Group | No | 18S | PERK | Dct | DDct | 2DDct |
|---|---|---|---|---|---|---|
| | 39 | 11.5 | 26.13 | 14.63 | −0.41 | 1.33 |
| | mean | 12 | 27 | 15 | 0 | 1.21 |
| | sd | 0.9 | 0.7 | 0.8 | 0.84 | 0.97 |
| | sem | 0.3 | 0.2 | 0.3 | 0.27 | 0.31 |
| | n | 10 | 10 | 10 | 10 | 10 |
| 5 mg/kg | 2 | 13.46 | 28.14 | 14.68 | −0.36 | 1.29 |
| | 5 | 13.11 | 29.05 | 15.94 | 0.9 | 0.54 |
| | 6 | 11.61 | 28.17 | 16.56 | 1.52 | 0.35 |
| | 8 | 13.35 | 27.81 | 14.46 | −0.58 | 1.5 |
| | 12 | 12.03 | 28.31 | 16.28 | 1.24 | 0.42 |
| | 19 | 13.35 | 29.19 | 15.84 | 0.8 | 0.58 |
| | 23 | 11.6 | 26.56 | 14.96 | −0.08 | 1.06 |
| | 36 | 11.79 | 26.19 | 14.4 | −0.64 | 1.56 |
| | 37 | 11.14 | 26.22 | 15.08 | 0.04 | 0.97 |
| | 38 | 11.12 | 26.5 | 15.38 | 0.34 | 0.79 |
| | mean | 12.3 | 27.6 | 15.4 | 0.32 | 0.91 |
| | sd | 1 | 1.2 | 0.8 | 0.77 | 0.44 |
| | sem | 0.3 | 0.4 | 0.2 | 0.24 | 0.14 |
| | n | 10 | 10 | 10 | 10 | 10 |
| 20 mg/kg | 3 | 12.91 | 27.9 | 14.99 | −0.05 | 1.04 |
| | 16 | 12.29 | 27.26 | 14.97 | −0.07 | 1.05 |
| | 21 | 12.2 | 26.9 | 14.7 | −0.34 | 1.27 |
| | 28 | 13.03 | 26.65 | 13.62 | −1.42 | 2.68 |
| | 32 | 11.49 | 27.25 | 15.76 | 0.72 | 0.61 |
| | 40 | 11.26 | 25.88 | 14.62 | −0.42 | 1.34 |
| | mean | 12.2 | 27 | 14.8 | −0.27 | 1.33 |
| | sd | 0.7 | 0.7 | 0.7 | 0.7 | 0.71 |
| | sem | 0.3 | 0.3 | 0.3 | 0.28 | 0.29 |
| | n | 6 | 6 | 6 | 6 | 6 |

TABLE 11B

ER and oxidative stress gene expression (21 days): NRF2

| Group | No | 18S | NRF2 | Dct | DDct | 2DDct |
|---|---|---|---|---|---|---|
| Vehicle | 7 | 12.96 | 24.42 | 11.46 | 0.52 | 0.7 |
| | 15 | 11.15 | 21.92 | 10.77 | −0.17 | 1.13 |
| | 17 | 11.14 | 23.26 | 12.12 | 1.18 | 0.44 |
| | 20 | 13.25 | 23.32 | 10.07 | −0.87 | 1.83 |
| | 24 | 11.65 | 22.91 | 11.26 | 0.32 | 0.8 |
| | 26 | 12.41 | 23.66 | 11.25 | 0.31 | 0.81 |
| | 27 | 13.25 | 22.13 | 8.88 | −2.06 | 4.17 |
| | 31 | 11.38 | 23 | 11.62 | 0.68 | 0.62 |
| | 35 | 11.26 | 22.61 | 11.35 | 0.41 | 0.75 |
| | 39 | 11.5 | 22.12 | 10.62 | −0.32 | 1.25 |
| | mean | 12 | 22.9 | 10.9 | 0 | 1.25 |
| | sd | 0.9 | 0.8 | 0.9 | 0.92 | 1.1 |
| | sem | 0.3 | 0.2 | 0.3 | 0.29 | 0.35 |
| | n | 10 | 10 | 10 | 10 | 10 |
| 5 mg/kg | 2 | 13.46 | 24.8 | 11.34 | 0.4 | 0.76 |
| | 5 | 13.11 | 25.07 | 11.96 | 1.02 | 0.49 |
| | 6 | 11.61 | 23.36 | 11.75 | 0.81 | 0.57 |
| | 8 | 13.35 | 23.36 | 10.01 | −0.93 | 1.91 |
| | 12 | 12.03 | 24.63 | 12.6 | 1.66 | 0.32 |
| | 19 | 13.35 | 25.61 | 12.26 | 1.32 | 0.4 |
| | 23 | 11.6 | 22.83 | 11.23 | 0.29 | 0.82 |
| | 36 | 11.79 | 22.7 | 10.91 | −0.03 | 1.02 |
| | 37 | 11.14 | 22.66 | 11.52 | 0.58 | 0.67 |
| | 38 | 11.12 | 22.62 | 11.5 | 0.56 | 0.68 |
| | mean | 12.3 | 23.8 | 11.5 | 0.57 | 0.76 |
| | sd | 1 | 1.1 | 0.7 | 0.72 | 0.45 |
| | sem | 0.3 | 0.4 | 0.2 | 0.23 | 0.14 |
| | n | 10 | 10 | 10 | 10 | 10 |
| 20 mg/kg | 3 | 12.91 | 24.24 | 11.33 | 0.39 | 0.76 |
| | 16 | 12.29 | 23.63 | 11.34 | 0.4 | 0.76 |
| | 21 | 12.2 | 23.27 | 11.07 | 0.13 | 0.91 |
| | 28 | 13.03 | 22.81 | 9.78 | −1.16 | 2.23 |
| | 32 | 11.49 | 23.05 | 11.56 | 0.62 | 0.65 |
| | 40 | 11.26 | 22.02 | 10.76 | −0.18 | 1.13 |
| | mean | 12.2 | 23.2 | 11 | 0.03 | 1.08 |

TABLE 11B-continued

ER and oxidative stress gene expression (21 days): NRF2

| Group | No | 18S | NRF2 | Dct | DDct | 2DDct |
|---|---|---|---|---|---|---|
| | sd | 0.7 | 0.8 | 0.6 | 0.65 | 0.59 |
| | sem | 0.3 | 0.3 | 0.3 | 0.26 | 0.24 |
| | n | 6 | 6 | 6 | 6 | 6 |

TABLE 12A

IL-6 expression (21 days)

| group | animal # | IL-6 (pg/mg tissue) |
|---|---|---|
| Vehicle | 7 | 875 |
| | 15 | 622 |
| | 17 | 1041 |
| | 20 | 713 |
| | 24 | 935 |
| | 26 | 1170 |
| | 27 | 794 |
| | 31 | 1250 |
| | 35 | 1183 |
| | 39 | 1218 |
| | mean | 980 |
| | sd | 225 |
| | sem | 71 |
| | n | 10 |
| 5 mg/kg | 2 | 1444 |
| | 5 | 845 |
| | 6 | 1107 |
| | 8 | 650 |
| | 12 | 1305 |
| | 19 | 957 |
| | 23 | 770 |
| | 36 | 1296 |
| | 37 | 883 |
| | 38 | 863 |
| | mean | 1012 |
| | sd | 263 |
| | sem | 83 |
| | n | 10 |
| 20 mg/kg | 3 | 904 |
| | 16 | 737 |
| | 21 | 760 |
| | 28 | 705 |
| | 32 | 970 |
| | 40 | 826 |
| | mean | 817 |
| | sd | 103 |
| | sem | 42 |
| | n | 6 |

TABLE 12B

IL-6 expression (9 days)

| group | animal # | IL-6 (pg/mg tissue) |
|---|---|---|
| 40 mg/kg | 25 | 1005 |
| | 30 | 569 |
| | 33 | 535 |
| | 34 | 566 |
| | mean | 669 |
| | sd | 225 |
| | sem | 112 |
| | n | 4 |

TABLE 13

Fibrosis gene expression (21 days): Col1a1

| Group | No | 18S | Col1a1 | Dct | DDct | 2DDct |
|---|---|---|---|---|---|---|
| Vehicle | 7 | 12.96 | 28.29 | 15.3 | 1.19 | 0.44 |
|  | 15 | 11.15 | 23.38 | 12.2 | −1.91 | 3.75 |
|  | 17 | 11.14 | 27.86 | 16.72 | 2.58 | 0.17 |
|  | 20 | 13.25 | 27.11 | 13.86 | −0.28 | 1.21 |
|  | 24 | 11.65 | 25.32 | 13.67 | −0.47 | 1.38 |
|  | 26 | 12.41 | 26.57 | 14.16 | 0.02 | 0.98 |
|  | 27 | 13.25 | 25.29 | 12.04 | −2.1 | 4.28 |
|  | 31 | 11.38 | 27.22 | 15.84 | 1.7 | 0.31 |
|  | 35 | 11.26 | 25.67 | 14.41 | 0.27 | 0.83 |
|  | 39 | 11.5 | 24.6 | 13.1 | −1.04 | 2.05 |
|  | mean | 12 | 26.1 | 14.1 | 0 | 1.54 |
|  | sd | 0.9 | 1.5 | 1.5 | 1.51 | 1.42 |
|  | sem | 0.3 | 0.5 | 0.5 | 0.48 | 0.45 |
|  | n | 10 | 10 | 10 | 10 | 10 |
| 5 mg/kg | 2 | 13.46 | 27.81 | 14.4 | 0.21 | 0.86 |
|  | 5 | 13.11 | 29.15 | 16.04 | 1.9 | 0.27 |
|  | 6 | 11.61 | 25.8 | 14.19 | 0.05 | 0.96 |
|  | 8 | 13.35 | 28.03 | 14.68 | 0.54 | 0.69 |
|  | 12 | 12.03 | 28.92 | 16.89 | 2.75 | 0.15 |
|  | 19 | 13.35 | 31.82 | 18.47 | 4.33 | 0.05 |
|  | 23 | 11.6 | 24.93 | 13.33 | −0.81 | 1.75 |
|  | 36 | 11.79 | 24.75 | 12.96 | −1.18 | 2.26 |
|  | 37 | 11.14 | 25.01 | 13.87 | −0.27 | 1.2 |
|  | 38 | 11.12 | 26.07 | 14.95 | 0.81 | 0.57 |
|  | mean | 12.3 | 27.2 | 15 | 0.84 | 0.88 |
|  | sd | 1 | 2.3 | 1.7 | 1.7 | 0.71 |
|  | sem | 0.3 | 0.7 | 0.5 | 0.54 | 0.22 |
|  | n | 10 | 10 | 10 | 10 | 10 |
| 20 mg/kg | 3 | 12.91 | 28.9 | 15.99 | 1.85 | 0.28 |
|  | 16 | 12.29 | 26.66 | 14.37 | 0.23 | 0.85 |
|  | 21 | 12.2 | 26.93 | 14.73 | 0.59 | 0.66 |
|  | 28 | 13.03 | 27.17 | 14.14 | 0 | 1 |
|  | 32 | 11.49 | 26.34 | 14.85 | 0.71 | 0.61 |
|  | 40 | 11.26 | 23.43 | 12.17 | −1.97 | 3.91* |
|  | mean | 12.2 | 26.6 | 14.4 | 0.24 | 0.68 |
|  | sd | 0.7 | 1.8 | 1.3 | 1.26 | 0.27 |
|  | sem | 0.3 | 0.7 | 0.5 | 0.51 | 0.12 |
|  | n | 6 | 6 | 6 | 6 | 5 |

NAFLD score analysis. A 0.5 cm³ piece of liver was fixed in 10% formalin for 48-72h, stored in ethanol 70° at 4° C., and processed for eosin/hematoxylin staining and NAFLD score analysis. One section (thickness 3-5 µm) per block was deposited on Superfrost+slides for hematoxylin-eosin staining. Individual slides having a single hepatic lobe section stained with H&E were digitized using a Nanozoomer from Hamamatsu. Sections were evaluated with knowledge of groups. Each section was evaluated and individually scored. A NAFLD scoring system (NAS) adapted from Kleiner et al. (Hepatology 41, 1313-21, 2005), Wu et al. (BMC Vet. Res. 10, 162, 2014), and Lee et al. (J. Lipid Res. 48, 1885-96, 2007). A total of four variables were qualitatively assessed and ranked with a score: (1) hepatocellular steatosis, (2) liver inflammation, (3) lobular fibrosis, and (4) hepatocyte ballooning. The criteria for score assignments are presented in the table below.

| Score | Steatosis | Inflammation | Fibrosis | Hepatocyte ballooning |
|---|---|---|---|---|
| 0 | <5% of liver parenchyma | no foci | none | none |
| 1 | 5-33% of liver parenchyma | <2 foci at 20x field | zone 3 and/or perisinusoidal fibrosis | minimal to mild focal involving fewer than 3 hepatocytes |
| 2 | 34-66% of liver parenchyma | 2-4 foci at 20x field | As grade 1 and portal fibrosis | moderate multifocal involving more than 3 hepatocytes |
| 3 | >66% of liver parenchyma | >4 foci at 20x field | As grade 2 and bridging fibrosis | prominent multifocal involving large number of hepatocytes |
| 4 | not applicable | not applicable | cirrhosis | not applicable |

NAS scores were determined based on histopathological analysis of steatosis, inflammation, hepatocyte ballooning, and fibrosis. The most remarkable lesion contributing to the NAS scores in the vehicle group and in the groups treated with Compound #37 at 5 mg/kg and 20 mg/kg was interstitial inflammation ranging from a Grade 1 to a Grade 3 in all animals in all three groups. A grade-3 inflammation was noted in 2/10 animals in the vehicle-treated group, 4/10 animals in the group treated with Compound #37 at 5 mg/kg, and 1/6 animals in the group treated with Compound #37 at 20 mg/kg. Inflammation was accompanied by limited periportal fibrosis (mostly Grade 1) in 9/10 animals in the vehicle-treated group, 10/10 animals in the group treated with Compound #37 at 5 mg/kg, and 3/6 animals in the group treated with Compound #37 at 20 mg/kg. Grade 1 hepatocellular steatosis was observed in 7/10 animals in the vehicle-treated group, 9/10 animals in the group treated with Compound #37 at 5 mg/kg, and 3/6 animals in the group treated with Compound #37 at 20 mg/kg. A grade 2 hepatocellular steatosis was also observed in one animal each in the vehicle-treated group and the group treated with Compound #37 at 5 mg/kg, but not in animals treated with Compound #37 at 20 mg/kg.

There was no inflammation noted in the animals treated with Compound #37 at 40 mg/kg. Inflammation was accompanied by limited periportal fibrosis but was not observed at day 9 in animals treated with Compound #37 at 40 mg/kg. The hepatocellular steatosis was more pronounced (Grade 2) in that group. The steatosis was accompanied by hepatocellular ballooning, which was inconsistently noted in vehicle-treated group and the group treated with Compound #37 at 5 mg/kg group, but was absent in the group treated with Compound #37 at 20 mg/kg.

Overall, the NAS scores in the vehicle-treated group and the group treated with Compound #37 at 5 mg/kg were slightly higher than that observed in the group treated with Compound #37 at 20 mg/kg, reflecting an apparent difference severity and extent of the inflammatory and lipidic changes. The group treated with Compound #37 at 20 mg/kg was the least severely affected.

Lesions of NAFLD observed in this study were consistent to that previously described and reviewed by Imajo et al.

(2013). The hyper-inflammatory response was accompanied by some evidence of fibrosis.

Although this experiment did not demonstrate a clear dose-dependent effect of treatment with Compound #37, treatment at 20 mg/kg appeared to be the most effective in reducing most of the liver injuries induced in this specific diet-induced NASH mouse model. Plasma ALT and ALT levels were reduced as well as liver steatosis. Finally NAS score assessed by histopathological analysis was also improved with reduced inflammation, steatosis, and hepatocyte ballooning as well as fibrosis.

The results are shown in Tables 14A and 14B.

TABLE 14A

NAS Scores (21 days)

| group | animal # | steatose | inflammation | fibrosis | hepatocyte ballooning | total |
|---|---|---|---|---|---|---|
| Vehicle | 7 | 1 | 2 | 1 | 0 | 4 |
|  | 15 | 2 | 1 | 1 | 2 | 6 |
|  | 17 | 1 | 1 | 0 | 0 | 2 |
|  | 20 | 1 | 2 | 1 | 0 | 4 |
|  | 24 | 1 | 3 | 1 | 0 | 5 |
|  | 26 | 0 | 1 | 1 | 0 | 2 |
|  | 27 | 1 | 3 | 1 | 0 | 5 |
|  | 31 | 1 | 2 | 1 | 0 | 4 |
|  | 35 | 0 | 2 | 1 | 0 | 3 |
|  | 39 | 1 | 2 | 1 | 0 | 4 |
|  | mean | 0.9 | 1.9 | 0.9 | 0.2 | 3.9 |
|  | sd | 0.57 | 0.74 | 0.32 | 0.63 | 1.29 |
|  | sem | 0.18 | 0.23 | 0.1 | 0.2 | 0.41 |
|  | n | 10 | 10 | 10 | 10 | 10 |
| 5 mg/kg | 2 | 1 | 1 | 1 | 1 | 4 |
|  | 5 | 1 | 2 | 1 | 1 | 5 |
|  | 6 | 1 | 3 | 1 | 0 | 5 |
|  | 8 | 1 | 1 | 1 | 0 | 3 |
|  | 12 | 1 | 1 | 1 | 0 | 3 |
|  | 19 | 2 | 1 | 1 | 1 | 5 |
|  | 23 | 1 | 3 | 2 | 0 | 6 |
|  | 36 | 1 | 3 | 1 | 0 | 5 |
|  | 37 | 1 | 3 | 2 | 0 | 6 |
|  | 38 | 1 | 2 | 1 | 0 | 4 |
|  | mean | 1.1 | 2 | 1.2 | 0.3 | 4.6 |
|  | sd | 0.3 | 0.9 | 0.4 | 0.5 | 1.1 |
|  | sem | 0.1 | 0.3 | 0.1 | 0.2 | 0.3 |
|  | n | 10 | 10 | 10 | 10 | 10 |
| 20 mg/kg | 3 | 1 | 1 | 0 | 0 | 2 |
|  | 16 | 0 | 2 | 1 | 0 | 3 |
|  | 21 | 0 | 2 | 1 | 0 | 3 |
|  | 28 | 1 | 3 | 1 | 0 | 5 |
|  | 32 | 0 | 1 | 0 | 0 | 1 |
|  | 40 | 1 | 1 | 0 | 0 | 2 |
|  | mean | 0.5 | 1.67 | 0.5 | 0 | 2.67 |
|  | sd | 0.55 | 0.82 | 0.55 | 0 | 1.37 |
|  | sem | 0.22 | 0.33 | 0.22 | 0 | 0.56 |
|  | n | 6 | 6 | 6 | 6 | 6 |

TABLE 14B

NAS Scores (9 days)

| group | animal # | steatose | inflammation | fibrosis | hepatocyte ballooning | total |
|---|---|---|---|---|---|---|
| 40 mg/kg | 25 | 2 | 0 | 0 | 1 | 3 |
|  | 30 | 2 | 0 | 0 | 1 | 3 |
|  | 33 | 2 | 0 | 0 | 1 | 3 |
|  | 34 | 2 | 0 | 0 | 1 | 3 |
|  | mean | 2 | 0 | 0 | 1 | 3 |
|  | sd | 0 | 0 | 0 | 0 | 0 |
|  | sem | 0 | 0 | 0 | 0 | 0 |
|  | n | 4 | 4 | 4 | 4 | 4 |

Summary of the Results and Discussion.

The Paigen diet in the C57Bl/6J mouse strain typically results in an initial acute weight loss that recovers over time (Hebbard & George, 2011; vendor historical unpublished data). Animals receiving this diet with Compound #37 were observed to have an added dose-dependent decrease in food intake within the first week of dosing that led to marked weight loss and resulting toxicity. The Compound #37 40 mg/kg/day treatment group (10 mice) exhibited a marked decrease in food intake and >20% mean weight loss over 4 days of treatment, leading to the death of 3 mice by day 7 and the death of an additional 3 mice by day 9. Dosing of this group was stopped on day 4 and the surviving mice were sacrificed on day 9, 1 hour after a final dose to analyze drug exposure. The Compound #37 20 mg/kg/day group (10 mice) also demonstrated decreased food intake and weight loss; 4 mice with the most pronounced weight loss died (1 on day 7, 2 on day 9, 1 on day 11). The other 6 mice in the group exhibited less dramatic weight loss, survived, and regained weight similar to vehicle group animals. No mice died in the Compound #37 5 mg/kg/day or vehicle control groups (10 mice each group).

The death of animals in the Compound #37 40 mg/kg/day and 20 mg/kg/day groups appears to be related to synergistic weight loss due to a combination of the Paigen diet and the inappetence effects of Compound #37 observed in repeat-dose toxicity studies in rats and dogs. By the end of the 3-week dosing period, no differences in weight were observed among the animals that survived the full study in the vehicle control, Compound #37 5 mg/kg/day, and Compound #37 20 mg/kg/day treatment groups (Table B3). Compound #37 mean plasma concentration 1 hour after final dose administration on day 21 was 20.4 μM (±4.33 μM) and 112 μM (±26.0 μM) for the 5 mg/kg and 20 mg/kg groups, respectively. The Compound #37 mean plasma concentration 1 hour after final dose administration for the 4 animals on day 9 in the 40 mg/kg group was 136 μM (±37.1 μM). These exposures at 1 hour after dosing are approximately 2-fold higher than those observed in healthy mice and may be related to altered Compound #37 metabolism in this acute liver injury model.

TABLE B3

| Treatment | | Days of Treatment | | | | | | | | | |
|---|---|---|---|---|---|---|---|---|---|---|---|
| | | 0 | 2 | 4 | 7 | 9 | 11 | 14 | 16 | 18 | 21 |
| Vehicle | Mean (g) | 27.5 | 26.9 | 25.9 | 25.3 | 24.6 | 24.3 | 24.1 | 24.6 | 25.0 | 25.6 |
| | SD | 1.7 | 2.1 | 1.6 | 1.5 | 2.1 | 2.6 | 2.7 | 2.6 | 2.2 | 1.3 |
| | N | 10 | 10 | 10 | 10 | 10 | 10 | 10 | 10 | 10 | 10 |
| MDV4463 5 mg/kg | Mean (g) | 27.8 | 26.6 | 26.3 | 26.9 | 26.5 | 25.9 | 25.8 | 25.1 | 25.4 | 25.8 |
| | SD | 1.6 | 1.5 | 1.4 | 2.0 | 1.5 | 1.7 | 2.0 | 2.2 | 2.5 | 2.0 |
| | N | 10 | 10 | 10 | 10 | 10 | 10 | 10 | 10 | 10 | 10 |
| MDV4463 20 mg/kg | Mean (g) | 27.7 | 25.7 | 23.9 | 23.7 | 25.6 | 27.2 | 27.2 | 26.9 | 27.3 | 27.0 |
| | SD | 1.5 | 1.4 | 2.9 | 4.2 | 4.5 | 1.4 | 1.2 | 1.4 | 1.5 | 1.7 |
| | N | 10 | 10 | 10 | 9 | 7 | 6 | 6 | 6 | 6 | 6 |

TABLE B3-continued

| | | Days of Treatment | | | | | | | | | |
|---|---|---|---|---|---|---|---|---|---|---|---|
| Treatment | | 0 | 2 | 4 | 7 | 9 | 11 | 14 | 16 | 18 | 21 |
| MDV4463 | Mean (g) | 28.0 | 25.8 | 22.03 | 19.73 | 23.28 | — | — | — | — | — |
| 40 mg/kg | SD | 1.4 | 1.2 | 0.8 | 1.3 | 1.4 | — | — | — | — | — |
| | N | 10 | 10 | 10 | 7 | 4 | — | — | — | — | — |

The severe food intake decrease and animal deaths confound the interpretation of the results in this cholate-based model. No consistent observations in hepatic lipid concentrations or SREBP-related target gene expression levels were evident in surviving animals receiving Compound #37 compared with the vehicle control group; however, lower plasma triglyceride and free fatty acid concentrations were observed in a dose-dependent manner. Of note, after 21 days of treatment in this model, liver transaminases were markedly increased for all treatment groups, consistent with the diet-induced liver injury, but trended toward lower values in the Compound #37 treatment groups compared with the vehicle control group (Table 5A). The 4 surviving animals in the 40 mg/kg group were found to have markedly elevated liver transaminases at the time of sacrifice on day 9 (mean AST and ALT>2500 U/L); however, no control animals were sacrificed at this time point for comparison.

Example B4. Effect of Compound #37 in an Obese Insulin-Resistant Mouse Diet-Induced NASH Model (DIN Model)

This example demonstrates that Compound #37 tends to improve insulin resistance and reduced liver fibrosis in a diet-induced NASH obese insulin resistant mice.

Male C57Bl/6J mice (8 weeks old) were housed in enriched ventilated cages (31×12.5×12.7 cm) throughout the experimental phase. Animals' cages litters were changed at least once a week. Animal were housed 5 per cage on inverted 12-hour light cycle (at 09:00 am lights off), 22±2° C. and 55±10% relative humidity. The acclimation period was 20 days. During the acclimation period, all mice were fed a standard diet (RM1 (E) 801492, SDS) and tap water ad libitum. After the acclimation period, mice were fed with the DIN diet (60% fat, cholesterol enriched) and fructose-enriched tap water ad libitum until the end of the experiment.

At 6 weeks of diet, mice were 4-hour fasted (09:00 am to 1:00 pm) and blood (150 µl/EDTA) was collected at 01:00 pm by retro-orbital bleeding under isoflurane anesthesia. Mice were then allocated in 2 homogenous groups (n=12/group) according to their plasma levels of ALT (average levels: 685U/L), AST (average levels: 627U/L) and HOMA-IR index (average value: 4.7), into 2 homogenous groups (see values at day 0 in Tables 15A and 15B ALT/AST and Tables 16A and 16B for HOMA-IR). Mice were then treated once daily by oral gavage with vehicle (Group 1) or Compound #37 at 20 mg/kg (Group 2) for 70 days.

Results. A non-significant trend towards lower body weight and body weight gain was observed in mice treated with Compound #37, with no major change observed regarding food intake. Water intake tended to be higher in mice treated with, resulting in a 17% increase in cumulative water intake (p<0.05 vs. vehicle). One animal in the 20 mg/kg/day treatment group died on day 48.

Although a trend towards lower AST plasma levels was observed in mice treated with Compound #37, no significant change was observed in plasma ALT/AST levels and area under the curve during the 70-day treatment (Tables 15A and 15B).

Blood glucose levels were not altered by Compound #37 treatment. However, plasma insulin levels tended to be reduced with Compound #37, leading to lower HOMA-IR index at day 42 and day 70 (50 and 40% reduction), although this trend was not significant. At the end of the treatment period, plasma leptin levels were significantly reduced by 38% with Compound #37 (p<0.05 vs. vehicle). These results are presented in Tables 16A and 16B.

Although mice treated with Compound #37 showed increased HDL-cholesterol by 31% (p<0.05 vs. vehicle), no significant change was observed in plasma lipids levels at the end of the treatment period. See Table 17.

Liver weight was significantly higher (by 21%) in mice treated with Compound #37. Hepatic total cholesterol levels were raised by 17% (p<0.05 vs. vehicle). However, liver fatty acids and triglycerides levels remained unchanged. See Table 18A. Hepatic MCP-1 levels were reduced by 70% (p<0.001 vs. vehicle) in mice treated with Compound #37; see Table 18B.

Slides having a single hepatic lobe section stained with H&E and Sims red were digitized using a Nanozoomer from Hamamatsu. Sections were evaluated with knowledge of groups. In agreement with the unchanged hepatic triglycerides levels, oil red O staining and % labeling was not changed with Compound #37. A substantial reduction in Sirius Red labeling was also observed, leading to a 61% reduction (p<0.001 vs. vehicle) in % labeling. These results are presented in Table 18B.

Each section was evaluated and individually scored using the modified NAFLD scoring system described above. The results of the NAS scoring are shown in Table 19. Although inflammation scores were low in both groups (0-1), NAS scoring (FIG. 10) showed a significant 81% increase in the inflammation score (p<0.05 vs. vehicle) for mice treated with Compound #37. In agreement with the Sirius Red % labeling, fibrosis score was reduced by 45%, although this did not reach significance (p=0.055 vs. vehicle). While steatosis and hepatocyte ballooning scores remained unchanged, total NAS score did not change with Compound #37.

The results of the gene expression analysis are presented in Tables 20A-20L. Hepatic expression levels of genes involved in lipid (FAS, SREBP1, ACC1, SCD1), cholesterol metabolism (HMG-CoAR, LDLR), in SREBP proteolysis (SCAP, INSIG1), in ER stress (PERK), oxidative stress (NRF2), and inflammation (MCP-1) were not changed. However, expression of collagen 1α1, involved in liver fibrosis, was reduced by 66% in mice treated with Compound #37 (p<0.05 vs. vehicle).

Conclusion. In the diet-induced NASH obese insulin resistant mice, Compound #37 tends to improve insulin resistance and reduce liver fibrosis.

TABLE 15A

Plasma ALT and AST Levels (Vehicle Group)

| group | animal # | days of treatment/ALAT (U/L) | | | | | | days of treatment/ASAT (U/L) | | | | | | ALAT U/L · day | ASAT U/L · day |
|---|---|---|---|---|---|---|---|---|---|---|---|---|---|---|---|
| | | 0 | 14 | 28 | 42 | 56 | 70 | 0 | 14 | 28 | 42 | 56 | 70 | | |
| Vehicle | 2 | 564 | 68 | 60 | 66 | 46 | 326 | 795 | 264 | 122 | 98 | 188 | 162 | 7910 | 11403 |
| | 5 | 214 | 48 | 58 | 84 | 80 | 66 | 278 | 98 | 134 | 198 | 206 | 112 | 3850 | 7182 |
| | 7 | 634 | 326 | 424 | 176 | 234 | 250 | 475 | 274 | 254 | 174 | 244 | 286 | 14308 | 11949 |
| | 9 | 403 | 588 | 264 | 430 | 324 | 490 | 356 | 804 | 194 | 328 | 372 | 392 | 17493 | 17122 |
| | 11 | 293 | 212 | 298 | 184 | 432 | 568 | 216 | 200 | 174 | 182 | 126 | 324 | 13909 | 8554 |
| | 12 | 1500 | 474 | 196 | 104 | 176 | 648 | 1315 | 484 | 150 | 156 | 142 | 594 | 21686 | 19887 |
| | 13 | 1145 | 252 | 118 | 74 | 212 | 372 | 825 | 186 | 114 | 86 | 110 | 318 | 15211 | 11473 |
| | 14 | 560 | 174 | 182 | 162 | 120 | 446 | 441 | 170 | 126 | 184 | 132 | 372 | 11508 | 9975 |
| | 15 | 235 | 176 | 926 | 100 | 86 | 264 | 216 | 300 | 198 | 120 | 266 | 280 | 12509 | 9660 |
| | 16 | 830 | 497 | 186 | 168 | 146 | 92 | 620 | 684 | 182 | 158 | 150 | 116 | 13433 | 13370 |
| | 20 | 638 | 290 | 212 | 242 | 194 | 996 | 1280 | 575 | 440 | 504 | 376 | 1354 | 18004 | 31703 |
| | 23 | 1110 | 74 | 608 | 134 | 48 | 80 | 840 | 108 | 154 | 104 | 96 | 124 | 14378 | 9982 |
| | mean | 677 | 265 | 294 | 160 | 175 | 383 | 638 | 346 | 187 | 191 | 214 | 370 | 13683 | 13522 |
| | sd | 401 | 178 | 252 | 100 | 116 | 271 | 382 | 235 | 89 | 117 | 102 | 340 | 4639 | 6743 |
| | sem | 116 | 51 | 73 | 29 | 33 | 78 | 110 | 68 | 26 | 34 | 34 | 98 | 1339 | 1946 |
| | n | 12 | 12 | 12 | 12 | 12 | 12 | 12 | 12 | 12 | 12 | 12 | 12 | 12 | 12 |

TABLE 15B

Plasma ALT and AST Levels (20 mg/kg Compound #37 group)

| group | animal # | days of treatment/ALAT (U/L) | | | | | | days of treatment/ASAT (U/L) | | | | | | ALAT U/L · day | ASAT U/L · day |
|---|---|---|---|---|---|---|---|---|---|---|---|---|---|---|---|
| | | 0 | 14 | 28 | 42 | 56 | 70 | 0 | 14 | 28 | 42 | 56 | 70 | | |
| 20 mg/kg | 1 | 830 | 690 | 160 | 66 | 534 | 142 | 725 | 440 | 222 | 130 | 182 | 182 | 16954 | 13167 |
| | 3 | 662 | 134 | 208 | 50 | 70 | 142 | 730 | 248 | 288 | 76 | 130 | 198 | 8862 | 11690 |
| | 4 | 260 | 252 | 38 | 370 | 74 | 104 | 283 | 428 | 68 | 174 | 164 | 192 | 7686 | 9163 |
| | 6 | 1065 | 106 | 136 | 322 | dead | dead | 860 | 126 | 190 | 296 | dead | dead | dead | dead |
| | 8 | 1520 | 250 | 176 | 68 | 276 | 364 | 1440 | 296 | 238 | 88 | 346 | 258 | 18578 | 18662 |
| | 10 | 698 | 252 | 118 | 280 | 80 | 1030 | 875 | 268 | 98 | 132 | 122 | 648 | 17206 | 15001 |
| | 17 | 955 | 218 | 96 | 52 | 48 | 326 | 584 | 206 | 84 | 80 | 92 | 162 | 11865 | 8456 |
| | 18 | 551 | 200 | 68 | 50 | 68 | 372 | 435 | 228 | 76 | 110 | 108 | 206 | 9163 | 8141 |
| | 19 | 226 | 92 | 58 | 136 | 52 | 210 | 217 | 124 | 80 | 140 | 60 | 180 | 5418 | 5607 |
| | 21 | 365 | 198 | 316 | 58 | 54 | 342 | 269 | 150 | 168 | 96 | 96 | 160 | 9331 | 6573 |
| | 22 | 625 | 256 | 226 | 168 | 112 | 1150 | 464 | 190 | 140 | 200 | 132 | 524 | 17759 | 11550 |
| | 24 | 563 | 410 | 154 | 92 | 130 | 358 | 500 | 288 | 102 | 106 | 112 | 376 | 11949 | 10388 |
| | mean | 693 | 255 | 146 | 143 | 136 | 413 | 615 | 249 | 146 | 136 | 126 | 281 | 12252 | 10763 |
| | sd | 365 | 161 | 79 | 117 | 147 | 350 | 343 | 104 | 74 | 63 | 37 | 165 | 4630 | 3830 |
| | sem | 105 | 46 | 23 | 34 | 44 | 106 | 99 | 30 | 21 | 18 | 13 | 50 | 1396 | 1155 |
| | n | 12 | 12 | 12 | 12 | 11 | 11 | 12 | 12 | 12 | 12 | 11 | 11 | 11 | 11 |

TABLE 16A

Blood Glucose and Plasma Insulin Levels

| group | animal # | blood glucose (mg/dL) | | | plasma insulin (μU/mL) | | |
|---|---|---|---|---|---|---|---|
| | | day 0 | day 42 | day 70 | day 0 | day 42 | day 70 |
| Vehicle | 2 | 97 | 135 | 159 | 21.8 | 26.0 | 14.1 |
| | 5 | 117 | 145 | 141 | 51.9 | 22.3 | 59.4 |
| | 7 | 123 | 109 | 153 | 7.8 | 12.1 | 13.2 |
| | 9 | 135 | 136 | 145 | 8.1 | 16.9 | 16.7 |
| | 11 | 118 | 144 | 172 | 9.6 | 31.0 | 13.6 |
| | 12 | 106 | 112 | 133 | 5.1 | 6.5 | 7.0 |
| | 13 | 92 | 166 | 154 | 13.1 | 9.5 | 18.1 |
| | 14 | 131 | 142 | 156 | 9.0 | 8.9 | 33.2 |
| | 15 | 117 | 138 | 109 | 9.9 | 16.2 | 39.9 |
| | 16 | 100 | 150 | 119 | 32.4 | 57.8 | 23.3 |
| | 20 | 96 | 90 | 111 | 26.7 | 62.8 | 6.0 |
| | 23 | 90 | 99 | 145 | 10.2 | 7.2 | 9.8 |
| | mean | 110 | 131 | 141 | 17.1 | 23.1 | 21.2 |
| | sd | 15 | 23 | 20 | 13.8 | 19 | 15.7 |
| | sem | 4 | 7 | 6 | 4 | 5.5 | 4.5 |
| | n | 12 | 12 | 12 | 12 | 12 | 12 |
| 20 mg/kg | 1 | 97 | 133 | 138 | 11.3 | 11.6 | 21.9 |
| | 3 | 113 | 139 | 132 | 14.7 | 9.5 | 8.0 |
| | 4 | 123 | 112 | 135 | 77.6 | 18.0 | 18.1 |
| | 6 | 106 | 126 | dead | 8.1 | 24.8 | dead |
| | 8 | 79 | 128 | 157 | 11.9 | 8.9 | 15.1 |
| | 10 | 113 | 132 | 136 | 6.9 | 11.8 | 11.5 |
| | 17 | 95 | 131 | 124 | 7.5 | 5.8 | 9.3 |
| | 18 | 114 | 138 | 127 | 13.6 | 8.2 | 20.6 |
| | 19 | 102 | 139 | 100 | 8.4 | 8.2 | 10.3 |
| | 21 | 89 | 151 | 114 | 7.5 | 10.0 | 13.4 |
| | 22 | 112 | 140 | 130 | 31.9 | 10.2 | 9.8 |
| | 24 | 103 | 127 | 141 | 10.7 | 10.7 | 12.9 |
| | mean | 104 | 133 | 130 | 17 | 11.5 | 13.7 |
| | sd | 12 | 10 | 15 | 20 | 5.1 | 4.7 |
| | sem | 4 | 3 | 4 | 6 | 1.5 | 1.4 |
| | n | 12 | 12 | 11 | 12 | 12 | 11 |

TABLE 16B

Homeostasis Model Assessment of Insulin Resistance and Plasma Leptin Levels

| group | animal # | HOMA-IR ([mM × μU/mL]/22.5) day 0 | day 42 | day 70 | plasma leptin (pg/mL) day 70 |
|---|---|---|---|---|---|
| Vehicle | 2 | 5.2 | 8.7 | 5.5 | 397 |
| | 5 | 15.0 | 8.0 | 20.7 | 311 |
| | 7 | 2.4 | 1.6 | 5.0 | 675 |
| | 9 | 2.7 | 5.7 | 6.0 | 842 |
| | 11 | 2.8 | 11.0 | 5.8 | 480 |
| | 12 | 1.3 | 1.8 | 2.3 | 95 |
| | 13 | 3.0 | 3.9 | 6.9 | 334 |
| | 14 | 2.9 | 3.1 | 12.8 | 653 |
| | 15 | 2.9 | 5.5 | 10.7 | 630 |
| | 16 | 8.0 | 21.4 | 6.8 | 490 |
| | 20 | 6.3 | 14.0 | 1.7 | 44 |
| | 23 | 2.3 | 1.8 | 3.5 | 165 |
| | mean | 4.6 | 7.2 | 7.3 | 426 |
| | sd | 3.8 | 5.9 | 5.3 | 249 |
| | sem | 1.1 | 1.7 | 1.5 | 72 |
| | n | 12 | 12 | 12 | 12 |
| 20 mg/kg | 1 | 2.7 | 3.8 | 7.5 | 454 |
| | 3 | 4.1 | 3.3 | 2.6 | 330 |
| | 4 | 23.6 | 5.0 | 6.0 | 202 |
| | 6 | 2.1 | 7.7 | dead | dead |
| | 8 | 2.3 | 2.8 | 5.8 | 280 |
| | 10 | 1.9 | 3.8 | 3.9 | 341 |
| | 17 | 1.8 | 1.9 | 2.8 | 144 |
| | 18 | 3.8 | 2.8 | 6.5 | 294 |
| | 19 | 2.1 | 2.8 | 2.5 | 46 |
| | 21 | 1.6 | 3.7 | 3.8 | 269 |
| | 22 | 8.8 | 3.5 | 3.1 | 374 |
| | 24 | 2.3 | 3.4 | 4.5 | 187 |
| | mean | 4.8 | 3.7 | 4.5 | 265 |
| | sd | 6.2 | 1.5 | 1.7 | 114 |
| | sem | 1.8 | 0.4 | 0.5 | 35 |
| | n | 12 | 12 | 11 | 11 |

TABLE 17

Plasma Lipid Levels

| Group | Animal # | cholesterol (g/L) | HDL cholesterol (g/L) | triglycerides (g/L) | free fatty acids (mM) |
|---|---|---|---|---|---|
| Vehicle | 2 | 1.50 | 1.01 | 0.50 | 0.56 |
| | 5 | 1.63 | 1.12 | 0.39 | 0.54 |
| | 7 | 1.94 | 1.20 | 0.40 | 0.65 |
| | 9 | 2.49 | 1.47 | 0.40 | 0.57 |
| | 11 | 2.04 | 1.41 | 0.40 | 0.67 |
| | 12 | 1.34 | 1.02 | 0.42 | 0.69 |
| | 13 | 1.61 | 0.92 | 0.40 | 0.84 |
| | 14 | 1.64 | 1.16 | 0.50 | 0.62 |
| | 15 | 1.98 | 1.22 | 0.60 | 0.81 |
| | 16 | 1.72 | 0.98 | 0.34 | 0.46 |
| | 20 | 2.75 | 0.58 | 1.03 | 1.08 |
| | 23 | 1.31 | 0.88 | 0.42 | 0.93 |
| | mean | 1.83 | 1.08 | 0.48 | 0.7 |
| | sd | 0.44 | 0.24 | 0.19 | 0.18 |
| | sem | 0.13 | 0.07 | 0.05 | 0.05 |
| | n | 12 | 12 | 12 | 12 |
| 20 mg/kg | 1 | 2.49 | 1.65 | 0.37 | 0.73 |
| | 3 | 2.36 | 1.68 | 0.3 | 0.63 |
| | 4 | 1.95 | 1.10 | 0.42 | 0.59 |
| | 6 | dead | dead | dead | dead |
| | 8 | 1.67 | 1.47 | 0.35 | 0.29 |
| | 10 | 2.12 | 1.90 | 0.40 | 0.65 |
| | 17 | 1.38 | 1.12 | 0.34 | 0.56 |
| | 18 | 1.62 | 1.43 | 0.45 | 0.71 |
| | 19 | 1.15 | 0.62 | 0.50 | 0.44 |
| | 21 | 1.57 | 1.47 | 0.47 | 0.59 |
| | 22 | 1.86 | 1.62 | 0.37 | 0.59 |
| | 24 | 1.90 | 1.56 | 0.39 | 0.67 |

TABLE 17-continued

Plasma Lipid Levels

| Group | Animal # | cholesterol (g/L) | HDL cholesterol (g/L) | triglycerides (g/L) | free fatty acids (mM) |
|---|---|---|---|---|---|
| | mean | 1.82 | 1.42 | 0.40 | 0.59 |
| | sd | 0.4 | 0.36 | 0.06 | 0.13 |
| | sem | 0.12 | 0.11 | 0.02 | 0.04 |
| | n | 11 | 11 | 11 | 11 |

TABLE 18A

Liver Lipid Levels

| Group | animal # | liver weight | cholesterol (μg/mg) | triglycerides (μg/mg) | fatty acids (nmol/mg) |
|---|---|---|---|---|---|
| Vehicle | 2 | 1.65 | 20.5 | 128.5 | 67.2 |
| | 5 | 1.72 | 20.0 | 62.4 | 41.3 |
| | 7 | 2.35 | 35.0 | 197.5 | 92.5 |
| | 9 | 2.61 | 25.6 | 165.2 | 67.8 |
| | 11 | 2.29 | 32.2 | 151.5 | 85.5 |
| | 12 | 1.57 | 18.8 | 103.3 | 48.9 |
| | 13 | 2.14 | 21.7 | 90.6 | 51.5 |
| | 14 | 2.44 | 30.4 | 181.3 | 75.2 |
| | 15 | 2.62 | 23.3 | 178.2 | 64.6 |
| | 16 | 2.08 | 18.7 | 85.7 | 45.3 |
| | 20 | 2.40 | 22.8 | 67.8 | 46.8 |
| | 23 | 1.60 | 20.0 | 107.0 | 45.3 |
| | mean | 2.12 | 24.1 | 126.6 | 61.0 |
| | sd | 0.39 | 5.5 | 47 | 17.1 |
| | sem | 0.11 | 1.6 | 13.6 | 4.9 |
| | n | 12 | 12 | 12 | 12 |
| 20 mg/kg | 1 | 3.24 | 27.4 | 262.5 | 72.2 |
| | 3 | 2.72 | 32.2 | 203.3 | 67.2 |
| | 4 | 1.97 | 25.8 | 72.2 | 56.2 |
| | 6 | dead | dead | dead | dead |
| | 8 | 2.74 | 28.4 | 162.3 | 82.8 |
| | 10 | 2.39 | 28.3 | 101.9 | 56.8 |
| | 17 | 1.97 | 27.1 | 53.6 | 47.8 |
| | 18 | 2.54 | 29.9 | 178.1 | 68.4 |
| | 19 | 2.44 | 20.7 | 48.9 | 43.9 |
| | 21 | 2.67 | 31.3 | 91.5 | 70.0 |
| | 22 | 3.05 | 34.0 | 195 | 76.7 |
| | 24 | 2.40 | 25.3 | 102.6 | 53.2 |
| | mean | 2.56 | 28.2 | 133.8 | 63.2 |
| | sd | 0.39 | 3.7 | 70.1 | 12.4 |
| | sem | 0.12 | 1.1 | 21.1 | 3.7 |
| | n | 11 | 11 | 11 | 11 |

TABLE 18B

MCP1 and % Labeling

| Group | animal # | MCP1 (pg/mg liver) | O red Oil labeling (%) | Sirius red labeling (%) |
|---|---|---|---|---|
| Vehicle | 2 | 1.96 | 8.8 | 0.6 |
| | 5 | 3.04 | 6.2 | 1.1 |
| | 7 | 3.3 | 28.8 | 1.2 |
| | 9 | 3.73 | 5.7 | 1.4 |
| | 11 | 3.31 | 10.6 | 1.9 |
| | 12 | 5.91 | 9.7 | 2.7 |
| | 13 | 2.79 | 10.8 | 1.6 |
| | 14 | 4.74 | 13.6 | 0.9 |
| | 15 | 1.87 | 8.3 | 1.0 |
| | 16 | 3.16 | 5.2 | 2.0 |
| | 20 | 31.66 | 5.1 | 6.6 |
| | 23 | 1.68 | 4.3 | 1.9 |
| | mean | 5.6 | 9.8 | 1.9 |
| | sd | 8.3 | 6.6 | 1.6 |
| | sem | 2.4 | 1.9 | 0.5 |
| | n | 12 | 12 | 12 |

TABLE 18B-continued

MCP1 and % Labeling

| Group | animal # | MCP1 (pg/mg liver) | O red Oil labeling (%) | Sirius red labeling (%) |
|---|---|---|---|---|
| 20 mg/kg | 1 | 1.34 | 12.9 | 0.5 |
| | 3 | 1.53 | 15.1 | 0.8 |
| | 4 | 0.60 | 0.9 | 0.8 |
| | 6 | dead | ND | ND |
| | 8 | 2.54 | 18.6 | 0.6 |
| | 10 | 1.76 | 19.3 | 1.0 |
| | 17 | 1.72 | 21.3 | 0.9 |
| | 18 | 1.42 | 0.3 | 0.8 |
| | 19 | 1.21 | 8.3 | 0.7 |
| | 21 | 1.78 | 19.5 | 0.6 |
| | 22 | 1.90 | 13.0 | 0.7 |
| | 24 | 2.59 | 4.2 | 0.8 |
| | mean | 1.7 | 12.1 | 0.7 |
| | sd | 0.6 | 7.7 | 0.1 |
| | sem | 0.2 | 2.3 | 0 |
| | n | 11 | 11 | 11 |

TABLE 19

NAS Scores

| group | animal # | steatosis | inflammation | fibrosis | hepatocyte ballooning | total |
|---|---|---|---|---|---|---|
| Vehicle | 2 | 1 | 0 | 1 | 1 | 3 |
| | 5 | 1 | 1 | 1 | 1 | 4 |
| | 7 | 3 | 0 | 2 | 3 | 8 |
| | 9 | 2 | 0 | 1 | 2 | 5 |
| | 11 | 2 | 1 | 1 | 2 | 6 |
| | 12 | 1 | 1 | 1 | 1 | 4 |
| | 13 | 2 | 0 | 1 | 2 | 5 |
| | 14 | 2 | 0 | 1 | 2 | 5 |
| | 15 | 3 | 0 | 1 | 3 | 7 |
| | 16 | 1 | 1 | 0 | 1 | 3 |
| | 20 | 2 | 1 | 3 | 2 | 8 |
| | 23 | 1 | 1 | 1 | 1 | 4 |
| | mean | 1.75 | 0.50 | 1.17 | 1.75 | 5.17 |
| | sd | 0.75 | 0.52 | 0.72 | 0.75 | 1.75 |
| | sem | 0.22 | 0.15 | 0.21 | 0.22 | 0.51 |
| | n | 12 | 12 | 12 | 12 | 12 |
| 20 mg/kg | 1 | 3 | 0 | 1 | 3 | 7 |
| | 3 | 3 | 1 | 1 | 3 | 8 |
| | 4 | 1 | 1 | 0 | 1 | 3 |
| | 8 | 2 | 1 | 0 | 2 | 5 |
| | 10 | 2 | 1 | 1 | 2 | 6 |
| | 17 | 1 | 1 | 1 | 1 | 4 |
| | 18 | 2 | 1 | 0 | 2 | 5 |
| | 19 | 1 | 1 | 0 | 1 | 3 |
| | 21 | 2 | 1 | 1 | 2 | 6 |
| | 22 | 2 | 1 | 1 | 2 | 6 |
| | 24 | 2 | 1 | 1 | 2 | 6 |
| | mean | 1.91 | 0.91 | 0.64 | 1.91 | 5.36 |
| | sd | 0.70 | 0.30 | 0.50 | 0.70 | 1.57 |
| | sem | 0.21 | 0.09 | 0.15 | 0.21 | 0.47 |
| | n | 11 | 11 | 11 | 11 | 11 |

TABLE 20A

Gene Expression: FAS

| | | FAS | | | | |
|---|---|---|---|---|---|---|
| group | animal # | 18S | FAS | Dct | DDct | $2^{DDct}$ |
| vehicle | 2 | 12.42 | 21.64 | 9.22 | 0.72 | 0.61 |
| | 5 | 12.38 | 20.75 | 8.37 | -0.13 | 1.09 |
| | 7 | 12.58 | 20.74 | 8.16 | -0.34 | 1.27 |
| | 9 | 12.32 | 20.89 | 8.57 | 0.07 | 0.95 |
| | 11 | 12.58 | 20.77 | 8.19 | -0.31 | 1.24 |
| | 12 | 12.11 | 23.11 | 11 | 2.50 | 0.18 |
| | 13 | 12.34 | 20.65 | 8.31 | -0.19 | 1.14 |
| | 14 | 12.37 | 18.82 | 6.45 | -2.05 | 4.14 |
| | 15 | 12.16 | 18.85 | 6.69 | -1.81 | 3.51 |
| | 16 | 12.59 | 21.25 | 8.66 | 0.16 | 0.90 |
| | 20 | 12.33 | 21.59 | 9.26 | 0.76 | 0.59 |
| | 23 | 12.52 | 21.64 | 9.12 | 0.62 | 0.65 |
| | mean | 12.4 | 20.9 | 8.5 | 0.00 | 1.36 |
| | sd | 0.2 | 1.2 | 1.2 | 1.19 | 1.20 |
| | sem | 0.0 | 0.3 | 0.3 | 0.34 | 0.35 |
| | n | 12 | 12 | 12 | 12 | 12 |
| 20 mg/kg | 1 | 12.55 | 19.75 | 7.2 | -1.30 | 2.46 |
| | 3 | 12.55 | 20.68 | 8.13 | -0.37 | 1.29 |
| | 4 | 12.84 | 22.79 | 9.95 | 1.45 | 0.37 |
| | 6 | ND | ND | ND | ND | ND |
| | 8 | 12.43 | 20.37 | 7.94 | -0.56 | 1.47 |
| | 10 | 12.35 | 22.33 | 9.98 | 1.48 | 0.36 |
| | 17 | 12.59 | 20.71 | 8.12 | -0.38 | 1.30 |
| | 18 | 11.73 | 20.54 | 8.81 | 0.31 | 0.81 |
| | 19 | 12.51 | 21.65 | 9.14 | 0.64 | 0.64 |
| | 21 | 11.5 | 21.62 | 10.12 | 1.62 | 0.33 |
| | 22 | 11.55 | 22.33 | 10.78 | 2.28 | 0.21 |
| | 24 | 12.35 | 20.03 | 7.68 | -0.82 | 1.77 |
| | mean | 12.3 | 21.2 | 8.9 | 0.40 | 1 |
| | sd | 0.5 | 1 | 1.2 | 1.18 | 0.72 |
| | sem | 0.1 | 0.3 | 0.4 | 0.35 | 0.22 |
| | n | 11 | 11 | 11 | 11 | 11 |

TABLE 20B

Gene Expression: SCD1

| | | SCD1 | | | | |
|---|---|---|---|---|---|---|
| group | animal # | 18S | SCD1 | Dct | DDct | $2^{DDct}$ |
| vehicle | 2 | 12.42 | 17.7 | 5.28 | -0.03 | 1.02 |
| | 5 | 12.38 | 17.75 | 5.37 | 0.06 | 0.96 |
| | 7 | 12.58 | 17.25 | 4.67 | -0.64 | 1.56 |
| | 9 | 12.32 | 18.04 | 5.72 | 0.41 | 0.75 |
| | 11 | 12.58 | 17.53 | 4.95 | -0.36 | 1.29 |
| | 12 | 12.11 | 18.91 | 6.8 | 1.49 | 0.36 |
| | 13 | 12.34 | 17.62 | 5.28 | -0.03 | 1.02 |
| | 14 | 12.37 | 16.47 | 4.1 | -1.21 | 2.32 |
| | 15 | 12.16 | 16.63 | 4.47 | -0.84 | 1.80 |
| | 16 | 12.59 | 18.4 | 5.81 | 0.5 | 0.71 |
| | 20 | 12.33 | 18.26 | 5.93 | 0.62 | 0.65 |
| | 23 | 12.52 | 17.91 | 5.39 | 0.08 | 0.95 |
| | mean | 12.4 | 17.7 | 5.3 | 0.00 | 1.12 |
| | sd | 0.2 | 0.7 | 0.7 | 0.72 | 0.55 |
| | sem | 0.0 | 0.2 | 0.2 | 0.21 | 0.16 |
| | n | 12 | 12 | 12 | 12 | 12 |
| 20 mg/kg | 1 | 12.55 | 17.05 | 4.5 | -0.81 | 1.76 |
| | 3 | 12.55 | 16.66 | 4.11 | -1.20 | 2.30 |
| | 4 | 12.84 | 18.93 | 6.09 | 0.78 | 0.58 |
| | 6 | ND | ND | ND | ND | ND |
| | 8 | 12.43 | 17.94 | 5.51 | 0.20 | 0.87 |
| | 10 | 12.35 | 17.92 | 5.57 | 0.26 | 0.84 |
| | 17 | 12.59 | 17.42 | 4.83 | -0.48 | 1.40 |
| | 18 | 11.73 | 16.42 | 4.69 | -0.62 | 1.54 |
| | 19 | 12.51 | 17.11 | 4.6 | -0.71 | 1.64 |
| | 21 | 11.5 | 17.53 | 6.03 | 0.72 | 0.61 |
| | 22 | 11.55 | 18.11 | 6.56 | 1.25 | 0.42 |
| | 24 | 12.35 | 16.3 | 3.95 | -1.36 | 2.57 |
| | mean | 12.3 | 17.4 | 5.1 | -0.18 | 1.32 |
| | sd | 0.5 | 0.8 | 0.9 | 0.87 | 0.72 |
| | sem | 0.1 | 0.2 | 0.3 | 0.26 | 0.22 |
| | n | 11 | 11 | 11 | 11 | 11 |

TABLE 20C

Gene Expression: SREBP1C

| group | animal # | 18S | SREBP1C | Dct | DDct | $2^{DDct}$ |
|---|---|---|---|---|---|---|
| vehicle | 2 | 12.42 | 26.04 | 13.62 | 0.26 | 0.84 |
|  | 5 | 12.38 | 25.85 | 13.47 | 0.11 | 0.93 |
|  | 7 | 12.58 | 25.84 | 13.26 | −0.10 | 1.07 |
|  | 9 | 12.32 | 26 | 13.68 | 0.32 | 0.8 |
|  | 11 | 12.58 | 25.98 | 13.4 | 0.04 | 0.97 |
|  | 12 | 12.11 | 26.29 | 14.18 | 0.82 | 0.57 |
|  | 13 | 12.34 | 26.15 | 13.81 | 0.45 | 0.73 |
|  | 14 | 12.37 | 24.53 | 12.16 | −1.20 | 2.30 |
|  | 15 | 12.16 | 25.26 | 13.1 | −0.26 | 1.20 |
|  | 16 | 12.59 | 26.19 | 13.6 | 0.24 | 0.85 |
|  | 20 | 12.33 | 25 | 12.67 | −0.69 | 1.62 |
|  | 23 | 12.52 | 25.92 | 13.4 | 0.04 | 0.97 |
|  | mean | 12.4 | 25.8 | 13.4 | 0.00 | 1.07 |
|  | sd | 0.2 | 0.5 | 0.5 | 0.53 | 0.47 |
|  | sem | 0.0 | 0.2 | 0.2 | 0.15 | 0.14 |
|  | n | 12 | 12 | 12 | 12 | 12 |
| 20 mg/kg | 1 | 12.55 | 25.53 | 12.98 | −0.38 | 1.30 |
|  | 3 | 12.55 | 25.64 | 13.09 | −0.27 | 1.21 |
|  | 4 | 12.84 | 27.5 | 14.66 | 1.30 | 0.41 |
|  | 6 | ND | ND | ND | ND | ND |
|  | 8 | 12.43 | 26.83 | 14.4 | 1.04 | 0.49 |
|  | 10 | 12.35 | 26.25 | 13.9 | 0.54 | 0.69 |
|  | 17 | 12.59 | 25.81 | 13.22 | −0.14 | 1.10 |
|  | 18 | 11.73 | 25.1 | 13.37 | 0.01 | 0.99 |
|  | 19 | 12.51 | 25.42 | 12.91 | −0.45 | 1.37 |
|  | 21 | 11.5 | 26.32 | 14.82 | 1.46 | 0.36 |
|  | 22 | 11.55 | 26.01 | 14.46 | 1.10 | 0.47 |
|  | 24 | 12.35 | 24.62 | 12.27 | −1.09 | 2.13 |
|  | mean | 12.3 | 25.9 | 13.6 | 0.28 | 0.96 |
|  | sd | 0.5 | 0.8 | 0.8 | 0.85 | 0.54 |
|  | sem | 0.1 | 0.2 | 0.3 | 0.25 | 0.16 |
|  | n | 11 | 11 | 11 | 11 | 11 |

TABLE 20D

Gene Expression: ACC1

| group | animal# | 18S | ACC1 | Dct | DDct | $2^{DDct}$ |
|---|---|---|---|---|---|---|
| vehicle | 2 | 12.42 | 28.34 | 15.92 | 0.04 | 0.97 |
|  | 5 | 12.38 | 28.51 | 16.13 | 0.25 | 0.84 |
|  | 7 | 12.58 | 28.12 | 15.54 | −0.34 | 1.27 |
|  | 9 | 12.32 | 28.17 | 15.85 | −0.03 | 1.02 |
|  | 11 | 12.58 | 28.43 | 15.85 | −0.03 | 1.02 |
|  | 12 | 12.11 | 29.9 | 17.79 | 1.91 | 0.27 |
|  | 13 | 12.34 | 28.36 | 16.02 | 0.14 | 0.91 |
|  | 14 | 12.37 | 26.48 | 14.11 | −1.77 | 3.42 |
|  | 15 | 12.16 | 26.85 | 14.69 | −1.19 | 2.29 |
|  | 16 | 12.59 | 28.75 | 16.16 | 0.28 | 0.83 |
|  | 20 | 12.33 | 29 | 16.67 | 0.79 | 0.58 |
|  | 23 | 12.52 | 28.38 | 15.86 | −0.02 | 1.02 |
|  | mean | 12.4 | 28.3 | 15.9 | 0.00 | 1.20 |
|  | sd | 0.2 | 0.9 | 0.9 | 0.91 | 0.84 |
|  | sem | 0.0 | 0.3 | 0.3 | 0.26 | 0.24 |
|  | n | 12 | 12 | 12 | 12 | 12 |
| 20 mg/kg | 1 | 12.55 | 27.74 | 15.19 | −0.69 | 1.62 |
|  | 3 | 12.55 | 28.17 | 15.62 | −0.26 | 1.20 |
|  | 4 | 12.84 | 31 | 18.16 | 2.28 | 0.21 |
|  | 6 | ND | ND | ND | ND | ND |
|  | 8 | 12.43 | 28.06 | 15.63 | −0.25 | 1.19 |
|  | 10 | 12.35 | 30.55 | 18.2 | 2.32 | 0.20 |
|  | 17 | 12.59 | 28.11 | 15.52 | −0.36 | 1.29 |
|  | 18 | 11.73 | 27.95 | 16.22 | 0.34 | 0.79 |
|  | 19 | 12.51 | 28.97 | 16.46 | 0.58 | 0.67 |
|  | 21 | 11.5 | 28.95 | 17.45 | 1.57 | 0.34 |
|  | 22 | 11.55 | 29.55 | 18 | 2.12 | 0.23 |
|  | 24 | 12.35 | 27.41 | 15.06 | −0.82 | 1.77 |
|  | mean | 12.3 | 28.8 | 16.5 | 0.62 | 0.86 |
|  | sd | 0.5 | 1.2 | 1.2 | 1.23 | 0.58 |

TABLE 20D-continued

Gene Expression: ACC1

| group | animal# | 18S | ACC1 | Dct | DDct | $2^{DDct}$ |
|---|---|---|---|---|---|---|
|  | sem | 0.1 | 0.4 | 0.4 | 0.37 | 0.18 |
|  | n | 11 | 11 | 11 | 11 | 11 |

TABLE 20E

Gene Expression: SCAP

| group | animal # | 18S | SCAP | Dct | DDct | $2^{DDct}$ |
|---|---|---|---|---|---|---|
| vehicle | 2 | 12.42 | 24.25 | 11.83 | −0.23 | 1.17 |
|  | 5 | 12.38 | 24.57 | 12.19 | 0.13 | 0.91 |
|  | 7 | 12.58 | 24.17 | 11.59 | −0.47 | 1.39 |
|  | 9 | 12.32 | 25.05 | 12.73 | 0.67 | 0.63 |
|  | 11 | 12.58 | 24.81 | 12.23 | 0.17 | 0.89 |
|  | 12 | 12.11 | 25 | 12.89 | 0.83 | 0.56 |
|  | 13 | 12.34 | 24.73 | 12.39 | 0.33 | 0.80 |
|  | 14 | 12.37 | 23.28 | 10.91 | −1.15 | 2.22 |
|  | 15 | 12.16 | 24.06 | 11.9 | −0.16 | 1.12 |
|  | 16 | 12.59 | 24.66 | 12.07 | 0.01 | 0.99 |
|  | 20 | 12.33 | 24.76 | 12.43 | 0.37 | 0.77 |
|  | 23 | 12.52 | 24.1 | 11.58 | −0.48 | 1.4 |
|  | mean | 12.4 | 24.5 | 12.1 | 0.00 | 1.07 |
|  | sd | 0.2 | 0.5 | 0.5 | 0.55 | 0.45 |
|  | sem | 0.0 | 0.1 | 0.2 | 0.16 | 0.13 |
|  | n | 12 | 12 | 12 | 12 | 12 |
| 20 mg/kg | 1 | 12.55 | 24.16 | 11.61 | −0.45 | 1.37 |
|  | 3 | 12.55 | 23.83 | 11.28 | −0.78 | 1.72 |
|  | 4 | 12.84 | 25.53 | 12.69 | 0.63 | 0.65 |
|  | 6 | ND | ND | ND | ND | ND |
|  | 8 | 12.43 | 24.98 | 12.55 | 0.49 | 0.71 |
|  | 10 | 12.35 | 24.54 | 12.19 | 0.13 | 0.91 |
|  | 17 | 12.59 | 24.11 | 11.52 | −0.54 | 1.46 |
|  | 18 | 11.73 | 23.32 | 11.59 | −0.47 | 1.39 |
|  | 19 | 12.51 | 23.79 | 11.28 | −0.78 | 1.72 |
|  | 21 | 11.5 | 24.21 | 12.71 | 0.65 | 0.64 |
|  | 22 | 11.55 | 24.38 | 12.83 | 0.77 | 0.59 |
|  | 24 | 12.35 | 23.73 | 11.38 | −0.68 | 1.60 |
|  | mean | 12.3 | 24.2 | 12.0 | −0.10 | 1.16 |
|  | sd | 0.5 | 0.6 | 0.6 | 0.63 | 0.46 |
|  | sem | 0.1 | 0.2 | 0.2 | 0.19 | 0.14 |
|  | n | 11 | 11 | 11 | 11 | 11 |

TABLE 20F

Gene Expression: INSIG1

| group | animal # | 18S | INSIG1 | Dct | DDct | $2^{DDct}$ |
|---|---|---|---|---|---|---|
| vehicle | 2 | 12.42 | 23.1 | 10.68 | −0.22 | 1.16 |
|  | 5 | 12.38 | 22.61 | 10.23 | −0.67 | 1.59 |
|  | 7 | 12.58 | 22.83 | 10.25 | −0.65 | 1.57 |
|  | 9 | 12.32 | 23.3 | 10.98 | 0.08 | 0.94 |
|  | 11 | 12.58 | 23.27 | 10.69 | −0.21 | 1.15 |
|  | 12 | 12.11 | 24.36 | 12.25 | 1.35 | 0.39 |
|  | 13 | 12.34 | 23.78 | 11.44 | 0.54 | 0.69 |
|  | 14 | 12.37 | 22.17 | 9.8 | −1.10 | 2.14 |
|  | 15 | 12.16 | 22.89 | 10.73 | −0.17 | 1.12 |
|  | 16 | 12.59 | 24.03 | 11.44 | 0.54 | 0.69 |
|  | 20 | 12.33 | 24.68 | 12.35 | 1.45 | 0.37 |
|  | 23 | 12.52 | 22.44 | 9.92 | −0.98 | 1.97 |
|  | mean | 12.4 | 23.3 | 10.9 | 0.00 | 1.15 |
|  | sd | 0.2 | 0.8 | 0.8 | 0.84 | 0.58 |
|  | sem | 0.0 | 0.2 | 0.2 | 0.24 | 0.17 |
|  | n | 12 | 12 | 12 | 12 | 12 |

TABLE 20F-continued

Gene Expression: INSIG1

| | | | INSIG1 | | | |
|---|---|---|---|---|---|---|
| group | animal # | 18S | INSIG1 | Dct | DDct | $2^{DDct}$ |
| 20 mg/kg | 1 | 12.55 | 22.4 | 9.85 | −1.05 | 2.07 |
| | 3 | 12.55 | 22.28 | 9.73 | −1.17 | 2.24 |
| | 4 | 12.84 | 24.1 | 11.26 | 0.36 | 0.78 |
| | 6 | ND | ND | ND | ND | ND |
| | 8 | 12.43 | 22.7 | 10.27 | −0.63 | 1.54 |
| | 10 | 12.35 | 22.65 | 10.3 | −0.60 | 1.51 |
| | 17 | 12.59 | 22.76 | 10.17 | −0.73 | 1.65 |
| | 18 | 11.73 | 22.09 | 10.36 | −0.54 | 1.45 |
| | 19 | 12.51 | 22.89 | 10.38 | −0.52 | 1.43 |
| | 21 | 11.5 | 22.76 | 11.26 | 0.36 | 0.78 |
| | 22 | 11.55 | 23.58 | 12.03 | 1.13 | 0.46 |
| | 24 | 12.35 | 21.74 | 9.39 | −1.51 | 2.84 |
| | mean | 12.3 | 22.7 | 10.5 | −0.44 | 1.52 |
| | sd | 0.5 | 0.7 | 0.8 | 0.77 | 0.7 |
| | sem | 0.1 | 0.2 | 0.2 | 0.23 | 0.21 |
| | n | 11 | 11 | 11 | 11 | 11 |

TABLE 20G

Gene Expression: HMGCOA

| | | | HMGCOA | | | |
|---|---|---|---|---|---|---|
| group | animal # | 18S | HMGCoA | Dct | DDct | $2^{DDct}$ |
| vehicle | 2 | 12.42 | 25.68 | 13.26 | 0.04 | 0.97 |
| | 5 | 12.38 | 25.07 | 12.69 | −0.53 | 1.44 |
| | 7 | 12.58 | 25.26 | 12.68 | −0.54 | 1.45 |
| | 9 | 12.32 | 26.03 | 13.71 | 0.49 | 0.71 |
| | 11 | 12.58 | 25.79 | 13.21 | −0.01 | 1.01 |
| | 12 | 12.11 | 26.44 | 14.33 | 1.11 | 0.46 |
| | 13 | 12.34 | 26.48 | 14.14 | 0.92 | 0.53 |
| | 14 | 12.37 | 24.43 | 12.06 | −1.16 | 2.24 |
| | 15 | 12.16 | 25.33 | 13.17 | −0.05 | 1.04 |
| | 16 | 12.59 | 26.00 | 13.41 | 0.19 | 0.88 |
| | 20 | 12.33 | 25.97 | 13.64 | 0.42 | 0.75 |
| | 23 | 12.52 | 24.87 | 12.35 | −0.87 | 1.83 |
| | mean | 12.4 | 25.6 | 13.2 | 0.00 | 1.11 |
| | sd | 0.2 | 0.6 | 0.7 | 0.69 | 0.54 |
| | sem | 0.0 | 0.2 | 0.2 | 0.20 | 0.15 |
| | n | 12 | 12 | 12 | 12 | 12 |
| 20 mg/kg | 1 | 12.55 | 25.35 | 12.8 | −0.42 | 1.34 |
| | 3 | 12.55 | 24.69 | 12.14 | −1.08 | 2.12 |
| | 4 | 12.84 | 26.62 | 13.78 | 0.56 | 0.68 |
| | 6 | ND | ND | ND | ND | ND |
| | 8 | 12.43 | 25.08 | 12.65 | −0.57 | 1.49 |
| | 10 | 12.35 | 25.92 | 13.57 | 0.35 | 0.79 |
| | 17 | 12.59 | 25.42 | 12.83 | −0.39 | 1.31 |
| | 18 | 11.73 | 24.76 | 13.03 | −0.19 | 1.14 |
| | 19 | 12.51 | 25.37 | 12.86 | −0.36 | 1.28 |
| | 21 | 11.5 | 25.99 | 14.49 | 1.27 | 0.41 |
| | 22 | 11.55 | 26.18 | 14.63 | 1.41 | 0.38 |
| | 24 | 12.35 | 24.72 | 12.37 | −0.85 | 1.8 |
| | mean | 12.3 | 25.5 | 13.2 | −0.03 | 1.16 |
| | sd | 0.5 | 0.6 | 0.8 | 0.82 | 0.55 |
| | sem | 0.1 | 0.2 | 0.2 | 0.25 | 0.17 |
| | n | 11 | 11 | 11 | 11 | 11 |

TABLE 20H

Gene Expression: LDLR

| | | | LDLR | | | |
|---|---|---|---|---|---|---|
| Group | animal # | 18S | LDLR | Dct | DDct | $2^{DDct}$ |
| Vehicle | 2 | 12.42 | 26.06 | 13.64 | 0.54 | 0.69 |
| | 5 | 12.38 | 24.71 | 12.33 | −0.77 | 1.70 |
| | 7 | 12.58 | 24.85 | 12.27 | −0.83 | 1.77 |
| | 9 | 12.32 | 26.25 | 13.93 | 0.83 | 0.56 |
| | 11 | 12.58 | 25.02 | 12.44 | −0.66 | 1.58 |
| | 12 | 12.11 | 26.93 | 14.82 | 1.72 | 0.30 |
| | 13 | 12.34 | 25.93 | 13.59 | 0.49 | 0.71 |
| | 14 | 12.37 | 24.05 | 11.68 | −1.42 | 2.67 |
| | 15 | 12.16 | 24.96 | 12.8 | −0.3 | 1.23 |
| | 16 | 12.59 | 25.41 | 12.82 | −0.28 | 1.21 |
| | 20 | 12.33 | 26.6 | 14.27 | 1.17 | 0.44 |
| | 23 | 12.52 | 25.08 | 12.56 | −0.54 | 1.45 |
| | mean | 12.4 | 25.5 | 13.1 | 0.00 | 1.19 |
| | sd | 0.2 | 0.9 | 0.9 | 0.94 | 0.69 |
| | sem | 0.0 | 0.2 | 0.3 | 0.27 | 0.20 |
| | n | 12 | 12 | 12 | 12 | 12 |
| 20 mg/kg | 1 | 12.55 | 24.92 | 12.37 | −0.73 | 1.65 |
| | 3 | 12.55 | 24.3 | 11.75 | −1.35 | 2.54 |
| | 4 | 12.84 | 27.14 | 14.3 | 1.2 | 0.43 |
| | 6 | ND | ND | ND | ND | ND |
| | 8 | 12.43 | 25.37 | 12.94 | −0.16 | 1.11 |
| | 10 | 12.35 | 25.85 | 13.5 | 0.4 | 0.76 |
| | 17 | 12.59 | 24.92 | 12.33 | −0.77 | 1.7 |
| | 18 | 11.73 | 23.76 | 12.03 | −1.07 | 2.09 |
| | 19 | 12.51 | 24.73 | 12.22 | −0.88 | 1.84 |
| | 21 | 11.5 | 24.47 | 12.97 | −0.13 | 1.09 |
| | 22 | 11.55 | 24.99 | 13.44 | 0.34 | 0.79 |
| | 24 | 12.35 | 23.63 | 11.28 | −1.82 | 3.52 |
| | mean | 12.3 | 24.9 | 12.6 | −0.45 | 1.59 |
| | sd | 0.5 | 1.0 | 0.9 | 0.88 | 0.90 |
| | sem | 0.1 | 0.3 | 0.3 | 0.26 | 0.27 |
| | n | 11 | 11 | 11 | 11 | 11 |

TABLE 20I

Gene Expression: PERK

| | | | PERK | | | |
|---|---|---|---|---|---|---|
| group | animal # | 18S | PERK | Dct | DDct | $2^{DDct}$ |
| Vehicle | 2 | 12.42 | 27.4 | 14.98 | 0.48 | 0.71 |
| | 5 | 12.38 | 27.25 | 14.87 | 0.37 | 0.77 |
| | 7 | 12.58 | 26.77 | 14.19 | −0.31 | 1.24 |
| | 9 | 12.32 | 26.82 | 14.5 | 0.00 | 1.00 |
| | 11 | 12.58 | 27.18 | 14.6 | 0.1 | 0.93 |
| | 12 | 12.11 | 27.22 | 15.11 | 0.61 | 0.65 |
| | 13 | 12.34 | 27.27 | 14.93 | 0.43 | 0.74 |
| | 14 | 12.37 | 25.93 | 13.56 | −0.94 | 1.91 |
| | 15 | 12.16 | 26.19 | 14.03 | −0.47 | 1.38 |
| | 16 | 12.59 | 27.55 | 14.96 | 0.46 | 0.72 |
| | 20 | 12.33 | 26.25 | 13.92 | −0.58 | 1.49 |
| | 23 | 12.52 | 26.82 | 14.30 | −0.20 | 1.15 |
| | mean | 12.4 | 26.9 | 14.50 | 0.00 | 1.06 |
| | sd | 0.2 | 0.5 | 0.5 | 0.5 | 0.39 |
| | sem | 0 | 0.2 | 0.1 | 0.14 | 0.11 |
| | n | 12 | 12 | 12 | 12 | 12 |
| 20 mg/kg | 1 | 12.55 | 26.78 | 14.23 | −0.27 | 1.2 |
| | 3 | 12.55 | 26.96 | 14.41 | −0.09 | 1.06 |
| | 4 | 12.84 | 28.95 | 16.11 | 1.61 | 0.33 |
| | 6 | ND | ND | ND | ND | ND |
| | 8 | 12.43 | 27.32 | 14.89 | 0.39 | 0.76 |
| | 10 | 12.35 | 27.3 | 14.95 | 0.45 | 0.73 |
| | 17 | 12.59 | 26.77 | 14.18 | −0.32 | 1.24 |
| | 18 | 11.73 | 26.58 | 14.85 | 0.35 | 0.78 |
| | 19 | 12.51 | 26.81 | 14.3 | −0.2 | 1.15 |
| | 21 | 11.5 | 27.25 | 15.75 | 1.25 | 0.42 |
| | 22 | 11.55 | 27.62 | 16.07 | 1.57 | 0.34 |
| | 24 | 12.35 | 25.25 | 12.9 | −1.6 | 3.02 |
| | mean | 12.3 | 27.1 | 14.8 | 0.29 | 1.00 |
| | sd | 0.5 | 0.9 | 0.9 | 0.95 | 075 |
| | sem | 0.1 | 0.2 | 0.3 | 0.29 | 0.23 |
| | n | 11 | 11 | 11 | 11 | 11 |

TABLE 20J

Gene Expression: NRF2

| Group | animal # | 18S | NRF2 | Dct | DDct | $2^{DDct}$ |
|---|---|---|---|---|---|---|
| Vehicle | 2 | 12.42 | 23.83 | 11.41 | 0.37 | 0.77 |
|  | 5 | 12.38 | 23.87 | 11.49 | 0.45 | 0.73 |
|  | 7 | 12.58 | 23.16 | 10.58 | −0.46 | 1.38 |
|  | 9 | 12.32 | 23.29 | 10.97 | −0.07 | 1.05 |
|  | 11 | 12.58 | 24.02 | 11.44 | 0.40 | 0.76 |
|  | 12 | 12.11 | 23.91 | 11.8 | 0.76 | 0.59 |
|  | 13 | 12.34 | 23.45 | 11.11 | 0.07 | 0.95 |
|  | 14 | 12.37 | 22.15 | 9.78 | −1.26 | 2.40 |
|  | 15 | 12.16 | 22.53 | 10.37 | −0.67 | 1.59 |
|  | 16 | 12.59 | 24.02 | 11.43 | 0.39 | 0.76 |
|  | 20 | 12.33 | 23.13 | 10.8 | −0.24 | 1.18 |
|  | 23 | 12.52 | 23.84 | 11.32 | 0.28 | 0.82 |
|  | mean | 12.4 | 23.4 | 11.0 | 0.00 | 1.08 |
|  | sd | 0.2 | 0.6 | 0.6 | 0.57 | 0.51 |
|  | sem | 0.0 | 0.2 | 0.2 | 0.17 | 0.15 |
|  | n | 12 | 12 | 12 | 12 | 12 |
| 20 mg/kg | 1 | 12.55 | 23.17 | 10.62 | −0.42 | 1.34 |
|  | 3 | 12.55 | 23.25 | 10.7 | −0.34 | 1.27 |
|  | 4 | 12.84 | 25.41 | 12.57 | 1.53 | 0.35 |
|  | 6 | ND | ND | ND | ND | ND |
|  | 8 | 12.43 | 23.7 | 11.27 | 0.23 | 0.85 |
|  | 10 | 12.35 | 23.66 | 11.31 | 0.27 | 0.83 |
|  | 17 | 12.59 | 23.47 | 10.88 | −0.16 | 1.12 |
|  | 18 | 11.73 | 22.83 | 11.1 | 0.06 | 0.96 |
|  | 19 | 12.51 | 23.25 | 10.74 | −0.3 | 1.23 |
|  | 21 | 11.5 | 23.73 | 12.23 | 1.19 | 0.44 |
|  | 22 | 11.55 | 23.44 | 11.89 | 0.85 | 0.56 |
|  | 24 | 12.35 | 22.25 | 9.9 | −1.14 | 2.21 |
|  | mean | 12.3 | 23.5 | 11.2 | 0.16 | 1.01 |
|  | sd | 0.5 | 0.8 | 0.8 | 0.78 | 0.52 |
|  | sem | 0.1 | 0.2 | 0.2 | 0.23 | 0.16 |
|  | n | 11 | 11 | 11 | 11 | 11 |

TABLE 20K

Gene Expression: MCP-1

| Group | animal # | 18S | MCP-1 | Dct | DDct | $2^{DDct}$ |
|---|---|---|---|---|---|---|
| Vehicle | 2 | 12.42 | 27.14 | 14.72 | 1.1 | 0.47 |
|  | 5 | 12.38 | 26.01 | 13.63 | 0.01 | 0.99 |
|  | 7 | 12.58 | 25.58 | 13 | −0.62 | 1.54 |
|  | 9 | 12.32 | 25.75 | 13.43 | −0.19 | 1.14 |
|  | 11 | 12.58 | 26.44 | 13.86 | 0.24 | 0.85 |
|  | 12 | 12.11 | 25.87 | 13.76 | 0.14 | 0.91 |
|  | 13 | 12.34 | 26.2 | 13.86 | 0.24 | 0.85 |
|  | 14 | 12.37 | 25.42 | 13.05 | −0.57 | 1.48 |
|  | 15 | 12.16 | 25.66 | 13.5 | −0.12 | 1.09 |
|  | 16 | 12.59 | 27.42 | 14.83 | 1.21 | 0.43 |
|  | 20 | 12.33 | 24.06 | 11.73 | −1.89 | 3.7 |
|  | 23 | 12.52 | 26.57 | 14.05 | 0.43 | 0.74 |
|  | mean | 12.4 | 26.0 | 13.6 | 0.00 | 1.18 |
|  | sd | 0.2 | 0.9 | 0.8 | 0.82 | 0.86 |
|  | sem | 0.0 | 0.3 | 0.2 | 0.24 | 0.25 |
|  | n | 12 | 12 | 12 | 12 | 12 |
| 20 mg/kg | 1 | 12.55 | 26.89 | 14.34 | 0.72 | 0.61 |
|  | 3 | 12.55 | 26.18 | 13.63 | 0.01 | 0.99 |
|  | 4 | 12.84 | 28.45 | 15.61 | 1.99 | 0.25 |
|  | 6 | ND | ND | ND | ND | ND |
|  | 8 | 12.43 | 26.02 | 13.59 | −0.03 | 1.02 |
|  | 10 | 12.35 | 25.89 | 13.54 | −0.08 | 1.06 |
|  | 17 | 12.59 | 26.25 | 13.66 | 0.04 | 0.97 |
|  | 18 | 11.73 | 26.62 | 14.89 | 1.27 | 0.41 |
|  | 19 | 12.51 | 28.83 | 16.32 | 2.7 | 0.15 |
|  | 21 | 11.5 | 27 | 15.5 | 1.88 | 0.27 |
|  | 22 | 11.55 | 27.29 | 15.74 | 2.12 | 0.23 |
|  | 24 | 12.35 | 24.14 | 11.79 | −1.83 | 3.55 |
|  | mean | 12.3 | 26.7 | 14.4 | 0.80 | 0.87 |
|  | sd | 0.5 | 1.3 | 1.3 | 1.33 | 0.96 |
|  | sem | 0.1 | 0.4 | 0.4 | 0.40 | 0.29 |
|  | n | 11 | 11 | 11 | 11 | 11 |

TABLE 20L

Gene Expression: Col1a1

| Group | animal # | 18S | Col1a1 | Dct | DDct | $2^{DDct}$ |
|---|---|---|---|---|---|---|
| Vehicle | 2 | 12.42 | 29.06 | 16.64 | 2.69 | 0.15 |
|  | 5 | 12.38 | 28.03 | 15.65 | 1.70 | 0.31 |
|  | 7 | 12.58 | 26.08 | 13.5 | −0.45 | 1.37 |
|  | 9 | 12.32 | 26.57 | 14.25 | 0.30 | 0.81 |
|  | 11 | 12.58 | 26.7 | 14.12 | 0.17 | 0.89 |
|  | 12 | 12.11 | 26.28 | 14.17 | 0.22 | 0.86 |
|  | 13 | 12.34 | 26.14 | 13.8 | −0.15 | 1.11 |
|  | 14 | 12.37 | 24.13 | 11.76 | −2.19 | 4.56 |
|  | 15 | 12.16 | 25.13 | 12.97 | −0.98 | 1.97 |
|  | 16 | 12.59 | 26.77 | 14.18 | 0.23 | 0.85 |
|  | 20 | 12.33 | 24.38 | 12.05 | −1.90 | 3.73 |
|  | 23 | 12.52 | 26.83 | 14.31 | 0.36 | 0.78 |
|  | mean | 12.4 | 26.3 | 14 | 0.00 | 1.45 |
|  | sd | 0.2 | 1.4 | 1.4 | 1.35 | 1.35 |
|  | sem | 0 | 0.4 | 0.4 | 0.39 | 0.39 |
|  | n | 12 | 12 | 12 | 12 | 12 |
| 20 mg/kg | 1 | 12.55 | 27.55 | 15 | 1.05 | 0.48 |
|  | 3 | 12.55 | 26.78 | 14.23 | 0.28 | 0.82 |
|  | 4 | 12.84 | 30.66 | 17.82 | 3.87 | 0.07 |
|  | 6 | ND | ND | ND | ND | ND |
|  | 8 | 12.43 | 28.81 | 16.38 | 2.43 | 0.19 |
|  | 10 | 12.35 | 27.72 | 15.37 | 1.42 | 0.37 |
|  | 17 | 12.59 | 28.24 | 15.65 | 1.7 | 0.31 |
|  | 18 | 11.73 | 26.86 | 15.13 | 1.18 | 0.44 |
|  | 19 | 12.51 | 28.61 | 16.1 | 2.15 | 0.23 |
|  | 21 | 11.5 | 27.64 | 16.14 | 2.19 | 0.22 |
|  | 22 | 11.55 | 29.03 | 17.48 | 3.53 | 0.09 |
|  | 24 | 12.35 | 25.17 | 12.82 | −1.13 | 2.19 |
|  | mean | 12.3 | 27.9 | 15.6 | 1.70 | 0.49 |
|  | sd | 0.5 | 1.4 | 1.4 | 1.41 | 0.60 |
|  | sem | 0.1 | 0.4 | 0.4 | 0.42 | 0.18 |
|  | n | 11 | 11 | 11 | 11 | 11 |

Example B5

Effect of Compound #37 on Plasma and Liver Lipid Levels in ob/ob Mice

This example demonstrates the effect of Compound #37 on plasma and liver lipid levels in ob/ob mice.

Groups of mice were either untreated (group 1) or treated for 8 weeks with vehicle (group 2), or with Compound #37 at 5 mg/kg (group 3), 10 mg/kg (group 4), or 20 mg/kg (group 5). Treatment was daily by oral gavage in vehicle (20% HPβCD). Values are presented as mean±standard error of the mean (sem). A t test was performed to compare the untreated group and the vehicle group. Then Compound #37-treated groups were compared to the vehicle-treated group with a 1-way ANOVA+Dunnett's post-test. When variances were significantly different, a Kruskaii-Wallis test was performed. For each test, a p<0.05 was considered significant. Of note, animal #39, group 1 was excluded from the statistical analysis, due to low values for all parameters measured. Some other values were considered as out-liners and excluded from the statistical analysis when the value was far below the mean minus 2 SD. Excluded values are marked with an asterisk in Tables 21-23.

Results. At the end of experiment, the ob/ob mice treated with vehicle alone, in comparison to the untreated mice, displayed a significant increase in plasma triglyceride levels ($p<0.01$) and, inversely, a significant plasma insulin level decrease ($p<0.01$). The plasma total cholesterol and non-esterified fatty acids levels were unchanged (Table 21).

Treatment with Compound #37 at 10 mg/kg treatment tended to decrease plasma triglycerides levels. Compound #37 decreased dose-dependently levels of non-esterified fatty acids and total cholesterol levels. Plasma insulin levels were unchanged with the treatment or tended to increase with treatment with Compound #37 at 20 mg/kg. See Table 21.

Treatment with 5 mg/kg of Compound #37 significantly decreased liver triglyceride and fatty acids levels, as shown in Table 22. This decrease was correlated with results obtained with Oil red O staining at the same dose; see Table 23.

The treatment was generally well tolerated over 8 weeks, with no significant differences in weight gain and food intake across all treatment groups (Compound #37P042). Compound #37 treatment resulted in a reduction in plasma triglyceride, as well as a statistically significant ($p<0.05$) dose-dependent reduction in plasma free fatty acids and total cholesterol concentrations. These plasma lipid results are consistent with SCAP/SREBP pathway inhibition seen in tissue-specific SCAP knockout mice (Horton et al, 2002) and with inhibition of SREBP in vivo (Moon et al, 2012).

Lipid accumulation was reduced in the livers of Compound #37-treated ob/ob mice (Compound #37P042), as indicated by a reduction in triglycerides, fatty acids, total cholesterol, and Oil Red O staining of hepatic neutral lipids; however, these reductions were variable (Compound #37P054, Table 2.6.2-2). Quantification of Oil Red O staining showed a decrease at the 5 mg/kg/day and 20 mg/kg/day doses; however, these decreases were not statistically significant. The 10 mg/kg/day dose resulted in no reduction in Oil Red O staining despite reducing plasma lipids. Compound #37 had no effect on hepatic cholesterol concentrations. The variability in these findings may be due to the severity of steatosis that develops in this model or the quantification methods used. Fasting blood glucose and insulin concentrations were highly variable across groups without significant changes from the vehicle control group.

Conclusion. Vehicle alone modified plasma triglycerides and insulin levels. Treatment with Compound #37 decreased in a dose-dependent manner non-esterified fatty acid levels and total cholesterol and tended to decrease triglycerides. At 5 mg/kg, Compound #37 significantly decreased liver triglycerides and fatty acids, indicating that treatment with Compound #37 improves liver steatosis in ob/ob mice.

TABLE 21

Plasma triglycerides, non-esterified free fatty acids, total cholesterol, and insulin levels

| Group | animal # | triglycerides (g/L) | non-esterified fatty acids (mM) | total cholesterol (g/L) | plasma insulin (µU/mL) |
|---|---|---|---|---|---|
| no treatment | 15 | 0.777 | 1.33 | 1.954 | 499.9 |
| | 17 | 0.728 | 1.009 | 1.903 | 643.5 |
| | 23 | 0.663 | 1.131 | 1.891 | 866.9 |
| | 25 | 0.973 | 0.886 | 1.802 | 511.4 |
| | 30 | 1.348 | 0.494 | 1.752 | 905.3 |
| | 33 | 0.908 | 0.552 | 1.676 | 1019.5 |
| | 36 | 0.875 | 0.777 | 2.055 | 783.6 |
| | 39 | 2.147* | 0.552* | 1.133* | 11.4* |
| | 48 | 1.984 | 0.873 | 2.055 | 310.3 |
| | mean | 1.0 | 0.9 | 1.9 | 695.1 |
| | sd | 0.4 | 0.3 | 0.1 | 244.0 |
| | sem | 0.2 | 0.1 | 0.0 | 86.3 |
| | n | 8 | 8 | 8 | 8 |
| vehicle | 1 | 1.576 | 1.562 | 2.232 | 16.5* |
| | 3 | 1.625 | 1.157 | 2.118 | 202.0 |
| | 12 | 2.115 | 1.221 | 1.827 | 121.3 |
| | 13 | 1.886 | 0.893 | 1.966 | 65.4 |
| | 22 | 1.152 | 0.803 | 1.764 | 496.8 |
| | 26 | 1.935 | 0.751 | 1.651 | 504.0 |
| | 28 | 1.674 | 0.88 | 1.663 | 464.6 |
| | 43 | 1.544 | 0.835 | 2.087 | 394.6 |
| | 44 | 1.788 | 0.848 | 2.029 | 170.9 |
| | mean | 1.7 | 1.0 | 1.9 | 302.4 |
| | sd | 0.3 | 0.3 | 0.2 | 181.1 |
| | sem | 0.1 | 0.1 | 0.1 | 64.0 |
| | n | 9 | 9 | 9 | 9 |
| 5 mg/kg | 4 | 1.283 | 1.028 | 1.587 | 198.7 |
| | 8 | 1.152 | 0.77 | 1.903 | 262.7 |
| | 10 | 1.038 | 0.616 | 1.916 | 181.1 |
| | 18 | 1.397 | 0.552 | 1.853 | 250.5 |
| | 19 | 1.593 | 0.68 | 2.017 | 118.7 |
| | 20 | 1.201 | 1.092 | 1.537 | 394.6 |
| | 40 | 1.397 | 0.783 | 2.08 | 24.6* |
| | 41 | 1.609 | 0.655 | 1.625 | 374.6 |
| | 47 | 2.408 | 0.539 | 1.347 | 512.6 |
| | 50 | 2.504 | 0.68 | 1.638 | 173.1 |
| | mean | 1.6 | 0.7 | 1.8 | 274.1 |
| | sd | 0.5 | 0.2 | 0.2 | 127.9 |
| | sem | 0.2 | 0.1 | 0.1 | 42.6 |
| | n | 10 | 10 | 10 | 10 |
| 10 mg/kg | 2 | 0.94 | 1.009 | 1.587 | 123.8 |
| | 6 | 1.12 | 0.474 | 1.865 | 457.7 |
| | 11 | 0.875 | 0.828 | 1.865 | 81.9 |
| | 14 | 1.218 | 0.7 | 1.891 | 949.0 |
| | 21 | 1.528 | 0.564 | 1.827 | 153.3 |
| | 29 | 1.299 | 0.951 | 1.827 | 62.6 |
| | 31 | 1.968 | 0.738 | 1.234 | 508.2 |
| | 42 | 1.381 | 0.661 | 1.891 | 904.4 |
| | 45 | 1.593 | 0.809 | 1.651 | 194.4 |
| | 46 | 0.777 | 0.307 | 1.183 | 137.5 |
| | mean | 1.3 | 0.7 | 1.7 | 357.3 |
| | sd | 0.4 | 0.2 | 0.3 | 336.0 |
| | sem | 0.1 | 0.1 | 0.1 | 106.2 |
| | n | 10 | 10 | 10 | 10 |
| 20 mg/kg | 5 | 0.875 | 0.429 | 1.234 | 447.3 |
| | 9 | 1.886 | 0.642 | 0.893 | 10.5 |
| | 16 | 1.511 | 0.494 | 1.499 | 730.1 |
| | 24 | 1.642 | 0.481 | 1.714 | 505.0 |
| | 27 | 1.854 | 0.423 | 1.663 | 254.3 |
| | 34 | 1.283 | 0.513 | 1.625 | 881.0 |
| | 35 | 1.308 | 0.423 | 1.587 | 810.7 |
| | 37 | 1.381 | 0.397 | 1.36 | 483.7 |
| | 38 | 1.511 | 0.687 | 1.272 | 62.6 |
| | 49 | 1.968 | 0.597 | 1.663 | 256.2 |
| | mean | 1.5 | 0.5 | 1.5 | 444.1 |
| | sd | 0.4 | 0.1 | 0.3 | 301.3 |
| | sem | 0.1 | 0.0 | 0.1 | 95.3 |
| | n | 10 | 10 | 10 | 10 |

TABLE 22

Liver triglycerides, fatty acids, and total cholesterol levels

| Group | animal # | triglycerides (µg/mg liver) | fatty acids (nmol/mg liver) | total cholesterol (µg/mg liver) |
|---|---|---|---|---|
| no treatment | 15 | 106.20 | 45.19 | 5.66 |
| | 17 | 124.97 | 45.88 | 14.51 |
| | 23 | 94.27 | 35.16 | 11.82 |
| | 25 | 116.95 | 42.26 | 13.05 |
| | 30 | 137.18 | 45.36 | 14.25 |
| | 33 | 128.14 | 51.02 | 14.52 |
| | 36 | 115.83 | 41.64 | 13.72 |
| | 39 | 11.203* | 12.58* | 9.83* |
| | 48 | 98.37 | 43.67 | 13.79 |
| | mean | 115.2 | 43.8 | 12.7 |
| | sd | 14.9 | 4.5 | 3.0 |
| | sem | 5.3 | 1.6 | 1.0 |
| | n | 8 | 8 | 8 |
| vehicle | 1 | 155.04 | 51.45 | 14.77 |
| | 3 | 132.12 | 53.84 | 13.67 |
| | 12 | 100.72 | 36.40 | 10.92 |
| | 13 | 126.81 | 47.45 | 17.15 |
| | 22 | 172.66 | 45.61 | 15.29 |
| | 26 | 119.53 | 41.60 | 12.06 |
| | 28 | 110.38 | 40.42 | 12.48 |
| | 43 | 102.33 | 53.25 | 13.47 |
| | 44 | 212.91 | 56.63 | 13.92 |
| | mean | 136.9 | 47.4 | 13.7 |
| | sd | 37.1 | 6.9 | 1.9 |
| | sem | 12.4 | 2.3 | 0.6 |
| | n | 9 | 9 | 9 |
| 5 mg/kg | 4 | 32.54 | 21.39 | 9.57 |
| | 8 | 89.34 | 38.65 | 13.21 |
| | 10 | 118.92 | 43.56 | 16.08 |
| | 18 | 123.01 | 43.68 | 15.08 |
| | 19 | 111.66 | 42.30 | 14.41 |
| | 20 | 54.15 | 26.81 | 9.18 |
| | 40 | 66.99 | 31.47 | 10.40 |
| | 41 | 69.20 | 34.22 | 12.19 |
| | 47 | 107.70 | 40.04 | 13.20 |
| | 50 | 29.81 | 36.50 | 13.39 |
| | mean | 80.3 | 35.9 | 12.5 |
| | sd | 34.9 | 7.5 | 2.3 |
| | sem | 11.0 | 2.4 | 0.7 |
| | n | 10 | 10 | 10 |
| 10 mg/kg | 2 | 71.81 | 29.78 | 11.02 |
| | 6 | 110.46 | 49.10 | 14.95 |
| | 11 | 96.59 | 42.91 | 15.25 |
| | 14 | 67.76 | 39.50 | 11.27 |
| | 21 | 106.16 | 43.38 | 14.07 |
| | 29 | 153.12 | 48.06 | 16.04 |
| | 31 | 128.22 | 58.06 | 17.20 |
| | 42 | 157.22 | 46.42 | 13.65 |
| | 45 | 124.56 | 53.47 | 14.90 |
| | 46 | 138.07 | 59.33 | 17.30 |
| | mean | 115.44 | 47.00 | 14.47 |
| | sd | 30.9 | 8.8 | 2.2 |
| | sem | 9.8 | 2.8 | 0.7 |
| | n | 10 | 10 | 10 |
| 20 mg/kg | 5 | 115.27 | 46.82 | 16.75 |
| | 9 | 10.45* | 11.67* | 7.14* |
| | 16 | 99.74 | 43.19 | 13.56 |
| | 24 | 160.82 | 56.93 | 17.52 |
| | 27 | 71.59 | 36.64 | 11.98 |
| | 34 | 95.60 | 43.21 | 14.67 |
| | 35 | 114.62 | 40.58 | 14.39 |
| | 37 | 92.80 | 33.97 | 13.53 |
| | 38 | 91.36 | 38.27 | 12.83 |
| | 49 | 115.09 | 41.87 | 9.07 |
| | mean | 106.3 | 42.4 | 13.8 |
| | sd | 24.9 | 6.7 | 2.5 |
| | sem | 8.3 | 2.2 | 0.8 |
| | n | 9 | 9 | 9 |

*excluded from statistical analysis

TABLE 23

Liver Oil Red O

| Group | animal # | oil-red-O quantification (%) |
|---|---|---|
| no treatment | 15 | 9.01 |
| | 17 | 14.17 |
| | 23 | 10.38 |
| | 25 | 21.79 |
| | 30 | 16.52 |
| | 33 | 17.11 |
| | 36 | 5.43 |
| | 39 | 0.19* |
| | 48 | 4.74 |
| | mean | 12.4 |
| | sd | 6.0 |
| | sem | 2.1 |
| | n | 8 |
| vehicle | 1 | 5.01 |
| | 3 | 10.20 |
| | 12 | 14.84 |
| | 13 | 5.99 |
| | 22 | 3.94 |
| | 26 | 5.55 |
| | 28 | 22.20 |
| | 43 | 19.93 |
| | 44 | 13.80 |
| | mean | 11.3 |
| | sd | 6.8 |
| | sem | 2.3 |
| | n | 9 |
| 5 mg/kg | 4 | 0.67 |
| | 8 | 2.91 |
| | 10 | 8.82 |
| | 18 | 9.22 |
| | 19 | 4.41 |
| | 20 | 6.15 |
| | 40 | 8.06 |
| | 41 | 8.93 |
| | 47 | 8.85 |
| | 50 | 9.33 |
| | mean | 6.7 |
| | sd | 3.1 |
| | sem | 1.0 |
| | n | 10 |
| 10 mg/kg | 2 | 19.18 |
| | 6 | 18.46 |
| | 11 | 13.25 |
| | 14 | 3.65 |
| | 21 | 8.46 |
| | 29 | 8.67 |
| | 31 | 16.07 |
| | 42 | 17.12 |
| | 45 | 16.00 |
| | 46 | 11.43 |
| | mean | 13.23 |
| | sd | 5.1 |
| | sem | 1.6 |
| | n | 10 |
| 20 mg/kg | 5 | 13.45 |
| | 9 | 0.42 |
| | 16 | 15.53 |
| | 24 | 9.89 |
| | 27 | 4.95 |
| | 34 | 8.17 |
| | 35 | 4.74 |
| | 37 | 7.06 |
| | 38 | 15.71 |
| | 49 | 5.38 |
| | mean | 8.5 |
| | sd | 5.1 |
| | sem | 1.6 |
| | n | 10 |

Example B6

Effect of Compound #37 in a Diet-Induced Chronic Steatosis/NASH Model

To investigate whether Compound #37 improves pre-existing steatosis/NASH pathology, a study was conducted using a 16-week diet-induced NASH mouse model. In this model, mice develop steatosis that progresses with inflammation and fibrosis that mimic many of the observed pathologies in human nonalcoholic fatty liver disease (NAFLD) and NASH (Hebbard & George, 2010). For 6 weeks, mice were fed a high-fat, high-cholesterol diet and provided drinking water containing fructose to induce liver pathology (Charlton et al, 2011). After 6 weeks, the mice were divided into 2 groups with similar mean aspartate aminotransferase (AST) and alanine aminotransferase (ALT) values (n=12 mice), although it should be noted that AST and ALT concentrations within both groups were higher and with greater variability than anticipated (e.g., mean ALT 677 U/L [SD, 401 U/L] in the vehicle control group and 693 U/L [SD, 365 U/L] in the Compound #37 group). After the animals were divided into 2 groups, the diet was continued for 10 additional weeks during which time 1 group received vehicle and the other was treated with 20 mg/kg/day Compound #37.

Compound #37 was generally well tolerated in this model with no important differences in weight gain between treatment groups after the first week of treatment. One animal in the Compound #37 treatment group died after 48 days of treatment with no obvious cause of death; gavage error in dosing could not be ruled out. This death rate is within historical norms for long-term diet-induced NASH studies at this vendor.

Overall, no consistent findings were observed in plasma or hepatic lipid concentrations, degree of steatosis, or SREBP-related target gene expression levels between treatment groups, although the degree of variability of liver injury in the animals at baseline makes the results difficult to interpret. No evidence of hepatotoxicity with Compound #37 was observed in this study; transaminase concentrations were similar between treatment groups throughout the study.

Figure 4:
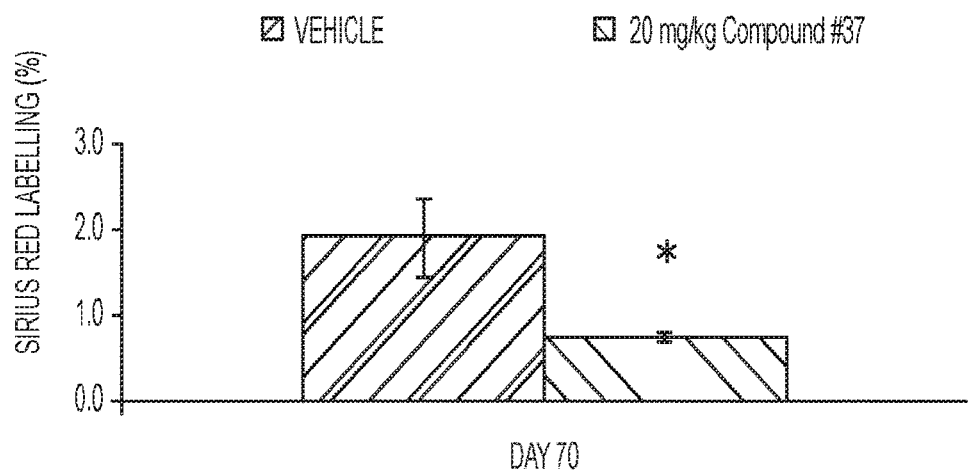
FIG. 4. Graph showing the effect of Compound #37 on collagen deposition in a diet-induced chronic NASH mouse model. Error bars indicate ±SEM.*, p<0.001 by Mann-Whitney test. NASH, nonalcoholic steatohepatitis.

Notably, while Compound #37 did not cause an overt reduction in liver lipid content, a significant reduction in the formation of collagen fiber formation was demonstrated by decreased Sirius Red staining (FIG. 4). Furthermore, mean liver collagen $\alpha 1$(I)mRNA was also significantly down-regulated by Compound #37 treatment (1.45% vs 0.49%; $p<0.05$), suggesting a potential effect on liver fibrosis.

Figure 5A:
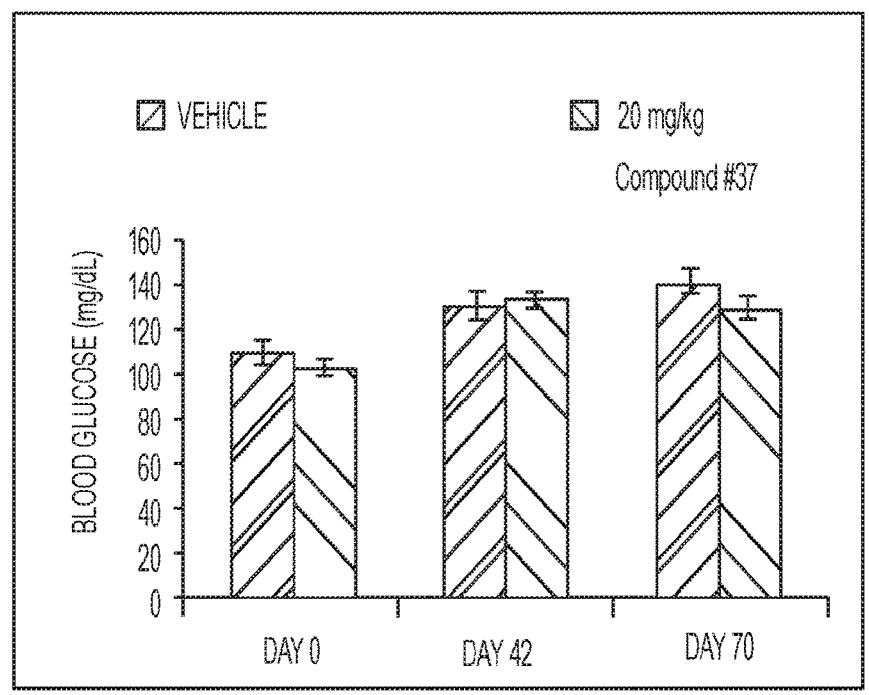
FIGS. 5A-C. HOMA-IR scores and blood glucose and plasma insulin concentrations in a diet-induced chronic NASH mouse model.
Figure 5B:
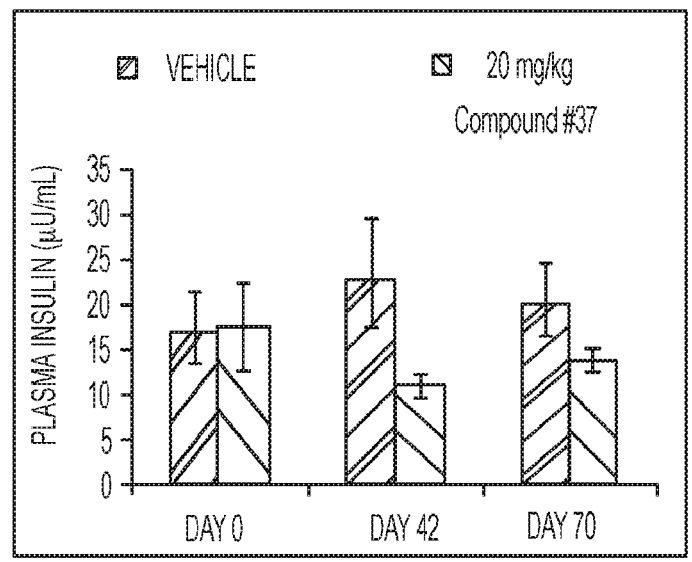
Figure 5C:
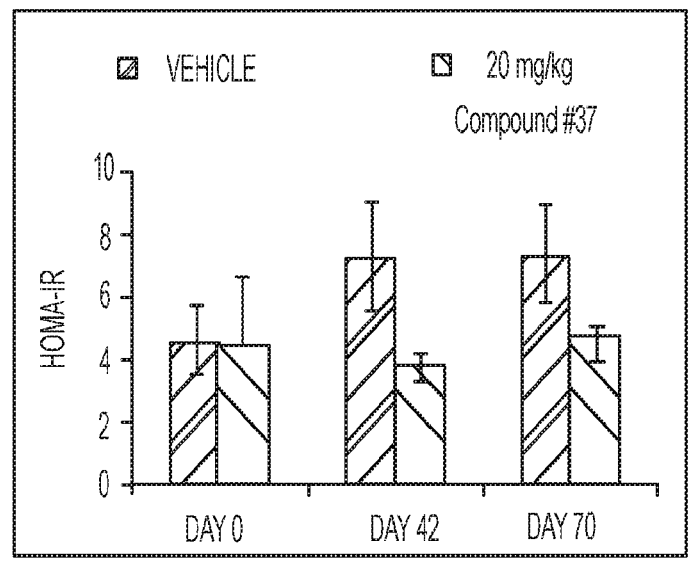

Compound #37 treatment also resulted in a trend toward lower homeostasis model assessment-estimated insulin resistance (HOMA-IR) scores due to reduced plasma insulin. Glucose concentrations were in the normal range and were largely unchanged for the Compound #37-treated mice, indicating an improvement in insulin sensitivity without concurrent hypoglycemia (FIGS. 5A-C). Compound #37-treated mice also had a 38% reduction in plasma leptin concentrations, a hormone associated with adiposity, but these findings were not statistically significant.

Example B7

Pharmacology Data From 28-Day Repeat-Dose Toxicity Studies in Healthy Rats and Dogs In addition to standard safety endpoints, pharmacology endpoints were assessed as part of a 28-day repeat-dose toxicity studies in healthy rats and dogs.

Figure 6:
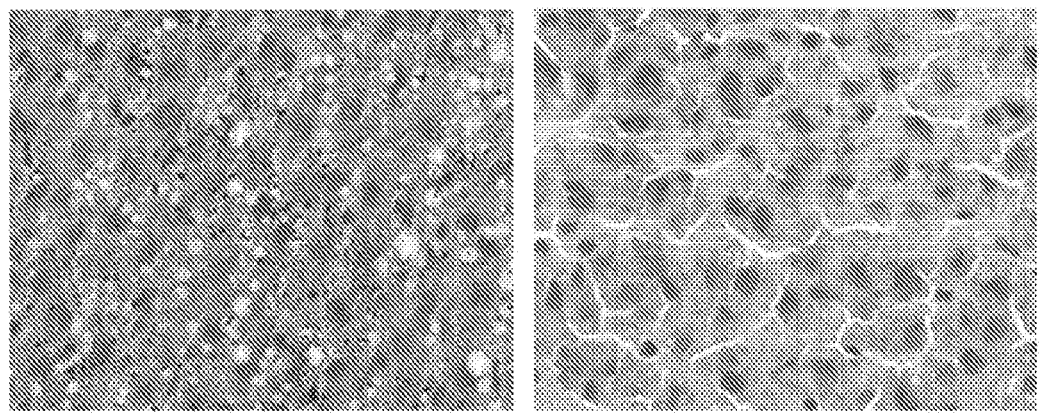
FIG. 6. Photomicrographs showing the effect of Compound #37 on liver Oil red O staining in healthy female rats after 28 days of treatment. Left panel, control; right panel, 100/75 mg/g/day Compound #37.

In the repeat-dose toxicity study in rats (Compound #37P018), Compound #37 was given at 0 (vehicle control), 50, 100/75, and 200/150 mg/kg/day for 28 days; some animals from each dose group continued into a 28-day recovery period. After 28 days of treatment, liver neutral lipids from treated and control animals were analyzed with Oil Red O staining. This analysis demonstrated a trend towards decreased concentrations of neutral lipids in the liver in an Compound #37 dose-dependent manner (summarized in Table B7; representative micrographs are presented in FIG. 6) without effects on liver glycogen.

TABLE B7

|  | ALT (U/L) | | AST (U/L) | |
| --- | --- | --- | --- | --- |
|  | Mean | SD | Mean | SD |
| Vehicle | 576.30 | 482.79 | 632.40 | 389.57 |
| Compound #37, 5 mg/kg | 419.30 | 181.14 | 449.44 | 121.87 |
| Compound #37, 20 mg/kg | 403.50 | 107.81 | 431.17 | 100.66 |

Figure 7:
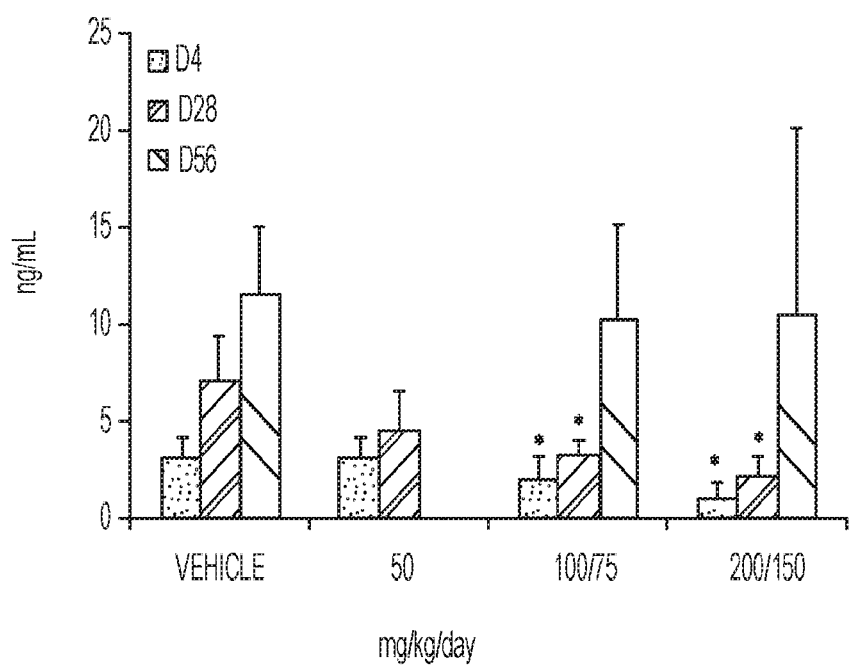
FIG. 7. Graph showing the effect of Compound #37 on leptin concentration staining in healthy female rats. D4, day 4; D28, day 28; D56, day 56.*, p<0.05.

The more pronounced effects in female rats compared with male rats is consistent with the observed higher plasma exposure (>4-fold higher area under the curve over 24 hours [AUC24h]) at day 28 in females compared with males. Evidence of an effect of Compound #37 on leptin concentrations was also observed in female rats in a dose-dependent manner. As animals gain weight, leptin concentrations naturally increase due to its origin from adipose tissue. Female rats treated with Compound #37 had lower concentrations of leptin compared with the vehicle control group during the treatment period (day 4 and day 28), which was not observed after treatment termination and recovery (day 56) (FIG. 7). In male rats, decreases in leptin concentrations were only observed at the highest dose group, likely due to lower systemic exposures of Compound #37 as noted above.

Figure 8A:
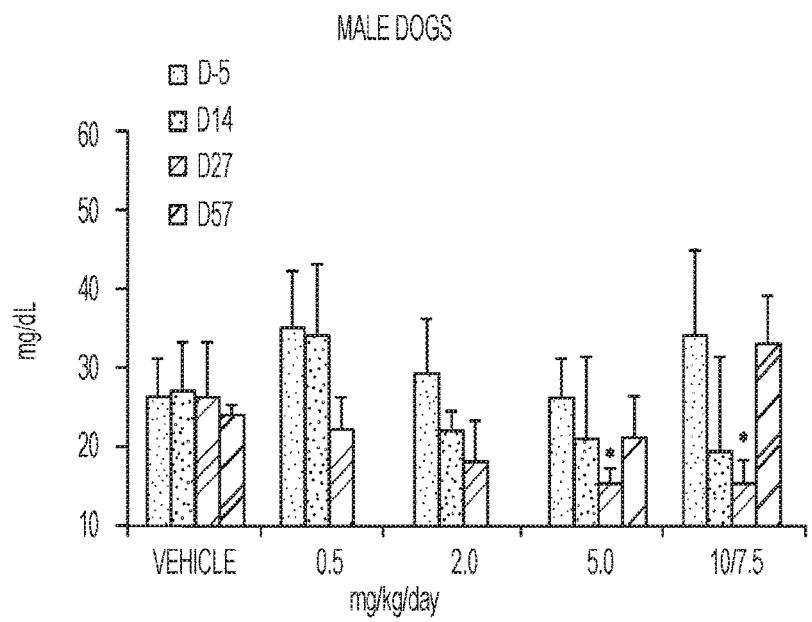
FIGS. 8A-B. Graphs showing the effect of Compound #37 on circulating triglyceride concentration in male and female dogs on days.
Figure 8B:
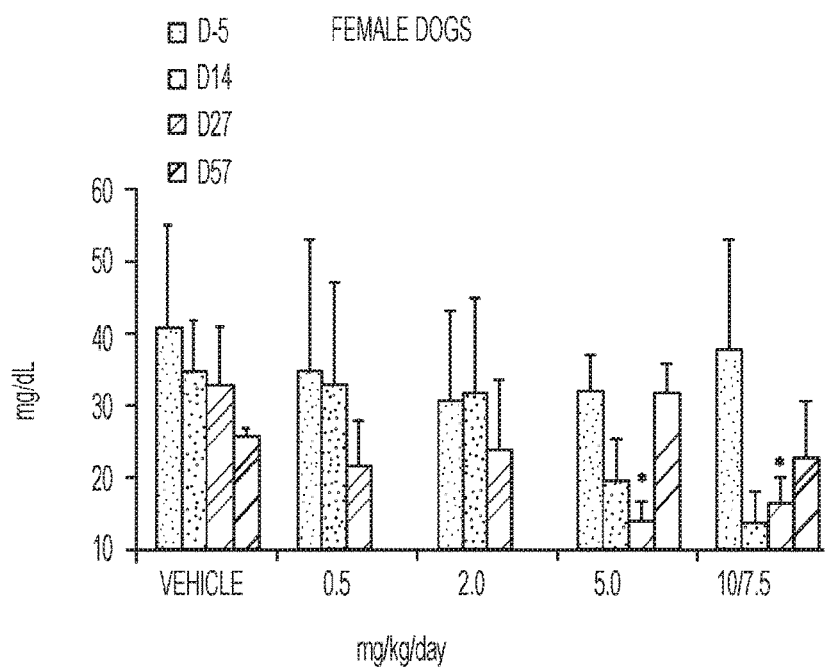
Figure 9A:
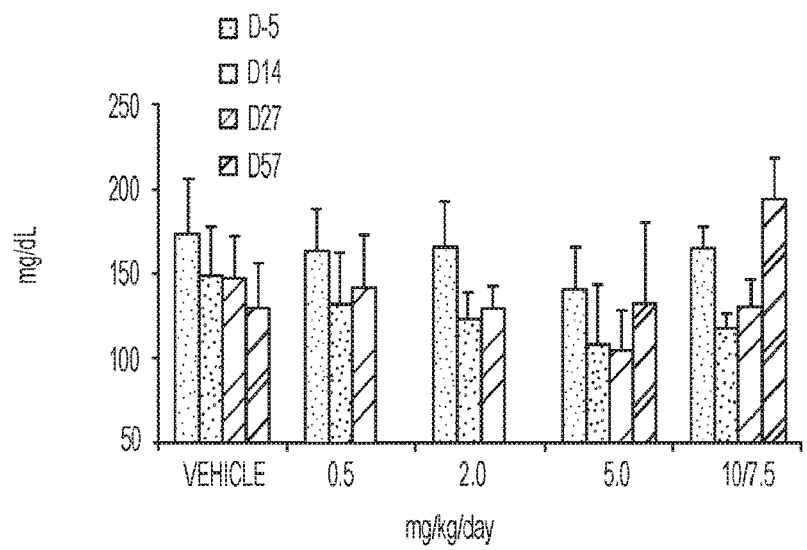
FIGS. 9A-B. Graphs showing the effect of Compound #37 on circulating total cholesterol concentration in male and female dogs on days.
Figure 9B:
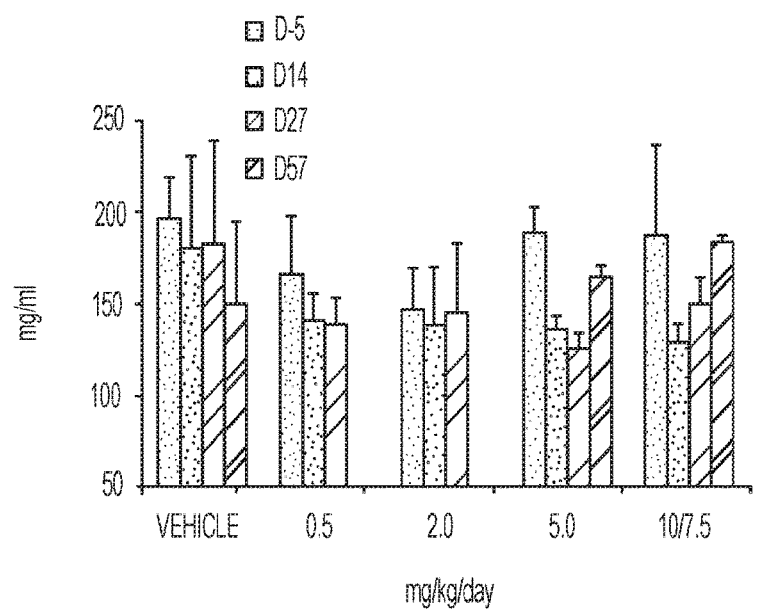

In the repeat-dose toxicity study in dogs, Compound #37 was given at 0 (vehicle control), 0.5, 2, 5, and 10/7.5 mg/kg/day for 28 days; some animals from each dose group continued into a 28-day recovery period (vehicle, 5, and 10/7.5 mg/kg/day groups only). Observations included trends of mild to moderate decreases in serum triglyceride (FIGS. 8A-B) and cholesterol concentrations (FIGS. 9A-B) at Compound #37 doses≥5 mg/kg/day. These Compound #37-related changes were reversible at the end of the 28-day recovery period. Findings were similar between male and female dogs, and consistent with the lack of sex differences in plasma exposure.

REFERENCES

Charlton et al., "Fast food diet mouse: novel small animal model of NASH with ballooning, progressive fibrosis, and high physiological fidelity to the human condition," Am J Physiol Gastrointest Liver Physiol. 2011 November; 301(5):G825-34.

Chavin et al., "Fatty acid synthase blockade protects steatotic livers from warm ischemia reperfusion injury and transplantation," Am J Transplant. 2004 September; 4(9): 1440-7.

Desai et al., "Atherogenic diet-induced hepatitis is partially dependent on murine TLR4," J Leukoc Biol. 2008 June; 83(6):1336-44.

Dubuquoy et al., "Prevention of liver damages by targeting different physiological mechanisms in two murine NASH models," Poster session presented at: World Diabetes Congress; 2013 Dec. 2-6; Melbourne, Australia. (poster P260).

Hebbard & George, "Animal models of nonalcoholic fatty liver disease," Nat Rev Gastroenterol Hepatol. 2011 January; 8(1):35-44. Review.

Horton et al., "SREBPs: activators of the complete program of cholesterol and fatty acid synthesis in the liver," J Clin Invest. 2002 May; 109(9):1125-31. Review.

Kamisuki et al., "A small molecule that blocks fat synthesis by inhibiting the activation of SREBP," Chem Biol. 2009 Aug. 28; 16(8):882-92.

Knowles et al., "Human hepatocellular carcinoma cell lines secrete the major plasma proteins and hepatitis B surface antigen," Science. 1980 Jul. 25; 209(4455):497-9.

Matsuda et al., "SREBP cleavage-activating protein (SCAP) is required for increased lipid synthesis in liver induced by cholesterol deprivation and insulin elevation," Genes Dev. 2001 May 15; 15(10):1206-16.

Moon et al., "The Scap/SREBP pathway is essential for developing diabetic fatty liver and carbohydrate-induced hypertriglyceridemia in animals," Cell Metab. 2012 Feb. 8; 15(2):240-6.

Nishina et al., "Effects of dietary fats from animal and plant sources on diet-induced fatty streak lesions in C57BL/6J mice," J Lipid Res. 1993 August; 34(8):1413-22.

Perfield et al., "Altered hepatic lipid metabolism contributes to nonalcoholic fatty liver disease in leptin-deficient Ob/Ob mice," J Obes. 2013; 2013:296537. Epub 2013 Jan. 16.

Shimomura et al., "Increased levels of nuclear SREP-1c associated with fatty livers in two mouse models of diabetes mellitus," J Biol Chem. 1999 Oct. 15; 274(42): 30028-32.

Vergnes et al., "Cholesterol and cholate components of an atherogenic diet induce distinct stages of hepatic inflammatory gene expression," J Biol Chem. 2003 Oct. 31; 278(44):42774-84.

The invention claimed is:

1. A method of treating liver fibrosis, comprising administering to a patient in need thereof an effective amount of the compound

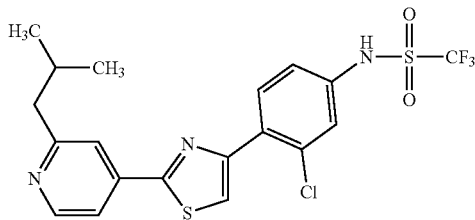 [SMILES: CC(C)Cc1cc(-c2nc(-c3ccc(NS(=O)(=O)C(F)(F)F)cc3Cl)cs2)ccn1]

or a pharmaceutically acceptable salt thereof.

2. The method of claim 1, wherein the patient has non-alcoholic steatohepatitis (NASH).

3. The method of claim 1, wherein administration of the compound or the pharmaceutically acceptable salt of the compound reduces the risk of NASH in the patient.

* * * * *